US010548967B2

(12) United States Patent
Mebatsion et al.

(10) Patent No.: US 10,548,967 B2
(45) Date of Patent: Feb. 4, 2020

(54) ATTENUATED SWINE INFLUENZA VACCINES AND METHODS OF MAKING AND USE THEREOF

(71) Applicant: BOEHRINGER INGELHEIM ANIMAL HEALTH USA INC., Duluth, GA (US)

(72) Inventors: Teshome Mebatsion, Watkinsville, GA (US); Taejoong Kim, Bogart, GA (US); Paul Michael Dorr, Columbia, MO (US); Martin Leonardo Liebstein-Bellia, Columbia, MO (US); Alton Timothy Leard, Lavonia, GA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/828,067

(22) Filed: Nov. 30, 2017

(65) Prior Publication Data

US 2018/0147276 A1    May 31, 2018

Related U.S. Application Data

(60) Provisional application No. 62/428,062, filed on Nov. 30, 2016.

(51) Int. Cl.
| | |
|---|---|
| *A61K 39/145* | (2006.01) |
| *C12N 7/00* | (2006.01) |
| *C12N 15/85* | (2006.01) |
| *A61K 39/00* | (2006.01) |

(52) U.S. Cl.
CPC .............. *A61K 39/145* (2013.01); *C12N 7/00* (2013.01); *C12N 15/85* (2013.01); *A61K 2039/5254* (2013.01); *A61K 2039/552* (2013.01); *A61K 2039/70* (2013.01); *C12N 2760/16022* (2013.01); *C12N 2760/16034* (2013.01)

(58) Field of Classification Search
CPC .......... A61K 39/145; A61K 2039/5254; A61K 2039/552; A61K 2039/70; A61K 39/12; C12N 7/00; C12N 15/85; C12N 2760/16022; C12N 2760/16034; C12N 2760/16111; C12N 2760/16134; C12N 2760/16162
See application file for complete search history.

(56) References Cited

U.S. PATENT DOCUMENTS

| | | | |
|---|---|---|---|
| 8,846,051 B2 | 9/2014 | Kew et al. | |
| 2010/0209454 A1* | 8/2010 | Wimmer | C07K 14/005 424/205.1 |
| 2012/0269849 A1* | 10/2012 | Wimmer | A61K 39/145 424/204.1 |
| 2012/0329091 A1* | 12/2012 | Pilpel | C07K 14/505 435/69.1 |
| 2013/0309263 A1* | 11/2013 | Calvert | A61K 39/12 424/186.1 |
| 2014/0155469 A1* | 6/2014 | Bahou | C07K 14/005 514/44 R |
| 2014/0356962 A1* | 12/2014 | Wimmer | C12N 7/00 435/471 |
| 2016/0354460 A1* | 12/2016 | Poon | C12N 7/00 |
| 2017/0196964 A1* | 7/2017 | Martinez-Sobrido | C07K 16/10 |
| 2018/0008689 A1* | 1/2018 | Vignuzzi | C12N 7/00 |
| 2018/0010136 A1* | 1/2018 | Hunt | C12N 15/67 |

OTHER PUBLICATIONS

Fan RL, Valkenburg SA, Wong CK, Li OT, Nicholls JM, Rabadan R, Peiris JS, Poon LL. Generation of Live Attenuated Influenza Virus by Using Codon Usage Bias. J Virol. Nov. 2015;89(21):10762-73. Epub Aug. 12, 2015.*
Nogales A, Baker SF, Ortiz-Riaño E, Dewhurst S, Topham DJ, Martínez-Sobrido L. Influenza A virus attenuation by codon deoptimization of the NS gene for vaccine development. J Virol. Sep. 2014;88(18):10525-40. Epub Jun. 25, 2014.*
Luan S, Pan W, Li T, Yang H, Zhang B, Li F, Chen L. [Rescued influenza A virus with codon deoptimized NS1 gene is attenuated both in vitro and in vivo]. Sheng Wu Gong Cheng Xue Bao. May 2009;25(5):720-6.*
Hause BM, Simonson RR. Influenza A virus (A/swine/North Carolina/3793/2008(H1N1)). Taxon 1144239. Segments 1-8, Accession Nos. JQ624664-JQ624671. Dep. Mar. 3, 2012.*
Altschul SF, Madden TL. 1997. Gapped BLAST and PSI-BLAST: a new generation of protein database search programs. Nucleic Acids Res. 25:3389-3402.
Bouvier 2008, The Biology of Influenza Viruses; https://www.ncbi.nlm.nih.gov/pmc/arti-cles/pmc3074182; describing the eight segments of influenza A and B.
Bragstad K et al. 2008. The evolution of human influenza A viruses from 1999 to 2006: A complete genome study. Virology J. 5:40.
Broadbent et al. Evaluation of the attenuation, immunogenicity, and efficacy of a live virus vaccine generated by codon-pair bias de-optimization of the 2009 pandemic H1N1 influenza virus, in ferrets. Vaccine vol. 34, Issue 4, Jan. 20, 2016, pp. 563-570.
Cai Z et al. 2010. A computational framework for influenza antigenic cartography. PLoS Computational Biology, 6(10): e1000949.
Coleman JR et al. Virus attenuation by genome-scale changes in codon pair bias. Science 2008. 320 (5884)1784-1787. PMID: 18583614.
Cottey R et al. 2001. Influenza virus. Curr. Protoc. Immunol. 19.11:1-32.
Das SR et al. 2011. Fitness costs limit influenza A virus hemagglutinin glycosylation as an immune evasion strategy. Proc. Natl. Acad. Sci. 108:E1417-E1422.

(Continued)

*Primary Examiner* — Rachel B Gill
(74) *Attorney, Agent, or Firm* — Judy Jarecki-Black; Suzanne Shope

(57) ABSTRACT

This disclosure provides attenuated swine influenza strains, particularly those produced via a reverse genetics approach, compositions comprising same, and methods of production and use thereof.

31 Claims, 14 Drawing Sheets

Specification includes a Sequence Listing.

(56) References Cited

OTHER PUBLICATIONS

Desselberger U et al. 1978. Biochemical evidence that "new" influenza virus strains in nature may arise by recombination (reassortment). Proc. Natl. Acad. Sci. 75:3341-3345.
Department of Health & Human Services, U.S. "Vaccine Types. Live-attenuated vaccines." https://www.vaccines.gov/basics/types/index.html; accessed Jan. 11, 2019.
Hause BM et al. 2010. Antigenic categorization of contemporary H3N2 swine influenza virus isolates using a high-throughput serum neutralization assay. J. Vet. Diagn. Invest. 22:352-359.
Hause BM et al. 2011 Genetic and antigenic characterization of recent human-like H1 (δ-cluster) swine influenza virus isolates. J. Swine Health Prod. 19:268-276.
Hay AJ et al. 2001. The evolution of human influenza viruses. Philos. T. R. Soc. B. 356:1861-1870.
Hensley SE et al. 2011. Influenza A virus hemagglutinin antibody escape promotes neuraminidase antigenic variation and drug resistance. PLoS One 6:e15190.
Hoffmann E et al. 2000. A DNA transfection system for generation of influenza A virus from eight plasmids. Proc. Natl. Acad. Sci. 97:6108-6113.
Hoffmann E et al. 2001. Universal primer set for the full length amplification of al influenza viruses. Arch. Virol. 146:2275-2289.
Karasin AI et al. 2006. Identification of human H1N2 and human-swine reassortant H1N2 and H1N1 influenza A viruses among pigs in Ontario, Canada (2003-2005). J. Clin. Microbiol. 44:1123-1126.
Klingbeil, et al. Protection of pigs against pandemic swine origin H1N1 influenza A virus infection by hemagglutinin- or neuraminidase-expressing attenuated pseudorabies virus recombinants. Virus Research vol. 199, Mar. 2, 2015, pp. 20-30.
Le Nouën C et al. Attenuation of Human Respiratory Syncytial Virus by Genome Scale Codon-Pair Deoptimization. Proc. Natl. Acad. Sci. USA Aug. 25, 2014. pii: 201411290. PMID: 25157129.
Long J et al. 2011. Evolution of H3N2 influenza virus in a guinea pig model. PLoS ONE 6:e20130.
Lorusso A et al. 2012. Contemporary epidemiology of North American lineage triple reassortant influenza A viruses in pigs. Curr. Top. Microbiol. Immunol. Jan. 22.
Mueller S et al. Live attenuated influenza virus vaccines by computer-aided rational design. Nat. Biotechn. 2010. 28:723-727. PMID: 20543832.
Sali A, Potterton L. 1995. Evaluation of comparative protein modeling by MODELLER. Proteins 23: 318-326.
Schild G et al. 1974. Antigenic variation in current influenza A viruses: evidence for a high frequency of antigenic 'drift' for the Hong Kong virus. Bull. World Health Organ. 51:1-11.
Scholtissek. Source for influenza pandemics. Eur. J. Epidemiol. (1994) 10:455-458.
Stengell M et al. 2011. Minor changes in the hemagglutinin of influenza A(H1N1)2009 virus alter its antigenic properties. PLoS One 6:e25848.
Vincent AL et al. 2009. Characterization of a newly emerged genetic cluster of H1N1 and H1N2 swine influenza virus in The United States. Virus Genes 39:176-185.
World Health Organization. "Live Attenuated Vaccines (LAV)." https://vaccine-safety-training.org/live-attenuated-vaccines.html; accessed Jan. 10, 2019.
Yang C et al. Deliberate reduction of hemagglutinin and neuraminidase expression of influenza virus leads to an ultra-protective influenza vaccine in mice. Proc. Natl., Acad. Sci. USA 2013. 110:9481-9486. PMID: 23690603.

\* cited by examiner

| Number | Type | Description |
|---|---|---|
| 1 | DNA/RNA | NS1 CDS of A/swine/NC/3793/2008(H1N1) - TRIG |
| 2 | PRT | NS1 of A/swine/NC/3793/2008(H1N1) - TRIG |
| 3 | DNA/RNA | M1 CDS of A/swine/NC/3793/2008(H1N1) - TRIG |
| 4 | PRT | M1 of A/swine/NC/3793/2008(H1N1) - TRIG |
| 5 | DNA/RNA | M2 CDS of A/swine/NC/3793/2008(H1N1) - TRIG |
| 6 | PRT | M2 of A/swine/NC/3793/2008(H1N1) - TRIG |
| 7 | DNA/RNA | NA CDS of A/swine/NC/3793/2008(H1N1) - TRIG |
| 8 | PRT | NA of A/swine/NC/3793/2008(H1N1) - TRIG |
| 9 | DNA/RNA | NP CDS of A/swine/NC/3793/2008(H1N1) - TRIG |
| 10 | PRT | NP of A/swine/NC/3793/2008(H1N1) - TRIG |
| 11 | DNA/RNA | HA CDS of A/swine/NC/3793/2008(H1N1) - TRIG |
| 12 | PRT | HA of A/swine/NC/3793/2008(H1N1) - TRIG |
| 13 | DNA/RNA | PA CDS of A/swine/NC/3793/2008(H1N1) - TRIG |
| 14 | PRT | PA of A/swine/NC/3793/2008(H1N1) - TRIG |
| 15 | DNA/RNA | PB1 CDS of A/swine/NC/3793/2008(H1N1) - TRIG |
| 16 | PRT | PB1 of A/swine/NC/3793/2008(H1N1) - TRIG |
| 17 | DNA/RNA | PB2 CDS of A/swine/NC/3793/2008(H1N1) - TRIG |
| 18 | PRT | PB2 of A/swine/NC/3793/2008(H1N1) - TRIG |
| 19 | DNA/RNA | M CDS (contains M1 & M2) of A/swine/NC/3793/2008(H1N1) - TRIG |
| 20 | DNA/RNA | NS CDS (contains NS1 & NS2) of A/swine/NC/3793/2008(H1N1) - TRIG |
| 21 | DNA/RNA | HA CDS (H1N1 SIV field isolate) |
| 22 | DNA/RNA | HA-DO (H1N1; de-optimized) |
| 23 | PRT | HA (H1N1 SIV field isolated/de-optimized) |
| 24 | DNA/RNA | NA CDS (H1N1 SIV field isolate) |
| 25 | DNA/RNA | NA-DO (H1N1; de-optimized) |
| 26 | PRT | NA (H1N1 SIV field isolated/de-optimized) |
| 27 | DNA/RNA | NS1-DO CDS of A/swine/NC/3793/2008(H1N1) – TRIG, de-optimized |
| 28 | DNA/RNA | HA CDS (H1N2 SIV field isolate) |
| 29 | DNA/RNA | HA-DO (H1N2; de-optimized) |
| 30 | PRT | HA (H1N2 SIV field isolated/de-optimized) |
| 31 | DNA/RNA | NA CDS (H1N2 SIV field isolate) |
| 32 | DNA/RNA | NA-DO (H1N2; de-optimized) |
| 33 | PRT | NA (H1N2 SIV field isolated/de-optimized) |
| 34 | DNA/RNA | HA CDS (H3N2 SIV field isolate) |
| 35 | DNA/RNA | HA-DO (H3N2; de-optimized) |
| 36 | PRT | HA (H3N2 SIV field isolated/de-optimized) |
| 37 | DNA/RNA | NA CDS (H3N2 SIV field isolate) |
| 38 | DNA/RNA | NA-DO (H3N2; de-optimized) |
| 39 | PRT | NA (H3N2 SIV field isolated/de-optimized) |

*FIG. 2*

| Number | Type | Description |
|---|---|---|
| 40 | DNA/RNA | NS2 CDS of A/Swine/NC/93523/01(H1N2) |
| 41 | PRT | NS2 of A/swine/NC/93523/01(H1N2) |
| 42 | DNA/RNA | NS1 CDS of A/Swine/NC/93523/01(H1N2) |
| 43 | PRT | NS1 of A/swine/NC/93523/01(H1N2) |
| 44 | DNA/RNA | M CDS of A/swine/NC/93523/01(H1N2) |
| 45 | PRT | M of A/swine/NC/93523/01(H1N2) |
| 46 | DNA/RNA | NA CDS of A/swine/NC/93523/01(H1N2) |
| 47 | PRT | NA of A/swine/NC/93523/01(H1N2) |
| 48 | DNA/RNA | NP CDS of A/swine/NC/93523/01(H1N2) |
| 49 | PRT | NP of A/swine/NC/93523/01(H1N2) |
| 50 | DNA/RNA | HA CDS of A/swine/NC/93523/01(H1N2) |
| 51 | PRT | HA of A/swine/NC/93523/01(H1N2) |
| 52 | DNA/RNA | PA CDS of A/swine/NC/93523/01(H1N2) |
| 53 | PRT | PA of A/swine/NC/93523/01(H1N2) |
| 54 | DNA/RNA | PB1 CDS of A/swine/NC/93523/01(H1N2) |
| 55 | PRT | PB1 of A/swine/NC/93523/01(H1N2) |
| 56 | DNA/RNA | PB2 CDS of A/swine/NC/93523/01(H1N2) |
| 57 | PRT | PB2 of A/swine/NC/93523/01(H1N2) |
| 58 | DNA/RNA | NS2 CDS of A/swine/NC/R08-001877-D08-013371/08(H3N2) |
| 59 | PRT | NS2 of A/swine/NC/R08-001877-D08-013371/08(H3N2) |
| 60 | DNA/RNA | NS1 CDS of A/swine/NC/R08-001877-D08-013371/08(H3N2) |
| 61 | PRT | NS1 of A/swine/NC/R08-001877-D08-013371/08(H3N2) |
| 62 | DNA/RNA | M1 CDS of A/swine/NC/R08-001877-D08-013371/08(H3N2) |
| 63 | PRT | M1 of A/swine/NC/R08-001877-D08-013371/08(H3N2) |
| 64 | DNA/RNA | M2 CDS of A/swine/NC/R08-001877-D08-013371/08(H3N2) |
| 65 | PRT | M2 of A/swine/NC/R08-001877-D08-013371/08(H3N2) |
| 66 | DNA/RNA | NA CDS of A/swine/NC/R08-001877-D08-013371/08(H3N2) |
| 67 | PRT | NA of A/swine/NC/R08-001877-D08-013371/08(H3N2) |
| 68 | DNA/RNA | NP CDS of A/swine/NC/R08-001877-D08-013371/08(H3N2) |
| 69 | PRT | NP of A/swine/NC/R08-001877-D08-013371/08(H3N2) |
| 70 | DNA/RNA | HA CDS of A/swine/NC/R08-001877-D08-013371/08(H3N2) |
| 71 | PRT | HA of A/swine/NC/R08-001877-D08-013371/08(H3N2) |
| 72 | DNA/RNA | PA CDS of A/swine/NC/R08-001877-D08-013371/08(H3N2) |
| 73 | PRT | PA of A/swine/NC/R08-001877-D08-013371/08(H3N2) |
| 74 | DNA/RNA | PB1 CDS of A/swine/NC/R08-001877-D08-013371/08(H3N2) |
| 75 | PRT | PB1 of A/swine/NC/R08-001877-D08-013371/08(H3N2) |
| 76 | DNA/RNA | PB2 CDS of A/swine/NC/R08-001877-D08-013371/08(H3N2) |
| 77 | PRT | PB2 of A/swine/NC/R08-001877-D08-013371/08(H3N2) |

*FIG. 2*
*(Continued)*

| Number | Type | Description |
|---|---|---|
| 78 | DNA/RNA | PB2 CDS + 5' and 3'UTR |
| 79 | DNA/RNA | PB1 CDS + 5' and 3'UTR |
| 80 | DNA/RNA | PA CDS + 5' and 3'UTR |
| 81 | DNA/RNA | NP CDS + 5' and 3'UTR |
| 82 | DNA/RNA | M CDS + 5' and 3'UTR |
| 83 | DNA/RNA | NS CDS + 5' and 3'UTR |
| 84 | DNA/RNA | HA of H1N1 CDS + 5' and 3'UTR |
| 85 | DNA/RNA | NA of H1N1 CDS + 5' and 3'UTR |
| 86 | DNA/RNA | HA of H1N2 CDS + 5' and 3'UTR |
| 87 | DNA/RNA | NA of H1N2 CDS + 5' and 3'UTR |
| 88 | DNA/RNA | HA of H3N2 CDS + 5' and 3'UTR |
| 89 | DNA/RNA | NA of H3N2 CDS + 5' and 3'UTR |
| 90 | DNA/RNA | NS1-DO of TRIG H1N1 CDS + 5' and 3'UTR |
| 91 | DNA/RNA | HA-DO of H1N1 CDS + 5' and 3'UTR |
| 92 | DNA/RNA | NA-DO of H1N1 CDS + 5' and 3'UTR |
| 93 | DNA/RNA | HA-DO of H1N2 CDS + 5' and 3'UTR |
| 94 | DNA/RNA | NA-DO of H1N2 CDS + 5' and 3'UTR |
| 95 | DNA/RNA | HA-DO of H3N2 CDS + 5' and 3'UTR |
| 96 | DNA/RNA | NA-DO of H3N2 CDS + 5' and 3'UTR |
| 97 | DNA/RNA | Bm-HA-Forward Primer |
| 98 | DNA/RNA | 3-Reverse Primer |
| 99 | DNA/RNA | 5-Forward Primer |
| 100 | DNA/RNA | Bm-HA-Reverse Primer |
| 101 | DNA/RNA | H3 ecto-domain Forward Primer |
| 102 | DNA/RNA | H3 ecto-domain Reverse Primer |
| 103 | DNA/RNA | Overlapping sequence of SEQ ID NOs: 98 & 99 |
| 104 | DNA/RNA | 3'UTR, SS, TMD, CTD, and 5'UTR of HA segment (H1N2-DO) |
| 105 | DNA/RNA | HA-DO (H1-H3 chimera) - Nucleotides 351 to 2450 of pHW2000 |
| 106 | PRT | HA-DO (H1-H3 chimera) |
| 107 | DNA | pHW2000 plasmid |
| 108 | DNA | pHW2000-TRIG-NS1-DO |
| 109 | DNA | pHW2000-H1N1-HA-DO |
| 110 | DNA | p pHW2000 Cloning Vector

Cloning site (BsmBI) sequences

```
                                    BsmBI
5'-TCCGAAGTTGGGGGGGAGGAGACGGTACCGTCTCCAATAACCCGGCGGCCC-3' SEQ ID NO:116
3'-AGGCTTCAACCCCCCCTCCTCTGCCATGGCAGAGGTTATTGGGCCGCCGGG-5' SEQ ID NO:117
                              BsmBI
```

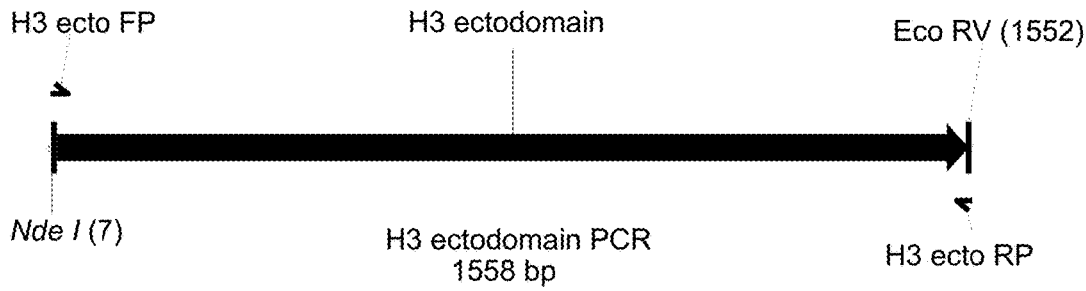

```
                NdeI
                ~~~~~~
    1   ACTACATATG CACAAAAACT TCCCGGAAGT GACAACAGCA TGGCAACGCT GTGCTTAGGA CATCATGCGG
   71   TCCCGAATGG AACGTTAGTC AAAACGATAA CGGATGATCA AATAGAAGTC ACGAATGCGA CGGAATTAGT
  141   CCAATCGTCG TCGACGGGAC GTATATGTAA TTCGCCGCAT CAAATATTAG ATGGAAAAAA TTGTACGTTA
  211   ATAGATGCGT TATTAGGAGA TCCGCATTGT GATGATTTTC AAAATAAAGA ATGGGATTTA TTTGTCGAAC
  281   GTTCGACGGC GTATTCGAAT TGTTATCCGT ATTATGTCCC GGATTATGCG TCGTTACGTT CGTTAGTCGC
  351   GTCGTCGGGA ACGTTAGAAT TTACGCAAGA ATCGTTTAAT TGGACGGGAG TCGCGCAAGA TGGATCGTCG
  421   TATGCGTGTC GTCGTGAATC GGTCAATTCG TTTTTTTCGC GTTTAAATTG GTTACATAAA TTAGATTATA
  491   AATATCCGGC GTTAAAAGTC ACGATGCCGA ATAATGATAA ATTTGATAAA TTATATATAT GGGGAGTCCA
  561   TCATCCGGGA ACGGATCGTG ATCAAACGAA TTTATATGTC CAAACGTCGG ACGTGTCAC GGTCTCGACG
  631   AAACGTTCGC AACAAACGGT CATACCGAAT ATAGGATCGC GTCCGTGGGT CCGTGGAGTC TCGTCGATAA
  701   TATCGATATA TTGGACGATA GTCAAACCGG GAGATATATT ATTAATAAAT TCGACGGGAA ATTTAATAGC
  771   GCCGCGTGGA TATTTTAAAT TACAATCGGG AAAATCGTCG ATAATGCGTT CGGATGCGCC GATAGGAATA
  841   TGTAATTCGG AATGTATAAC GCCGAATGGA TCGATACCGA ATGATAAACC GTTTCAAAAT GTCAATCGTA
  911   TAACCTATGG AGCGTGTCCG CGTTATGTCA AACAAAATAC GTTAAAATTA GCGACGGGAA TGCGTAATGT
  981   CCCGGAAAAA CAAACGCGTG AATATTTGG AGCGATAGCG GGATTTATAG AAAATGGATG GAAGGAATG
 1051   GTCGATGGAT GGTATGGATT TCGTCATCAA AATTCGGAAG GAACGGGACA AGCGGCGGAT TTAAAATCGA
 1121   CGCGTGCGGC GATAAATCAA ATAACGGGAA AATTAAATCG TGTCATAAAA AAAACGAATG AAAAATTTCA
 1191   TCAAATAGAA AAAGAATTTT CGGAAGTCGA AGGACGTATA CAAGATTTAG AAAAATATGT CGAAGATACG
 1261   AAAATAGATT TATGGTCGTA TAATGCGGAA TTATTAGTCG CGTTAGAAAA TCAACATACG ATAGATTTAA
 1331   CGGATTCGGA AATGAATAAA TTATTTGAAC GTACGCGTAA ACAATTACGT GAAAATGCGG AAGATATGGG
 1401   AAATGGATGT TTTAAAATAT ATCATAAATG TGATAATGCG TGTATAGGAT CGATACGTAA TGGAACGTAT
 1471   GATCATGATG TCTATCGTGA TGAAGCGTTA AATAATCGTT TTCAAATAAA AGGAGTCCAA TTAAAATCGG
             EcoRV
             ~~ ~~~~~~
 1541   GATATAAAGA TATCTTAA
```

FIG. 7

BOLD = 3'UTR from H1N2

*Italics* = signal sequences from H1N2

Light Grey = ectodomain from H3N2

*Light grey + Italics* = transmembrane domain from H1N2

Underline = cytoplasmic tail from H1N2

*Underline + Italics* = 5' UTR from H1N2

\*Numbering is with respect to the pHW2000-HA-DO (H1-H3 chimera) plasmid

```
 351  GGCTAACTAG AGAACCCACT GCTTACTGGC TTATCGAAAT TAATACGACT CACTATAGGG AGACCCAAGC
 421  TGTTAACGCT AGCAGTTAAC CGGAGTACTG GTCGACCTCC GAAGTTGGGG GGGAGCAAAA GCAGGGGAAA
 491  AATAAAAGCA ACCAAAATGA AAGTAAAACT AATGGTTCTG TTATGTACAT TTACAGCTAC ATATGCACAA
 561  AAACTTCCCG GAAGTGACAA CAGCATGGCA ACGCTGTGCT TAGGACATCA TGCGGTCCCG AATGGAACGT
 631  TAGTCAAAAC GATAACGGAT GATCAAATAG AAGTCACGAA TGCGACGGAA TTAGTCCAAT CGTCGTCGAC
 701  GGGACGTATA TGTAATTCGC CGCATCAAAT ATTAGATGGA AAAAATTGTA CGTTAATAGA TGCGTTATTA
 771  GGAGATCCGC ATTGTGATGA TTTTCAAAAT AAAGAATGGG ATTTATTTGT CGAACGTTCG ACGGCGTATT
 841  CGAATTGTTA TCCGTATTAT GTCCCGGATT ATGCGTCGTT ACGTTCGTTA GTCGCGTCGT CGGGAACGTT
 911  AGAATTTACG CAAGAATCGT TTAATTGGAC GGGAGTCGCG CAAGATGGAT CGTCGTATGC GTGTCGTCGT
 981  GAATCGGTCA ATTCGTTTTT TCGCGTTTTA AATTGGTTAC ATAAATTAGA TTATAAATAT CCGGCGTTAA
1051  AAGTCACGAT GCCGAATAAT GATAAATTTG ATAAATTATA TATATGGGGA GTCCATCATC CGGGAACGGA
1121  TCGTGATCAA ACGAATTTAT ATGTCCAAAC GTCGGGACGT GTCACGGTCT CGACGAAACG TTCGCAACAA
1191  ACGGTCATAC CGAATATAGG ATCGCGTCCG TGGGTCCGTG GAGTCTCGTC GATAATATCG ATATATTGGA
1261  CGATAGTCAA ACCGGAGAGAT ATATTATTAA TAAATTCGAC GGGAAATTTA ATAGCGCCGC GTGGATATTT
1331  TAAATTACAA TCGGGAAAAT CGTCGATAAT GCGTTCGGAT GCGCCGATAG GAATATGTAA TTCGGAATGT
1401  ATAACGCCGA ATGCATCGAT ACCGAATGAT AAACCGTTTC AAAATGTCAA TCGTATAACC TATGGAGCGT
1471  GTCCGCGTTA TGTCAAACAA AATACGTTAA AATTAGCGAC GGGAATGCGT AATGTCCCGG AAAAACAAAC
1541  GCGTGGAATA TTTGGAGCGA TAGCGGGATT TATAGAAAAT GGATGGGAAG GAATGGTCGA TGGATGGTAT
1611  GGATTTCGTC ATCAAAATTC GGAAGGAACG GGACAAGCGG CGGATTTAAA ATCGACGCGT GCGGCGATAA
1681  ATCAAATAAC GGGAAAATTA AATCGTGTCA TAAAAAAAAC GAATGAAAAA TTTCATCAAA TAGAAAAAGA
1751  ATTTTCGGAA GTCGAAGGAC GTATACAAGA TTTAGAAAAA TATGTCGAAG ATACGAAAAT AGATTTATGG
1821  TCGTATAATG CGGAATTATT AGTCGCGTTA GAAAATCAAC ATACGATAGA TTTAACGGAT TCGGAAATGA
1891  ATAAATTATT TGAACGTACG CGTAAACAAT TACGTGAAAA TGCGGAAGAT ATGGGAAATG GATGTTTAA
1961  AATATATCAT AAATGTGATA ATGCGTGTAT AGGATCGATA CGTAATGGAA CCTATGATCA TGATGTCTAT
2031  CGTGATGAAG CGTTAAATAA TCGTTTCAA ATAAAAGGAG TCCAATTAAA ATCGGGATAT AAAGATATCT
2101  TAGCGATATA TTCGACGGTC GGGTCGTCCC TAGTTCTTTT AGTCTCCCTG GGGCAATCA GCTTCTGGAT
2171  GTGTTCCAAT GGGTCTTTAC AGTGTAGAAT ATGCATCTAA GACCAGAATT TCAGAAATAT AAGGAAAAAC
2241  ACCCTTGTTT CTACTAATAA CCCGGCGGCC CAAAATGCCG ACTCGGAGCG AAAGATATAC CTCCCCCGGG
2311  GCCGGGAGGT CGCGTCACCG ACCACGCCGC CGGCCCAGGC GACGCGCGAC ACGGACACCT GTCCCCAAAA
2381  ACGCCACCAT CGCAGCCACA CACGGAGCGC CCGGGGCCCT CTGGTCAACC CCAGGACACA CGCGGGAGCA
```

(SEQ ID NO:105)

SEQUENCE LISTING

<160> NUMBER OF SEQ ID NOS: 117

<210> SEQ ID NO 1
<211> LENGTH: 657
<212> TYPE: DNA
<213> ORGANISM: swine influenza virus

<400> SEQUENCE: 1

```
atggactcca atactgtgtc aagctttcag gtagactgtt tcctttggca catccgcaaa        60
cgatttgcag acaatggatt gggtgatgcc ccattccttg atcggctccg ccgagatcaa       120
aagtccctaa aaggaagggg caacaccctt agcctagaca tcgaaacagc cactcttgtt       180
gggaaacaaa ttgttgagtg gattttgaaa gaggaatcca gcgatatact taagatgacc       240
```

```
attgcatctg tgcctacttc gcgctaccta gctgacatga ccctcgagga aatgtcacga    300
gactggttca tgctaatgcc taggcaaaag ataataggcc ctcttttgtgt gcgagtggac   360 caggcgatca tggaaaagaa catcatactg aaagcgaact tcagtgtgat ctttaaccga    420
ttagagactt tgatactact aagggctttc actgaggagg gagcaatcgt tggagaaatt   480
tcaccattac cttatcttcc aggacatact aatgaggatg tcaaaaatgc agttggggtc   540
ctcatcggag ggcttgaatg gaatggtaac acggttcgag gctctgaaaa tctacagaga   600
ttcgcttgga gaaaccataa tgaggatggg agatcttcac tacctccaga acagaaa      657
```

<210> SEQ ID NO 2
<211> LENGTH: 219
<212> TYPE: PRT
<213> ORGANISM: swine influenza virus

<400> SEQUENCE: 2

```
Met Asp Ser Asn Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
        35                  40                  45

Thr Leu Ser Leu Asp Ile Glu Thr Ala Thr Leu Val Gly Lys Gln Ile
    50                  55                  60

Val Glu Trp Ile Leu Lys Glu Glu Ser Ser Asp Ile Leu Lys Met Thr
65                  70                  75                  80

Ile Ala Ser Val Pro Thr Ser Arg Tyr Leu Ala Asp Met Thr Leu Glu
                85                  90                  95

Glu Met Ser Arg Asp Trp Phe Met Leu Met Pro Arg Gln Lys Ile Ile
            100                 105                 110

Gly Pro Leu Cys Val Arg Val Asp Gln Ala Ile Met Glu Lys Asn Ile
        115                 120                 125

Ile Leu Lys Ala Asn Phe Ser Val Ile Phe Asn Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Tyr Leu Pro Gly His Thr Asn Glu Asp Val Lys Asn
                165                 170                 175

Ala Val Gly Val Leu Ile Gly Gly Leu Glu Trp Asn Gly Asn Thr Val
            180                 185                 190

Arg Gly Ser Glu Asn Leu Gln Arg Phe Ala Trp Arg Asn His Asn Glu
        195                 200                 205

Asp Gly Arg Ser Ser Leu Pro Pro Glu Gln Lys
    210                 215
```

<210> SEQ ID NO 3
<211> LENGTH: 756
<212> TYPE: DNA
<213> ORGANISM: swine influenza virus

<400> SEQUENCE: 3

```
atgagtcttc taaccgaggt cgaaacgtat gttctctcta tcgtcccgtc aggccccctc     60
aaagccgaga tagcacagag gctcgaagac gtttttgcag ggaaaaacac cgatcttgag    120
gctctcatgg aatggctaaa gacaagacca atcctgtcac ctctgactaa agggatttta    180
```

```
gggtttgtgt tcacgctcac cgtgcccagt gagcgaggac tgcagcgtag acgttttgtc    240
cagaatgccc tcaatgggaa tggtgaccca acaacatgg acaaggcggt aaaactgtac     300
aggaaactaa aagggaaat aacattccat ggggccaagg aagtagcgct cagttactct     360
gctggtgcac ttgccagttg catgggcctc atatacaaca gaatgggac tgtcgccact     420
gaggtggcat ttggtctggt atgcgcaacc tgtgaacaaa ttgctgattc tcagcatcga    480
tctcatagac aaatggtgac aacaaccaat ccactaatca ggcacgagaa cagaatggta    540
atagccagca caacagctaa ggccatggaa caaatggctg atcaagtga acaagcagca     600
gaggctatgg aggttgccag tcaggctaga caaatggtac aggcaatgag aacaattggg    660
actcacccta gttccagcac tggtctaaaa gatgatcttc ttgaaaattt acaggcctat    720
cagaaacgga tgggagtgca aatgcaacga ttcaag                              756
```

```
<210> SEQ ID NO 4
<211> LENGTH: 252
<212> TYPE: PRT
<213> ORGANISM: swine influenza virus

<400> SEQUENCE: 4
```

```
Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Ala Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Ile Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
    210                 215                 220

Ser Ser Thr Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

```
<210> SEQ ID NO 5
<211> LENGTH: 291
```

<212> TYPE: DNA
<213> ORGANISM: swine influenza virus

<400> SEQUENCE: 5
atgagtcttc taaccgaggt cgaaacgcct atcagaaacg gatgggagtg caaatgcaac 60
gattcaagtg atcctctcat tgatgccgca agcatcattg gtattttgca cctgatattg 120
tggattcttg atcgtctttt tttcaaatgc atctaccgtc gctttaaata cggtctgcaa 180
agagggcctt ctacggaagg agtgccggag tccatgaggg aagaatatcg gcagaaacag 240
cagagtgctg tggatgttga cgatggtcat tttgtcaaca tagtgctaga g 291

<210> SEQ ID NO 6
<211> LENGTH: 97
<212> TYPE: PRT
<213> ORGANISM: swine influenza virus

<400> SEQUENCE: 6

Met Ser Leu Leu Thr Glu Val Glu Thr Pro Ile Arg Asn Gly Trp Glu
1 5 10 15

Cys Lys Cys Asn Asp Ser Ser Asp Pro Leu Ile Asp Ala Ala Ser Ile
20 25 30

Ile Gly Ile Leu His Leu Ile Leu Trp Ile Leu Asp Arg Leu Phe Phe
35 40 45

Lys Cys Ile Tyr Arg Arg Phe Lys Tyr Gly Leu Gln Arg Gly Pro Ser
50 55 60

Thr Glu Gly Val Pro Glu Ser Met Arg Glu Glu Tyr Arg Gln Lys Gln
65 70 75 80

Gln Ser Ala Val Asp Val Asp Asp Gly His Phe Val Asn Ile Val Leu
85 90 95

Glu

<210> SEQ ID NO 7
<211> LENGTH: 1407
<212> TYPE: DNA
<213> ORGANISM: swine influenza virus

<400> SEQUENCE: 7
atgaatacaa atcaaagaat aataaccatt gggacagttt gtctgatagt tggaataatt 60
agtctattgt tacagatagg aaacatggtt tcgttatgga tcagccattc aattcagact 120
gaagggaaaa atcatactga gatgtgcaat caaaatgtca ttacatatgt aaataacaca 180
tgggtgaacc gaacttatgt aaacattagc aataccaaaa ttgttaatgt acaggacgtg 240
gtttcagtaa tattaaccgg caattcctct ctctgcccaa taagtgggtg ggctatatac 300
agcaaagaca atagcataag gattggttct aaaggggaca tttttgtcat aagagaacca 360
ttcatttcat gctctcactt ggaatgcaga actttttttc tgacccaagg cgctttgctg 420
aatgacaagc attctaatgg aaccgtcaag gacaggagtc cctatagaac tttaatgagc 480
tgtcccatcg gtgaagctcc atctccatat aactcaaggt tcgaatcagt tgcttggtca 540
gcaagtgcat gccatgatgg gatgggatgg ctaacaatcg gaatctccgg tccagataat 600
ggagcagtag ctgttttaaa atacaacggt ataataacag atacaataaa aagttggaga 660
aacaaaatat taagaacaca agagtcagaa tgtgtttgta tgaacggttc ttgttttact 720
gtattaactg atggcccaag caatgggcaa gcatcgtaca aaatattcaa gatggaaaaa 780
ggaaaaataa ttaaatcaat tgagctggat gcacccaatt accactatga ggaatgctcc 840

-continued

```
tgttatcctg atgcaggcaa agtaatgtgt gtttgcagag acaactggca tgcctcgaac    900
cggccatggg tctctttcga tcagaatctt aattatcaaa tagggtacat atgcagtggg    960
gttttcggtg ataacccgcg ttctaatgat ggaaagggca attgtggccc agtacattct    1020
aatggagcaa atgagtgaa aggattctca tataaatatg gtaatggtgt ttggatagga    1080
aggactaaaa gtatcaactc cagaagtgga tttgaaatga tttgggatcc aaatgggtgg    1140
actggaactg atagtagttt ctctatgaag caggatatta tagcattaac tgattggtca    1200
ggatacagtg gaagttttgt ccaacatcct gaattaacag gaatgaattg cataaggccc    1260
tgtttctggg tagaattaat cagagggcaa cccaaggaaa acaccatctg gctagcggaa    1320
agcagcatct ctttctgtgg tgtaaatggt gaaaccgcaa gctggtcatg gccagacgga    1380
gctgatctgc cattcaccat tgacaag                                        1407
```

<210> SEQ ID NO 8
<211> LENGTH: 469
<212> TYPE: PRT
<213> ORGANISM: swine influenza virus

<400> SEQUENCE: 8

```
Met Asn Thr Asn Gln Arg Ile Ile Thr Ile Gly Thr Val Cys Leu Ile
1               5                   10                  15

Val Gly Ile Ile Ser Leu Leu Gln Ile Gly Asn Met Val Ser Leu
            20                  25                  30

Trp Ile Ser His Ser Ile Gln Thr Glu Gly Lys Asn His Thr Glu Met
        35                  40                  45

Cys Asn Gln Asn Val Ile Thr Tyr Val Asn Asn Thr Trp Val Asn Arg
    50                  55                  60

Thr Tyr Val Asn Ile Ser Asn Thr Lys Ile Val Asn Val Gln Asp Val
65                  70                  75                  80

Val Ser Val Ile Leu Thr Gly Asn Ser Ser Leu Cys Pro Ile Ser Gly
                85                  90                  95

Trp Ala Ile Tyr Ser Lys Asp Asn Ser Ile Arg Ile Gly Ser Lys Gly
            100                 105                 110

Asp Ile Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Val Cys Met Asn Gly Ser Cys Phe Thr
225                 230                 235                 240

Val Leu Thr Asp Gly Pro Ser Asn Gly Gln Ala Ser Tyr Lys Ile Phe
                245                 250                 255

Lys Met Glu Lys Gly Lys Ile Lys Ser Ile Glu Leu Asp Ala Pro
            260                 265                 270
```

```
                Asn Tyr His Tyr Glu Glu Cys Ser Cys Tyr Pro Asp Ala Gly Lys Val
                                275                 280                 285

Met Cys Val Cys Arg Asp Asn Trp His Ala Ser Asn Arg Pro Trp Val
                290                 295                 300

Ser Phe Asp Gln Asn Leu Asn Tyr Gln Ile Gly Tyr Ile Cys Ser Gly
                305                 310                 315                 320

Val Phe Gly Asp Asn Pro Arg Ser Asn Asp Gly Lys Gly Asn Cys Gly
                                325                 330                 335

Pro Val His Ser Asn Gly Ala Asn Gly Val Lys Gly Phe Ser Tyr Lys
                                340                 345                 350

Tyr Gly Asn Gly Val Trp Ile Gly Arg Thr Lys Ser Ile Asn Ser Arg
                                355                 360                 365

Ser Gly Phe Glu Met Ile Trp Asp Pro Asn Gly Trp Thr Gly Thr Asp
                370                 375                 380

Ser Ser Phe Ser Met Lys Gln Asp Ile Ile Ala Leu Thr Asp Trp Ser
                385                 390                 395                 400

Gly Tyr Ser Gly Ser Phe Val Gln His Pro Glu Leu Thr Gly Met Asn
                                405                 410                 415

Cys Ile Arg Pro Cys Phe Trp Val Glu Leu Ile Arg Gly Gln Pro Lys
                                420                 425                 430

Glu Asn Thr Ile Trp Ala Ser Gly Ser Ser Ile Ser Phe Cys Gly Val
                                435                 440                 445

Asn Gly Glu Thr Ala Ser Trp Ser Trp Pro Asp Gly Ala Asp Leu Pro
                                450                 455                 460

Phe Thr Ile Asp Lys
                465

<210> SEQ ID NO 9
<211> LENGTH: 1512
<212> TYPE: DNA
<213> ORGANISM: swine influenza virus

<400> SEQUENCE: 9
atgagtgaca tcgaagccat ggcgtctcaa ggcaccaaac gatcatatga acaaatggag      60
actggtggtg aacgccagga tgccacagaa atcagagcat ctgtcggaag aatgattggt     120
ggaatcggga aattctacat ccaaatgtgc actgaactca aactcagtga ctatgaggga     180
cgactaatcc aaaatagcat aacaatagag agaatggtgc tctctgcttt tgatgagaga     240
agaaataaat acctagaaga gcatcccagt gctgggaaag accctaagaa actggaggga     300
cccatatata gaagagtaga cggaaagtgg atgagagaac tcattcttta tgacaaagaa     360
gaaataagga gagtttggcg ccaggcaaac aatggtgatg atgcaacagc tggtcttact     420
catatcatga tttggcattc caatctgaat gatgccacgt accagagaac aagagcactt     480
gttcgcaccg gaatggatcc cagaatgtgc tctctaatgc aaggttcaac acttcccaga     540
aggtctggag cagcaggtgc tgcagtgaaa ggagttggaa cataacaat ggaattaatc      600 agaatgatca acgggggat caatgaccga aatttctgga gaggtgaaaa tggaagaagg      660
acaaggattg catatgaaag aatgtgcaat attctcaaag gaaaatttca gacagctgcc     720
caaagggcaa tgatggatca agtgagagaa agtcggaacc cagggaacgc tgagattgaa     780
gatctcattt tcctggcacg gtcagcactt atcctaaggg gatcagttgc acataagtct     840
tgcctgcctg cttgcgtgta tgggcttgca gtgcaagtg gcatgacttt gaaagggaa      900 gggtattcgc tggtcgggat agacccattt aaattactcc agaacagtca agtgttcagc     960
```

```
ctggtaagac caaatgaaaa cccagctcac aagagtcaat tagtgtggat ggcatgccac    1020
tctgctgcat ttgaggatct aagggtctca gtttcataa gagggaagaa agtgattcca    1080
aggggaaagc tttccacaag aggggttcag attgcttcaa atgagaatgt ggaagccatg    1140
gattccaata ccttagagct gagaagcaga tactgggcta taaggaccag aagtggagga    1200
aatactaatc aacagaaagc atccgcaggc cagatcagtg tgcaacctac attctcagtg    1260
caacggaatc tccctttga aagagcaacc gttatggcag ctttcagcgg aaacaatgaa    1320
ggacggacat ccgatatgcg gacagaaatt ataaggatga tggaaaatgc aaaaccagaa    1380
gatttgtcct tccaggggcg gggagtcttc gagctctcgg acgaaaaggc aacgagcccg    1440
atcgtgcctt cctttgacat gagtaatgaa gggtcttatt tcttcggaga caatgcagag    1500
gagtatgaca gt                                                       1512
```

<210> SEQ ID NO 10
<211> LENGTH: 504
<212> TYPE: PRT
<213> ORGANISM: swine influenza virus

<400> SEQUENCE: 10

```
Met Ser Asp Ile Glu Ala Met Ala Ser Gln Gly Thr Lys Arg Ser Tyr
 1               5                  10                  15

Glu Gln Met Glu Thr Gly Gly Glu Arg Gln Asp Ala Thr Glu Ile Arg
             20                  25                  30

Ala Ser Val Gly Arg Met Ile Gly Gly Ile Gly Lys Phe Tyr Ile Gln
         35                  40                  45

Met Cys Thr Glu Leu Lys Leu Ser Asp Tyr Glu Gly Arg Leu Ile Gln
 50                  55                  60

Asn Ser Ile Thr Ile Glu Arg Met Val Leu Ser Ala Phe Asp Glu Arg
 65                  70                  75                  80

Arg Asn Lys Tyr Leu Glu Glu His Pro Ser Ala Gly Lys Asp Pro Lys
                 85                  90                  95

Lys Thr Gly Gly Pro Ile Tyr Arg Arg Val Asp Gly Lys Trp Met Arg
            100                 105                 110

Glu Leu Ile Leu Tyr Asp Lys Glu Glu Ile Arg Arg Val Trp Arg Gln
        115                 120                 125

Ala Asn Asn Gly Asp Asp Ala Thr Ala Gly Leu Thr His Ile Met Ile
    130                 135                 140

Trp His Ser Asn Leu Asn Asp Ala Thr Tyr Gln Arg Thr Arg Ala Leu
145                 150                 155                 160

Val Arg Thr Gly Met Asp Pro Arg Met Cys Ser Leu Met Gln Gly Ser
                165                 170                 175

Thr Leu Pro Arg Arg Ser Gly Ala Ala Gly Ala Ala Val Lys Gly Val
            180                 185                 190

Gly Thr Ile Thr Met Glu Leu Ile Arg Met Ile Lys Arg Gly Ile Asn
        195                 200                 205

Asp Arg Asn Phe Trp Arg Gly Glu Asn Gly Arg Thr Arg Ile Ala
    210                 215                 220

Tyr Glu Arg Met Cys Asn Ile Leu Lys Gly Lys Phe Gln Thr Ala Ala
225                 230                 235                 240

Gln Arg Ala Met Met Asp Gln Val Arg Glu Ser Arg Asn Pro Gly Asn
                245                 250                 255

Ala Glu Ile Glu Asp Leu Ile Phe Leu Ala Arg Ser Ala Leu Ile Leu
            260                 265                 270
```

```
Arg Gly Ser Val Ala His Lys Ser Cys Leu Pro Ala Cys Val Tyr Gly
                275                 280                 285
Leu Ala Val Ala Ser Gly His Asp Phe Glu Arg Glu Gly Tyr Ser Leu
    290                 295                 300
Val Gly Ile Asp Pro Phe Lys Leu Leu Gln Asn Ser Gln Val Phe Ser
305                 310                 315                 320
Leu Val Arg Pro Asn Glu Asn Pro Ala His Lys Ser Gln Leu Val Trp
                325                 330                 335
Met Ala Cys His Ser Ala Ala Phe Glu Asp Leu Arg Val Ser Ser Phe
                340                 345                 350
Ile Arg Gly Lys Lys Val Ile Pro Arg Gly Lys Leu Ser Thr Arg Gly
                355                 360                 365
Val Gln Ile Ala Ser Asn Glu Asn Val Glu Ala Met Asp Ser Asn Thr
    370                 375                 380
Leu Glu Leu Arg Ser Arg Tyr Trp Ala Ile Arg Thr Arg Ser Gly Gly
385                 390                 395                 400
Asn Thr Asn Gln Gln Lys Ala Ser Ala Gly Gln Ile Ser Val Gln Pro
                405                 410                 415
Thr Phe Ser Val Gln Arg Asn Leu Pro Phe Glu Arg Ala Thr Val Met
                420                 425                 430
Ala Ala Phe Ser Gly Asn Asn Glu Gly Arg Thr Ser Asp Met Arg Thr
    435                 440                 445
Glu Ile Ile Arg Met Met Glu Asn Ala Lys Pro Glu Asp Leu Ser Phe
450                 455                 460
Gln Gly Arg Gly Val Phe Glu Leu Ser Asp Glu Lys Ala Thr Ser Pro
465                 470                 475                 480
Ile Val Pro Ser Phe Asp Met Ser Asn Glu Gly Ser Tyr Phe Phe Gly
                485                 490                 495
Asp Asn Ala Glu Glu Tyr Asp Ser
                500

<210> SEQ ID NO 11
<211> LENGTH: 1698
<212> TYPE: DNA
<213> ORGANISM: swine influenza virus

<400> SEQUENCE: 11
atgaaggcaa tactagtagt cctgctatat acatttacaa ccgcaaatgc cgacacatta     60
tgcataggtt atcatgcgaa caattcaact gacaccgtag acacagtgct agaaaaaaat    120
gtaacagtaa cacactctgt caaccttcta gaaacaggc ataatgggaa actatgtaaa    180
ctaagagggg tagctccatt gcatttgggt aaatgtaaca ttgctggctg ctcctggga     240 aatccagagt gtgagtcaat ctccaaagca agctcatggt cctacattgt ggaaacatct    300
aattcagaca atgggacgtg ttacccagga gatttcatca attatgagga gctaagagag    360
cagttgagct cagtgtcatc atttgaaaga tttgagatat ccccatgac aagttcatgg    420 cccaatcatg acacgaacag aggtgtgacg gcagcatgtc ctcacgctgg acaaatagc    480 ttctacaaaa atttaatatg gctggtcaaa aaggaaatt cataccccaa gatcaacaaa    540
tcctacatta caacaaaga gaagaagtt ctcgtgctat gggccataca tcatccacct    600
accaatgccg accaacaaag cctctaccaa aatgcagatg cctatgtttt tgtggggtca    660
tcaagataca gcaggaagtt cgagccagaa atagcaacaa gacccaaggt gagagaccaa    720
gcagggagaa tgaactatta ctggacattg gtagagcctg agacaagat aacattcgaa    780
```

```
gcaactggaa atctagtggt accgagatat gccttcgcat tgaaaagaaa ttctggatct      840
ggtattatca tttcagatac atcagtccac gattgtgata cgacttgtca gacacccaat      900
ggtgctataa acaccagcct cccatttcaa aatatacatc agtcacaat tggagaatgt       960 ccaaaatatg taaaaagtac taaactgaga atggccacag gattaaggaa tatcccgtct     1020
attcaatcta gaggcctgtt tggggccatt gctggcttta ttgaagggg ctggacagga      1080 atgatagacg gatggtacgg ttaccaccat caaaatgagc agggatcagg atatgcagcc     1140
gacctgaaaa gcacacagaa tgccattgac gggatcacta caaggtaaa ttctgttatt     1200 gaaaagatga acacacaatt cacagcagta ggtaaagagt tcagccactt ggaaagaaga     1260
atagagaatt taaataaaaa ggttgatgat ggttttctag atatttggac ttacaatgcc     1320
gaactgttgg ttctgttgga gaatgaaaga actttggatt accacgattc aaatgtgaaa     1380
aacttatatg aaaaagtaag aagccaacta aaaaacaatg ccaaagaaat tggaaatggc     1440
tgctttgaat tttaccacaa atgtgatgac acgtgtatgg aaagcgtcaa aaatgggact     1500
tatgattacc caaaatactc agaggaagca aaactaaaca gagaggaaat agatggggta     1560
aagttggaat caacaagggt ttaccaaatt ttggcgatct attcaacggt cgccagttca     1620
ttggtactgg tagtctccct gggggcaatc agtttctgga tgtgctctaa tgggtcgcta     1680
cagtgcagaa tatgtatt                                                   1698
```

```
<210> SEQ ID NO 12
<211> LENGTH: 566
<212> TYPE: PRT
<213> ORGANISM: swine influenza virus

<400> SEQUENCE: 12
```

```
Met Lys Ala Ile Leu Val Val Leu Leu Tyr Thr Phe Thr Thr Ala Asn
 1               5                   10                  15

Ala Asp Thr Leu Cys Ile Gly Tyr His Ala Asn Asn Ser Thr Asp Thr
                 20                  25                  30

Val Asp Thr Val Leu Glu Lys Asn Val Thr Val Thr His Ser Val Asn
             35                  40                  45

Leu Leu Glu Asn Arg His Asn Gly Lys Leu Cys Lys Leu Arg Gly Val
         50                  55                  60

Ala Pro Leu His Leu Gly Lys Cys Asn Ile Ala Gly Trp Leu Leu Gly
 65                  70                  75                  80

Asn Pro Glu Cys Glu Ser Ile Ser Lys Ala Ser Ser Trp Ser Tyr Ile
                 85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Met Thr Ser Ser Trp Pro Asn His Asp
    130                 135                 140

Thr Asn Arg Gly Val Thr Ala Ala Cys Pro His Ala Gly Thr Asn Ser
145                 150                 155                 160

Phe Tyr Lys Asn Leu Ile Trp Leu Val Lys Lys Gly Asn Ser Tyr Pro
                165                 170                 175

Lys Ile Asn Lys Ser Tyr Ile Asn Asn Lys Glu Lys Glu Val Leu Val
            180                 185                 190

Leu Trp Ala Ile His His Pro Pro Thr Asn Ala Asp Gln Gln Ser Leu
        195                 200                 205
```

```
Tyr Gln Asn Ala Asp Ala Tyr Val Phe Val Gly Ser Ser Arg Tyr Ser
210                 215                 220

Arg Lys Phe Glu Pro Glu Ile Ala Thr Arg Pro Lys Val Arg Asp Gln
225                 230                 235                 240

Ala Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
                260                 265                 270

Ala Leu Lys Arg Asn Ser Gly Ser Gly Ile Ile Ile Ser Asp Thr Ser
                275                 280                 285

Val His Asp Cys Asp Thr Thr Cys Gln Thr Pro Asn Gly Ala Ile Asn
290                 295                 300

Thr Ser Leu Pro Phe Gln Asn Ile His Pro Val Thr Ile Gly Glu Cys
305                 310                 315                 320

Pro Lys Tyr Val Lys Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
                355                 360                 365

His His Gln Asn Glu Gln Gly Ser Gly Tyr Ala Ala Asp Leu Lys Ser
                370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Ser His
                405                 410                 415

Leu Glu Arg Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
                435                 440                 445

Glu Arg Thr Leu Asp Tyr His Asp Ser Asn Val Lys Asn Leu Tyr Glu
                450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asp Thr Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Val Tyr
                515                 520                 525

Gln Ile Leu Ala Ile Tyr Ser Thr Val Ala Ser Ser Leu Val Leu Val
                530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 13
<211> LENGTH: 2148
<212> TYPE: DNA
<213> ORGANISM: swine influenza virus

<400> SEQUENCE: 13
atggaagact ttgtgcgaca atgcttc

-continued

```
atgaaagaat atggagaaga tccgaaaatt gaaactaaca aattcgctgc aatatgcaca    120
cacttggaag tatgtttcat gtattcagat ttccatttca ttgacgagcg ggtgaatca    180
atcattgtag aatctggtga tccaaatgca ttactgaagc accgatttga gataattgaa    240
ggacgagacc ggaccatggc ctggacagta gtgaacagta tctgcaacac cacaggggta    300
gagaagccta aatttcttcc ggatttatac gactacaaag aaaatcggtt cattgaaatt    360
ggagtgacac gaagggaggt ccacatatac tacctagaga aagccaacaa aataaaatcc    420
gagaagacac acattcacat tttttcattc actggagagg agatggccac caaagcagac    480
tacacccttg atgaagaaag cagggcaaga atcaaaacca ggcttttcac cataagacaa    540
gaaatggcaa gtaggggtct atgggattcc tttcgtcagt ccgaaagagg cgaggagaca    600
attgaagaaa gatttgaaat tacaggaacc atgcgcagac ttgccgacca aagtctccca    660
ccgaacttct ccagtcttga aaactttaga gcttatgtag atgggttcga accaaacggc    720
tgcattgagg gcaagctttc tcaaatgtca aaagaagtga gcgcccaaat tgaacccttc    780
ttgaagacaa caccacgccc tctaaaattg cctgatgggc ctccttgctc tcagcggtca    840
aagttcttgc tgatggatgc tctgaaacta agtattgaag acccgagtca tgaaggagaa    900
ggaataccac tatatgatgc aatcaagtgc atgaagacat tttttggctg gaaagaaccc    960
aacataatca aaccacatga gaaaggcata aaccccaatt acctactggc ttggaagcag   1020
gtgctagcag agctccaaga cattgaaaat gaagagaaga tcccaaagac aaagaacatg   1080
aggagaacaa gccaattgaa gtgggcactc ggtgagaata tggcaccaga gaaagtagat   1140
tttgatgact gcaaagatgt tggtgatctt aaacagtatg acagcgacga gccagagccc   1200
agatctctag caagttgggt ccaaaatgaa ttcaacaagg catgtgaatt gaccgattca   1260
agctggatag aacttgatga gataggagaa gatattgcac cgattgaaca catcgcaagt   1320
atgaggagga actattttac agcagaagtg tcccattgta gggctacgga atacataatg   1380
aagggagtgt acataaacac ggctttgctt aatgcatctt gtgcagccat ggatgacttt   1440
cagctgatcc caatgataag caaatgcagg accaaagaag gaagacgaaa aacaaatctg   1500
tatgggttca ttataaaagg aaggtcccat ctgaggaatg atactgacgt ggtgaacttt   1560
gtaagcatgg agttctccct caccgacccg agactggagc cacacaaatg ggaaaaatac   1620
tgtgttcttg aaataggaga catgctcctg aggactgcga taggccaagt gtcgaggccc   1680
atgttcttat atgtgagaac caatggaacc tccaagatca agatgaaatg gggcatggaa   1740
atgaggcgct gccttcttca atctcttcag cagattgaga gcatgattga ggctgagtct   1800
tctgtaaaag agaaagacat gaccaaggaa ttttttgaaa acaaatcgga aacatggcca   1860
attggagaat cacccaaagg agtggaggaa ggctctattg ggaaagtgtg caggacctta   1920
ctggcaaaat ctgtattcaa cagtctatac gcgtctccac aacttgaggg attttcggct   1980
gaatcgagaa agttgcttct cattgttcag gcacttaggg acaacctgga acctggaacc   2040
ttcgatcttg gggggctata tgaagcaatc gaggagtgcc tgattaatga tccctgggtt   2100
ttgcttaatg catcttggtt caactccttc ctcacacatg cactgaaa                2148
```

<210> SEQ ID NO 14
<211> LENGTH: 716
<212> TYPE: PRT
<213> ORGANISM: swine influenza virus

<400> SEQUENCE: 14

Met Glu Asp Phe Val Arg Gln Cys Phe Asn Pro Met Ile Val Glu Leu

-continued

```
1               5                   10                  15
Ala Glu Lys Ala Met Lys Glu Tyr Gly Glu Asp Pro Lys Ile Glu Thr
                20                  25                  30
Asn Lys Phe Ala Ala Ile Cys Thr His Leu Glu Val Cys Phe Met Tyr
                35                  40                  45
Ser Asp Phe His Phe Ile Asp Glu Arg Gly Glu Ser Ile Ile Val Glu
                50                  55                  60
Ser Gly Asp Pro Asn Ala Leu Leu Lys His Arg Phe Glu Ile Ile Glu
65                  70                  75                  80
Gly Arg Asp Arg Thr Met Ala Trp Thr Val Val Asn Ser Ile Cys Asn
                    85                  90                  95
Thr Thr Gly Val Glu Lys Pro Lys Phe Leu Pro Asp Leu Tyr Asp Tyr
                    100                 105                 110
Lys Glu Asn Arg Phe Ile Glu Ile Gly Val Thr Arg Arg Glu Val His
                    115                 120                 125
Ile Tyr Tyr Leu Glu Lys Ala Asn Lys Ile Lys Ser Glu Lys Thr His
130                 135                 140
Ile His Ile Phe Ser Phe Thr Gly Glu Glu Met Ala Thr Lys Ala Asp
145                 150                 155                 160
Tyr Thr Leu Asp Glu Glu Ser Arg Ala Arg Ile Lys Thr Arg Leu Phe
                    165                 170                 175
Thr Ile Arg Gln Glu Met Ala Ser Arg Gly Leu Trp Asp Ser Phe Arg
                    180                 185                 190
Gln Ser Glu Arg Gly Glu Glu Thr Ile Glu Glu Arg Phe Glu Ile Thr
                    195                 200                 205
Gly Thr Met Arg Arg Leu Ala Asp Gln Ser Leu Pro Pro Asn Phe Ser
                210                 215                 220
Ser Leu Glu Asn Phe Arg Ala Tyr Val Asp Gly Phe Glu Pro Asn Gly
225                 230                 235                 240
Cys Ile Glu Gly Lys Leu Ser Gln Met Ser Lys Glu Val Ser Ala Gln
                    245                 250                 255
Ile Glu Pro Phe Leu Lys Thr Thr Pro Arg Pro Leu Lys Leu Pro Asp
                    260                 265                 270
Gly Pro Pro Cys Ser Gln Arg Ser Lys Phe Leu Leu Met Asp Ala Leu
                    275                 280                 285
Lys Leu Ser Ile Glu Asp Pro Ser His Glu Gly Glu Gly Ile Pro Leu
                290                 295                 300
Tyr Asp Ala Ile Lys Cys Met Lys Thr Phe Phe Gly Trp Lys Glu Pro
305                 310                 315                 320
Asn Ile Ile Lys Pro His Glu Lys Gly Ile Asn Pro Asn Tyr Leu Leu
                    325                 330                 335
Ala Trp Lys Gln Val Leu Ala Glu Leu Gln Asp Ile Glu Asn Glu Glu
                    340                 345                 350
Lys Ile Pro Lys Thr Lys Asn Met Arg Arg Thr Ser Gln Leu Lys Trp
                    355                 360                 365
Ala Leu Gly Glu Asn Met Ala Pro Glu Lys Val Asp Phe Asp Asp Cys
                370                 375                 380
Lys Asp Val Gly Asp Leu Lys Gln Tyr Asp Ser Asp Glu Pro Glu Pro
385                 390                 395                 400
Arg Ser Leu Ala Ser Trp Val Gln Asn Glu Phe Asn Lys Ala Cys Glu
                    405                 410                 415
Leu Thr Asp Ser Ser Trp Ile Glu Leu Asp Glu Ile Gly Glu Asp Ile
                    420                 425                 430
```

-continued

```
Ala Pro Ile Glu His Ile Ala Ser Met Arg Arg Asn Tyr Phe Thr Ala
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
    530                 535                 540
Ile Gly Asp Met Leu Leu Arg Thr Ala Ile Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
Glu Ser Met Ile Glu Ala Glu Ser Ser Val Lys Glu Lys Asp Met Thr
        595                 600                 605
Lys Glu Phe Phe Glu Asn Lys Ser Glu Thr Trp Pro Ile Gly Glu Ser
    610                 615                 620
Pro Lys Gly Val Glu Glu Gly Ser Ile Gly Lys Val Cys Arg Thr Leu
625                 630                 635                 640
Leu Ala Lys Ser Val Phe Asn Ser Leu Tyr Ala Ser Pro Gln Leu Glu
                645                 650                 655
Gly Phe Ser Ala Glu Ser Arg Lys Leu Leu Leu Ile Val Gln Ala Leu
            660                 665                 670
Arg Asp Asn Leu Glu Pro Gly Thr Phe Asp Leu Gly Gly Leu Tyr Glu
        675                 680                 685
Ala Ile Glu Glu Cys Leu Ile Asn Asp Pro Trp Val Leu Leu Asn Ala
    690                 695                 700
Ser Trp Phe Asn Ser Phe Leu Thr His Ala Leu Lys
705                 710                 715

<210> SEQ ID NO 15
<211> LENGTH: 2271
<212> TYPE: DNA
<213> ORGANISM: swine influenza virus

<400> SEQUENCE: 15
atggatgtca acccgactct acttttccta aaggttccag cgcaaaatgc cataagcacc      60
acattccctt atactggaga tcctccatac agccatggaa caggaacagg atacaccatg     120
gacacagtca acagaacaca ccagtattca gaaaaaggga aatggacgac aaacacagag     180
actggggcac cccagctcaa cccgattgat ggaccactac ccgatgataa tgaaccaagt     240
gggtatgcac aaacagactg tgtcctggag gccatggctt tccttgaaga atcccaccca     300
gggatatttg agaattcatg ccttgaaaca atggaaattg tccaacaaac aagggtggat     360
aaactaactc aaggtcgcca gacttatgat tggacattaa acagaaatca accggcagca     420
actgcattgg ccaacaccat agaagttttt agatcaaacg gtctaacagc taatgagtca     480
```

-continued

| | |
|---|---|
| ggaaggctaa tagatttcct aaaggatgta atggaatcaa tggataagga ggaaatagag | 540 |
| ataacaacac attttcaaag aaaaaggaga gtaagagaca acatgaccaa gaagatggtc | 600 |
| acacaaagaa caatagggaa gaaaaaacaa aaattgaata agagaagtta tctaataaga | 660 |
| gcactgacat tgaatacgat gaccaaagat gcagagagag gcaagttaaa aaggagggct | 720 |
| atcgcaacac ctgggatgca gattagaggg ttcgtgtact tgttgagac tttagctaga | 780 |
| agcatctgcg aaaagcttga acagtccgga ctcccagtag ggggcaatga aaagaaagcc | 840 |
| aaattggcaa atgttgtgag aaagatgatg actaattcac aagacacaga gctttctttc | 900 |
| acaatcactg gagataacac taatggaat gaaaaccaga atcctcgaat gttcctggcg | 960 |
| atgatcacat acattaccag aaatcaaccc gagtggttca gaaacatact gagtatgca | 1020 |
| ccaataatgt tctcaaacaa aatggcaaga ctaggaaaag ggtacatgtt cgagagtaaa | 1080 |
| agaatgaagc tccgaacaca ggtaccagca gaaatgctag caagcattga tcttaagtat | 1140 |
| ttcaatgaat caacaaggaa gaaaattgag aaaataaggc ctctcctaat agatggcaca | 1200 |
| gcatcattga gccctgggat gatgatgggc atgttcaaca tgctaagtac ggttttggga | 1260 |
| gtctcaatac tgaatcttgg acaaaagaaa tacaccagga caacatactg gtgggatgga | 1320 |
| ctccaatcct cagacgattt tgccctcata gtaaatgcac caaatcatga gggaatacaa | 1380 |
| gcaggagtgg atagattcta caggacctgc aagttagtag ggatcaacat gagcaaaaag | 1440 |
| aagtcctata taaataagac tgggacattt gaattcacaa gctttttta tcgctatggg | 1500 |
| tttgtagcta atttagcat ggagctgccc agttttggag tgtctggaat aaacgaatca | 1560 |
| gctgatatga gcatcggagt aacagtgata agaacaacaa tgataaataa tgatcttgga | 1620 |
| cctgcaacag cccagatggc cctccagttg ttcatcaaag actacagata cacatataga | 1680 |
| tgccatagag gggacacaca aatccagacg agaagatcat tcgagctaaa gagcctgtgg | 1740 |
| aatcaaactc aatcaaaggc aggattatta gtatctgatg gaggaccaaa tttatacaat | 1800 |
| atccggaatc ttcacattcc tgaagtctgc ttaaaatggg agctaatgga tgaggattat | 1860 |
| cggggaagac tttgtaatcc cctgaatccc tttgtcagcc ataaagagat tgattctgta | 1920 |
| aacagtgctg tggtgatgcc agcccatggt ccagccaaaa gtatggagta tgatgccgtt | 1980 |
| gcaactacac actcctggat tcccaagagg aaccgctcta ttctcaacac aagccaaagg | 2040 |
| ggaattcttg aggatgaaca gatgtaccag aagtgctgca acctgttcga gaaattttc | 2100 |
| cctagtagtt catacagaag accagttgga atttctagca tggtggaggc catggtgtct | 2160 |
| agggcccgga ttgatgccag gattgacttc gagtctggac ggattaagaa agaagagttc | 2220 |
| tctgagatca tgaagatctg ttccaccatt gaagaactca gacggcaaaa g | 2271 |

<210> SEQ ID NO 16
<211> LENGTH: 757
<212> TYPE: PRT
<213> ORGANISM: swine influenza virus

<400> SEQUENCE: 16

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

-continued

```
Gln Leu Asn Pro Ile Asp Gly Pro Leu Pro Asp Asn Glu Pro Ser
 65                  70                  75                  80

Gly Tyr Ala Gln Thr Asp Cys Val Leu Glu Ala Met Ala Phe Leu Glu
                 85                  90                  95

Glu Ser His Pro Gly Ile Phe Glu Asn Ser Cys Leu Thr Met Glu
            100                 105                 110

Ile Val Gln Gln Thr Arg Val Asp Lys Leu Thr Gln Gly Arg Gln Thr
                115                 120                 125

Tyr Asp Trp Thr Leu Asn Arg Asn Gln Pro Ala Ala Thr Ala Leu Ala
        130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Lys Leu Asn Lys Arg Ser Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
            340                 345                 350

Lys Gly Tyr Met Phe Glu Ser Lys Arg Met Lys Leu Arg Thr Gln Val
        355                 360                 365

Pro Ala Glu Met Leu Ala Ser Ile Asp Leu Lys Tyr Phe Asn Glu Ser
        370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Arg Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Val Gly Ile Asn Met Ser Lys Lys
465                 470                 475                 480
```

Lys Ser Tyr Ile Asn Lys Thr Gly Thr Phe Glu Phe Thr Ser Phe Phe
            485                 490                 495
Tyr Arg Tyr Gly Phe Val Ala Asn Phe Ser Met Glu Leu Pro Ser Phe
        500                 505                 510
Gly Val Ser Gly Ile Asn Glu Ser Ala Asp Met Ser Ile Gly Val Thr
    515                 520                 525
Val Ile Lys Asn Asn Met Ile Asn Asn Asp Leu Gly Pro Ala Thr Ala
530                 535                 540
Gln Met Ala Leu Gln Leu Phe Ile Lys Asp Tyr Arg Tyr Thr Tyr Arg
545                 550                 555                 560
Cys His Arg Gly Asp Thr Gln Ile Gln Thr Arg Arg Ser Phe Glu Leu
                565                 570                 575
Lys Ser Leu Trp Asn Gln Thr Gln Ser Lys Ala Gly Leu Leu Val Ser
            580                 585                 590
Asp Gly Gly Pro Asn Leu Tyr Asn Ile Arg Asn Leu His Ile Pro Glu
        595                 600                 605
Val Cys Leu Lys Trp Glu Leu Met Asp Glu Asp Tyr Arg Gly Arg Leu
    610                 615                 620
Cys Asn Pro Leu Asn Pro Phe Val Ser His Lys Glu Ile Asp Ser Val
625                 630                 635                 640
Asn Ser Ala Val Val Met Pro Ala His Gly Pro Ala Lys Ser Met Glu
                645                 650                 655
Tyr Asp Ala Val Ala Thr Thr His Ser Trp Ile Pro Lys Arg Asn Arg
            660                 665                 670
Ser Ile Leu Asn Thr Ser Gln Arg Gly Ile Leu Glu Asp Glu Gln Met
        675                 680                 685
Tyr Gln Lys Cys Cys Asn Leu Phe Glu Lys Phe Phe Pro Ser Ser Ser
    690                 695                 700
Tyr Arg Arg Pro Val Gly Ile Ser Ser Met Val Glu Ala Met Val Ser
705                 710                 715                 720
Arg Ala Arg Ile Asp Ala Arg Ile Asp Phe Glu Ser Gly Arg Ile Lys
                725                 730                 735
Lys Glu Glu Phe Ser Glu Ile Met Lys Ile Cys Ser Thr Ile Glu Glu
            740                 745                 750
Leu Arg Arg Gln Lys
        755

<210> SEQ ID NO 17
<211> LENGTH: 2277
<212> TYPE: DNA
<213> ORGANISM: swine influenza virus

<400> SEQUENCE: 17
atggagagaa taaagaaact aagagatctg atgtcgcagt ctcgcactcg cgagatactc        60
acaaagacca ctgtggacca tatggccata atcaaaaagt acacatcagg aaggcaagag       120
aagaaccccg cactcagaat gaagtggatg atggcaatga atacccaat  tacagcagac       180 aagagaataa tggacatgat tccagagagg aatgaacaag acaaaccct  ctggagcaaa       240 acaaacgatg ctggatcgga ccgtgtgatg gtatcacccc tggccgtaac atggtggaat       300
aggaatggcc aacaacaag  cacagttcac taccctaagg tatataaaac ttatttcgaa       360
aagatcgaaa ggttaaaaca tggtatcttt ggccctgtcc acttcagaaa tcaagttaaa       420
ataagaagga gggttgacac aaaccctggt catgcagatc tcagtgccaa ggaggcacag       480
gatgtgatca tggaagttgt tttcccaaat gaagtggggg caagagtact gacgtcagag       540

```
tcacagctga caataacaaa ggaaaagaaa gaagagctcc aggattgtaa gattgctccc      600
ctgatggtgg catacatgct agaaagagag ttggttcgca agacgaggtt tctcccggtg      660
gctggtggaa caagcagtgt ttatattgaa gtgctacact taactcaggg aacatgctgg      720
gaacaaatgt acactccagg aggagaagtg agaaatgatg atgttgacca agtttttgat      780
atcgctgcta aaacatagt aagaagagca gcagtgtcag cagacccatt agcatctctc      840
ttggaaatgt gccacagcac acagattgga ggaataagga tggtggacat ccttagacag      900
aacccaacgg aggaacaagc cgtagacata tgcaaggcag caatggggct gaggattagc      960
tcttctttca gctttggtgg gttcaccttc aaaagaacaa gcggatcatc agttaagaaa     1020
gaagaagaag tgctcacggg caacctccaa acactgaaaa taagagtaca tgaaggatat     1080
gaagaattca caatggtagg gagaagagca actgctattc tcagaaaagc aaccaggaga     1140
ttgatccagt aatagtaag tgggagagac gatcaatcaa ttgctgaggc aataattgta     1200
gccatggtat tttcacaaga ggattgcatg atcaaggcag ttaggggcga tctgaacttt     1260
gtcaataggg caaaccagcg actgaatccc atgcaccaac tcttgaggca tttccaaaaa     1320
gatgcaaaag tgcttttcca gaactgggga attgaaccca tcgacagtgt gatgggaatg     1380
atcgggatat tgcctgatat gacccccaagc acggaaatgt cgctgagagg tataagagtc     1440
agcaaaatgg gagtagatga gtattccagc acggagagag tggtagtgag cattgaccga     1500
tttttgagag ttcgggatca acgagggaac gtactattgt cccccgaaga ggtcagcgag     1560
acacaaggaa ctgagaaatt gacaataact tattcgtcat caatgatgtg ggagatcaat     1620
ggtcctgagt cagtgctggt caacacttat caatggatca aaggaattg ggaaagcttg     1680
aaaattcaat ggtcacaaga tcccacgatg ttatacaaca aaatggaatt tgaaccattc     1740
cagtctcttg tccctaaggc aaccagaagt cgttacagtg gattcgtgag gacactgttc     1800
cagcaaatgc gggatgtgct tggaacattt gacactgtcc aaataataaa acttctcccc     1860
tttgctgctg ctccaccgga acagagtagg atacagttct cctcgctgac tgtgaatgtg     1920
agaggatcag ggctgaggat actggtaaga ggcaattctc cagtgttcaa ttacaacaaa     1980
gcaaccaaaa ggcttacaat tcttggaaaa gatgcaggtg cattgactga agatccagat     2040
gaaggcacag ctggagtgga gtctgctgtc ctgaggggat cctcatttt gggtaaagaa     2100
gacaagagat atggcccagc attaagcatc aatgaactga gcaatcttgc aaaaggagag     2160
aaggctaatg tgttaattgg gcaaggagac gtggtgttgg taatgaaacg gaaacggaac     2220
tctagcatac ttactgacag ccagacagcg accaaaagaa ttcggatggc catcaat       2277
```

<210> SEQ ID NO 18
<211> LENGTH: 759
<212> TYPE: PRT
<213> ORGANISM: swine influenza virus

<400> SEQUENCE: 18

```
Met Glu Arg Ile Lys Glu Leu Arg Asp Leu Met Ser Gln Ser Arg Thr
 1               5                  10                  15

Arg Glu Ile Leu Thr Lys Thr Thr Val Asp His Met Ala Ile Ile Lys
                20                  25                  30

Lys Tyr Thr Ser Gly Arg Gln Glu Lys Asn Pro Ala Leu Arg Met Lys
            35                  40                  45

Trp Met Met Ala Met Lys Tyr Pro Ile Thr Ala Asp Lys Arg Ile Met
        50                  55                  60
```

```
Asp Met Ile Pro Glu Arg Asn Glu Gln Gly Gln Thr Leu Trp Ser Lys
 65                  70                  75                  80

Thr Asn Asp Ala Gly Ser Asp Arg Val Met Val Ser Pro Leu Ala Val
                 85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Ile Glu Arg Leu Lys His Gly
        115                 120                 125

Ile Phe Gly Pro Val His Phe Arg Asn Gln Val Lys Ile Arg Arg Arg
    130                 135                 140

Val Asp Thr Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Val
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Asp Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Ser Val Met Gly Met Ile Gly Ile Leu
    450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
```

|        |        |        | 485    |        |        |        | 490    |        |        |        | 495    |        |
|--------|--------|--------|--------|--------|--------|--------|--------|--------|--------|--------|--------|--------|

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Ser Leu
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Thr Arg Ser Arg Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
        610                 615                 620

Pro Pro Glu Gln Ser Arg Ile Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Ile Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asn Ser Ser Ile Leu Thr Asp Ser Gln Thr Ala Thr Lys
            740                 745                 750

Arg Ile Arg Met Ala Ile Asn
        755

<210> SEQ ID NO 19
<211> LENGTH: 979
<212> TYPE: DNA
<213> ORGANISM: swine influenza virus

<400> SEQUENCE: 19

| atgagtcttc taaccgaggt cgaaacgtat gttctctcta tcgtcccgtc aggccccctc | 60  |
| aaagccgaga tagcacagag gctcgaagac gttttgcag ggaaaaacac cgatcttgag  | 120 |
| gctctcatgg aatggctaaa gacaagacca atcctgtcac ctctgactaa agggatttta | 180 |
| gggtttgtgt tcacgctcac cgtgcccagt gagcgaggac tgcagcgtag acgttttgtc | 240 |
| cagaatgccc tcaatgggaa tggtgaccca acaacatgg acaaggcggt aaaactgtac  | 300 |
| aggaaactaa aagggaaat aacattccat ggggccaagg aagtagcgct cagttactct  | 360 |
| gctggtgcac ttgccagttg catgggcctc atatacaaca gaatggggac tgtcgccact | 420 |
| gaggtggcat ttggtctggt atgcgcaacc tgtgaacaaa ttgctgattc tcagcatcga | 480 |
| tctcatagac aaatggtgac aacaaccaat ccactaatca ggcacgagaa cagaatggta | 540 |

| | |
|---|---|
| atagccagca caacagctaa ggccatggaa caaatggctg atcaagtga acaagcagca | 600 |
| gaggctatgg aggttgccag tcaggctaga caaatggtac aggcaatgag aacaattggg | 660 |
| actcacccta gttccagcac tggtctaaaa gatgatcttc ttgaaaattt acaggcctat | 720 |
| cagaaacgga tgggagtgca aatgcaacga ttcaagtgat cctctcattg atgccgcaag | 780 |
| catcattggt attttgcacc tgatattgtg gattcttgat cgtcttttt tcaaatgcat | 840 |
| ctaccgtcgc tttaaatacg gtctgcaaag agggccttct acggaaggag tgccggagtc | 900 |
| catgagggaa gaatatcggc agaaacagca gagtgctgtg gatgttgacg atggtcattt | 960 |
| tgtcaacata gtgctagag | 979 |

<210> SEQ ID NO 20
<211> LENGTH: 835
<212> TYPE: DNA
<213> ORGANISM: swine influenza virus

<400> SEQUENCE: 20

| | |
|---|---|
| atggactcca atactgtgtc aagctttcag gtagactgtt tcctttggca catccgcaaa | 60 |
| cgatttgcag acaatggatt gggtgatgcc ccattccttg atcggctccg ccgagatcaa | 120 |
| aagtccctaa aggaagggg caacacccctt agcctagaca tcgaaacagc cactcttgtt | 180 |
| gggaaacaaa ttgttgagtg gatttttgaaa gaggaatcca gcgatatact taagatgacc | 240 |
| attgcatctg tgcctacttc gcgctaccta gctgacatga ccctcgagga aatgtcacga | 300 |
| gactggttca tgctaatgcc taggcaaaag ataataggcc ctctttgtgt gcgagtggac | 360 |
| caggcgatca tggaaaagaa catcatactg aaagcgaact tcagtgtgat ctttaaccga | 420 |
| ttagagactt tgatactact aagggctttc actgaggagg gagcaatcgt tggagaaatt | 480 |
| tcaccattac cttatcttcc aggacatact aatgaggatg tcaaaaatgc agttggggtc | 540 |
| ctcatcggag ggcttgaatg gaatggtaac acggttcgag gctctgaaaa tctacagaga | 600 |
| ttcgcttgga gaaaccataa tgaggatggg agatcttcac tacctccaga acagaaatga | 660 |
| aaagtggcga gagcaattgg gacagaaatt tgaggaaata agatggttaa ttgaagaaat | 720 |
| acggcacaga ttgaaagcga cagaaaatag tttcgagcaa ataacattta tgcaagcctt | 780 |
| acaactactg cttgaagtag aacaagagat aaggactttc tcgtttcagc ttatt | 835 |

<210> SEQ ID NO 21
<211> LENGTH: 1698
<212> TYPE: DNA
<213> ORGANISM: swine influenza virus

<400> SEQUENCE: 21

| | |
|---|---|
| atgaaggcaa tactagtagt tctgctatat acatttgcaa cctcaaatgc agacacatta | 60 |
| tgtataggtt atcatgcgaa caattcaaca gacactgtag acacagtact agaaaagaat | 120 |
| gtaacagtaa cacactctgt taaccttcta agacaagc ataacgggaa actatgcaaa | 180 |
| ctaagagggg tagccccatt gcatttgggt aaatgtaaca ttgctggctg gatcctggga | 240 |
| aatccagagt gtgaatcact ctccacagca agctcatggt cctacattgt ggaaacatct | 300 |
| agttcaggca atggaacgtg ttacccagga gatttcatcg attatgagga gctaagagag | 360 |
| caattgagct cagtgtcatc atttgaaagg tttgagatat tccccaagac aagttcatgg | 420 |
| cccaatcatg aatcgaacaa aggtgtaacg gcagcatgtc ctcatgctgg agaaaaaagc | 480 |
| ttctacaaaa atttaatatg gctagttaaa aaaggaaact catacccaaa gctcagcaaa | 540 |
| tcctacatta tgataaagg gaaagaagtc ctcgtgctat ggggcattca ccatccatct | 600 |

-continued

```
actagtgctg accaacaaag tctctatcag aatgcagatg catatgtttt tgtggggaca    660
tcaagataca gcaagaagtt caagccggaa atagcaataa gacccaaagt gagggatcaa    720
gaagggagaa tgaactatta ctggacacta gtagagccgg gagacaaaat aacattcgaa    780
gcaactggaa atctagtggt accgagatat gcattcgcaa tggaaagaaa tgctggatct    840
ggtattatca tttcagatac accagtccac gattgcaata caacttgtca gacacccaag    900
ggtgctataa acaccagcct tccttttcag aatatacatc cgatcacaat tggaaaatgt    960
ccaaaatatg taaaaagcac aaaattgaga ctggccacag gattgaggaa tgtcccgtct   1020
attcaatcta gaggcctatt tggggccatt gccggtttca ttgaaggggg gtggacaggg   1080
atggtagatg gatggtacgg ttatcaccat caaaatgagc aggggtcagg atatgcagcc   1140
gacctgaaga gcacacagaa tgccattgac gagattacta acaaagtaaa ttctgttatt   1200
gaaaagatga atacacagtt cacagcagta ggtaaagagt tcaaccacct ggaaaaaaga   1260
atagagaatt taaataaaaa agttgatgat ggtttcctgg acatttggac ttacaatgcc   1320
gaactgttgg ttctattgga aaatgaaaga actttggact accacgattc aaatgtgaag   1380
aacttatatg aaaaggtaag aagccagtta aaaaacaatg ccaaggaaat tggaaacggc   1440
tgctttgaat tttaccacaa atgcgataac acgtgcatgg aaagtgtcaa aaatgggact   1500
tatgactacc caaaatactc agaggaagca aaattaaaca gagaagaaat agatggggta   1560
aagctggaat caacaaggat ttaccagatt ttggcgatct attcaactgt cgccagttca   1620
ttggtactgg tagtctccct gggggcaatc agtttctgga tgtgctctaa tgggtctcta   1680
cagtgtagaa tatgtatt                                                 1698
```

```

<210> SEQ ID NO 22
<211> LENGTH: 1698
<212> TYPE: DNA
<213> ORGANISM: Artificial Sequence
<220> FEATURE:
<223> OTHER INFORMATION: HA-DO (de-optimized)

<400> SEQUENCE: 22

```

```
atgaaggcaa tactagtagt tctgctatat acatttgcaa cctcaaatgc agacacatta     60
tgtataggtt atcatgcgaa caattcaaca gatacggtcg atacggtctt agaaaaaaat    120
gtcacggtca cgcattcggt caatttatta gaagataaac ataatggaaa attatgtaaa    180
ttacgtggag tcgcgccgtt acatttagga aaatgtaata tagcgggatg gatattagga    240
aatccggaat gtgaatcgtt atcgacggcg tcgtcgtggt cgtatatagt cgaaacgtcg    300
tcgtcgggaa atggaacgtg ttatccggga gattttatag attatgaaga attacgtgaa    360
caattatcgt cggtctcgtc gtttgaacgt tttgaaatat ttccgaaaac gtcgtcgtgg    420
ccgaatcatg aatcgaataa aggagtcacg gcggcgtgtc cgcatgcggg agaaaaatcg    480
ttttataaaa atttaatatg gctagtcaaa aaaggaaatt cgtatccgaa attatcgaaa    540
tcgtatataa atgataaagg aaaagaagtc ttagtcttat ggggaataca tcatccgtcg    600
acgtcggcgg atcaacaatc gttatatcaa aatgcggatg cgtatgtctt tgtcggaacg    660
tcgcgttatt cgaaaaaatt taaaccggaa atagcgatac gtccgaaagt ccgtgatcaa    720
gaaggacgca tgaattatta ttggacgcta gtcgaaccgg gagataaaat aacgtttgaa    780
gcgacgggaa atttagtcgt cccgcgttat gcgtttgcga tggaacgtaa tgcgggatcg    840
ggaataataa tatcggatac gccggtccat gattgtaata cgacgtgtca aacgccgaaa    900
```

```
ggagcgataa atacgtcgtt accgtttcaa aatatacatc cgataacgat aggaaaatgt    960
ccgaaatatg tcaaatcgac gaaattacgt ttagcgacgg gattacgtaa tgtcccgtcg   1020
atacaatcgc gtggattatt tggagcgata gcgggattta tagaaggagg atggacggga   1080
atggtcgatg gatggtatgg atatcatcat caaaatgaac aaggatcggg atatgcggcg   1140
gatttaaaat cgacgcaaaa tgcgatagat gaaataacga ataaagtcaa ttcggtcata   1200
gaaaaaatga atacgcaatt tacggcggtc ggaaaagaat ttaatcattt agaaaaacgt   1260
atagaaaatt taaataaaaa agtcgatgat ggatttttag atatatggac gtataatgcg   1320
gaattattag tcttattaga aaatgaacgt acgttagatt atcatgattc gaatgtcaaa   1380
aatttatatg aaaaagtccg ttcgcaatta aaaaataatg cgaaagaaat aggaaatgga   1440
tgttttgaat tttatcataa atgtgataat acgtgtatgg aatcggtcaa aaatggaacg   1500
tatgattatc cgaaatattc ggaagaagcg aaattaaatc gtgaagaaat agatggagtc   1560
aaattagaat cgacgcgtat atatcaaata ttagcgatat attcgacggt cgcgtcgtca   1620
ttggtactgg tagtctccct gggggcaatc agtttctgga tgtgctctaa tgggtctcta   1680
cagtgtagaa tatgtatt                                                 1698
```

<210> SEQ ID NO 23
<211> LENGTH: 566
<212> TYPE: PRT
<213> ORGANISM: swine influenza virus

<400> SEQUENCE: 23

```
Met Lys Ala Ile Leu Val Val Leu Leu Tyr Thr Phe Ala Thr Ser Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Gly Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Glu
    130                 135                 140

Ser Asn Lys Gly Val Thr Ala Ala Cys Pro His Ala Gly Glu Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Thr Ser Arg Tyr Ser
    210                 215                 220

Lys Lys Phe Lys Pro Glu Ile Ala Ile Arg Pro Lys Val Arg Asp Gln
```

-continued

```
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 24
<211> LENGTH: 1407
<212> TYPE: DNA
<213> ORGANISM: swine influenza virus

<400> SEQUENCE: 24

```
atgaatccaa accaaaagat aataaccatt ggttcggtct gtatgacaat tggaatggct      60
aacttaatat tacaaattgg aaacataatc tcaatatgga ttagccactc aattcaactt     120
gggaatcaaa atcagattga aacatgcaat caaagcgtca ttacttatga aaacaacact     180
```

-continued

```
tgggtaaatc agacatatgt taacatcagc aacaccaact ttgctgctgg acagtcagtg    240
gtttccgtga aattagcggg caattcctct ctctgccctg ttagtggatg ggctatatac    300
agtaaagaca acagtgtaag aatcggttcc aagggggatg tgtttgtcat aagggaacca    360
ttcatatcat gctccccctt ggaatgcaga accttcttct tgactcaagg ggccttgcta    420
aatgacaaac attccaatgg aaccattaaa gacaggagcc catatcgaac cctaatgagc    480
tgtcctattg gtgaagttcc ctctccatac aactcaagat ttgagtcagt cgcttggtca    540
gcaagtgctt gtcatgatgg catcaattgg ctaacaattg gaatttctgg cccagacaat    600
ggggcagtgg ctgtgttaaa gtacaacggc ataataacag acactatcaa gagttggaga    660
aacaatatat tgagaacaca agagtctgaa tgtgcatgtg taaatggttc ttgctttact    720
gtaatgaccg atggaccaag taatggacag gcctcataca agatcttcag aatagaaaag    780
ggaaagatag tcaaatcagt cgaaatgaat gcccctaatt atcactatga ggaatgctcc    840
tgttatcctg attctagtga aatcacatgt gtgtgcaggg ataactggca tggctcgaat    900
cgaccgtggg tgtctttcaa ccagaatctg gaatatcaga taggatacat atgcagtggg    960
attttcggag acaatccacg ccctaatgat aagacaggca gttgtggtcc agtatcgtct   1020
aatggagcaa atggagtaaa agggttttca ttcaaatacg gcaatggtgt ttggataggg   1080
agaactaaaa gcattagttc aagaaacggt tttgagatga tttgggatcc gaacggatgg   1140
actgggacag acaataactt ctcaataaag caagatatcg taggaataaa tgagtggtca   1200
ggatatagcg ggagttttgt tcagcatcca gaactaacag ggctggattg tataagacct   1260
tgcttctggg ttgaactaat cagagggcga cccaaagaga acacaatctg gactagcggg   1320
agcagcatat ccttttgtgg tgtaaacagt gacactgtgg gttggtcttg gccagacggt   1380
gctgagttgc catttaccat tgacaag                                       1407
```

```
<210> SEQ ID NO 25
<211> LENGTH: 1407
<212> TYPE: DNA
<213> ORGANISM: Artificial Sequence
<220> FEATURE:
<223> OTHER INFORMATION: NA-DO (de-optimized)

<400> SEQUENCE: 25
atgaatccaa accaaaagat aataaccatt ggttcggtct gtatgacaat tggaatggct     60
aacttaatat tacaaattgg aaacataatc tcaatatgga tttcgcattc gatacaatta    120
ggaaatcaaa atcaaataga aacgtgtaat caatcggtca taacgtatga aaataatacg    180
tgggtcaatc aaacgtatgt caatatatcg aatacgaatt ttgcggcggg acaatcggtc    240
gtatcggtca aattagcggg aaattcgtcg ttatgtccgg tctcgggatg ggcgatatat    300
tcgaaagata attcggtccg tataggatcg aaaggagatg tctttgtcat acgtgaaccg    360
tttatatcgt gttcgccgtt agaatgtcgt acgttttttt taacgcaagg agcgttatta    420
aatgataaac attcgaatgg aacgataaaa gatcgttcgc cgtatcgtac gttaatgtcg    480
tgtccgatag gagaagtccc gtcgccgtat aattcgcgtt ttgaatcggt cgcgtggtcg    540
gcgtcggcgt gtcatgatgg aataaattgg ttaacgatag gaatatcggg accggataat    600
ggagcggtcg cggtcttaaa atataatgga ataataacgg atacgataaa atcgtggcgt    660
aataatatat tacgtacgca agaatcggaa tgtgcgtgtg tcaatggatc gtgttttacg    720
gtcatgacgg atggaccgtc gaatggacaa gcgtcgtata aaatatttcg tatagaaaaa    780
ggaaaaatag tcaaatcggt cgaaatgaat gcgccgaatt atcattatga agaatgttcg    840
```

```
tgttatccgg attcgtcgga aataacgtgt gtctgtcgtg ataattggca tggatcgaat    900
cgtccgtggg tctcgtttaa tcaaaattta gaatatcaaa taggatatat atgttcggga    960
atatttggag ataatccgcg tccgaatgat aaaacgggat cgtgtggacc ggtctcgtcg   1020
aatggagcga atggagtcaa aggattttcg tttaaatatg gaaatggagt ctggatagga   1080
cgtacgaaat cgatatcgtc gcgtaatgga tttgaaatga tatgggatcc gaatggatgg   1140
acgggaacgg ataataattt ttcgataaaa caagatatag tcggaataaa tgaatggtcg   1200
ggatattcgg gatcgtttgt ccaacatccg gaattaacgg gattagattg tatacgtccg   1260
tgtttttggg tcgaattaat acgtggacgt ccgaaagaaa atacgatatg gactagcggg   1320
agcagcatat ccttttgtgg tgtaaacagt gacactgtgg gttggtcttg gccagacggt   1380
gctgagttgc catttaccat tgacaag                                        1407
```

<210> SEQ ID NO 26
<211> LENGTH: 469
<212> TYPE: PRT
<213> ORGANISM: swine influenza virus

<400> SEQUENCE: 26

```
Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270
```

Asn Tyr His Tyr Glu Glu Cys Ser Cys Tyr Pro Asp Ser Glu Ile
            275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 27
<211> LENGTH: 657
<212> TYPE: DNA
<213> ORGANISM: Artificial Sequence
<220> FEATURE:
<223> OTHER INFORMATION: NS1 DO CDS of A/swine/NC/3793/2008(H1N1) -
      TRIG, de-optimized

<400> SEQUENCE: 27
atggactcca atactgtgtc aagctttcag gtagactgtt tcctttggca catccgcaaa      60
cgatttgcag acaatggatt gggtgatgcc ccattccttg atcggctccg ccagatcaa     120 aaatcgttaa aaggacgtgg aaatacgtta tcgttagata tagaaacggc gacgctagtc    180
ggaaaacaaa tagtcgaatg gatattaaaa gaagaatcgt cggatatatt aaaaatgacg    240
atagcgtcgg tcccgacgtc gcgttattta gcggatatga cgttagaaga aatgtcgcgt    300
gattggttta tgttaatgcc gcgtcaaaaa ataataggac cgttatgtgt ccgtgtcgat    360
caagcgataa tggaaaaaaa tataatatta aaagcgaatt tttcggtcat atttaatcgt    420
ttagaaacgt taatattatt acgtgcgttt acgaggagg gagcaatcgt tggagaaatt    480
tcaccattac cttatcttcc aggacatact aatgaggatg tcaaaaatgc agttggggtc    540
ctcatcggag ggcttgaatg gaatggtaac acggttcgag gctctgaaaa tctacagaga    600
ttcgcttgga gaaaccataa tgaggatggg agatcttcac tacctccaga acagaaa      657

<210> SEQ ID NO 28
<211> LENGTH: 1695
<212> TYPE: DNA
<213> ORGANISM: swine influenza virus -continued

<400> SEQUENCE: 28

```
atgaaagtaa aactaatggt tctgttatgt acatttacag ctacatatgc agacacaata     60
tgtgtaggct accatgccaa caactcaact gacactgttg acacagtact tgagaagaat    120
gtgacagtga cacactctgt caacctactt gaggacagcc acaatggaaa actatgtcta    180
ctaaaaggaa tagctccact acaattgggt agttgcagcg ttgccggatg gatcttagga    240
aacccagagt gcgaattgct gatttccaag gaatcttggt cctacattgt agaaacacca    300
aatcctgaga atggaacatg ttacccaggg tatttcacag actatgaaga actgagggag    360
caattgagtt cagtatcttc atttaagagg ttcgaaatat tccccaaaga gagctcatgg    420
cccaaccaca ccgtaaccgg agtgtcatca tcatgctccc ataacgggaa aagcagcttc    480
tacagaaatt tgctatggct gacggtgaag aacggtctgt acccaaacct gagcaagtcc    540
tatacaaaca aaaaggagaa agaagtcctt gtactatggg gtgttcatca cccatctaac    600
ataggggacc aaagggccct ctatcataca gaaaatgctt atgtctctgt agtgtcttca    660
cattatagca gaagattcac cccagaaata gccaaaagac ccaaggtgag aaatcaggaa    720
ggaagaatca actactactg gaccctgcta gaacccgggg atacaataat atttgaggca    780
aatggaaatc taatagcacc aaggtatgcc ttcgaactga gtaagggttt tggatcagga    840
atcatcacat caaatgcacc aatgggtgaa tgtaatgcaa agtgtcaaac acctcaggga    900
gctataaaca gcagtcttcc tttccagaat gtacacccag taacaatagg agagtgccca    960
aagtatgtca aaagtgcaaa attaaggatg gttacaggac taaggaacac cccatccatt   1020
caatccagag gtttgtttgg agccattgcc ggtttcattg aaggagggtg gactggaatg   1080
gtagatggtt ggtatggtta tcaccatcag aatgagcaag gatctgggta tgctgcagac   1140
caacaaagca cacaaaatgc cattaatggg attacaaaca aggtgaattc tgtgattgaa   1200
aaaatgaaca ctcaattcac agctgtgggc aaagaattca acaaactgga aagaagaatg   1260
gaaaacttaa ataaaaaggt tgatgatggg tttctagaca tttggacata taatgcagaa   1320
ttgttagttc tactggaaaa tgaaaggact ttggatttcc atgactccaa cgtgaagaat   1380
ctgtatgaga aagtaaaaag ccaattaaaa aataatgcca aagaaatagg aaacgggtgt   1440
tttgaattct atcataagtg taacgatgaa tgcatggaga gtgtgaaaaa tggaacttat   1500
gactatccaa aatattccga agaatcaaag ttaaacaggg agaaaattga tggagtgaaa   1560
ttggaatcaa tgggagtcta taatatcctg gcgatctact caacagtcgc cagttcccta   1620
gttcttttag tctccctggg ggcaatcagc ttctggatgt gttccaatgg gtctttacag   1680
tgtagaatat gcatc                                                    1695
```

<210> SEQ ID NO 29
<211> LENGTH: 1695
<212> TYPE: DNA
<213> ORGANISM: Artificial Sequence
<220> FEATURE:
<223> OTHER INFORMATION: HA-DO (H1N2; de-optimized)

<400> SEQUENCE: 29

```
atgaaagtaa aactaatggt tctgttatgt acatttacag ctacatatgc agacacaata     60
tgtgtaggct accatgccaa caactcaact gatacggtcg atacggtctt agaaaaaaat    120
gtcacggtca cgcattcggt caatttatta gaagattcgc ataatggaaa attatgttta    180
ttaaaaggaa tagcgccgtt acaattagga tcgtgttcgg tcgcgggatg gatattagga    240
aatccggaat gtgaattatt aatatcgaaa gaatcgtggt cgtatatagt cgaaacgccg    300
```

```
aatccggaaa atggaacgtg ttatccggga tattttacgg attatgaaga attacgtgaa      360
caattatcgt cggtctcgtc gtttaaacgt tttgaaatat ttccgaaaga atcgtcgtgg      420
ccgaatcata cggtcacggg agtctcgtcg tcgtgttcgc ataatggaaa atcgtcgttt      480
tatcgtaatt tattatggtt aacggtcaaa aatggattat atccgaattt atcgaaatcg      540
tatacgaata aaaagaaaa agaagtctta gtcttatggg gagtccatca tccgtcgaat       600
ataggagatc aacgtgcgtt atatcatacg gaaaatgcgt atgtctcggt cgtatcgtcg      660
cattattcgc gtcgttttac gccggaaata gcgaaacgtc cgaaagtccg taatcaagaa      720
ggacgtataa attattattg gacgttatta gaaccgggag atacgataat atttgaagcg      780
aatggaaatt taatagcgcc gcgttatgcg tttgaattat cgaaaggatt tggatcggga      840
ataataacgt cgaatgcgcc gatgggagaa tgtaatgcga aatgtcaaac gccgcaagga      900
gcgataaatt cgtcgttacc gtttcaaaat gtccatccgg tcacgatagg agaatgtccg      960
aaatatgtca aatcggcgaa attacgtatg gtcacgggat acgtaatac gccgtcgata     1020 caatcgcgtg gattatttgg agcgatagcg ggatttatag aaggaggatg gacgggaatg     1080
gtcgatggat ggtatggata tcatcatcaa aatgaacaag gatcgggata tgcggcggat     1140
caacaatcga cgcaaaatgc gataaatgga ataacgaata aagtcaattc ggtcatagaa     1200
aaaatgaata cgcaatttac ggcggtcgga aaagaattta ataaattaga acgtcgtatg     1260
gaaaatttaa ataaaaagt cgatgatgga ttttagata tatggacgta taatgcggaa      1320
ttattagtct tattagaaaa tgaacgtacg ttagattttc atgattcgaa tgtcaaaaat     1380
ttatatgaaa aagtcaaatc gcaattaaaa aataatgcga agaaatagg aaatggatgt      1440 tttgaatttt atcataaatg taatgatgaa tgtatggaat cggtcaaaaa tggaacgtat     1500
gattatccga atatattcgga agaatcgaaa ttaaatcgtg aaaaaataga tggagtcaaa     1560
ttagaatcga tgggagtcta taatatatta gcgatatatt cgacggtcgc gtcgtcccta     1620 gttctttttag tctccctggg ggcaatcagc ttctggatgt gttccaatgg gtcttacag      1680 tgtagaatat gcatc                                                       1695
```

<210> SEQ ID NO 30
<211> LENGTH: 565
<212> TYPE: PRT
<213> ORGANISM: swine influenza virus

<400> SEQUENCE: 30

Met Lys Val Lys Leu Met Val Leu Leu Cys Thr Phe Thr Ala Thr Tyr
1               5                   10                  15

Ala Asp Thr Ile Cys Val Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Ser Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Thr Asp Tyr Glu Glu Leu Arg Glu Gln Leu Ser Ser Val Ser Ser Phe

```
              115                 120                 125
Lys Arg Phe Glu Ile Phe Pro Lys Glu Ser Ser Trp Pro Asn His Thr
              130                 135                 140
Val Thr Gly Val Ser Ser Cys Ser His Asn Gly Lys Ser Phe
145                 150                 155                 160
Tyr Arg Asn Leu Leu Trp Leu Thr Val Lys Asn Gly Leu Tyr Pro Asn
                  165                 170                 175
Leu Ser Lys Ser Tyr Thr Asn Lys Lys Glu Lys Glu Val Leu Val Leu
              180                 185                 190
Trp Gly Val His His Pro Ser Asn Ile Gly Asp Gln Arg Ala Leu Tyr
              195                 200                 205
His Thr Glu Asn Ala Tyr Val Ser Val Val Ser Ser His Tyr Ser Arg
              210                 215                 220
Arg Phe Thr Pro Glu Ile Ala Lys Arg Pro Lys Val Arg Asn Gln Glu
225                 230                 235                 240
Gly Arg Ile Asn Tyr Tyr Trp Thr Leu Leu Glu Pro Gly Asp Thr Ile
                  245                 250                 255
Ile Phe Glu Ala Asn Gly Asn Leu Ile Ala Pro Arg Tyr Ala Phe Glu
              260                 265                 270
Leu Ser Lys Gly Phe Gly Ser Gly Ile Ile Thr Ser Asn Ala Pro Met
              275                 280                 285
Gly Glu Cys Asn Ala Lys Cys Gln Thr Pro Gln Gly Ala Ile Asn Ser
              290                 295                 300
Ser Leu Pro Phe Gln Asn Val His Pro Val Thr Ile Gly Glu Cys Pro
305                 310                 315                 320
Lys Tyr Val Lys Ser Ala Lys Leu Arg Met Val Thr Gly Leu Arg Asn
                  325                 330                 335
Thr Pro Ser Ile Gln Ser Arg Gly Leu Phe Gly Ala Ile Ala Gly Phe
              340                 345                 350
Ile Glu Gly Gly Trp Thr Gly Met Val Asp Gly Trp Tyr Gly Tyr His
              355                 360                 365
His Gln Asn Glu Gln Gly Ser Gly Tyr Ala Ala Asp Gln Gln Ser Thr
              370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                  405                 410                 415
Glu Arg Arg Met Glu Asn Leu Asn Lys Lys Val Asp Asp Gly Phe Leu
                  420                 425                 430
Asp Ile Trp Thr Tyr Asn Ala Glu Leu Leu Val Leu Leu Glu Asn Glu
              435                 440                 445
Arg Thr Leu Asp Phe His Asp Ser Asn Val Lys Asn Leu Tyr Glu Lys
              450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                  485                 490                 495
Asn Gly Thr Tyr Asp Tyr Pro Lys Tyr Ser Glu Glu Ser Lys Leu Asn
                  500                 505                 510
Arg Glu Lys Ile Asp Gly Val Lys Leu Glu Ser Met Gly Val Tyr Asn
              515                 520                 525
Ile Leu Ala Ile Tyr Ser Thr Val Ala Ser Ser Leu Val Leu Leu Val
              530                 535                 540
```

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 31
<211> LENGTH: 1407
<212> TYPE: DNA
<213> ORGANISM: swine influenza virus

<400> SEQUENCE: 31

| | | | | | | |
|---|---|---|---|---|---|---|
| atgaatccaa | atcaaaagat | aataacgatt | ggctctgttt | ctcttactat | tgccacaatg | 60 |
| tgcttcctta | tgcaaattgc | catcctggta | actaatgtaa | cattgcactt | caatcaatat | 120 |
| gaatgcaact | accccccaaa | caaccaagta | atactgtgtg | aaccaacaat | aatagaaaga | 180 |
| aacataacag | agatagtgta | tctgaccaac | accaccatag | agaaggaaat | atgccccaaa | 240 |
| ctagcagaat | acagaaattg | gtcaaagccg | caatgtaaaa | ttacagggtt | tgcaccttt | 300 |
| tccaaggaca | attcgattag | ctttctgct | ggtggggaca | tttgggtgac | gagagaacct | 360 |
| tatgtgtcat | gcgatcctga | taagtgttat | cagtttgccc | ttggacaagg | aacaacatta | 420 |
| aacaacaggc | attcaaatga | cacagtacat | gataggaccc | cttatcgaac | cctattgatg | 480 |
| aatgagttgg | gtattccatt | ccatttgggg | accaaacaag | tgtgcatagc | atggtccagc | 540 |
| tcaagttgtc | atgatggaaa | agcatggctt | cacgtttgta | ttactgggca | tgatgaaaat | 600 |
| gcaactgcca | gcatcattta | caatggaaga | cttgtagata | gtattggttc | atggtccaaa | 660 |
| aaaatactca | ggacacagga | gtcggaatgt | gtttgcatca | atggaacttg | tacagtagta | 720 |
| atgactgatg | ggagtgcttc | aggaatagct | gacactaaaa | tattattcat | tgaagagggg | 780 |
| aaaatcgttc | atattagccc | attgttagga | agtgctcagc | atgtagagga | gtgctcctgt | 840 |
| tatccccgat | atcctggtgt | cagatgcatc | tgtagagaca | actggaaagg | ttccaataga | 900 |
| cccgtcgtag | atataaatgt | aaaggattat | agcattgttt | ccagttatgt | gtgctcagga | 960 |
| cttgttggag | atacacccag | aaaagacgac | agatccagca | gtagcgattg | tctgaatcct | 1020 |
| aacaatgagg | aagggggggca | tggagtgaaa | ggctgggcct | tgatgatgg | aaatgatgtg | 1080 |
| tggatgggaa | gaacaatcaa | cgagacgtta | cgctcaggtt | atgaaacctt | caaagtcatt | 1140 |
| gaaggctggt | ccaaacctaa | ttccaaattg | cagataaata | ggcaagtcat | agttgaaaga | 1200 |
| ggtgataggt | ccggttattc | tggcattttc | tctgttgaag | gcaaaagctg | tatcaatcgg | 1260 |
| tgcttttatg | tggagttgat | aagaggaagg | aaacaggaaa | ctgcagtatg | gtggacgtca | 1320 |
| aacagtattg | ttgtgttttg | tggcacctca | ggtacatatg | aacaggctc | atggcctgat | 1380 |
| ggggcgaaca | tcaatctcat | gcctgta | | | | 1407 |

<210> SEQ ID NO 32
<211> LENGTH: 1407
<212> TYPE: DNA
<213> ORGANISM: Artificial Sequence
<220> FEATURE:
<223> OTHER INFORMATION: NA-DO (H1N2; de-optimized)

<400> SEQUENCE: 32

| | | | | | | |
|---|---|---|---|---|---|---|
| atgaatccaa | atcaaaagat | aataacgatt | ggctctgttt | ctcttactat | tgccacaatg | 60 |
| tgcttcctta | tgcaaattgc | catcctggta | actaatgtaa | cattgcactt | caatcaatat | 120 |
| gaatgtaatt | atccgccgaa | taatcaagtc | atattatgtg | aaccgacgat | aatagaacgt | 180 |

```
aatataacgg aaatagtcta tttaacgaat acgacgatag aaaagaaat atgtccgaaa      240 ttagcggaat atcgtaattg gtcgaaaccg caatgtaaaa taacgggatt tgcgccgttt      300
tcgaaagata attcgatacg tttatcggcg ggaggagata tatgggtcac gcgtgaaccg      360
tatgtctcgt gtgatccgga taaatgttat caatttgcgt taggacaagg aacgacgtta      420
aataatcgtc attcgaatga tacggtccat gatcgtacgc cgtatcgcac gttattaatg      480
aatgaattag gaataccgtt tcatttagga acgaaacaag tctgtatagc gtggtcgtcg      540
tcgtcgtgtc atgatggaaa agcgtggtta catgtctgta taacgggaca tgatgaaaat      600
gcgacggcgt cgataatata taatggacgt ttagtcgatt cgataggatc gtggtcgaaa      660
aaaatattac gtacgcaaga atcggaatgt gtctgtataa atggaacgtg tacggtcgtc      720
atgacggatg gatcggcgtc gggaatagcg gatacgaaaa tattatttat agaagaagga      780
aaaatagtcc atatatcgcc gttattagga tcggcgcaac atgtcgaaga atgttcgtgt      840
tatccgcgtt atccgggagt ccgttgtata tgtcgtgata attggaaagg atcgaatcgt      900
ccggtcgtcg atataaatgt caaagattat tcgatagtct cgtcgtatgt ctgttcggga      960
ttagtcggag atacgccgcg taaagatgat cgttcgtcgt cgtcggattg tttaaatccg     1020
aataatgaag aaggaggaca tggagtcaaa ggatgggcgt tgatgatgg aaatgatgtc     1080 tggatgggac gtacgataaa tgaaacgtta cgttcgggat atgaaacgtt aaagtcata      1140 gaaggatggt cgaaaccgaa ttcgaaatta caaataaatc gtcaagtcat agtcgaacgt     1200
ggagatcgtt cgggatattc gggaatattt tcggtcgaag gaaaatcgtg tataaatcgt     1260 tgttttatg tcgaattaat acgtggacgt aaacaagaaa ctgcagtatg gtggacgtca     1320
aacagtattg ttgtgttttg tggcacctca ggtacatatg aacaggctc atggcctgat      1380 ggggcgaaca tcaatctcat gcctgta                                         1407
```

<210> SEQ ID NO 33
<211> LENGTH: 469
<212> TYPE: PRT
<213> ORGANISM: swine influenza virus

<400> SEQUENCE: 33

Met Asn Pro Asn Gln Lys Ile Ile Thr Ile Gly Ser Val Ser Leu Thr
1               5                   10                  15

Ile Ala Thr Met Cys Phe Leu Met Gln Ile Ala Ile Leu Val Thr Asn
            20                  25                  30

Val Thr Leu His Phe Asn Gln Tyr Glu Cys Asn Tyr Pro Pro Asn Asn
        35                  40                  45

Gln Val Ile Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Ile Pro Phe His Leu Gly Thr Lys Gln Val Cys Ile
              165                 170                 175

Ala Trp Ser Ser Ser Cys His Asp Gly Lys Ala Trp Leu His Val
        180                 185                 190

Cys Ile Thr Gly His Asp Glu Asn Ala Thr Ala Ser Ile Ile Tyr Asn
            195                 200                 205

Gly Arg Leu Val Asp Ser Ile Gly Ser Trp Ser Lys Lys Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Ile Ala Asp Thr Lys Ile Leu Phe
            245                 250                 255

Ile Glu Glu Gly Lys Ile Val His Ile Ser Pro Leu Leu Gly Ser Ala
            260                 265                 270

Gln His Val Glu Glu Cys Ser Cys Tyr Pro Arg Tyr Pro Gly Val Arg
        275                 280                 285

Cys Ile Cys Arg Asp Asn Trp Lys Gly Ser Asn Arg Pro Val Val Asp
        290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asp Asp Arg Ser Ser Ser Ser Asp
            325                 330                 335

Cys Leu Asn Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
        355                 360                 365

Thr Leu Arg Ser Gly Tyr Glu Thr Phe Lys Val Ile Glu Gly Trp Ser
        370                 375                 380

Lys Pro Asn Ser Lys Leu Gln Ile Asn Arg Gln Val Ile Val Glu Arg
385                 390                 395                 400

Gly Asp Arg Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Gln
            420                 425                 430

Glu Thr Ala Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
        450                 455                 460

Asn Leu Met Pro Val
465

<210> SEQ ID NO 34
<211> LENGTH: 1698
<212> TYPE: DNA
<213> ORGANISM: swine influenza virus

<400> SEQUENCE: 34
atgaagacta tcattgcttt tagctgcgtt ttatgtttga ttttcgctca aaaacttccc      60
ggaagtgaca cagcatggc aacgctgtgc ctgggacacc atgcagtacc aaacggaacg     120
ttagtgaaaa caatcacgga tgaccaaatt gaagtgacta atgctactga gctggttcag     180
agttcctcaa caggtagaat atgcaacagt cctcaccaaa tccttgatgg gaaaaattgc     240
acactgatag atgctctatt gggagaccct cattgtgatg acttccaaaa caaggaatgg     300

```
gacctttttg ttgaacgaag cacagcctac agcaactgtt acccttatta tgtgccggat    360
tatgcctccc ttaggtcact agttgcatca tccggcaccc tggaatttac ccaagaaagc    420
ttcaattgga ctggagttgc tcaagatgga tcaagctatg cttgcagaag ggaatctgtt    480
aacagtttct ttagtagatt gaattggttg cataaattgg attacaaata tccagcgctg    540
aaagtaacta tgccgaacaa tgacaaattc gacaaattgt acatttgggg ggttcaccac    600
ccgggcactg acagggacca aaccaaccta tatgttcaaa catcagggag agttacagtc    660
tccaccaaaa gaagccaaca aactgtaatc ccaaatatcg ggtctagacc ctgggtaagg    720
ggtgtctcca gcataataag catctattgg acaatagtaa aaccgggaga catacttttg    780
attaacagca cagggaatct aattgcccct cggggttact tcaaattaca aagtgggaaa    840
agctcaataa tgagatcaga tgcacccatt ggcatctgca attctgaatg cattactcca    900
aatggaagca ttcccaacga caaacctttt caaaatgtaa acaggatcac ttatggggcc    960
tgtcccagat atgttaagca aaacaccctg aaattggcaa caggaatgcg gaatgtacca   1020
gagaaacaaa ccagaggcat atttggcgca atcgcaggtt tcatagaaaa tggttgggaa   1080
gggatggtgg acggttggta cggtttcagg catcaaaatt ctgaaggcac aggacaagca   1140
gcagatctta aaagcactcg tgcagcaatc aaccaaatca ccgggaaact aaatagagta   1200
atcaagaaaa cgaacgagaa attccatcag atcgaaaaag aattctcaga agtagaaggg   1260
agaattcagg acctagagaa atacgttgaa gacactaaaa tagacctctg gtcttacaac   1320
gcggagcttc ttgttgccct ggagaaccaa cacacaattg atttaactga ctcagaaatg   1380
aacaaactgt tcgaaagaac aagaaagcaa ttgcgggaaa atgctgagga catgggcaat   1440
ggttgcttca aaatatacca caaatgtgac aatgcctgca taggatcaat cagaaatgga   1500
acttatgacc atgatgtata cagagatgag gcattaaaca atcggttcca gatcaaaggt   1560
gttcagctga agtcaggata caaagattgg atcctatgga tttcctttgc catatcatgc   1620
tttttgcttt gtgttgttct gctggggttc attatgtggg cctgccaaaa aggcaacatt   1680
aggtgcaaca tttgcatt                                                 1698
```

<210> SEQ ID NO 35
<211> LENGTH: 1698
<212> TYPE: DNA
<213> ORGANISM: Artificial Sequence
<220> FEATURE:
<223> OTHER INFORMATION: HA-DO (H3N2; de-optimized)

<400> SEQUENCE: 35

```
atgaagacta tcattgcttt tagctgcgtt ttatgtttga ttttcgctca aaaacttccc     60
ggaagtgaca acagcatggc aacgctgtgc ttaggacatc atgcggtccc gaatggaacg    120
ttagtcaaaa cgataacgga tgatcaaata gaagtcacga atgcgacgga attagtccaa    180
tcgtcgtcga cgggacgtat atgtaattcg ccgcatcaaa tattagatgg aaaaaattgt    240
acgttaatag atgcgttatt aggagatccg cattgtgatg attttcaaaa taaagaatgg    300
gatttatttg tcgaacgttc gacggcgtat tcgaattgtt atccgtatta tgtcccggat    360
tatgcgtcgt tacgttcgtt agtcgcgtcg tcgggaacgt tagaatttac gcaagaatcg    420
tttaattgga cgggagtcgc gcaagatgga tcgtcgtatg cgtgtcgtcg tgaatcggtc    480
aattcgtttt tttcgcgttt aaattggtta cataaattag attataaata tccggcgtta    540
aaagtcacga tgccgaataa tgataaattt gataaattat atatatgggg agtccatcat    600
ccgggaacgg atcgtgatca aacgaattta tatgtccaaa cgtcgggacg tgtcacggtc    660
```

-continued

```
tcgacgaaac gttcgcaaca aacggtcata ccgaatatag gatcgcgtcc gtgggtccgt    720
ggagtctcgt cgataatatc gatatattgg acgatagtca aaccgggaga tatattatta    780
ataaattcga cgggaaattt aatagcgccg cgtggatatt ttaaattaca atcgggaaaa    840
tcgtcgataa tgcgttcgga tgcgccgata ggaatatgta attcggaatg tataacgccg    900
aatggatcga taccgaatga taaaccgttt caaaatgtca atcgtataac ctatggagcg    960
tgtccgcgtt atgtcaaaca aaatacgtta aaattagcga cgggaatgcg taatgtcccg   1020
gaaaaacaaa cgcgtggaat atttggagcg atagcgggat ttatagaaaa tggatgggaa   1080
ggaatggtcg atgatggta tggatttcgt catcaaaatt cggaaggaac gggacaagcg   1140
gcggatttaa aatcgacgcg tgcggcgata aatcaaataa cgggaaaatt aaatcgtgtc   1200
ataaaaaaaa cgaatgaaaa atttcatcaa atagaaaaag aattttcgga agtcgaagga   1260
cgtatacaag atttagaaaa atatgtcgaa gatacgaaaa tagatttatg gtcgtataat   1320
gcggaattat tagtcgcgtt agaaaatcaa catacgatag atttaacgga ttcgaaaatg   1380
aataaattat ttgaacgtac gcgtaaacaa ttacgtgaaa atgcggaaga tatgggaaat   1440
ggatgtttta aaatatatca taatgtgat aatgcgtgta taggatcgat acgtaatgga   1500
acgtatgatc atgatgtcta tcgtgatgaa gcgttaaata atcgttttca aataaaagga   1560
gtccaattaa aatcgggata taagattgg atattatgga tatcgtttgc gatatcgtgc   1620
tttttgcttt gtgttgttct gctggggttc attatgtggg cctgccaaaa aggcaacatt   1680
aggtgcaaca tttgcatt                                                1698
```

<210> SEQ ID NO 36
<211> LENGTH: 566
<212> TYPE: PRT
<213> ORGANISM: swine influenza virus

<400> SEQUENCE: 36

```
Met Lys Thr Ile Ile Ala Phe Ser Cys Val Leu Cys Leu Ile Phe Ala
1               5                   10                  15

Gln Lys Leu Pro Gly Ser Asp Asn Ser Met Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Arg Ile Cys Asn Ser Pro His Gln Ile Leu Asp Gly Lys Asn Cys
65                  70                  75                  80

Thr Leu Ile Asp Ala Leu Leu Gly Asp Pro His Cys Asp Asp Phe Gln
                85                  90                  95

Asn Lys Glu Trp Asp Leu Phe Val Glu Arg Ser Thr Ala Tyr Ser Asn
            100                 105                 110

Cys Tyr Pro Tyr Tyr Val Pro Asp Tyr Ala Ser Leu Arg Ser Leu Val
        115                 120                 125

Ala Ser Ser Gly Thr Leu Glu Phe Thr Gln Glu Ser Phe Asn Trp Thr
    130                 135                 140

Gly Val Ala Gln Asp Gly Ser Ser Tyr Ala Cys Arg Arg Glu Ser Val
145                 150                 155                 160

Asn Ser Phe Phe Ser Arg Leu Asn Trp Leu His Lys Leu Asp Tyr Lys
                165                 170                 175

Tyr Pro Ala Leu Lys Val Thr Met Pro Asn Asn Asp Lys Phe Asp Lys
```

```
                180             185             190
Leu Tyr Ile Trp Gly Val His His Pro Gly Thr Asp Arg Asp Gln Thr
            195                 200             205

Asn Leu Tyr Val Gln Thr Ser Gly Arg Val Thr Val Ser Thr Lys Arg
    210                 215                 220

Ser Gln Gln Thr Val Ile Pro Asn Ile Gly Ser Arg Pro Trp Val Arg
225                 230                 235                 240

Gly Val Ser Ser Ile Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Leu Gln Ser Gly Lys Ser Ser Ile Met Arg Ser Asp Ala
        275                 280                 285

Pro Ile Gly Ile Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
    370                 375                 380

Ser Thr Arg Ala Ala Ile Asn Gln Ile Thr Gly Lys Leu Asn Arg Val
385                 390                 395                 400

Ile Lys Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Arg Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Gln Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Lys Gly Asn Ile
545                 550                 555                 560

Arg Cys Asn Ile Cys Ile
                565

<210> SEQ ID NO 37
<211> LENGTH: 1407
<212> TYPE: DNA
<213> ORGANISM: swine influenza virus
```

<400> SEQUENCE: 37

```
atgaatccaa atcaaaagat aataacaatt ggctctgttt ctctcctcat tgccacaata      60
tgcttcctta tgcaaattgc catcctggta actactgtaa cattgcattt caagcagcat     120
gattgcaact cctccccaaa caaccaagta atgctgtgtg aaccaacaat aatagaaaga     180
aacacaacag agattgtgta tctgaccaac ataactatag agaaggaaat atgccccaaa     240
ctagcagaat acagaaattg gtcaaagcct caatgtaaca ttacaggatt tgcacctttc     300
tctaaggaca attcgattcg ctttccgct ggcggggaca tctgggtgac aagagaacct     360
tatgtgtcgt gcgatcctga caagtgttat caatttgccc ttgggcaggg aacaacacta     420
aacaacggtc attcaaatga cactgtacat gataggaccc cttaccgaac cctattgatg     480
aatgaattgg gtgttccatt tcatttgggg accaggcaag tgtgcatagc atggtccagc     540
tcaagttgtc acgatggaaa agcatggttg catgtttgta taactgggga tgataaaaat     600
gcaactgcta gcttcattta caatgggagg cttgtagata gtattggttc atggtccaaa     660
aatatactca gaacccagga gtcggaatgc gtttgtatca atggaacttg tacagtagta     720
atgactgatg gagcgcttc aggaaaagct gatactaaag tactattcat tgaggaggga     780
aaaatcgttc atattagcac attgtcagga agtgctcagc atgtcgagga gtgctcctgt     840
tatcctcgat atcctggtgt cagatgtgtc tgtagagaca actggaaagg ctccaacagg     900
cccatcgtag acataaatgt aaaggattat agtattgttt ccagttatgt atgctcagga     960
cttgttggag acacacccag aaaaaacgac agattcagca gtagccattg ccaagatcct    1020
aacaatgagg aaggaggtca tggggtgaaa ggctgggcct tgatgatgg aaatgacgtg     1080
tggatgggaa gaacgatcaa cgagaaatta cgctcaggtt atgaaacctt caaagtcatc    1140
gaaggctggt ccaaacctaa ctccaaatta cagacaaata ggcaagtcat agttgaaaga    1200
ggtaacaggt ccggttattc tggtatttc tccgttgaag gcaaaagctg catcaatcgg    1260
tgttttatg tggagttgat aagggaagg aaagaggaaa ctaaagtctg gtggacctca    1320
aacagtattg ttgtgctttg tggcacctca ggtacatatg aacaggctc atggcctgat    1380
ggggcggata tcaatctcat gcctata                                        1407
```

<210> SEQ ID NO 38
<211> LENGTH: 1407
<212> TYPE: DNA
<213> ORGANISM: Artificial Sequence
<220> FEATURE:
<223> OTHER INFORMATION: NA-DO (H3N2; de-optimized)

<400> SEQUENCE: 38
atgaatccaa atcaaaagat aataacaatt ggctctgttt ctctcctcat tgccacaata 60
tgcttcctta tgcaaattgc catcctggta actactgtaa cattgcattt caaacaacat 120
gattgtaatt cgtcgccgaa taatcaagtc atgttatgtg aaccgacgat aatagaacgt 180
aatacgacgg aaatagtcta tttaacgaat ataacgatag aaaaagaaat atgtccgaaa 240
ttagcggaat atcgtaattg gtcgaaaccg caatgtaata taacgggatt tgcgccgttt 300
tcgaaagata attcgatacg tttatcggcg ggaggagata tatgggtcac gcgtgaaccg 360
tatgtctcgt gtgatccgga taaatgttat caatttgcgt taggacaagg aacgacgtta 420
aataatggac attcgaatga tacggtccat gatcgtacgc cgtatcgcac gttattaatg 480
aatgaattag gagtcccgtt tcatttagga acgcgtcaag tctgtatagc gtggtcgtcg 540

```
tcgtcgtgtc atgatggaaa agcgtggtta catgtctgta taacgggaga tgataaaaat    600
gcgacggcgt cgtttatata taatggacgt ttagtcgatt cgataggatc gtggtcgaaa    660
aatatattac gtacgcaaga atcggaatgt gtctgtataa atggaacgtg tacggtcgtc    720
atgacggatg gatcggcgtc gggaaaagcg gatacgaaag tcttatttat agaagaagga    780
aaaatagtcc atatatcgac gttatcggga tcggcgcaac atgtcgaaga atgttcgtgt    840
tatccgcgtt atccgggagt ccgttgtgtc tgtcgtgata attggaaagg atcgaatcgt    900
ccgatagtcg atataaatgt caaagattat tcgatagtct cgtcgtatgt ctgttcggga    960
ttagtcggag atacgccgcg taaaaatgat cgttttcgt cgtcgcattg tcaagatccg    1020
aataatgaag aaggaggaca tggagtcaaa ggatgggcgt tgatgatgg aaatgatgtc    1080 tggatgggac gtacgataaa tgaaaaatta cgttcgggat atgaaacgtt taaagtcata    1140
gaaggatggt cgaaaccgaa ttcgaaatta caaacgaatc gtcaagtcat agtcgaacgt    1200
ggaaatcgtt cgggatattc gggaatattt tcggtcgaag gaaatcgtg tataaatcgt    1260 tgtttttatg tcgaattaat acgtggacgt aaagaagaaa ctaaagtctg gtggacctca    1320
aacagtattg ttgtgctttg tggcacctca ggtacatatg gaacaggctc atggcctgat    1380
ggggcggata tcaatctcat gcctata                                        1407
```

<210> SEQ ID NO 39
<211> LENGTH: 469
<212> TYPE: PRT
<213> ORGANISM: swine influenza virus

<400> SEQUENCE: 39

```
Met Asn Pro Asn Gln Lys Ile Ile Thr Ile Gly Ser Val Ser Leu Leu
1               5                   10                  15

Ile Ala Thr Ile Cys Phe Leu Met Gln Ile Ala Ile Leu Val Thr Thr
            20                  25                  30

Val Thr Leu His Phe Lys Gln His Asp Cys Asn Ser Pro Asn Asn
        35                  40                  45

Gln Val Met Leu Cys Glu Pro Thr Ile Ile Glu Arg Asn Thr Thr Glu
    50                  55                  60

Ile Val Tyr Leu Thr Asn Ile Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Ile Gly Ser Trp Ser Lys Asn Ile Leu Arg
    210                 215                 220
```

-continued

Thr Gln Glu Ser Glu Cys Val Cys Ile Asn Gly Thr Cys Thr Val Val
225 230 235 240

Met Thr Asp Gly Ser Ala Ser Gly Lys Ala Asp Thr Lys Val Leu Phe
245 250 255

Ile Glu Glu Gly Lys Ile Val His Ile Ser Thr Leu Ser Gly Ser Ala
260 265 270

Gln His Val Glu Glu Cys Ser Cys Tyr Pro Arg Tyr Pro Gly Val Arg
275 280 285

Cys Val Cys Arg Asp Asn Trp Lys Gly Ser Asn Arg Pro Ile Val Asp
290 295 300

Ile Asn Val Lys Asp Tyr Ser Ile Val Ser Ser Tyr Val Cys Ser Gly
305 310 315 320

Leu Val Gly Asp Thr Pro Arg Lys Asn Asp Arg Phe Ser Ser Ser His
325 330 335

Cys Gln Asp Pro Asn Asn Glu Glu Gly Gly His Gly Val Lys Gly Trp
340 345 350

Ala Phe Asp Asp Gly Asn Asp Val Trp Met Gly Arg Thr Ile Asn Glu
355 360 365

Lys Leu Arg Ser Gly Tyr Glu Thr Phe Lys Val Ile Glu Gly Trp Ser
370 375 380

Lys Pro Asn Ser Lys Leu Gln Thr Asn Arg Gln Val Ile Val Glu Arg
385 390 395 400

Gly Asn Arg Ser Gly Tyr Ser Gly Ile Phe Ser Val Glu Gly Lys Ser
405 410 415

Cys Ile Asn Arg Cys Phe Tyr Val Glu Leu Ile Arg Gly Arg Lys Glu
420 425 430

Glu Thr Lys Val Trp Trp Thr Ser Asn Ser Ile Val Val Leu Cys Gly
435 440 445

Thr Ser Gly Thr Tyr Gly Thr Gly Ser Trp Pro Asp Gly Ala Asp Ile
450 455 460

Asn Leu Met Pro Ile
465

<210> SEQ ID NO 40
<211> LENGTH: 363
<212> TYPE: DNA
<213> ORGANISM: swine influenza virus

<400> SEQUENCE: 40
atggactcca acactgtgtc aagctttcag gacatactga agaggatgtc aaaaatgcag 60
ttggggtcct catcggagga cttgaatgga atggtaacac ggttcgagtc cctgaaaatc 120
tacagagatt cgcttggaga aaccgtaatg aggatgggag accttcacta cctccagagc 180
agaaatgaaa aatggcgaga gcaattggga cagaaatttg aggaaattag gtggttaatt 240
gaagaagtgc ggcacagatt gaaagcgaca gagaatagtt tcgaacaaat aacatttatg 300
caagccttac aactactgct tgaagtagaa caagagataa gaactttctc gtttcagctt 360
att 363

<210> SEQ ID NO 41
<211> LENGTH: 121
<212> TYPE: PRT
<213> ORGANISM: swine influenza virus

<400> SEQUENCE: 41

```
Met Asp Ser Asn Thr Val Ser Ser Phe Gln Asp Ile Leu Lys Arg Met
1               5                   10                  15

Ser Lys Met Gln Leu Gly Ser Ser Glu Asp Leu Asn Gly Met Val
            20                  25                  30

Thr Arg Phe Glu Ser Leu Lys Ile Tyr Arg Asp Ser Leu Gly Glu Thr
            35                  40                  45

Val Met Arg Met Gly Asp Leu His Tyr Leu Gln Ser Arg Asn Glu Lys
50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Ala Thr Glu Asn Ser Phe Glu Gln
                85                  90                  95

Ile Thr Phe Met Gln Ala Leu Gln Leu Leu Leu Glu Val Glu Gln Glu
                100                 105                 110

Ile Arg Thr Phe Ser Phe Gln Leu Ile
                115                 120

<210> SEQ ID NO 42
<211> LENGTH: 657
<212> TYPE: DNA
<213> ORGANISM: swine influenza virus

<400> SEQUENCE: 42
atggactcca acactgtgtc aagctttcag gtagactgtt tcctttggca tatccgcaaa      60
cggtttgcag acaatggatt gggtgatgcc ccattccttg atcggctccg ccgagatcaa     120
aagtccctaa aaggaagagg caacacccct ggcctcgaca tcgaaacagc cactcttgtt     180
gggaaacaaa ttgtggagtg gattttgaaa gaggaatcca gcgagacact aagatgacc     240 attgcatctg tacctacttc gcgctactta gctgacatga ccctcgagga atgtcacga     300 gactggttca tgctcatgcc taggcaaaag ataataggct ctcttttgtgt gcgaatggac     360 caggcgatca tggaaaagaa catcatactg aaagcgaact tcagtgtgat cttcaaccga     420
ttagagactt tgatactact aagggctttc actgaggagg gagcaatcgt tggagaaatt     480
tcaccattac cttctcttcc aggacatact gaagaggatg tcaaaaatgc agttggggtc     540
ctcatcggag gacttgaatg gaatggtaac acggttcgag tccctgaaaa tctacagaga     600
ttcgcttgga gaaaccgtaa tgaggatggg agaccttcac tacctccaga gcagaaa       657

<210> SEQ ID NO 43
<211> LENGTH: 219
<212> TYPE: PRT
<213> ORGANISM: swine influenza virus

<400> SEQUENCE: 43

Met Asp Ser Asn Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
            35                  40                  45

Thr Leu Gly Leu Asp Ile Glu Thr Ala Thr Leu Val Gly Lys Gln Ile
            50                  55                  60

Val Glu Trp Ile Leu Lys Glu Glu Ser Ser Glu Thr Leu Lys Met Thr
65                  70                  75                  80

Ile Ala Ser Val Pro Thr Ser Arg Tyr Leu Ala Asp Met Thr Leu Glu
                85                  90                  95
```

Glu Met Ser Arg Asp Trp Phe Met Leu Met Pro Arg Gln Lys Ile Ile
            100                 105                 110

Gly Ser Leu Cys Val Arg Met Asp Gln Ala Ile Met Glu Lys Asn Ile
            115                 120                 125

Ile Leu Lys Ala Asn Phe Ser Val Ile Phe Asn Arg Leu Glu Thr Leu
            130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Val Gly Val Leu Ile Gly Gly Leu Glu Trp Asn Gly Asn Thr Val
            180                 185                 190

Arg Val Pro Glu Asn Leu Gln Arg Phe Ala Trp Arg Asn Arg Asn Glu
            195                 200                 205

Asp Gly Arg Pro Ser Leu Pro Pro Glu Gln Lys
            210                 215

<210> SEQ ID NO 44
<211> LENGTH: 756
<212> TYPE: DNA
<213> ORGANISM: swine influenza virus

<400> SEQUENCE: 44
atgagtcttc taaccgaggt cgaaacgtat gttctctcta tcgttccgtc aggccccctc      60
aaagccgaga tagcacagag actcgaagac gtttttgcag ggaaaaacac cgatcttgag     120
gctctcatgg aatggctaaa gacaagacca atcctgtcac ctctgactaa ggggatttta     180
gggtttgtgt tcacgctcac cgtgcccagt gagcgaggac tgcagcgtag acgctttgtc     240
cagaatgccc tcaatgggaa tggtgacccg aacaacatgg acaaagcagt caaactgtac     300
aggaaactca aagggaaat aacattccat ggggccaaag aagtagcgct cagttactct     360
gctggtgcgc ttgccagttg catgggtctc atatacaaca gaatggggac tgtcaccact     420
gaggtggcct ttggtctagt atgcgcaacc tgtgaacaga ttgctgattc ccagcatcga     480
tctcatagac aaatggtgac aacaaccaat ccactaatca ggcacgagaa cagaatggtg     540
atagccagca aacagctaa agccatggaa caaatggctg gatcaagcga caagcagca     600 gaggctatgg aggttgccag ccaggctaga caaatggtac aggcaatgag aacaattggg     660
actcacccta gttccagcgc tggtctaaaa gatgatcttc ttgaaaattt acaggcctat     720
cagaaacgga tgggagtgca aatgcaacga ttcaag                                756

<210> SEQ ID NO 45
<211> LENGTH: 252
<212> TYPE: PRT
<213> ORGANISM: swine influenza virus

<400> SEQUENCE: 45

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
        50                  55                  60

```
Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Lys Ala
                 85                  90                  95

Val Lys Leu Tyr Arg Lys Leu Lys Arg Glu Ile Thr Phe His Gly Ala
            100                 105                 110

Lys Glu Val Ala Leu Ser Tyr Ser Ala Gly Ala Leu Ala Ser Cys Met
        115                 120                 125

Gly Leu Ile Tyr Asn Arg Met Gly Thr Val Thr Thr Glu Val Ala Phe
130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Ile Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Thr Ile Gly Thr His Pro Ser
210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

<210> SEQ ID NO 46
<211> LENGTH: 1407
<212> TYPE: DNA
<213> ORGANISM: swine influenza virus

<400> SEQUENCE: 46

```
atgaatccaa atcaaaagat aataacgatt ggctctgtct ctctcactat tgccacaatg     60
tgcctcctta tgcaaattgc catcctggta actactgtaa cattgcattt caagcaatat    120
gaatgcaact ccccccccaaa caaccaagta atactgtgtg aaccaacaat aatagaaaga    180
aacataacag agatagtgta tctgaccaac accaccatag agaaggaaat gtgccccaag    240
ctagcagaat acagaagttg gtcaaagccg caatgtaaaa ttacaggatt tgcacctttt    300
tccaaggaca attcgattag ctttccgct ggtggggaca tttgggtgac aagagaacct    360
tatgtgtcat gcgatcctga caagtgttac caatttgccc ttggacaggg aacaacacta    420
aacaacaggc attcaaatga cacagtacat gataggaccc cttatcgaac cctattgatg    480
aatgagttgg gtgttccatt tcatttggga accaagcaag tgtgcatagc atggtccagc    540
tcaagttgtc atgatggaaa agcatggctg catgtttgtg taactgggca tgatgaaaat    600
gcaactgcta gcttcattta cgatgggagg ctggtagata tattggttc atggaccaaa    660
aaaatcctca ggacccatga gtcggaatgc gtttgtatca atggaacttg tacagtagta    720
atgactgatg gagtgcttc aggaagagct gatactaaaa tattattcat tgaggagggg    780
aaaatcgttc atattagccc attgttggga agtgctcagc atgttgagga gtgctcctgt    840
tatcctcgat atcctggtgt cagatgtgtc tgcagagaca actggaaagg ctccaatagg    900
cccgtcgtag atataaatgt aaaggattat agcattgttt ccagttatgt gtgctcagga    960
cttgttggag acacacccag aaaaaacgac agatccagca gtagcagttg cctgaatcct   1020
accaatgagg aaggggggtca tggagtgaaa ggctgggcct ttgatgatgg aaatgacgtg   1080
```

-continued

```
tggatgggaa gaacgatcag cgagaaatta cgctcaggtt atgaaacctt caaagtcatt    1140
gaaggctggt ccaaacccaa ctccaaattg cagataaata ggcaagtcat agttgacaga    1200
ggtgataggt ccggttattc tggcattttc tctgttgaag caaaagctg catcaatcgg     1260 tgcttttatg tggagttgat aaggggaagg aaacaggaaa ctgaagtatg gtggacctca    1320
aacagtattg ttgtgttttg tggcacctca ggtacatatg aacaggctc atggcctgat     1380 ggggcggaca tcaatctcat gcctata                                         1407
```

<210> SEQ ID NO 47
<211> LENGTH: 469
<212> TYPE: PRT
<213> ORGANISM: swine influenza virus

<400> SEQUENCE: 47

```
Met Asn Pro Asn Gln Lys Ile Ile Thr Ile Gly Ser Val Ser Leu Thr
1               5                   10                  15

Ile Ala Thr Met Cys Leu Leu Met Gln Ile Ala Ile Leu Val Thr Thr
            20                  25                  30

Val Thr Leu His Phe Lys Gln Tyr Glu Cys Asn Ser Pro Pro Asn Asn
        35                  40                  45

Gln Val Ile Leu Cys Glu Pro Thr Ile Ile Glu Arg Asn Ile Thr Glu
    50                  55                  60

Ile Val Tyr Leu Thr Asn Thr Thr Ile Glu Lys Glu Met Cys Pro Lys
65                  70                  75                  80

Leu Ala Glu Tyr Arg Ser Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Val Thr Gly His Asp Glu Asn Ala Thr Ala Ser Phe Ile Tyr Asp
        195                 200                 205

Gly Arg Leu Val Asp Ser Ile Gly Ser Trp Thr Lys Lys Ile Leu Arg
    210                 215                 220

Thr His Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Leu Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Val Val Asp
    290                 295                 300

Ile Asn Val Lys Asp Tyr Ser Ile Val Ser Ser Tyr Val Cys Ser Gly
```

```
                305                 310                 315                 320
Leu Val Gly Asp Thr Pro Arg Lys Asn Asp Arg Ser Ser Ser Ser
                325                 330                 335

Cys Leu Asn Pro Thr Asn Glu Glu Gly Gly His Gly Val Lys Gly Trp
                340                 345                 350

Ala Phe Asp Asp Gly Asn Asp Val Trp Met Gly Arg Thr Ile Ser Glu
                355                 360                 365

Lys Leu Arg Ser Gly Tyr Glu Thr Phe Lys Val Ile Glu Gly Trp Ser
            370                 375                 380

Lys Pro Asn Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
                420                 425                 430

Glu Thr Glu Val Trp Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
            450                 455                 460

Asn Leu Met Pro Ile
465

<210> SEQ ID NO 48
<211> LENGTH: 1512
<212> TYPE: DNA
<213> ORGANISM: swine influenza virus

<400> SEQUENCE: 48
atgagtgaca tcgaagccat ggcgtctcaa ggcaccaaac gatcatatga acagatggag      60
actggtgggg aacgccagga tgccacagaa atcagagcat ctgtcggaag aatgattggt     120
ggaatcggga gattctacat ccaaatgtgc actgaactca aactcagtga ctatgaggga     180
cgactaatcc aaaatagcat aacaatagag agaatggtgc tctctgcttt tgatgagaga     240
agaaataagt acctagaaga gcatcccagt gctgggaagg atcctaagaa actggaggga     300
cccatatata agagagtaga cggaaagtgg atgagagaac tcatcccttt agacaaagaa     360
gaaataagga gagtttggcg ccaagcaaac aatggtgaag atgcaacagc tggtctttact     420 catatcatga tttggcattc aatctgaat gatgccacgt atcagagaac aagagcactt     480
gttcgcaccg gaatggatcc agaatgtgc tctctgatgc aaggttcaac acttcccaga     540
aggtctgggg ccgcaggtgc tgcagtgaaa ggagttggaa caatagcaat ggagttaatc     600
agaatgatca acgtggaat caatgaccga aacttctgga ggggtgaaaa tggacgaagg     660
acaaggactg catatgaaag gatgtgcaat attctcaaag gaaaatttca gacagctgcc     720
cagagagcaa tgatggatca agtgagagaa agtcggaacc caggaaacgc tgagattgaa     780
gatctcattt tcctggcacg gtcagcactt attctaaggg gatcagttgc acataagtct     840
tgcctgcctg cttgtgtgta tgggcttgca gtagcaagtg ggcatgactt tgaagggaa     900 gggtattcac tggttgggat agacccattt aaattacttc aaacagtca agtgttcagc     960 ctgataagac caaatgaaaa cccagctcac aagagtcaat tggtgtggat ggcatgccac    1020
tctgctgcat ttgaggattt gagagtatca gtttcataa gggggaagaa ggtgattcca    1080
agaggaaagc tttccacaag aggggttcag attgcttcaa atgaaaatgt ggaagccatg    1140
gactccaata ccctagaact gagaagcaga tactgggcca taggaccag gagtgggaa    1200
```
aataccaatc aacagaaggc atccgcgggc cagatcagtg tgcaacctac attctcagta 1260
caacggaacc tccctttga aagagcaacc gttttggcag ctttcagcgg gaacaatgaa 1320
ggacggacat ccgatatgcg aacagaagtt ataaggatga tggaaagtgc aaagccagaa 1380
gatttgtcct tccaggggcg gggagtcttc gagctctcgg acgaaaaggc aacgagcccg 1440
atcgtgcctt cctttgacat gagtaatgaa gggtcttatt tcttcggaga caatgcagag 1500
gagtatgaca gt 1512

<210> SEQ ID NO 49
<211> LENGTH: 498
<212> TYPE: PRT
<213> ORGANISM: swine influenza virus

<400> SEQUENCE: 49

Met Ala Ser Gln Gly Thr Lys Arg Ser Tyr Glu Gln Met Glu Thr Gly
1 5 10 15

Gly Glu Arg Gln Asp Ala Thr Glu Ile Arg Ala Ser Val Gly Arg Met
20 25 30

Ile Gly Gly Ile Gly Arg Phe Tyr Ile Gln Met Cys Thr Glu Leu Lys
35 40 45

Leu Ser Asp Tyr Glu Gly Arg Leu Ile Gln Asn Ser Ile Thr Ile Glu
50 55 60

Arg Met Val Leu Ser Ala Phe Asp Glu Arg Arg Asn Lys Tyr Leu Glu
65 70 75 80

Glu His Pro Ser Ala Gly Lys Asp Pro Lys Lys Thr Gly Gly Pro Ile
85 90 95

Tyr Arg Arg Val Asp Gly Lys Trp Met Arg Glu Leu Ile Leu Tyr Asp
100 105 110

Lys Glu Glu Ile Arg Arg Val Trp Arg Gln Ala Asn Asn Gly Glu Asp
115 120 125

Ala Thr Ala Gly Leu Thr His Ile Met Ile Trp His Ser Asn Leu Asn
130 135 140

Asp Ala Thr Tyr Gln Arg Thr Arg Ala Leu Val Arg Thr Gly Met Asp
145 150 155 160

Pro Arg Met Cys Ser Leu Met Gln Gly Ser Thr Leu Pro Arg Arg Ser
165 170 175

Gly Ala Ala Gly Ala Ala Val Lys Gly Val Gly Thr Ile Ala Met Glu
180 185 190

Leu Ile Arg Met Ile Lys Arg Gly Ile Asn Asp Arg Asn Phe Trp Arg
195 200 205

Gly Glu Asn Gly Arg Arg Thr Arg Thr Ala Tyr Glu Arg Met Cys Asn
210 215 220

Ile Leu Lys Gly Lys Phe Gln Thr Ala Ala Gln Arg Ala Met Met Asp
225 230 235 240

Gln Val Arg Glu Ser Arg Asn Pro Gly Asn Ala Glu Ile Glu Asp Leu
245 250 255

Ile Phe Leu Ala Arg Ser Ala Leu Ile Leu Arg Gly Ser Val Ala His
260 265 270

Lys Ser Cys Leu Pro Ala Cys Val Tyr Gly Leu Ala Val Ala Ser Gly
275 280 285

His Asp Phe Glu Arg Glu Gly Tyr Ser Leu Val Gly Ile Asp Pro Phe
290 295 300

Lys Leu Leu Gln Asn Ser Gln Val Phe Ser Leu Ile Arg Pro Asn Glu 305 310 315 320

Asn Pro Ala His Lys Ser Gln Leu Val Trp Met Ala Cys His Ser Ala
325 330 335

Ala Phe Glu Asp Leu Arg Val Ser Ser Phe Ile Arg Gly Lys Lys Val
340 345 350

Ile Pro Arg Gly Lys Leu Ser Thr Arg Gly Val Gln Ile Ala Ser Asn
355 360 365

Glu Asn Val Glu Ala Met Asp Ser Asn Thr Leu Glu Leu Arg Ser Arg
370 375 380

Tyr Trp Ala Ile Arg Thr Arg Ser Gly Gly Asn Thr Asn Gln Gln Lys
385 390 395 400

Ala Ser Ala Gly Gln Ile Ser Val Gln Pro Thr Phe Ser Val Gln Arg
405 410 415

Asn Leu Pro Phe Glu Arg Ala Thr Val Leu Ala Ala Phe Ser Gly Asn
420 425 430

Asn Glu Gly Arg Thr Ser Asp Met Arg Thr Glu Val Ile Arg Met Met
435 440 445

Glu Ser Ala Lys Pro Glu Asp Leu Ser Phe Gln Gly Arg Gly Val Phe
450 455 460

Glu Leu Ser Asp Glu Lys Ala Thr Ser Pro Ile Val Pro Ser Phe Asp
465 470 475 480

Met Ser Asn Glu Gly Ser Tyr Phe Phe Gly Asp Asn Ala Glu Glu Tyr
485 490 495

Asp Ser

<210> SEQ ID NO 50
<211> LENGTH: 1695
<212> TYPE: DNA
<213> ORGANISM: swine influenza virus

<400> SEQUENCE: 50
atgaaggcaa tactagtagt cttgctatat acatttacaa ccgcaaaagc agacacatta 60
tgtataggtt accatgcaaa caattcaact gacactgtag acacagtact agaaaagaat 120
gtaacagtaa cacactctgt taaccttcta gaagacaggc ataacgggaa actatgtaaa 180
ctaagagggg tagccccatt gcatttgggt aaatgtaaca ttgctggatg gctcctggga 240
aatccagagt gtgaatcact cttcacagca agctcatggt cttacattgt ggaaacacct 300
aattcagaca atgggacgtg ttacccagga gatttcatca attatgaaga gctaagagag 360
cagttgagct cagtctcatc atttgaaaga tttgagatat tccccaagac aagttggccc 420
aatcatgaca cgaacagagg tgtgacggca gcatgtcctc atgctggagc aaatagcttc 480
tacagaaatt taatatggct ggttgaaaaa gaaaattcat acccaaagct cagcaaatcc 540
tatatcaaca ataaggagat ggaagtcctc gtgctatggg gcattcacca cccatctacc 600
agtgccgacc aacgaagtct ctaccagaat gcagatgcct atgtttttgt ggggtcatca 660
agatacagca agaagttcaa gccagaaata gcaataagac ccaaggtgag ggatcaagca 720
gggagaatga actattactg gacactagta gagcctggag ataaaataac attcgaagca 780
actggaaatc tagtggtacc gagatatgcc ttcgcaatga aaagaggttc aggatctggt 840
attatcattt cagatacatc agttcacgat tgtaacacga cttgtcagac acccaagggt 900
gctataaaca ccagcctccc atttcagaat gtacatccag tcacgattgg agaatgtcca 960
aaatatgtca aaagcacaaa attgagaatg gccacaggat taaggaatat cccgtctatt 1020

```
caatctagag gcctgtttgg tgccattgcc ggctttattg agggggggatg gacaggaatg    1080 atagatggat ggtacggtta tcaccatcaa aatgagcagg gatcaggata tgcagctgac    1140
ctaaagagca cacagaatgc cattgacggg atcactaaca aagtaaattc tgttattgaa    1200
aagatgaaca cacaattcac agcagtgggt aaagagttca accacctgga aaaagaata    1260 gagaatttaa ataaaaaggt tgatgatggt tttctggatg tttggactta caatgctgag    1320
ctattggttc tgttggaaaa tgaaagaact ttggattacc acgattcaaa tgtgaagaac    1380
ttatatgaaa aagtaagaag ccagctaaaa aacaatgcca aggaaattgg aaatggctgc    1440
tttgaatttt accacaaatg tgatgacaca tgcatggaaa gcgtcaaaaa tgggacttat    1500
gattacccaa aatactcaga ggaagcaaaa ctaaacagag aggaaataga cggggtaaaa    1560
ctggaatcaa caaggattta ccagattttg gcgatctatt caactgtcgc cagttcattg    1620
gtactggtag tctccctggg ggcaatcagt ttctggatgt gctctaatgg gtctttacag    1680
tgcagaatat gtatt                                                     1695

<210> SEQ ID NO 51
<211> LENGTH: 565
<212> TYPE: PRT
<213> ORGANISM: swine influenza virus

<400> SEQUENCE: 51

Met Lys Ala Ile Leu Val Val Leu Leu Tyr Thr Phe Thr Thr Ala Lys
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Arg His Asn Gly Lys Leu Cys Lys Leu Arg Gly Val
    50                  55                  60

Ala Pro Leu His Leu Gly Lys Cys Asn Ile Ala Gly Trp Leu Leu Gly
65                  70                  75                  80

Asn Pro Glu Cys Glu Ser Leu Phe Thr Ala Ser Ser Trp Ser Tyr Ile
                85                  90                  95

Val Glu Thr Pro Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Trp Pro Asn His Asp Thr
    130                 135                 140

Asn Arg Gly Val Thr Ala Ala Cys Pro His Ala Gly Ala Asn Ser Phe
145                 150                 155                 160

Tyr Arg Asn Leu Ile Trp Leu Val Glu Lys Asn Ser Tyr Pro Lys
                165                 170                 175

Leu Ser Lys Ser Tyr Ile Asn Asn Lys Glu Met Glu Val Leu Val Leu
            180                 185                 190

Trp Gly Ile His His Pro Ser Thr Ser Ala Asp Gln Arg Ser Leu Tyr
        195                 200                 205

Gln Asn Ala Asp Ala Tyr Val Phe Val Gly Ser Ser Arg Tyr Ser Lys
    210                 215                 220

Lys Phe Lys Pro Glu Ile Ala Ile Arg Pro Lys Val Arg Asp Gln Ala
225                 230                 235                 240

Gly Arg Met Asn Tyr Tyr Trp Thr Leu Val Glu Pro Gly Asp Lys Ile
                245                 250                 255
```

```
Thr Phe Glu Ala Thr Gly Asn Leu Val Val Pro Arg Tyr Ala Phe Ala
            260                 265                 270

Met Lys Arg Gly Ser Gly Ser Gly Ile Ile Ile Ser Asp Thr Ser Val
        275                 280                 285

His Asp Cys Asn Thr Thr Cys Gln Thr Pro Lys Gly Ala Ile Asn Thr
    290                 295                 300

Ser Leu Pro Phe Gln Asn Val His Pro Val Thr Ile Gly Glu Cys Pro
305                 310                 315                 320

Lys Tyr Val Lys Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Val Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asp Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 52
<211> LENGTH: 2148
<212> TYPE: DNA
<213> ORGANISM: swine influenza virus

<400> SEQUENCE: 52
atggaagact ttgtgcgaca atgcttcaat ccaatgatcg tcgagcttgc ggaaaaggca    60
atgaaagaat atgagaaga tccgaaaatc gaaaccaaca aattcgctgc aatatgcaca   120
cacttggaag tctgtttcat gtattcagat ttccatttca tcgacgaacg gggtgaatca   180
ataattgtag aatctggtga tccaaatgca ttactgaagc accgatttga gataattgaa   240
ggaagagacc gaaccatggc ctggacagtg gtgaatagta tctgcaacac cacaggggta   300
```

```
gagaagccta aatttcttcc ggatttgtat gattacaaag agaaccgatt cattgaaatt      360
ggagtgacac ggagggaggt ccacatatac tacctagaga aagccaacaa aataaaatcc      420
gagaagacac acattcacat tttttcattc actggagagg agatggccac cagagcggac      480
tacacccttg atgaagagag cagggcaaga atcaaaacca ggcttttcac cataagacaa      540
gaaatggcca gtagggtct atgggattcc tttcgtcaat ccgagagagg cgaagagaca       600
attgaagaaa gatttgaaat tacaggaacc atgcgcaggc ttgccgacca aagtctccca      660
ccgaacttct ccagccttga aaactttaga gcctatgtag atggattcga accgaacggc      720
tgcattgagg gcaagctttc tcaaatgtca aagaagtga cgccaaaat tgaaccattc        780 ttgaagacga caccacgccc cctcagattg cctggtgggc ctccttgctc tcagcggtca      840
aagttcctgc tgatggatgc tctgaaacta agtattgaag acccgagtca tgagggggaa      900
gggataccac tatatgatgc aatcaaatgc atgaagacat ttttggctg gaaagagcct      960 aacataatca aaccacatga aaaggcataa acccccaatt acctcctggc ttggaagcag     1020
gtgctagcag agctgcagga cattgaaaat gaagagaaga tcccaaaaac aaagaacatg     1080
aagagaacga gccaattgaa gtgggcactc ggtgagaata tggcaccaga gaaagtagac     1140
tttgatgagt gcaaagatgt tggtgatctt aaacagtatg acagcgatga gccagagccc     1200
agatctctag caagctgggt ccaaaatgaa ttcaataagg catgtgaatt gaccgattca     1260
agctggatag aacttgatga gataggagaa gatgttgccc cgattgaaca catcgcaagc     1320
atgaggagga actattttac agcagaagtg tcccattgca gggctactga atacataatg     1380
aagggagtgt acataaatac ggctttgctc aatgcatctt gcgcagccat ggatgacttc     1440
cagctgatcc caatgataag caaatgtagg accaaagaag gaagacggaa acaaatctg     1500 tatgggttca ttataaaagg aagtctcat ttgagaaatg atactgacgt ggtgaacttt     1560
gtaagcatgg agttctccct cactgacccg aaactggagc cacacaaatg gaaaagtac     1620 tgtgttcttg aaataggaga tatgctcctg aggactgcga taggccaagt gtcgaggccc     1680
atgttcctat atgtgagaac caatggaacc tctaagatca agatgaaatg gggcatggaa     1740
atgaggcgct gccttcttca gtctcttcag cagattgaga gcatgattga agcagagtct     1800
tctgtcaaag agaaagacat gaccaaggaa ttctttgaaa ccaaatcgga aacatggcca     1860
atcggagaat cacccaaagg agtggaggaa ggctctattg ggaaagtgtg caggaccta     1920 ctggcaaaat ctgtattcaa tagtctatac gcgtctccac aacttgaggg gttttcggct     1980
gaatcgagaa aattgcttct cattgtccag gcacttaggg acaacctgga acctggaacc     2040
ttcgatcttg gggggctata tgaagcaatc gaggagtgcc tgattaatga tccctgggtt     2100
ttgcttaatg catcttggtt caactccttc ctcacacatg cactgaaa               2148
```

<210> SEQ ID NO 53
<211> LENGTH: 716
<212> TYPE: PRT
<213> ORGANISM: swine influenza virus

<400> SEQUENCE: 53

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45
```

```
Ser Asp Phe His Phe Ile Asp Glu Arg Gly Glu Ser Ile Ile Val Glu
 50                  55                  60
Ser Gly Asp Pro Asn Ala Leu Leu Lys His Arg Phe Glu Ile Ile Glu
 65                  70                  75                  80
Gly Arg Asp Arg Thr Met Ala Trp Thr Val Val Asn Ser Ile Cys Asn
                 85                  90                  95
Thr Thr Gly Val Glu Lys Pro Lys Phe Leu Pro Asp Leu Tyr Asp Tyr
             100                 105                 110
Lys Glu Asn Arg Phe Ile Glu Ile Gly Val Thr Arg Glu Val His
             115                 120                 125
Ile Tyr Tyr Leu Glu Lys Ala Asn Lys Ile Lys Ser Glu Lys Thr His
130                 135                 140
Ile His Ile Phe Ser Phe Thr Gly Glu Glu Met Ala Thr Arg Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Ser Arg Gly Leu Trp Asp Ser Phe Arg
            180                 185                 190
Gln Ser Glu Arg Gly Glu Glu Thr Ile Glu Glu Arg Phe Glu Ile Thr
        195                 200                 205
Gly Thr Met Arg Arg Leu Ala Asp Gln Ser Leu Pro Pro Asn Phe Ser
210                 215                 220
Ser Leu Glu Asn Phe Arg Ala Tyr Val Asp Gly Phe Glu Pro Asn Gly
225                 230                 235                 240
Cys Ile Glu Gly Lys Leu Ser Gln Met Ser Lys Glu Val Ser Ala Lys
                245                 250                 255
Ile Glu Pro Phe Leu Lys Thr Thr Pro Arg Pro Leu Arg Leu Pro Gly
            260                 265                 270
Gly Pro Pro Cys Ser Gln Arg Ser Lys Phe Leu Leu Met Asp Ala Leu
        275                 280                 285
Lys Leu Ser Ile Glu Asp Pro Ser His Glu Gly Glu Gly Ile Pro Leu
290                 295                 300
Tyr Asp Ala Ile Lys Cys Met Lys Thr Phe Phe Gly Trp Lys Glu Pro
305                 310                 315                 320
Asn Ile Ile Lys Pro His Glu Lys Gly Ile Asn Pro Asn Tyr Leu Leu
                325                 330                 335
Ala Trp Lys Gln Val Leu Ala Glu Leu Gln Asp Ile Glu Asn Glu Glu
            340                 345                 350
Lys Ile Pro Lys Thr Lys Asn Met Lys Arg Thr Ser Gln Leu Lys Trp
        355                 360                 365
Ala Leu Gly Glu Asn Met Ala Pro Glu Lys Val Asp Phe Asp Glu Cys
370                 375                 380
Lys Asp Val Gly Asp Leu Lys Gln Tyr Asp Ser Asp Glu Pro Glu Pro
385                 390                 395                 400
Arg Ser Leu Ala Ser Trp Val Gln Asn Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu His Ile Ala Ser Met Arg Arg Asn Tyr Phe Thr Ala
        435                 440                 445
Glu Val Ser His Cys Arg Ala Thr Glu Tyr Ile Met Lys Gly Val Tyr
450                 455                 460
Ile Asn Thr Ala Leu Leu Asn Ala Ser Cys Ala Ala Met Asp Asp Phe
```

```
                465                 470                 475                 480
            Gln Leu Ile Pro Met Ile Ser Lys Cys Arg Thr Lys Glu Gly Arg Arg
                            485                 490                 495

Lys Thr Asn Leu Tyr Gly Phe Ile Ile Lys Gly Arg Ser His Leu Arg
                        500                 505                 510

Asn Asp Thr Asp Val Val Asn Phe Val Ser Met Glu Phe Ser Leu Thr
                        515                 520                 525

Asp Pro Lys Leu Glu Pro His Lys Trp Glu Lys Tyr Cys Val Leu Glu
                    530                 535                 540

Ile Gly Asp Met Leu Leu Arg Thr Ala Ile Gly Gln Val Ser Arg Pro
            545                 550                 555                 560

Met Phe Leu Tyr Val Arg Thr Asn Gly Thr Ser Lys Ile Lys Met Lys
                            565                 570                 575

Trp Gly Met Glu Met Arg Arg Cys Leu Leu Gln Ser Leu Gln Gln Ile
                        580                 585                 590

Glu Ser Met Ile Glu Ala Glu Ser Ser Val Lys Glu Lys Asp Met Thr
                        595                 600                 605

Lys Glu Phe Phe Glu Thr Lys Ser Glu Thr Trp Pro Ile Gly Glu Ser
                    610                 615                 620

Pro Lys Gly Val Glu Glu Gly Ser Ile Gly Lys Val Cys Arg Thr Leu
            625                 630                 635                 640

Leu Ala Lys Ser Val Phe Asn Ser Leu Tyr Ala Ser Pro Gln Leu Glu
                            645                 650                 655

Gly Phe Ser Ala Glu Ser Arg Lys Leu Leu Leu Ile Val Gln Ala Leu
                        660                 665                 670

Arg Asp Asn Leu Glu Pro Gly Thr Phe Asp Leu Gly Gly Leu Tyr Glu
                        675                 680                 685

Ala Ile Glu Glu Cys Leu Ile Asn Asp Pro Trp Val Leu Leu Asn Ala
                    690                 695                 700

Ser Trp Phe Asn Ser Phe Leu Thr His Ala Leu Lys
            705                 710                 715

<210> SEQ ID NO 54
<211> LENGTH: 2271
<212> TYPE: DNA
<213> ORGANISM: swine influenza virus

<400> SEQUENCE: 54
atggatgtca atccgactct acttttccta agggttccag cgcaaaatgc cataagcacc      60
acattccctt atactggaga tcctccatac agccatggaa caggaacagg atacaccatg     120
gacacagtca acagaacaca ccaatattca gagaagggaa gtggacgaca aaacacagag     180 acagggcac cccagctcaa cccgattgat ggaccactac ctgaggataa tgaaccaagt     240
ggatatgcac aaacagactg tgttctggag gccatggctt tccttgaaga tcccacccca     300
gggatatttg agaattcatg ccttgagaca tggaagttg ttcaacaaac aagggtggat     360
aaactaactc aaggtcgcca gacttatgat tggacattaa acagaaatca accggcagca     420
actgcattgg caaacaccat agaagttttt agatcaaatg gtctaacagc taatgagtca     480
ggaaggctaa tagatttcct aaaggatgta atggaatcaa tggataaaga ggaaatagag     540
ataacaacac actttcaaag aaaaaggaga gtaagagaca acatgaccaa gaagatggtc     600
acacaaagaa caataggaaa gaaaaaacaa agaatgaata gagaggtta tctaataaga     660 gcactaacat tgaatacgat gaccaaagat gcagagagag caaattaaa aagaagggct     720
```

```
atcgcaacac ctgggatgca aattagaggg ttcgtgtact ttgttgaaac tttagctaga    780
agcatttgcg aaaagctgga acagtctgga ctcccagtag ggggcaatga aaagaaggcc    840
aaattggcaa atgttgtgag aaagatgatg actaattcac aagacacaga gctttctttc    900
acaatcactg gggacaacac taagtggaat gaaaatcaaa atcctcgaat gttcctggcg    960
atgattacat atatcaccag aaatcaaccc gaatggttca gaaacatcct gagcatggca   1020
cccataatgt tctcaaacaa aatggcaagg ctaggaaaag ggtacatgtt cgagagtaaa   1080
agaatgaagc tccgaacaca ataccatca gaaatgctag caagcattga cctgaagtat    1140
ttcaatgaat caacaaggaa gaaaattgag aaaataaggc ctcttctaat agatggcaca   1200
gcatcattga gccctggaat gatgatgggc atgttcaaca tgctaagtac ggttttggga   1260
gtctcaatac tgaatcttgg acaaaagaaa tacaccaaga caacgtactg gtgggatggg   1320
cttcaatcct ccgacgattt tgtcctcata gtgaatgcat caaatcatga gggaatacaa   1380
gcaggagtgg atagattcta caggacctgc aagttagtgg aatcaacat gagcaaaaag    1440 aagtcctata taaataagac agggacattt gaattcacaa gctttttta tcgctatgga    1500 tttgtggcta attttagcat ggagctgccc agttttggag tgtctggaat aaatgaatca   1560
gctgatatga gtattggagt aacaatgata agaacaaca tgataaacaa tgaccttgga    1620
cctgcaacag cccagatggc ccttcaattg ttcatcaaag actacagata cacatatagg   1680
tgccatagag agacacaca aattcagacg agaagatcat tcgagctaaa gaagctgtgg    1740
gatcaaaccc aatcaaggc aggactatta gtatctgatg gaggaccaaa cttatacaat    1800
atccggaatc ttcacattcc tgaagtctgc ttaaaatggg agctaatgga tgagggttat   1860
cggggaagac tttgtaatcc cctgaatcct tttgtcagcc ataaagagat tgattctgta   1920
aacaatgctg tggtgatgcc agcccatggt ccagccaaaa gcatggaata tgatgccgtt   1980
gcaactacac actcctggat tcccaagagg aaccgctcta ttctcaacac aagccaaagg   2040
ggaattcttg aggatgaaca gatgtaccag aagtgctgca acctgttcga gaaattttc    2100 cctagtagtt catacaggag accggttgga atttctagca tggtggaggc catggtgtct   2160
agagcccgga ttgatgccag aattgacttc gagtctggac ggattaagaa agaagagttc   2220
tctgagatca tgaagatctg ttccaccatt gaagaactca gacggcaaaa a            2271
```

<210> SEQ ID NO 55
<211> LENGTH: 757
<212> TYPE: PRT
<213> ORGANISM: swine influenza virus

<400> SEQUENCE: 55

```
Met Asp Val Asn Pro Thr Leu Leu Phe Leu Arg Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Lys Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
```

```
              100                 105                 110
Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
            130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
                180                 185                 190

Asp Asn Met Thr Lys Lys Met Val Thr Gln Arg Thr Ile Gly Lys Lys
            195                 200                 205

Lys Gln Arg Met Asn Lys Arg Gly Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
                340                 345                 350

Lys Gly Tyr Met Phe Glu Ser Lys Arg Met Lys Leu Arg Thr Gln Ile
            355                 360                 365

Pro Ser Glu Met Leu Ala Ser Ile Asp Leu Lys Tyr Phe Asn Glu Ser
            370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Val
            435                 440                 445

Leu Ile Val Asn Ala Ser Asn His Glu Gly Ile Gln Ala Gly Val Asp
            450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525
```

```
Met Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Gly Tyr Arg Gly Arg Leu
    610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755

<210> SEQ ID NO 56
<211> LENGTH: 2277
<212> TYPE: DNA
<213> ORGANISM: swine influenza virus

<400> SEQUENCE: 56
atggagagaa taaggaact aagagatcta atgtcgcagt cccgcactcg cgagatactc     60
actaagacca ctgtggacca tatggccata atcaaaaagt acacatcagg aaggcaagag    120
aagaatcccg cactcagaat gaagtggatg atggcaatga atacccaat tacagcagac     180 aagagaataa tgggcatgat tccagagagg aatgaacaag acaaaccct ctggagcaaa     240 acaaacgatg ctggatcaga acgcgtgatg gtatcacctc tggccgtaac atggtggaat    300
agaaatggcc aacaacaag tacagttcac taccctaagg tatataaaac ttatttcgaa     360
aaagtcgaaa ggttaaaaca tggtaccttt ggccctgtcc acttcagaaa tcaagttaaa    420
ataagaagga gagttgacac aaaccctggt cacgcagatc tcagtgccaa ggaggcacag    480
gatgtgatca tggaagttgt tttcccaaat gaagtggggg caagaatact gacatcagag    540
tcacagctga caataacaaa ggagaagaaa gaagagctcc aggattgtaa aattgctccc    600
ttgatggtgg catacatgct agaaagagag ttggtccgta aaacgaggtt tctcccggtg    660
gctggtggaa caggcagtgt ttatattgag gtgctgcact taacccaggg aacatgctgg    720
gagcagatgt acactccagg aggagaagtg agaaatgatg atgttgacca agttttgatt    780
```

-continued

```
atcgctgcta gaaacatagt aagaagagca gcagtgtcag cagacccatt agcatctctc    840
ttggaaatgt gccacagcac acagattgga ggaataagga tggtagacat ccttagacag    900
aatccaacag aggaacaagc cgtagacata tgcaaggcag caatgggggtt gaggattagc   960 tcatctttca gctttggtgg gttcactttc aaaagaacaa gcggatcatc agtcaagaaa   1020
gaagaagaaa tgctcacagg caacctccaa acactgaaaa taagagtaca tgaaggatat   1080
gaagaattca caatggtagg gagaagagca acagctattc tcagaaaggc aaccaggaga   1140
ttgatccagt taatagtaag tgggagagac gagcagtcaa ttgctgaggc aataattgtg   1200
gccatggtat tttcacaaga agattgcatg atcaaggcag ttaggggcga tctgaacttt   1260 gtcataggg caaaccagcg actgaatccc atgcaccaac tcttgagaca tttccaaaaa   1320
gatgcgaaag tgcttttcca gaactgggga attgaaccta tcgacaatgt gatgggaatg   1380
attggaatat tgcccgatat gacccccaagc acggagatgt cgctgagagg gataagagtc   1440
agcaaaatgg gagtagatga atactccagc acggagagag tggtagtgag cattgaccga   1500 ttttttgaggg ttcgggatca acgagggaac gtactattgt ctcccgaaga ggtcagcgag   1560
acacaaggaa cggagaagtt gacaataact tattcgtcat caatgatgtg ggagatcaat   1620
ggtcctgagt cagtgctggt caacacttat caatggatca tcaggaactg ggaaactgtg   1680
aaaattcaat ggtcacaaga ccccacgatg ttatacaaca aaatggaatt tgaaccattt   1740
cagtctcttg tccctaaggc aaccagaagc cgatacagtg gattcgtaag gacactgttc   1800
cagcaaatgc gggatgtgct tggaacattt gacactgtcc aaataataaa acttctccca   1860
tttgctgctg ctccaccaga acagagtagg atgcagtttt cctcattgac tgtgaatgtg   1920
agaggatcag ggttgaggat actggtgaga ggcaattctc cagtattcaa ttacaacaag   1980
gcaaccaaaa ggcttacagt tcttgggaaa gatgcaggtg cattgactga agatccagat   2040
gaaggcacag ctggggtgga gtctgctgtc ctgagaggat ttctcatttt gggcaaagaa   2100
gacaagagat atggaccagc attaagcatc aatgaactga gcaatcttgc aagaggagag   2160
aaggctaatg tgctaattgg gcaaggagac gtagtgttgg taatgaaacg gaaacgagac   2220
tctagcatac ttactgacag ccagacagcg accaaaagaa ttcggatggc catcaat      2277
```

<210> SEQ ID NO 57
<211> LENGTH: 759
<212> TYPE: PRT
<213> ORGANISM: swine influenza virus

<400> SEQUENCE: 57

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Met
    50                  55                  60

Gly Met Ile Pro Glu Arg Asn Glu Gln Gly Gln Thr Leu Trp Ser Lys
65                  70                  75                  80

Thr Asn Asp Ala Gly Ser Glu Arg Val Met Val Ser Pro Leu Ala Val
                85                  90                  95

Thr Trp Trp Asn Arg Asn Gly Pro Thr Thr Ser Thr Val His Tyr Pro
            100                 105                 110
```

Lys Val Tyr Lys Thr Tyr Phe Glu Lys Val Glu Arg Leu Lys His Gly
            115                 120                 125

Thr Phe Gly Pro Val His Phe Arg Asn Gln Val Lys Ile Arg Arg Arg
        130                 135                 140

Val Asp Thr Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ala Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Gly Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Lys Glu Glu Glu Met Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Asn Val Met Gly Met Ile Gly Ile Leu
    450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

```
Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Thr Arg Ser Arg Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Arg Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 58
<211> LENGTH: 372
<212> TYPE: DNA
<213> ORGANISM: swine influenza virus

<400> SEQUENCE: 58
atggactcca atactgtgtc aagctttcag ctcttccagg acatactaat gaggatgtca      60
aaaatgcagt gggggtcctc atcggaggac ttgaatggaa tggtaacacg gttcgaggct     120
ctgaaaatct acagagattc gcttggagaa accgtaatga aatgggaga ccttcattac      180 ctccagaaca gaaatgaaaa gtggcgagag caattgggac agaaatttga ggaaataaga     240
tggttaattg aagaagtacg gcacagattg aaagcgacag aaaatagttt cgaacaaata     300
acatttatgc aagccttaca actactgctt gaagtagaac aagagataag gactttctcg     360
tttcagctta tt                                                         372

<210> SEQ ID NO 59
<211> LENGTH: 121
<212> TYPE: PRT
<213> ORGANISM: swine influenza virus

<400> SEQUENCE: 59

Met Asp Ser Asn Thr Val Ser Ser Phe Gln Asp Ile Leu Met Arg Met
1               5                   10                  15

Ser Lys Met Gln Leu Gly Ser Ser Ser Glu Asp Leu Asn Gly Met Val
```

```
            20                  25                  30
Thr Arg Phe Glu Ala Leu Lys Ile Tyr Arg Asp Ser Leu Gly Glu Thr
            35                  40                  45

Val Met Arg Met Gly Asp Leu His Tyr Leu Gln Asn Arg Asn Glu Lys
        50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Ala Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
            115                 120

<210> SEQ ID NO 60
<211> LENGTH: 657
<212> TYPE: DNA
<213> ORGANISM: swine influenza virus

<400> SEQUENCE: 60
atggactcca atactgtgtc aagctttcag gtagactgtt tcctttggca catccgcaaa      60
cggtttgcag acaatggatt gggtgatgcc ccgttccttg atcggctccg ccgagatcaa     120
aagtccctga aggaagagg caacacccctt agcctagaca tcgaaacagc cactcttgtt     180
gggaaacaaa ttgttgagtg gattttgaaa gaggaatcca gcgatacact taagatgacc     240
attgcatctg tacctacttc gcgctaccta gctgacatga ccctcgagga aatgtcacga     300
gactggttca tgctcatgcc taggcaaaag ataataggcc ctctttgtgt gcgaatggac     360
caggcgatca tggaaaagaa catcatactg aaagcgaact tcagtgtgat ctttaaccga     420
ttagagactt tgatactact aagggctttc actgaggagg gagcaatcgt tggagaaatt     480
tcaccattac cttctcttcc aggacatact aatgaggatg tcaaaaatgc agttggggtc     540
ctcatcggag gacttgaatg gaatggtaac acggttcgag gctctgaaaa tctacagaga     600
ttcgcttgga gaaaccgtaa tgagaatggg agaccttcat acctccaga acagaaa        657

<210> SEQ ID NO 61
<211> LENGTH: 219
<212> TYPE: PRT
<213> ORGANISM: swine influenza virus

<400> SEQUENCE: 61

Met Asp Ser Asn Thr Val Ser Ser Phe Gln Val Asp Cys Phe Leu Trp
1               5                   10                  15

His Ile Arg Lys Arg Phe Ala Asp Asn Gly Leu Gly Asp Ala Pro Phe
            20                  25                  30

Leu Asp Arg Leu Arg Arg Asp Gln Lys Ser Leu Lys Gly Arg Gly Asn
        35                  40                  45

Thr Leu Ser Leu Asp Ile Glu Thr Ala Thr Leu Val Gly Lys Gln Ile
    50                  55                  60

Val Glu Trp Ile Leu Lys Glu Glu Ser Ser Asp Thr Leu Lys Met Thr
65                  70                  75                  80

Ile Ala Ser Val Pro Thr Ser Arg Tyr Leu Ala Asp Met Thr Leu Glu
                85                  90                  95

Glu Met Ser Arg Asp Trp Phe Met Leu Met Pro Arg Gln Lys Ile Ile
            100                 105                 110
```

```
Gly Pro Leu Cys Val Arg Met Asp Gln Ala Ile Met Glu Lys Asn Ile
            115                 120                 125
Ile Leu Lys Ala Asn Phe Ser Val Ile Phe Asn Arg Leu Glu Thr Leu
        130                 135                 140
Ile Leu Leu Arg Ala Phe Thr Glu Glu Gly Ala Ile Val Gly Glu Ile
145                 150                 155                 160
Ser Pro Leu Pro Ser Leu Pro Gly His Thr Asn Glu Asp Val Lys Asn
                165                 170                 175
Ala Val Gly Val Leu Ile Gly Gly Leu Glu Trp Asn Gly Asn Thr Val
            180                 185                 190
Arg Gly Ser Glu Asn Leu Gln Arg Phe Ala Trp Arg Asn Arg Asn Glu
        195                 200                 205
Asn Gly Arg Pro Ser Leu Pro Pro Glu Gln Lys
    210                 215
```

<210> SEQ ID NO 62
<211> LENGTH: 756
<212> TYPE: DNA
<213> ORGANISM: swine influenza virus

<400> SEQUENCE: 62

```
atgagtcttc taaccgaggt cgaaacgtat gttctctcta tcgtcccgtc aggccccctc      60
aaagccgaga tagcacagag actcgaagac gttttttgcag ggaaaaacac cgatcttgag    120
gctctcatgg aatggctaaa gacaagacca atcctgtcac ctctgactaa ggggatttta    180
gggtttgtgt tcacgctcac cgtgcccagt gagcgaggac tgcagcgtag acgttttgtc    240
cagaatgccc tcaatgggaa tggtgacccg aacaacatgg acaaggcggt caaactgtac    300
aggaaactaa aagggaaat aacattccat ggggccaagg aagtagcgct cagttactct    360
gctggtgcac ttgccagttg catgggcctc atatacaaca gaatggggac tgtcgccact    420
gaggtggcat ttggtctggt atgcgcaacc tgtgaacaga ttgctgattc tcagcatcga    480
tctcatagac aaatggtgac aacaaccaat ccactaatca ggcacgagaa cagaatggta    540
atagccagca aacagctaa ggccatggaa caaatggctg atcaagtga acaagcagca    600
gaggctatgg aggttgccag ccaggctaga caaatgtac aggcaatgag aacaattggg    660
actcacccta gttccagcac tggtctaaaa gatgatcttc ttgaaaattt acaggcctat    720
cagaaacgga tgggagtgca aatgcaacga ttcaag                              756
```

<210> SEQ ID NO 63
<211> LENGTH: 252
<212> TYPE: PRT
<213> ORGANISM: swine influenza virus

<400> SEQUENCE: 63

```
Met Ser Leu Leu Thr Glu Val Glu Thr Tyr Val Leu Ser Ile Val Pro
1               5                   10                  15
Ser Gly Pro Leu Lys Ala Glu Ile Ala Gln Arg Leu Glu Asp Val Phe
            20                  25                  30
Ala Gly Lys Asn Thr Asp Leu Glu Ala Leu Met Glu Trp Leu Lys Thr
        35                  40                  45
Arg Pro Ile Leu Ser Pro Leu Thr Lys Gly Ile Leu Gly Phe Val Phe
    50                  55                  60
Thr Leu Thr Val Pro Ser Glu Arg Gly Leu Gln Arg Arg Arg Phe Val
65                  70                  75                  80
Gln Asn Ala Leu Asn Gly Asn Gly Asp Pro Asn Asn Met Asp Lys Ala
```

```
                    85                  90                  95
Val Lys Leu Tyr Arg Lys Leu Lys Arg Glu Ile Thr Phe His Gly Ala
            100                 105                 110
Lys Glu Val Ala Leu Ser Tyr Ser Ala Gly Ala Leu Ala Ser Cys Met
            115                 120                 125
Gly Leu Ile Tyr Asn Arg Met Gly Thr Val Ala Thr Glu Val Ala Phe
            130                 135                 140
Gly Leu Val Cys Ala Thr Cys Glu Gln Ile Ala Asp Ser Gln His Arg
145                 150                 155                 160
Ser His Arg Gln Met Val Thr Thr Asn Pro Leu Ile Arg His Glu
                165                 170                 175
Asn Arg Met Val Ile Ala Ser Thr Thr Ala Lys Ala Met Glu Gln Met
                180                 185                 190
Ala Gly Ser Ser Glu Gln Ala Ala Glu Ala Met Glu Val Ala Ser Gln
                195                 200                 205
Ala Arg Gln Met Val Gln Ala Met Arg Thr Ile Gly Thr His Pro Ser
            210                 215                 220
Ser Ser Thr Gly Leu Lys Asp Asp Leu Leu Glu Asn Leu Gln Ala Tyr
225                 230                 235                 240
Gln Lys Arg Met Gly Val Gln Met Gln Arg Phe Lys
                245                 250

<210> SEQ ID NO 64
<211> LENGTH: 291
<212> TYPE: DNA
<213> ORGANISM: swine influenza virus

<400> SEQUENCE: 64
atgagtcttc taaccgaggt cgaaacgcct atcagaaacg gatgggagtg caaatgcaac      60
gattcaagtg atcctctcat tgatgccgca agcatcattg gattttgca cctgatattg      120 tggattcttg atcgtctttt tttcaaatgc atttaccgtc gctttaaata cggtctgcaa      180
agagggcctt ctacggaagg agtgccggag tccatgaggg aagaatatcg cagaaacag      240 cagagtgctg tggatgttga cgatggtcat tttgtcaaca tagtgctaga g             291

<210> SEQ ID NO 65
<211> LENGTH: 97
<212> TYPE: PRT
<213> ORGANISM: swine influenza virus

<400> SEQUENCE: 65

Met Ser Leu Leu Thr Glu Val Glu Thr Pro Ile Arg Asn Gly Trp Glu
1               5                   10                  15
Cys Lys Cys Asn Asp Ser Ser Asp Pro Leu Ile Asp Ala Ala Ser Ile
                20                  25                  30
Ile Gly Ile Leu His Leu Ile Leu Trp Ile Leu Asp Arg Leu Phe Phe
            35                  40                  45
Lys Cys Ile Tyr Arg Arg Phe Lys Tyr Gly Leu Gln Arg Gly Pro Ser
        50                  55                  60
Thr Glu Gly Val Pro Glu Ser Met Arg Glu Glu Tyr Arg Gln Lys Gln
65                  70                  75                  80
Gln Ser Ala Val Asp Val Asp Asp Gly His Phe Val Asn Ile Val Leu
                85                  90                  95
Glu
```

<210> SEQ ID NO 66
<211> LENGTH: 1407
<212> TYPE: DNA
<213> ORGANISM: swine influenza virus

<400> SEQUENCE: 66

```
atgaatccaa atcaaaagat aataacaatt ggctctgttt ctctcatcat tgccacaata      60
tgcttcttta tgcaaattgc catcctggta actactgtaa cattgcattt caagcagcat     120
gactgcaact ccccccaaa caaccaagta atgctgtgtg aaccaacaat aatagaaaga     180
aacactacag aaattgtgta tttgaccaac accaccatag aaaggaaat atgccccaaa      240
ctagcagaat acagaaattg gtcaaagccg caatgtaaca tcacaggatt tgcacctttt      300
tctaaggaca attcgattcg actttccgct ggtggagaca tctgggtgac aagagaacct     360
tatgtgtcat gcgatcctga caagtgttat caatttgccc ttgggcaggg aacaacacta     420
aacaacgggc attcaaatga cactgtacat gataggaccc cttaccgaac cctattgatg      480
aatgaattgg gtgttccatt ccatttggga accaggcaag tgtgcatagc atggtccagc     540
tcaagttgtc acgatggaaa agcatggctg catgtttgta taactgggga tgataaaaat     600
gcaactgcta gtttcattta caatgggagg cttgtagata tattggttc atggtccaaa     660
aatatactca gaacccagga gtcggaatgc gtttgtatca atggaacttg tacagtagta     720
atgactgatg ggagcgcttc aggaaaagct gatactaaaa tactattcat tgaggagggg     780
aaaatcgttc atattagcac attgtcagga agtgctcagc atgtcgagga gtgctcctgt     840
tatcctcgat atcctggtgt cagatgtgtc tgcagagaca actggaaagg ctccaatagg      900
cccatcgtag atataaatgt aaaggattat agcattgttt ccagttatgt atgctcggga     960
cttgttggag acacacccag aaaaaacgac agcttcagca gtagccattg cctagatcct    1020
aacaatgagg aaggtggtca tggagtgaaa ggctgggcct tgatgatgg aaatgacgtg     1080
tggatgggaa gaacgatcag cgagaagtca cgctcaggtt atgaaaccttt caaagtcatc    1140
gaaggctggt ccaaacctaa ttccaaatta cagacaaata ggcaagtcat agttgaaaga    1200
ggtaaaaggt ccggttattc tggtatttc tccgttgaag caaaagctg catcaatcgg     1260
tgcttttatg tagagttgat aaggggaagg aaagaggaaa ctaaagtctg gtggacctca    1320
aacagtattg ttgtgttttg tggcacctca ggtacatatg aacaggctc atggcctgat    1380
ggggcggata tcaatctcat gcctata                                       1407
```

<210> SEQ ID NO 67
<211> LENGTH: 469
<212> TYPE: PRT
<213> ORGANISM: swine influenza virus

<400> SEQUENCE: 67

```
Met Asn Pro Asn Gln Lys Ile Ile Thr Ile Gly Ser Val Ser Leu Ile
1               5                   10                  15

Ile Ala Thr Ile Cys Phe Phe Met Gln Ile Ala Ile Leu Val Thr Thr
            20                  25                  30

Val Thr Leu His Phe Lys Gln His Asp Cys Asn Ser Pro Pro Asn Asn
        35                  40                  45

Gln Val Met Leu Cys Glu Pro Thr Ile Ile Glu Arg Asn Thr Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
```

85                  90                  95
Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Gly His
        130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
                180                 185                 190

Cys Ile Thr Gly Asp Asp Lys Asn Ala Thr Ala Ser Phe Ile Tyr Asn
            195                 200                 205

Gly Arg Leu Val Asp Ser Ile Gly Ser Trp Ser Lys Asn Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Ile Ser Thr Leu Ser Gly Ser Ala
                260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
        290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Phe Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Ser Glu
            355                 360                 365

Lys Ser Arg Ser Gly Tyr Glu Thr Phe Lys Val Ile Glu Gly Trp Ser
        370                 375                 380

Lys Pro Asn Ser Lys Leu Gln Thr Asn Arg Gln Val Ile Val Glu Arg
385                 390                 395                 400

Gly Lys Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
            420                 425                 430

Glu Thr Lys Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 68
<211> LENGTH: 1494
<212> TYPE: DNA
<213> ORGANISM: swine influenza virus

<400> SEQUENCE: 68

```
atggcgtctc aaggcaccaa acgatcatat gaacaaatgg agactggtgg tgaacgccaa    60
gatgccacag aaatcagagc atctgtcgga agaatgattg gtggaatcgg gaaattctac   120
atccaaatgt gcactgaact caaactcagt gactatgagg gacgactaat ccaaaatagc   180
ataacaatag agagaatggt gctctctgct tttgatgaga agaaataa atacctagaa    240
gagcatccca gtgctgggaa ggatcctaag aaaactggag acccatata tagaagagta   300
gacggaaagt ggatgagaga actcattctt tatgacaaag aagaataag gagaatttgg   360
cgccaggcaa acaatggtga tgatgcaaca gctggtctta ctcatatcat gatttggcat   420
tccaatctga atgatgccac gtaccagaga acaagagcac ttgttcgcac cggaatggat   480
cccagaatgt gctctctaat gcaaggttca acacttccca aaggtctgg ggcagcaggt    540
gctgcagtga aggagttgg aacaataaca atggaattaa tcagaatgat caaaggggg    600
atcaatgacc gaaacttctg gagaggtgaa aatggaagaa ggacaaggat tgcatatgaa   660
agaatgtgca atattctcaa aggaaaattt cagacagctg cccaaagggc aatgatggat   720
caagtaagag aaagtcggaa cccaggaaat gctgagattg aagatctcat ttttctggca   780
cggtcagcac ttatcctaag gggatcagtt gcacataagt cttgcctgcc tgcttgtgtg   840
tatgggcttg cagtggcaag tgggcatgac tttgaaaggg aagggtattc gctggtaggg   900
atagaccat ttaaattact ccagaacagt caagtgttca gcctgataag accaaatgaa    960
aacccagctc acaagagtca attagtgtgg atagcatgcc actctgctgc atttgaggat  1020
ctaagggtct caagtttcat aagagggaag aaagtgattc aaggggggaa gctttccaca  1080
agagggattc agattgcttc aaatgagaat gtggaagcca tggattccaa taccttagag  1140
ctgagaagca gatactgggc cataaggacc agaagtggag gaaataccaa tcaacagaaa  1200
gcatccgcag gccagatcag tgtgcaacct acattctcag tgcaacggaa tctcccttt   1260
gaaagagcaa ccgttatggc agctttcagc gggaacaatg aaggacggac atccgatatg  1320
cgaacagaaa ttataaggat gatggaaat gcaaaaccag aagatttgtc cttccagggg  1380
cggggagtct tcgagctctc ggacgaaaag gcaacgagcc cgatcgtgcc ttcctttgac  1440
atgagtaatg aagggtctta tttcttcgga gacaatgcag aggagtatga cagt        1494
```

<210> SEQ ID NO 69
<211> LENGTH: 498
<212> TYPE: PRT
<213> ORGANISM: swine influenza virus

<400> SEQUENCE: 69

```
Met Ala Ser Gln Gly Thr Lys Arg Ser Tyr Glu Gln Met Glu Thr Gly
1               5                   10                  15

Gly Glu Arg Gln Asp Ala Thr Glu Ile Arg Ala Ser Val Gly Arg Met
            20                  25                  30

Ile Gly Gly Ile Gly Lys Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95
```

Tyr Arg Arg Val Asp Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
            165                 170                 175

Gly Ala Ala Gly Ala Val Lys Gly Val Gly Thr Ile Thr Met Glu
        180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Ile Ala Tyr Glu Arg Met Cys Asn
        210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
            245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
        290                 295                 300

Lys Leu Leu Gln Asn Ser Gln Val Phe Ser Leu Ile Arg Pro Asn Glu
305                 310                 315                 320

Asn Pro Ala His Lys Ser Gln Leu Val Trp Ile Ala Cys His Ser Ala
            325                 330                 335

Ala Phe Glu Asp Leu Arg Val Ser Ser Phe Ile Arg Gly Lys Lys Val
        340                 345                 350

Ile Pro Arg Gly Lys Leu Ser Thr Arg Gly Ile Gln Ile Ala Ser Asn
        355                 360                 365

Glu Asn Val Glu Ala Met Asp Ser Asn Thr Leu Glu Leu Arg Ser Arg
370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
        405                 410                 415

Asn Leu Pro Phe Glu Arg Ala Thr Val Met Ala Ala Phe Ser Gly Asn
        420                 425                 430

Asn Glu Gly Arg Thr Ser Asp Met Arg Thr Glu Ile Ile Arg Met Met
        435                 440                 445

Glu Asn Ala Lys Pro Glu Asp Leu Ser Phe Gln Gly Arg Gly Val Phe
        450                 455                 460

Glu Leu Ser Asp Glu Lys Ala Thr Ser Pro Ile Val Pro Ser Phe Asp
465                 470                 475                 480

Met Ser Asn Glu Gly Ser Tyr Phe Phe Gly Asp Asn Ala Glu Glu Tyr
            485                 490                 495

Asp Ser

<210> SEQ ID NO 70

<211> LENGTH: 1698
<212> TYPE: DNA
<213> ORGANISM: swine influenza virus

<400> SEQUENCE: 70

```
atgaagacta tcattgcttt tagctacatt ttatgtctga ttttcgctca aaaacttccc      60
ggaagtgaca acagcatggc aacgctatgc ctaggacacc atgcagtacc aaacggaacg     120
ttagtgaaaa caatcacgga tgaccaaatt gaagtgacta atgctactga gctggtccaa     180
agttcctcaa caggtagaat atgcaacagt cctcaccaaa tccttgatgg gaaaaattgc     240
acactgatag atgctctatt gggagaccct cattgtgatg acttccaaaa caaggaatgg     300
gaccttttg ttgaacgaag cacagcctac agcaactgct accttatta tgtgccggat      360
tatgcctccc ttaggtcact agttgcctca tccggcaccc tggaattcac ccaagaaagc     420
ttcaattgga ctggagttgc tcaagatgga tcaagctatg cttgcagaag gaaatctgtt     480
aacagtttct ttagtagatt aaattggttg cataatctga attacaaata ccagcgctg      540
aacgtaacta tgccaaacaa tgacaaattt gacaaattgt acatttgggg ggttcaccac     600
ccgggtacgg acaggaccaa accaaccta tatgttcaag catcagggag ggttacagtc     660
tccaccaaaa gaagccaaca aactgtaatc ccgaatatcg gatctagacc ctgggtaagg     720
ggtgtctcca gcataataag catctattgg acaatagtaa aaccgggaga catacttttg     780
attaacagca cagggaatct aattgcccct cggggttact tcaaaataca agtggggaaa     840
agctcaataa tgaggtcaga tgcacccatt ggcaactgca attctgaatg cattactcca     900
aatggaagca ttcccaatga caaaccttt caaaatgtaa acaggatcac atatggggcc     960
tgtcccagat atgtgaagca aaacactctg aaattggcaa cagggatgcg gaatgtacca    1020
gagaaacaaa ctagaggcat attcggcgca atcgcaggtt tcatagaaaa tggttgggag    1080
gggatggtgg acggttggta cggtttcagg catcaaaatt ctgaaggcac aggacaagca    1140
gcagatctta aaagcactca agcagcagtc aaccaaatca ccgggaaact aaatagagta    1200
atcaagaaaa cgaacgagaa attccatcag atcgaaaaag aattctcaga agtagaaggg    1260
agaattcagg acctagagaa atacgttgaa gacactaaaa tagatctctg gtcttacaac    1320
gcggagcttc ttgttgcccct ggagaaccaa catacaattg atttaactga ctcagaaatg    1380
aacaaactgt tcgaaagaac aaggaagcaa ctgcgggaaa atgctgagga catgggcaat    1440
ggttgcttca aaatatacca caagtgtgac aatgcctgca taggatcaat cagaaatgga    1500
acttatgacc atgatgtata cagagacgag gcattaaaca atcgattcca gatcaaaggt    1560
gttcagctga agtcaggata caagattgga atcctatgga tttcctttgc catatcatgc    1620
tttttgcttt gtgttgttct gctggggttc atcatgtggg cctgccaaaa aggcaacatt    1680
aggtgcaaca tttgcatt                                                 1698
```

<210> SEQ ID NO 71
<211> LENGTH: 566
<212> TYPE: PRT
<213> ORGANISM: swine influenza virus

<400> SEQUENCE: 71

```
Met Lys Thr Ile Ile Ala Phe Ser Tyr Ile Leu Cys Leu Ile Phe Ala
1               5                   10                  15

Gln Lys Leu Pro Gly Ser Asp Asn Ser Met Ala Thr Leu Cys Leu Gly
            20                  25                  30

His His Ala Val Pro Asn Gly Thr Leu Val Lys Thr Ile Thr Asp Asp
```

-continued

```
                35                  40                  45
Gln Ile Glu Val Thr Asn Ala Thr Glu Leu Val Gln Ser Ser Ser Thr
         50                  55                  60
Gly Arg Ile Cys Asn Ser Pro His Gln Ile Leu Asp Gly Lys Asn Cys
 65                  70                  75                  80
Thr Leu Ile Asp Ala Leu Leu Gly Asp Pro His Cys Asp Asp Phe Gln
                 85                  90                  95
Asn Lys Glu Trp Asp Leu Phe Val Glu Arg Ser Thr Ala Tyr Ser Asn
            100                 105                 110
Cys Tyr Pro Tyr Tyr Val Pro Asp Tyr Ala Ser Leu Arg Ser Leu Val
            115                 120                 125
Ala Ser Ser Gly Thr Leu Glu Phe Thr Gln Glu Ser Phe Asn Trp Thr
            130                 135                 140
Gly Val Ala Gln Asp Gly Ser Ser Tyr Ala Cys Arg Arg Lys Ser Val
145                 150                 155                 160
Asn Ser Phe Phe Ser Arg Leu Asn Trp Leu His Asn Leu Asn Tyr Lys
                165                 170                 175
Tyr Pro Ala Leu Asn Val Thr Met Pro Asn Asn Asp Lys Phe Asp Lys
            180                 185                 190
Leu Tyr Ile Trp Gly Val His His Pro Gly Thr Asp Arg Asp Gln Thr
            195                 200                 205
Asn Leu Tyr Val Gln Ala Ser Gly Arg Val Thr Val Ser Thr Lys Arg
            210                 215                 220
Ser Gln Gln Thr Val Ile Pro Asn Ile Gly Ser Arg Pro Trp Val Arg
225                 230                 235                 240
Gly Val Ser Ser Ile Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Gln Ser Gly Lys Ser Ser Ile Met Arg Ser Asp Ala
            275                 280                 285
Pro Ile Gly Asn Cys Asn Ser Glu Cys Ile Thr Pro Asn Gly Ser Ile
            290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
            355                 360                 365
Phe Arg His Gln Asn Ser Glu Gly Thr Gly Gln Ala Ala Asp Leu Lys
            370                 375                 380
Ser Thr Gln Ala Ala Val Asn Gln Ile Thr Gly Lys Leu Asn Arg Val
385                 390                 395                 400
Ile Lys Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
            450                 455                 460
```

| | | | | | | | | | | | |
|---|---|---|---|---|---|---|---|---|---|---|---|
|Glu|Arg|Thr|Arg|Lys|Gln|Leu|Arg|Glu|Asn|Ala|Glu|Asp|Met|Gly|Asn|
|465| | | |470| | | |475| | | |480| | | |

Gly Cys Phe Lys Ile Tyr His Lys Cys Asp Asn Ala Cys Ile Gly Ser
                        485                        490                        495

Ile Arg Asn Gly Thr Tyr Asp His Asp Val Tyr Arg Asp Glu Ala Leu
            500                        505                        510

Asn Asn Arg Phe Gln Ile Lys Gly Val Gln Leu Lys Ser Gly Tyr Lys
                515                        520                        525

Asp Trp Ile Leu Trp Ile Ser Phe Ala Ile Ser Cys Phe Leu Leu Cys
        530                        535                        540

Val Val Leu Leu Gly Phe Ile Met Trp Ala Cys Gln Lys Gly Asn Ile
545                    550                        555                        560

Arg Cys Asn Ile Cys Ile
                565

<210> SEQ ID NO 72
<211> LENGTH: 2148
<212> TYPE: DNA
<213> ORGANISM: swine influenza virus

<400> SEQUENCE: 72

```
atggaagact tgtgcgaca  atgcttcaat  ccaatgatcg  tcgagcttgc  ggaaaaggca     60
atgaagaat  atggagagga  ttcgaaaatc  gaaaccaaca  aattcgctgc  aatatgcacg    120
cacttggaag  tctgtttcat  gtattcggat  ttccatttca  ttgacgaaca  gggtgaatca   180
atcattatag  aatctggtga  tccaaatgca  ttgctgaagc  accgatttga  gataattgaa    240
ggaagagaca  ggactatggc  ctggacagta  gtgaacagta  tctgcaacac  cacaggggta    300
gagaagccta  aatttcttcc  ggatttatac  gactacaaag  aaaaccgatt  cgttgaaatt     360
ggagtgacac  gaagggaggt  ccacatatac  tacctagaga  agccaacaa   gataaaatcc    420
gagaagacac  acattcatat  tttttcattc  actggagagg  agatggccac  caaagcggac    480
tacacccttg  atgaagagag  cagggcaaga  atcaaaacca  ggctcttcac  cataagacaa    540
gagatggcca  gtaggggtct  atgggattcc  tttcgtcagt  ccgagagagg  cgaagagaca    600
attgaagaaa  gatttgaaat  tacaggaacc  atgcgcaggc  ttgccgacca  agtctcccca    660
ccgaacttct  ccagccttga  aaactttaga  gcctatgtag  atgggttcga  accaaacggc    720
tgcattgagg  gcaagctttc  tcaaatgtca  aagaagtga  gtgcccaaat  tgaaccattc    780
ttgaagacaa  caccacaccc  tctcagattg  cctaatgggc  ctccttgctc  tcagcggtca    840
aagttcttgc  tgatggatgc  tctgaaacta  agtattgaag  acccgagtca  tgagggagaa    900
ggaataccac  tatatgatgc  aatcaagtgc  atgaagacat  tttttggctg  gaaagagcct    960
aacataatca  aaccacatga  aaaggcata   accccaatt   atctactggc  ttggaagcag   1020
gtgctagcag  agctccagga  cattgaaaat  gaagagaaga  tcccaaagac  aaagaacatg   1080
aagagaacaa  gccaattgaa  gtgggcactt  ggtgagaata  tggcaccaga  gaaagtagat   1140
tttgatgact  gcaaagatgt  cggtgatctc  aaacagtatg  acagcgatga  gccagagccc   1200
agatctctag  caagctgggt  ccaaaatgag  ttcaacaagg  catgtgaatt  gaccgattca   1260
agctggatag  aacttgatga  gataggagaa  gatgttgccc  cgattgaaca  catcgcaagc   1320
atgaggagga  actattttac  agcagaagtg  tcccattgca  gggctactga  atacataatg   1380
aagggagtgt  acataaatac  ggctctactt  aatgcatctt  gtgcagccat  ggatgacttt   1440
cagctgatcc  caatgataag  caaatgtaga  accaagaag  gaagacgaaa  aacaaatctg   1500
```

```
tatggtttca ttataaaagg aaggtcccat ctgagaaatg atactgacgt ggtgaacttt   1560
gtaagcatgg agttctccct cactgacccg agactggagc cacacaaatg ggaaaagtac   1620
tgtgttcttg aaataggaga catgctcctg aggactgcga taggccaagt gtcgaggccc   1680
atgttcctat atgtgagaac caatggaacc tccaagatca agatgaaatg ggcatggaa    1740 atgaggcgct gcctcctcca gtctcttcag cagattgaga gcatgattga ggctgagtct   1800
tctgtcaaag agaaagacat gaccaaggaa ttctttgaaa acaaatcgga aacatggcca   1860
atcggagaat cacccaaagg agtggaggaa ggctctattg ggaaagtgtg caggacctta   1920
ctggcaaaat ctgtattcaa cagtctatac gcgtctccac aacttgaagg gttttcggct   1980
gaatcgagaa aattgctcct cattgttcag gcacttaggg acaacttgga acctggaacc   2040
ttcgatcttg gggggctata tgaagcaatc gaggagtgcc tgattaatga tccctgggtt   2100
ttgcttaatg catcttggtt caactccttc ctcacacatg cactgaaa                2148
```

<210> SEQ ID NO 73
<211> LENGTH: 716
<212> TYPE: PRT
<213> ORGANISM: swine influenza virus

<400> SEQUENCE: 73

```
Met Glu Asp Phe Val Arg Gln Cys Phe Asn Pro Met Ile Val Glu Leu
1               5                   10                  15

Ala Glu Lys Ala Met Lys Glu Tyr Gly Glu Asp Ser Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Gln Gly Glu Ser Ile Ile Ile Glu
    50                  55                  60

Ser Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Val Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Ser Ala Gln
                245                 250                 255
```

Ile Glu Pro Phe Leu Lys Thr Thr Pro His Pro Leu Arg Leu Pro Asn
            260                 265                 270

Gly Pro Pro Cys Ser Gln Arg Ser Lys Phe Leu Leu Met Asp Ala Leu
            275                 280                 285

Lys Leu Ser Ile Glu Asp Pro Ser His Glu Gly Glu Gly Ile Pro Leu
            290                 295                 300

Tyr Asp Ala Ile Lys Cys Met Lys Thr Phe Phe Gly Trp Lys Glu Pro
305                 310                 315                 320

Asn Ile Ile Lys Pro His Glu Lys Gly Ile Asn Pro Asn Tyr Leu Leu
                325                 330                 335

Ala Trp Lys Gln Val Leu Ala Glu Leu Gln Asp Ile Glu Asn Glu Glu
            340                 345                 350

Lys Ile Pro Lys Thr Lys Asn Met Lys Arg Thr Ser Gln Leu Lys Trp
            355                 360                 365

Ala Leu Gly Glu Asn Met Ala Pro Glu Lys Val Asp Phe Asp Asp Cys
            370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
            595                 600                 605

Lys Glu Phe Phe Glu Asn Lys Ser Glu Thr Trp Pro Ile Gly Glu Ser
            610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu

|  |  | 675 |  |  | 680 |  |  | 685 |  |
| --- | --- | --- | --- | --- | --- | --- | --- | --- | --- |

Ala Ile Glu Glu Cys Leu Ile Asn Asp Pro Trp Val Leu Leu Asn Ala
    690             695             700

Ser Trp Phe Asn Ser Phe Leu Thr His Ala Leu Lys
705             710             715

<210> SEQ ID NO 74
<211> LENGTH: 2271
<212> TYPE: DNA
<213> ORGANISM: swine influenza virus

<400> SEQUENCE: 74

| atggatgtca atccgactct acttttccta aaggttccag cgcagaatgc cataagcacc | 60 |
|---|---|
| acattccctt atactggaga tcctccatac agccatggaa caggaacagg atacaccatg | 120 |
| gacacagtca acagaacaca ccaatattca gaaaaaggga atggacgac aaacacagag | 180 |
| actggggcac cccagctcaa tccgattgat ggaccactac ctgaagataa tgaaccaagt | 240 |
| ggatatgcac aaacagactg tgttctggag gccatggctt tccttgaaga tcccacccca | 300 |
| gggatatttg agaattcatg ccttgaaaca atggaaattg tccaacaaac aagggtggat | 360 |
| aaactaactc agggtcgcca gacttatgat tggacattga tagaaatca accggcagca | 420 |
| actgcattgg ccaacaccat agaagttttt agatcaaatg gtctaacagc taatgagtca | 480 |
| ggaaggctaa tagatttctt aaagatgta atggaatcaa tggataaaga ggaaatagag | 540 |
| ataacgacac actttcaaag aaaaaggaga taagggaca catgaccaa gaagatggtc | 600 |
| acgcaaagaa caatagggaa gaaaaacaa agagtgtata gaaaagtta tctaataaga | 660 |
| gcactgacat tgaatacgat gaccaaagat gcagagagag gcaaattaaa aaggagggct | 720 |
| attgcaacac ctgggatgca aattagaggg ttcgtgtact tgttgagac tttagctaga | 780 |
| agcatttgcg aaaagcttga acagtccgga ctcccagtag ggggcaatga aaagaaagct | 840 |
| aaattggcaa acgttgtgag aaagatgatg actaattcac aagacacaga gctttctttc | 900 |
| acaatcactg ggacaacac taaatggaat gaaaaccaaa atcctcgaat gttcctggcg | 960 |
| atgattacat acatcaccag aaatcaaccc gagtggttca gaaacatcct gagcatggca | 1020 |
| cccataatgt tctcaaacaa aatggcaaga ctagggaaag ggtacatgtt cgagagtaaa | 1080 |
| agaatgaggc tccgaacaca gataccagca gaaatgctag caagcattga cctgaagtat | 1140 |
| ttcaatgaat caacaaagaa gaaaattgag aaaataaggc ctctcctaat agatggcaca | 1200 |
| gcatcattga gccctgggat gatgatgggc atgttcaaca tgctaagtac ggttttggga | 1260 |
| gtctcgatac tgaatcttgg acaaaagaaa tacacaagga caacatactg gtgggacgga | 1320 |
| ctccaatcct ccgacgattt tgccctcata gtaaatgcac caaatcatga gggaatacaa | 1380 |
| gcaggagtgg atagattcta caggacctgc aagttagtag aatcaacat gagcaaaaag | 1440 |
| aagtcctata taaataagac tgggacattt gaattcacaa gctttttta tcgctatggg | 1500 |
| tttgtagcta atttagcat ggagctgccc agttttggag tgtctggaat aaacgaatca | 1560 |
| gctgatatga gtattggagt aacagtgata agaacaaca tgataaacaa tgatcttgga | 1620 |
| cctgcaacag cccagatggc ccttcagttg ttcatcaaag actacagata cacatataga | 1680 |
| tgccatagag gggacacaca aatccagacg agaagatcat tcgagctaaa gaagctgtgg | 1740 |
| gatcaaaccc aatcaaaggc aggattatta gtatctgatg gaggaccaaa tttatacaat | 1800 |
| atccggaatc ttcacattcc tgaagtctgc ttaaatgggc agctaatgga tgaggattac | 1860 |
| cggggaagac tttgcaatcc cctgaatccc tttgtcagcc ataaagagat tgattctgta | 1920 |

```
aacagtgctg tggtgatgcc agcccatggt ccagccaaaa gcatggaata tgatgccgtt   1980
acaactacac actcctggat tcccaagagg aaccgctcta ttctcaacac aagccaaagg   2040
ggaattcttg aggatgaaca gatgtaccag aagtgctgca acctgttcga gaaatttttc   2100
cctagtagtt catacaggag accggttgga atttctagca tggtagaggc catggtgtct   2160
agggcccgga ttgatgccag gattgacttc gagtctggac ggattaagaa agaagagttc   2220
tctgagatca tgaagatctg ttccaccatt gaagaactca gacggcaaaa g            2271
```

<210> SEQ ID NO 75
<211> LENGTH: 757
<212> TYPE: PRT
<213> ORGANISM: swine influenza virus

<400> SEQUENCE: 75

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ile Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Ile Arg
            180                 185                 190

Asp Asn Met Thr Lys Lys Met Val Thr Gln Arg Thr Ile Gly Lys Lys
        195                 200                 205

Lys Gln Arg Val Tyr Lys Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
```

```
                305                 310                 315                 320
            Met Ile Thr Tyr Ile Thr Arg Asn Gln Pro Glu Trp Phe Arg Asn Ile
                            325                 330                 335
            Leu Ser Met Ala Pro Ile Met Phe Ser Asn Lys Met Ala Arg Leu Gly
                        340                 345                 350
            Lys Gly Tyr Met Phe Glu Ser Lys Arg Met Arg Leu Arg Thr Gln Ile
                        355                 360                 365
            Pro Ala Glu Met Leu Ala Ser Ile Asp Leu Lys Tyr Phe Asn Glu Ser
                        370                 375                 380
            Thr Lys Lys Lys Ile Glu Lys Ile Arg Pro Leu Leu Ile Asp Gly Thr
            385                 390                 395                 400
            Ala Ser Leu Ser Pro Gly Met Met Gly Met Phe Asn Met Leu Ser
                            405                 410                 415
            Thr Val Leu Gly Val Ser Ile Leu Asn Leu Gly Gln Lys Lys Tyr Thr
                        420                 425                 430
            Arg Thr Thr Tyr Trp Trp Asp Gly Leu Gln Ser Ser Asp Asp Phe Ala
                        435                 440                 445
            Leu Ile Val Asn Ala Pro Asn His Glu Gly Ile Gln Ala Gly Val Asp
                450                 455                 460
            Arg Phe Tyr Arg Thr Cys Lys Leu Val Gly Ile Asn Met Ser Lys Lys
            465                 470                 475                 480
            Lys Ser Tyr Ile Asn Lys Thr Gly Thr Phe Glu Phe Thr Ser Phe Phe
                            485                 490                 495
            Tyr Arg Tyr Gly Phe Val Ala Asn Phe Ser Met Glu Leu Pro Ser Phe
                        500                 505                 510
            Gly Val Ser Gly Ile Asn Glu Ser Ala Asp Met Ser Ile Gly Val Thr
                        515                 520                 525
            Val Ile Lys Asn Asn Met Ile Asn Asn Asp Leu Gly Pro Ala Thr Ala
                        530                 535                 540
            Gln Met Ala Leu Gln Leu Phe Ile Lys Asp Tyr Arg Tyr Thr Tyr Arg
            545                 550                 555                 560
            Cys His Arg Gly Asp Thr Gln Ile Gln Thr Arg Arg Ser Phe Glu Leu
                            565                 570                 575
            Lys Lys Leu Trp Asp Gln Thr Gln Ser Lys Ala Gly Leu Leu Val Ser
                        580                 585                 590
            Asp Gly Gly Pro Asn Leu Tyr Asn Ile Arg Asn Leu His Ile Pro Glu
                        595                 600                 605
            Val Cys Leu Lys Trp Glu Leu Met Asp Glu Asp Tyr Arg Gly Arg Leu
                        610                 615                 620
            Cys Asn Pro Leu Asn Pro Phe Val Ser His Lys Glu Ile Asp Ser Val
            625                 630                 635                 640
            Asn Ser Ala Val Val Met Pro Ala His Gly Pro Ala Lys Ser Met Glu
                            645                 650                 655
            Tyr Asp Ala Val Thr Thr Thr His Ser Trp Ile Pro Lys Arg Asn Arg
                        660                 665                 670
            Ser Ile Leu Asn Thr Ser Gln Arg Gly Ile Leu Glu Asp Glu Gln Met
                        675                 680                 685
            Tyr Gln Lys Cys Cys Asn Leu Phe Glu Lys Phe Phe Pro Ser Ser Ser
                        690                 695                 700
            Tyr Arg Arg Pro Val Gly Ile Ser Ser Met Val Glu Ala Met Val Ser
            705                 710                 715                 720
            Arg Ala Arg Ile Asp Ala Arg Ile Asp Phe Glu Ser Gly Arg Ile Lys
                            725                 730                 735
```

Lys Glu Glu Phe Ser Glu Ile Met Lys Ile Cys Ser Thr Ile Glu Glu
            740                 745                 750

Leu Arg Arg Gln Lys
        755

<210> SEQ ID NO 76
<211> LENGTH: 2277
<212> TYPE: DNA
<213> ORGANISM: swine influenza virus

<400> SEQUENCE: 76

| | |
|---|---|
| atggagagaa taaaagaact aagagatcta atgtcgcagt cccgcactcg cgagatactc | 60 |
| actaagacca ctgtggacca tatggccata atcaaaaagt acacatcagg aaggcaagag | 120 |
| aagaaccccg cactcagaat gaagtggatg atggcaatga aatacccaat tacagcagac | 180 |
| aagagaataa tggacatgat tccagagagg aatgaacaag acaaaccct ctggagcaaa | 240 |
| acaaacgatg ctggatcgga ccgtgtgatg gtatcacccc tggccgtaac atggtggaat | 300 |
| aggaatggcc caacaacaag cacagttcac taccctaagg tatataaaac ttatttcgaa | 360 |
| aaagtcgaaa ggttaaaaca tggtaccttt ggccctgtcc acttcagaaa tcaagttaaa | 420 |
| ataagaagga gggttgacac aaaccctggt catgcagatc tcagtgccaa ggaggcacag | 480 |
| gatgtgatca tggaagttgt tttcccaaat gaagtggggg caagaatact gacatcagag | 540 |
| tcacagctga caataacaaa agaaagaaa aagaactcc aggattgtaa aattgctccc | 600 |
| ttgatggtgg catacatgct agaaagagag ttggttcgta agacgaggtt tctcccggtg | 660 |
| gcaggtggaa caagcagtgt ttatattgaa gtgctgcact taactcaggg aacatgctgg | 720 |
| gagcaaatgt acactccagg aggagaagtg agaaatgatg atgttgacca aagtttgatt | 780 |
| atcgctgcta gaaacatagt aagaagagca gcagtgtcag cagacccatt agcatctctc | 840 |
| ttggaaatgt gccacagcac acagattgga ggaataagga tggtggacat ccttagacag | 900 |
| aacccaacgg aggaacaagc cgtagacata tgcaaggcag caatgggct gaggattagc | 960 |
| tcctctttca gctttggtgg gttcaccttc aaaagaacaa gcggatcatc agttaagaag | 1020 |
| gaagaagaag tgctcacggg caacctccaa acactgaaaa taagagtaca tgaaggatat | 1080 |
| gaagaattca caatggtcgg aaaagagca acagctattc tcagaaaagc aaccaggagg | 1140 |
| ttgatccagt taatagtaag tgggagagac gatcaatcaa ttgctgaggc aataattgtg | 1200 |
| gccatggtat tttcacaaga ggattgcatg atcaaggcag ttagggcga tctgaacttt | 1260 |
| gtcaataggg caaccagcg actgaatccc atgcaccaac tcttgaggca tttccaaaaa | 1320 |
| gatgcaaaag tgcttttcca gaactgggga attgaaccca tcgacagtgt gatgggaatg | 1380 |
| atcgggatat tgcctgatat gaccccaagc acggaaatgt cgctgagagg tataagagtc | 1440 |
| agcaaaatgg gagtagatga gtattccagc acggagagag tggtagtgag cattgaccga | 1500 |
| tttttgagag ttcgggatca acgagggaac gtactattgt ctcccgaaga ggtcagcgag | 1560 |
| acacaaggaa ctgagaaatt gacaataact tattcgtcat caatgatgtg ggagatcaat | 1620 |
| ggtcctgagt cagtgctggt caacacttat caatggatca taaggaactg gaaaagcttg | 1680 |
| aaaattcaat ggtcacaaga tcccacgatg ttatacaaca aaatggaatt tgaaccattc | 1740 |
| cagtctcttg tccctaaggc aatcagaagt cgttacagtg gattcgtaag gacactgttc | 1800 |
| cagcaaatgc gggatgtgct tggaacattt gacactgtcc aaataataaa actcctcccc | 1860 |
| tttgctgctg ctccacctga acagagtagg atgcagttct cctcgctgac tgtgaatgtg | 1920 |

-continued

```
agaggatcag ggctgaggat actggtaaga ggcaattctc cagtgttcaa ttacaacaaa    1980
gcaaccaaaa ggcttacaat tcttgggaaa gatgcaggtg cattgactga agatccagat    2040
gaaggcacag ctggagtgga gtctgctgtc ctgaggggat tcctcatttt gggtaaagaa    2100
gacaagagat atgcccagc attaagcatc aatgaactga gcaatcttgc aaaaggggag     2160
aaggctaatg tgctaattgg gcaaggagac gtggtgttgg taatgaaacg gaaacgggac    2220
tctagcatac ttactgacag ccagacagcg accaaaagaa ttcggatggc atcaat        2277
```

<210> SEQ ID NO 77
<211> LENGTH: 759
<212> TYPE: PRT
<213> ORGANISM: swine influenza virus

<400> SEQUENCE: 77

Met Glu Arg Ile Lys Glu Leu Arg Asp Leu Met Ser Gln Ser Arg Thr
1 5 10 15

Arg Glu Ile Leu Thr Lys Thr Thr Val Asp His Met Ala Ile Ile Lys
20 25 30

Lys Tyr Thr Ser Gly Arg Gln Glu Lys Asn Pro Ala Leu Arg Met Lys
35 40 45

Trp Met Met Ala Met Lys Tyr Pro Ile Thr Ala Asp Lys Arg Ile Met
50 55 60

Asp Met Ile Pro Glu Arg Asn Glu Gln Gly Gln Thr Leu Trp Ser Lys
65 70 75 80

Thr Asn Asp Ala Gly Ser Asp Arg Val Met Val Ser Pro Leu Ala Val
85 90 95

Thr Trp Trp Asn Arg Asn Gly Pro Thr Thr Ser Thr Val His Tyr Pro
100 105 110

Lys Val Tyr Lys Thr Tyr Phe Glu Lys Val Glu Arg Leu Lys His Gly
115 120 125

Thr Phe Gly Pro Val His Phe Arg Asn Gln Val Lys Ile Arg Arg Arg
130 135 140

Val Asp Thr Asn Pro Gly His Ala Asp Leu Ser Ala Lys Glu Ala Gln
145 150 155 160

Asp Val Ile Met Glu Val Val Phe Pro Asn Glu Val Gly Ala Arg Ile
165 170 175

Leu Thr Ser Glu Ser Gln Leu Thr Ile Thr Lys Glu Lys Lys Glu Glu
180 185 190

Leu Gln Asp Cys Lys Ile Ala Pro Leu Met Val Ala Tyr Met Leu Glu
195 200 205

Arg Glu Leu Val Arg Lys Thr Arg Phe Leu Pro Val Ala Gly Gly Thr
210 215 220

Ser Ser Val Tyr Ile Glu Val Leu His Leu Thr Gln Gly Thr Cys Trp
225 230 235 240

Glu Gln Met Tyr Thr Pro Gly Gly Glu Val Arg Asn Asp Asp Val Asp
245 250 255

Gln Ser Leu Ile Ile Ala Ala Arg Asn Ile Val Arg Arg Ala Ala Val
260 265 270

Ser Ala Asp Pro Leu Ala Ser Leu Leu Glu Met Cys His Ser Thr Gln
275 280 285

Ile Gly Gly Ile Arg Met Val Asp Ile Leu Arg Gln Asn Pro Thr Glu
290 295 300

Glu Gln Ala Val Asp Ile Cys Lys Ala Ala Met Gly Leu Arg Ile Ser
305 310 315 320

```
Ser Ser Phe Ser Phe Gly Gly Phe Thr Phe Lys Arg Thr Ser Gly Ser
            325                 330                 335

Ser Val Lys Lys Glu Glu Val Leu Thr Gly Asn Leu Gln Thr Leu
        340                 345                 350

Lys Ile Arg Val His Glu Gly Tyr Glu Glu Phe Thr Met Val Gly Lys
            355                 360                 365

Arg Ala Thr Ala Ile Leu Arg Lys Ala Thr Arg Leu Ile Gln Leu
        370                 375                 380

Ile Val Ser Gly Arg Asp Asp Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu Pro Ile Asp Ser Val Met Gly Met Ile Gly Ile Leu
        450                 455                 460

Pro Asp Met Thr Pro Ser Thr Glu Met Ser Leu Arg Gly Ile Arg Val
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Ser Leu
545                 550                 555                 560

Lys Ile Gln Trp Ser Gln Asp Pro Thr Met Leu Tyr Asn Lys Met Glu
                565                 570                 575

Phe Glu Pro Phe Gln Ser Leu Val Pro Lys Ala Ile Arg Ser Arg Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
        610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
                645                 650                 655

Asn Tyr Asn Lys Ala Thr Lys Arg Leu Thr Ile Leu Gly Lys Asp Ala
            660                 665                 670

Gly Ala Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Lys Arg Tyr
        690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735
```

-continued

```
Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 78
<211> LENGTH: 2341
<212> TYPE: DNA
<213> ORGANISM: swine influenza virus

<400> SEQUENCE: 78
agcgaaagca ggtcaaatat attcaatatg gagagaataa aagaactaag agatctgatg      60
tcgcagtctc gcactcgcga gatactcaca aagaccactg tggaccatat ggccataatc     120
aaaaagtaca catcaggaag gcaagagaag aaccccgcac tcagaatgaa gtggatgatg     180
gcaatgaaat acccaattac agcagacaag agaataatgg acatgattcc agagaggaat     240
gaacaaggac aaaccctctg gagcaaaaca aacgatgctg gatcggaccg tgtgatggta     300
tcacccctgg ccgtaacatg gtggaatagg aatggcccaa caacaagcac agttcactac     360
cctaaggtat ataaaactta tttcgaaaag atcgaaaggt taaaacatgg tatctttggc     420
cctgtccact tcagaaatca agttaaaata agaaggaggg ttgacacaaa ccctggtcat     480
gcagatctca gtgccaagga ggcacaggat gtgatcatgg aagttgtttt cccaaatgaa     540
gtgggggcaa gagtactgac gtcagagtca cagctgacaa taacaaagga aaagaaagaa     600
gagctccagg attgtaagat tgctcccctg atggtggcat acatgctaga aagagagttg     660
gttcgcaaga cgaggtttct cccggtggct ggtggaacaa gcagtgttta tattgaagtg     720
ctacacttaa ctcagggaac atgctgggaa caaatgtaca ctccaggagg agaagtgaga     780
aatgatgatg ttgaccaaag tttgattatc gctgctagaa acatagtaag aagagcagca     840
gtgtcagcag acccattagc atctctcttg gaaatgtgcc acagcacaca gattggagga     900
ataaggatgg tggacatcct tagacagaac ccaacggagg aacaagccgt agacatatgc     960
aaggcagcaa tggggctgag gattagctct tctttcagct ttggtgggtt caccttcaaa    1020
agaacaagcg gatcatcagt taagaaagaa gaagaagtgc tcacgggcaa cctccaaaca    1080
ctgaaaataa gagtacatga aggatatgaa gaattcacaa tggtagggag aagagcaact    1140
gctattctca gaaaagcaac caggagattg atccagttaa tagtaagtgg gagagacgat    1200
caatcaattg ctgaggcaat aattgtagcc atggtatttt cacaagagga ttgcatgatc    1260
aaggcagtta ggggcgatct gaactttgtc aatagggcaa accagcgact gaatcccatg    1320
caccaactct tgaggcattt ccaaaaagat gcaaaagtgc ttttccagaa ctggggaatt    1380
gaacccatcg acagtgtgat gggaatgatc gggatattgc ctgatatgac cccaagcacg    1440
gaaatgtcgc tgagaggtat aagagtcagc aaaatgggag tagatgagta ttccagcacg    1500
gagagagtgg tagtgagcat tgaccgattt ttgagagttc gggatcaacg agggaacgta    1560
ctattgtccc ccgaagaggt cagcgagaca caaggaactg agaaattgac aataacttat    1620
tcgtcatcaa tgatgtggga gatcaatggt cctgagtcag tgctggtcaa cacttatcaa    1680
tggatcataa ggaattggga aagcttgaaa attcaatggt cacaagatcc cacgatgtta    1740
tacaacaaaa tggaatttga accattccag tctcttgtcc ctaaggcaac cagaagtcgt    1800
tacagtggat tcgtgaggac actgttccag caaatgcggg atgtgcttgg aacatttgac    1860
actgtccaaa taataaaact tctccccttt gctgctgctc caccggaaca gagtaggata    1920
cagttctcct cgctgactgt gaatgtgaga ggatcagggc tgaggatact ggtaagaggc    1980
```

```
aattctccag tgttcaatta caacaaagca accaaaaggc ttacaattct tggaaaagat      2040
gcaggtgcat tgactgaaga tccagatgaa ggcacagctg gagtggagtc tgctgtcctg      2100 agggattcc tcattttggg taaagaagac aagagatatg cccagcatt aagcatcaat       2160 gaactgagca atcttgcaaa aggagagaag gctaatgtgt taattgggca aggagacgtg      2220
gtgttggtaa tgaaacggaa acggaactct agcatactta ctgacagcca gacagcgacc      2280
aaaagaattc ggatggccat caattagtgt cgaattgttt aaaaacgacc ttgtttctac      2340
t                                                                     2341

<210> SEQ ID NO 79
<211> LENGTH: 2341
<212> TYPE: DNA
<213> ORGANISM: swine influenza virus

<400> SEQUENCE: 79
agcgaaagca ggcaaaccat ttgaatggat gtcaacccga ctctactttt cctaaaggtt        60
ccagcgcaaa atgccataag caccacattc ccttatactg gagatcctcc atacagccat       120
ggaacaggaa caggatacac catggacaca gtcaacagaa cacccagta ttcagaaaaa        180 gggaaatgga cgacaaacac agagactggg gcaccccagc tcaacccgat tgatggacca       240
ctacccgatg ataatgaacc aagtgggtat gcacaaacag actgtgtcct ggaggccatg       300
gctttccttg aagaatccca cccagggata tttgagaatt catgccttga aacaatggaa       360
attgtccaac aaacaagggt ggataaacta actcaaggtc gccagactta tgattggaca       420
ttaaacagaa atcaaccggc agcaactgca ttggccaaca ccatagaagt ttttagatca       480
aacggtctaa cagctaatga gtcaggaagg ctaatagatt tcctaaagga tgtaatggaa       540
tcaatggata aggaggaaat agataacaac acacattttc aaagaaaaag gagagtaaga       600
gacaacatga ccaagaagat ggtcacacaa agaacaatag gaagaaaaa acaaaaattg       660 aataagagaa gttatctaat aagagcactg acattgaata cgatgaccaa agatgcagag       720
agaggcaagt taaaaggag gctatcgca cacctggga tgcagattag agggttcgtg         780
tactttgttg agactttagc tagaagcatc tgcgaaaagc ttgaacagtc cggactccca       840
gtagggggca atgaaaagaa agccaaattg gcaaatgttg tgagaaagat gatgactaat       900
tcacaagaca cagagctttc tttcacaatc actggagata cactaaatg gaatgaaaac       960 cagaatcctc gaatgttcct ggcgatgatc acatacatta ccagaaatca acccgagtgg      1020
ttcagaaaca tactgagtat ggcaccaata atgttctcaa acaaaatggc aagactagga       1080 aagggtaca tgttcgagag taaaagaatg aagctccgaa cacaggtacc agcagaaatg       1140
ctagcaagca ttgatcttaa gtatttcaat gaatcaacaa ggaagaaaat tgagaaaata     1200
aggcctctcc taatagatgg cacagcatca ttgagccctg gatgatgat gggcatgttc      1260 aacatgctaa gtacggtttt gggagtctca atactgaatc ttggacaaaa gaaatacacc      1320
aggacaacat actggtggga tggactccaa tcctcagacg atttgccct catagtaaat       1380 gcaccaaatc atgagggaat acaagcagga gtggatagat tctacaggac ctgcaagtta      1440
gtagggatca acatgagcaa aaagaagtcc tatataaata agactgggac atttgaattc      1500
acaagctttt tttatcgcta tgggtttgta gctaatttta gcatggagct gcccagtttt      1560
ggagtgtctg gaataaacga atcagctgat atgagcatcg gagtaacagt gataagaac       1620 aacatgataa ataatgatct tggacctgca acagcccaga tggccctcca gttgttcatc      1680
```

| | |
|---|---|
| aaagactaca gatacacata tagatgccat agaggggaca cacaaatcca gacgagaaga | 1740 |
| tcattcgagc taaagagcct gtggaatcaa actcaatcaa aggcaggatt attagtatct | 1800 |
| gatggaggac caaatttata caatatccgg aatcttcaca ttcctgaagt ctgcttaaaa | 1860 |
| tgggagctaa tggatgagga ttatcgggga agactttgta atcccctgaa tccctttgtc | 1920 |
| agccataaag agattgattc tgtaaacagt gctgtggtga tgccagccca tggtccagcc | 1980 |
| aaaagtatgg agtatgatgc cgttgcaact acacactcct ggattcccaa gaggaaccgc | 2040 |
| tctattctca acacaagcca aaggggaatt cttgaggatg aacagatgta ccagaagtgc | 2100 |
| tgcaacctgt tcgagaaatt tttccctagt agttcataca aagaccagt tggaatttct | 2160 |
| agcatggtgg aggccatggt gtctagggcc cggattgatg ccaggattga cttcgagtct | 2220 |
| ggacggatta agaagaaga gttctctgag atcatgaaga tctgttccac cattgaagaa | 2280 |
| ctcagacggc aaaagtaatg aatttagctt gtccttcatg aaaaaatgcc ttgtttctac | 2340 |
| t | 2341 |

<210> SEQ ID NO 80
<211> LENGTH: 2233
<212> TYPE: DNA
<213> ORGANISM: swine influenza virus

<400> SEQUENCE: 80

| | |
|---|---|
| agcgaaagca ggtactgatc caaaatggaa gactttgtgc gacaatgctt caatccaatg | 60 |
| atcgtcgagc ttgcggaaaa ggcaatgaaa gaatatggag aagatccgaa aattgaaact | 120 |
| aacaaattcg ctgcaatatg cacacacttg aagtatgtt tcatgtattc agatttccat | 180 |
| ttcattgacg agcggggtga atcaatcatt gtagaatctg gtgatccaaa tgcattactg | 240 |
| aagcaccgat ttgagataat tgaaggacgg gaccggacca tggcctggac agtagtgaac | 300 |
| agtatctgca acaccacagg ggtagagaag cctaaatttc ttccggattt atacgactac | 360 |
| aaagaaaatc ggttcattga aattggagtg acacgaaggg aggtccacat atactaccta | 420 |
| gagaaagcca acaaaataaa atccgagaag acacacattc attttttc attcactgga | 480 |
| gaggagatgg ccaccaaagc agactacacc cttgatgaag aaagcagggc aagaatcaaa | 540 |
| accaggcttt tcaccataag acaagaaatg gcaagtaggg gtctatggga ttcctttcgt | 600 |
| cagtccgaaa gaggcgagga gacaattgaa gaaagatttg aaattacagg aaccatgcgc | 660 |
| agacttgccg accaaagtct cccaccgaac ttctccagtc ttgaaaactt tagagcttat | 720 |
| gtagatgggt tcgaaccaaa cggctgcatt gagggcaagc tttctcaaat gtcaaaagaa | 780 |
| gtgagcgccc aaattgaacc cttcttgaag acaacaccac gccctctaaa attgcctgat | 840 |
| gggcctcctt gctctcagcg gtcaaagttc ttgctgatgg atgctctgaa actaagtatt | 900 |
| gaagacccga gtcatgaagg agaaggaata ccactatatg atgcaatcaa gtgcatgaag | 960 |
| acattttttg ctggaaaaga acccaacata atcaaaccac atgagaaagg cataaacccc | 1020 |
| aattacctac tggcttggaa gcaggtgcta gcagagctcc aagacattga aaatgaagag | 1080 |
| aagatcccaa agacaaagaa catgaggaga acaagccaat tgaagtgggc actcggtgag | 1140 |
| aatatggcac cagagaaagt agattttgat gactgcaaag atgttggtga tcttaaacag | 1200 |
| tatgacagcg acgagccaga gcccagatct ctagcaagtt gggtccaaaa tgaattcaac | 1260 |
| aaggcatgtg aattgaccga ttcaagctgg atagaacttg atgagatagg agaagatatt | 1320 |
| gcaccgattg aacacatcgc aagtatgagg aggaactatt ttacagcaga agtgtccat | 1380 |
| tgtagggcta cggaatacat aatgaaggga gtgtacataa acacggcttt gcttaatgca | 1440 |

-continued tcttgtgcag ccatggatga ctttcagctg atcccaatga taagcaaatg caggaccaaa 1500
gaaggaagac gaaaaacaaa tctgtatggg ttcattataa aaggaaggtc ccatctgagg 1560
aatgatactg acgtggtgaa ctttgtaagc atggagttct ccctcaccga cccgagactg 1620
gagccacaca aatgggaaaa atactgtgtt cttgaaatag gagacatgct cctgaggact 1680
gcgataggcc aagtgtcgag gcccatgttc ttatatgtga gaaccaatgg aacctccaag 1740
atcaagatga aatggggcat ggaaatgagg cgctgccttc ttcaatctct tcagcagatt 1800
gagagcatga ttgaggctga gtcttctgta aaagagaaag acatgaccaa ggaatttttt 1860
gaaaacaaat cggaaacatg gccaattgga gaatcaccca aaggagtgga ggaaggctct 1920
attgggaaag tgtgcaggac cttactggca aaatctgtat tcaacagtct atacgcatct 1980
ccacaacttg agggattttc ggctgaatcg agaaagttgc ttctcattgt tcaggcactt 2040
agggacaacc tggaacctgg aaccttcgat cttggggggc tatatgaagc aatcgaggag 2100
tgcctgatta atgatccctg ggttttgctt aatgcatctt ggttcaactc cttcctcaca 2160
catgcactga aatagttgtg gcaatgctac tatttgctat ccatactgtc caaaaaagta 2220
ccttgtttct act 2233

<210> SEQ ID NO 81
<211> LENGTH: 1565
<212> TYPE: DNA
<213> ORGANISM: swine influenza virus

<400> SEQUENCE: 81
agcaaaagca gggtagataa tcactcaatg agtgacatcg aagccatggc atctcaaggc 60
accaaacgat catatgaaca aatggagact ggtggtgaac gccaggatgc cacagaaatc 120
agagcatctg tcggaagaat gattggtgga atcgggaaat tctacatcca aatgtgcact 180
gaactcaaac tcagtgacta tgagggacga ctaatccaaa atagcataac aatagagaga 240
atggtgctct ctgcttttga tgagagaaga aataaatacc tagaagagca tcccagtgct 300
gggaaagacc ctaagaaaac tggaggaccc atatatagaa gagtagacgg aaagtggatg 360
agagaactca ttctttatga caaagaagaa ataaggagag tttggcgcca ggcaaacaat 420
ggtgatgatg caacagctgg tcttactcat atcatgattt ggcattccaa tctgaatgat 480
gccacgtacc agagaacaag agcacttgtt cgcaccggaa tggatcccag aatgtgctct 540
ctaatgcaag gttcaacact tcccagaagg tctggagcag caggtgctgc agtgaaagga 600
gttggaacaa taacaatgga attaatcaga atgatcaaac gggggatcaa tgaccgaaat 660
ttctggagag gtgaaaatgg aagaaggaca aggattgcat atgaaagaat gtgcaatatt 720
ctcaaaggaa aatttcagac agctgcccaa agggcaatga tggatcaagt gagagaaagt 780
cggaacccag ggaacgctga gattgaagat ctcattttcc tggcacggtc agcacttatc 840
ctaaggggat cagttgcaca taagtcttgc ctgcctgctt gcgtgtatgg gcttgcagtg 900
gcaagtgggc atgactttga aagggaaggg tattcgctgg tcgggataga cccatttaaa 960
ttactccaga acagtcaagt gttcagcctg gtaagaccaa atgaaaaccc agctcacaag 1020
agtcaattag tgtggatggc atgccactct gctgcatttg aggatctaag ggtctcaagt 1080
ttcataagag ggaagaaagt gattccaagg ggaaagcttt ccacaagagg ggttcagatt 1140
gcttcaaatg agaatgtgga agccatggat tccaatacct tagagctgag aagcagatac 1200
tgggctataa ggaccagaag tggaggaaat actaatcaac agaaagcatc cgcaggccag 1260

```
atcagtgtgc aacctacatt ctcagtgcaa cggaatctcc cttttgaaag agcaaccgtt    1320
atggcagctt tcagcggaaa caatgaagga cggacatccg atatgcggac agaaattata    1380
aggatgatgg aaaatgcaaa accagaagat ttgtccttcc aggggcgggg agtcttcgag    1440
ctctcggacg aaaaggcaac gagcccgatc gtgccttcct ttgacatgag taatgaaggg    1500
tcttatttct tcggagacaa tgcagaggag tatgacagtt gatgaaaaat acccttgttt    1560
ctact                                                                1565

<210> SEQ ID NO 82
<211> LENGTH: 1027
<212> TYPE: DNA
<213> ORGANISM: swine influenza virus

<400> SEQUENCE: 82
agcaaaagca ggtagatgtt taaagatgag tcttctaacc gaggtcgaaa cgtatgttct      60
ctctatcgtc ccgtcaggcc ccctcaaagc cgagatagca cagaggctcg aagacgtttt     120
tgcagggaaa aacaccgatc ttgaggctct catggaatgg ctaaagacaa gaccaatcct     180
gtcacctctg actaaaggga ttttaggggtt tgtgttcacg ctcaccgtgc ccagtgagcg     240
aggactgcag cgtagacgtt ttgtccagaa tgccctcaat gggaatggtg acccaaacaa     300
catggacaag gcggtaaaac tgtacaggaa actaaaaagg gaaataacat tccatggggc     360
caaggaagta gcgctcagtt actctgctgg tgcacttgcc agttgcatgg cctcatata      420 caacagaatg gggactgtcg ccactgaggt ggcatttggt ctggtatgcg caacctgtga     480
acaaattgct gattctcagc atcgatctca tagacaaatg gtgacaacaa ccaatccact     540
aatcaggcac gagaacagaa tggtaatagc cagcacaaca gctaaggcca tggaacaaat     600
ggctggatca agtgaacaag cagcagaggc tatggaggtt gccagtcagg ctagacaaat     660
ggtacaggca atgagaacaa ttgggactca ccctagttcc agcactggtc taaaagatga     720
tcttcttgaa aatttacagg cctatcagaa acggatggga gtgcaaatgc aacgattcaa     780
gtgatcctct cattgatgcc gcaagcatca ttggtatttt gcacctgata ttgtggattc     840
ttgatcgtct ttttttcaaa tgcatctacc gtcgctttaa atacggtctg caaagagggc     900
cttctacgga aggagtgccg gagtccatga gggaagaata tcggcagaaa cagcagagtg     960
ctgtggatgt tgacgatggt cattttgtca acatagtgct agagtaaaaa actaccttgt    1020
ttctact                                                              1027

<210> SEQ ID NO 83
<211> LENGTH: 890
<212> TYPE: DNA
<213> ORGANISM: swine influenza virus

<400> SEQUENCE: 83
agcaaaagca gggtgacaaa gacataatgg actccaatac tgtgtcaagc tttcaggtag      60 actgttttcct ttggcacatc cgcaaacgat ttgcagacaa tggattgggt gatgccccat    120
tccttgatcg gctccgccga gatcaaaagt ccctaaaagg aaggggcaac acccttagcc    180
tagacatcga aacagccact cttgttggga acaaattgt tgagtggatt ttgaaagagg    240
aatccagcga tatacttaag atgaccattg catctgtgcc tacttcgcgc tacctagctg    300
acatgaccct cgaggaaatg tcacgagact ggttcatgct aatgcctagg caaaagataa    360
taggccctct ttgtgtgcga gtggaccagg cgatcatgga aagaacatc atactgaaag    420 cgaacttcag tgtgatcttt aaccgattag agactttgat actactaagg ctttcactg    480
```

```
aggagggagc aatcgttgga gaaatttcac cattaccttg tcttccagga catactaatg      540
aggatgtcaa aaatgcagtt ggggtcctca tcggagggct tgaatggaat ggtaacacgg      600
ttcgaggctc tgaaaatcta cagagattcg cttggagaaa ccataatgag gatgggagat      660
cttcactacc tccagaacag aaatgaaaag tggcgagagc aattgggaca gaaatttgag      720
gaaataagat ggttaattga agaaatacgg cacagattga aagcgacaga aaatagtttc      780
gagcaaataa catttatgca agccttacaa ctactgcttg aagtagaaca agagataagg      840
actttctcgt ttcagcttat ttaatgataa aaaacaccct tgtttctact                 890

<210> SEQ ID NO 84
<211> LENGTH: 1778
<212> TYPE: DNA
<213> ORGANISM: swine influenza virus

<400> SEQUENCE: 84
agcaaaagca gggaaaaata aaagcaacca aaatgaaggc aatactagta gttctgctat       60
atacatttgc aacctcaaat gcagacacat tatgtatagg ttatcatgcg aacaattcaa      120
cagacactgt agacacagta ctagaaaaga atgtaacagt aacacactct gttaaccttc      180
tagaagacaa gcataacggg aaactatgca actaagagg ggtagcccca ttgcatttgg      240
gtaaatgtaa cattgctggc tggatcctgg gaaatccaga gtgtgaatca ctctccacag      300
caagctcatg gtcctacatt gtggaaacat ctagttcagg caatggaacg tgttacccag      360
gagatttcat cgattatgag gagctaagag agcaattgag ctcagtgtca tcatttgaaa      420
ggtttgagat attccccaag acaagttcat ggcccaatca tgaatcgaac aaaggtgtaa      480
cggcagcatg tcctcatgct ggagaaaaaa gcttctacaa aaatttaata tggctagtta      540
aaaaaggaaa ctcatacca aagctcagca atcctacat taatgataaa gggaaagaag      600
tcctcgtgct atgggggcatt caccatccat ctactagtgc tgaccaacaa agtctctatc      660
agaatgcaga tgcatatgtt tttgtgggga catcaagata cagcaagaag ttcaagccgg      720
aaatagcaat aagacccaaa gtgagggatc aagaagggag aatgaactat tactggacac      780
tagtagagcc gggagacaaa ataacattcg aagcaactgg aaatctagtg gtaccgagat      840
atgcattcgc aatggaaaga aatgctggat ctggtattat catttcagat acaccagtcc      900
acgattgcaa tacaacttgt cagacaccca agggtgctat aaacaccagc cttcctttc       960 agaatataca tccgatcaca attggaaaat gtccaaaata tgtaaaaagc acaaaattga     1020
gactggccac aggattgagg aatgtcccgt ctattcaatc tagaggccta tttggggcca     1080
ttgccggttt cattgaaggg gggtggacag ggatggtaga tggatggtac ggttatcacc     1140
atcaaaatga gcaggggtca ggatatgcag ccgacctgaa gagcacacag aatgccattg     1200
acgagattac taacaaagta aattctgtta ttgaaaagat gaatacacag ttcacagcag     1260
taggtaaaga gttcaaccac ctggaaaaaa gaatagagaa tttaaataaa aagttgatg      1320 atggtttcct ggacatttgg acttacaatg ccgaactgtt ggttctattg gaaaatgaaa     1380
gaactttgga ctaccacgat tcaaatgtga agaacttata tgaaaaggta agaagccagt     1440
taaaaaacaa tgccaaggaa attggaaacg gctgctttga attttaccac aaatgcgata     1500
acacgtgcat ggaaagtgtc aaaaatggga cttatgacta cccaaaatac tcagaggaag     1560
caaaattaaa cagagaagaa atagatgggg taaagctgga atcaacaagg atttaccaga     1620
ttttggcgat ctattcaact gtcgccagtt cattggtact ggtagtctcc ctgggggcaa     1680
```

```
tcagtttctg atgtgctct  aatgggtctc tacagtgtag aatatgtatt taacattagg    1740
atttcagaaa catgagaaaa aacacccttg tttctact                            1778

<210> SEQ ID NO 85
<211> LENGTH: 1458
<212> TYPE: DNA
<213> ORGANISM: swine influenza virus

<400> SEQUENCE: 85
agcaaaagca ggagtttaaa atgaatccaa accaaaagat aataaccatt ggttcggtct     60
gtatgacaat tggaatggct aacttaatat tacaaattgg aaacataatc tcaatatgga    120
ttagccactc aattcaactt gggaatcaaa atcagattga acatgcaat caaagcgtca     180 ttacttatga aaacaacact tgggtaaatc agacatatgt taacatcagc aacaccaact    240 tgctgctgg acagtcagtg gtttccgtga aattagcggg caattcctct ctctgccctg     300
ttagtggatg ggctatatac agtaaagaca acagtgtaag aatcggttcc aagggggatg    360
tgtttgtcat aagggaacca ttcatatcat gctcccccttt ggaatgcaga accttcttct    420
tgactcaagg ggccttgcta aatgacaaac attccaatgg aaccattaaa gacaggagcc    480
catatcgaac cctaatgagc tgtcctattg gtgaagttcc ctctccatac aactcaagat    540
ttgagtcagt cgcttggtca gcaagtgctt gtcatgatgg catcaattgg ctaacaattg    600
gaatttctgg cccagacaat ggggcagtgg ctgtgttaaa gtacaacggc ataataacag    660
acactatcaa gagttggaga aacaatatat tgagaacaca agagtctgaa tgtgcatgtg    720
taaatggttc ttgctttact gtaatgaccg atggaccaag taatgacag gcctcataca    780 agatcttcag aatagaaaag ggaaagatag tcaaatcagt cgaaatgaat gcccctaatt    840
atcactatga ggaatgctcc tgttatcctg attctagtga aatcacatgt gtgtgcaggg    900
ataactggca tggctcgaat cgaccgtggg tgtctttcaa ccagaatctg gaatatcaga    960
taggatacat atgcagtggg attttcggag acaatccacg ccctaatgat aagacaggca    1020
gttgtggtcc agtatcgtct aatggagcaa atggagtaaa agggttttca ttcaaatacg    1080
gcaatggtgt ttggataggg agaactaaaa gcattagttc aagaaacggt ttgagatga    1140 tttgggatcc gaacggatgg actgggacag acaataactt ctcaataaag caagatatcg    1200
taggaataaa tgagtggtca ggatatagcg ggagttttgt tcagcatcca gaactaacag    1260
ggctggattg tataagacct tgcttctggg ttgaactaat cagagggcga cccaaagaga    1320
acacaatctg gactagcggg agcagcatat cctttgtgg tgtaaacagt gacactgtgg    1380
gttggtcttg gccagacggt gctgagttgc catttaccat tgacaagtaa tttgttcaaa    1440
aaactccttg tttctact                                                 1458

<210> SEQ ID NO 86
<211> LENGTH: 1776
<212> TYPE: DNA
<213> ORGANISM: swine influenza virus

<400> SEQUENCE: 86
agcaaaagca ggggaaaat aaaagcaacc aaaatgaaag taaaactaat ggttctgtta     60
tgtacattta cagctacata tgcagacaca atatgtgtag ctaccatgc caacaactca    120 actgacactg ttgacacagt acttgagaag aatgtgacag tgacacactc tgtcaaccta    180
cttgaggaca gccacaatgg aaaactatgt ctactaaaag gaatagctcc actcaattg    240 ggtagttgca gcgttgccgg atggatctta ggaaacccag agtgcgaatt gctgatttcc    300
```

```
aaggaatctt ggtcctacat tgtagaaaca ccaaatcctg agaatggaac atgttaccca        360
gggtatttca cagactatga agaactgagg gagcaattga gttcagtatc ttcatttaag        420
aggttcgaaa tattccccaa agagagctca tggcccaacc acaccgtaac cggagtgtca        480
tcatcatgct cccataacgg gaaaagcagc ttctacagaa atttgctatg gctgacggtg        540
aagaacggtc tgtacccaaa cctgagcaag tcctatacaa acaaaaagga gaagaagtc         600 cttgtactat ggggtgttca tcacccatct aacataggg accaagggc cctctatcat         660 acagaaaatg cttatgtctc tgtagtgtct tcacattata gcagaagatt caccccagaa        720
atagccaaaa gacccaaggt gagaaatcag gaaggaagaa tcaactacta ctggaccctg        780
ctagaacccg gggatacaat aatatttgag gcaaatggaa atctaatagc accaaggtat        840
gccttcgaac tgagtaaggg ttttggatca ggaatcatca catcaaatgc accaatgggt        900
gaatgtaatg caaagtgtca aacacctcag ggagctataa acagcagtct cctttccag         960 aatgtacacc cagtaacaat aggagagtgc ccaaagtatg tcaaaagtgc aaaattaagg       1020
atggttacag gactaaggaa cacccccatcc attcaatcca gaggtttgtt tggagccatt       1080
gccggtttca ttgaaggagg gtggactgga atggtagatg gttggtatgg ttatcaccat       1140
cagaatgagc aaggatctgg gtatgctgca gaccaacaaa gcacacaaaa tgccattaat       1200
gggattacaa acaaggtgaa ttctgtgatt gaaaaaatga acactcaatt cacagctgtg       1260
ggcaaagaat tcaacaaact ggaaagaaga atggaaaact taaataaaaa ggttgatgat       1320
gggtttctag acatttggac atataatgca gaattgttag ttctactgga aaatgaaagg       1380
actttggatt tccatgactc caacgtgaag aatctgtatg agaaagtaaa aagccaatta       1440
aaaaataatg ccaaagaaat aggaaacggg tgttttgaat tctatcataa gtgtaacgat       1500
gaatgcatgg agagtgtgaa aaatggaact tatgactatc caaaatattc cgaagaatca       1560
aagttaaaca gggagaaaat tgatggagtg aaattggaat caatgggagt ctataatatc       1620
ctggcgatct actcaacagt cgccagttcc ctagttcttt tagtctccct gggggcaatc       1680
agcttctgga tgtgttccaa tgggtcttta cagtgtagaa tatgcatcta agaccagaat       1740
ttcagaaata taaggaaaaa caccttgtt tctact                                  1776

<210> SEQ ID NO 87
<211> LENGTH: 1458
<212> TYPE: DNA
<213> ORGANISM: swine influenza virus

<400> SEQUENCE: 87
agcaaaagca ggagtttaaa atgaatccaa atcaaaagat aataacgatt ggctctgttt         60
ctcttactat tgccacaatg tgcttcctta tgcaaattgc catcctggta actaatgtaa        120
cattgcactt caatcaatat gaatgcaact accccccaaa caaccaagta atactgtgtg        180
aaccaacaat aatagaaaga acataacag agatagtgta tctgaccaac accaccatag        240
agaaggaaat atgccccaaa ctagcagaat acagaaattg gtcaaagccg caatgtaaaa        300
ttacagggtt tgcaccttt tccaaggaca attcgattag ctttctgct ggtggggaca         360 tttgggtgac gagagaacct tatgtgtcat gcgatcctga taagtgttat cagtttgccc        420
ttggacaagg aacaacatta aacaacaggc attcaaatga cacagtacat gataggaccc        480
cttatcgaac cctattgatg aatgagttgg gtattccatt ccatttgggg accaaacaag        540
tgtgcatagc atggtccagc tcaagttgtc atgatggaaa agcatggctt cacgtttgta       600
```

```
ttactgggca tgatgaaaat gcaactgcca gcatcattta caatggaaga cttgtagata      660
gtattggttc atggtccaaa aaaatactca ggacacagga gtcggaatgt gtttgcatca      720
atggaacttg tacagtagta atgactgatg ggagtgcttc aggaatagct gacactaaaa      780
tattattcat tgaagagggg aaaatcgttc atattagccc attgttagga agtgctcagc      840
atgtagagga gtgctcctgt tatccccgat atcctggtgt cagatgcatc tgtagagaca      900
actggaaagg ttccaataga cccgtcgtag atataaatgt aaaggattat agcattgttt      960
ccagttatgt gtgctcagga cttgttggag atacacccag aaaagacgac agatccagca     1020
gtagcgattg tctgaatcct aacaatgagg aaggggggca tggagtgaaa ggctgggcct     1080
ttgatgatgg aaatgatgtg tggatgggaa gaacaatcaa cgagacgtta cgctcaggtt     1140
atgaaacctt caaagtcatt gaaggctggt ccaaacctaa ttccaaattg cagataaata     1200
ggcaagtcat agttgaaaga ggtgataggt ccggttattc tggcattttc tctgttgaag     1260
gcaaaagctg tatcaatcgg tgcttttatg tggagttgat aagaggaagg aaacaggaaa     1320
ctgcagtatg gtggacgtca aacagtattg ttgtgttttg tggcacctca ggtacatatg     1380
gaacaggctc atggcctgat ggggcgaaca tcaatctcat gcctgtataa tttattcaaa     1440
aaactccttg tttctact                                                   1458

<210> SEQ ID NO 88
<211> LENGTH: 1762
<212> TYPE: DNA
<213> ORGANISM: swine influenza virus

<400> SEQUENCE: 88
agcaaaagca gggatatttt ctattaacca tgaagactat cattgctttt agctgcgttt       60
tatgtttgat tttcgctcaa aaacttcccg gaagtgacaa cagcatggca acgctgtgcc      120
tgggacacca tgcagtacca aacggaacgt tagtgaaaac aatcacggat gaccaaattg      180
aagtgactaa tgctactgag ctggttcaga gttcctcaac aggtagaata tgcaacagtc      240
ctcaccaaat ccttgatggg aaaaattgca cactgataga tgctctattg ggagaccctc      300
attgtgatga cttccaaaac aaggaatggg accttttgt tgaacgaagc acagcctaca      360
gcaactgtta cccttattat gtgccggatt atgcctccct aggtcacta gttgcatcat      420 ccggcacccct ggaatttacc caagaaagct tcaattggac tggagttgct caagatggat      480
caagctatgc ttgcagaagg gaatctgtta acagtttctt tagtagattg aattggttgc      540 ataaaattgga ttacaaatat ccagcgctga aagtaactat gccgaacaat gacaaattcg      600
acaaattgta catttggggg gttcaccacc cgggcactga cagggaccaa accaacctat      660
atgttcaaac atcagggaga gttacagtct ccaccaaaag aagccaacaa actgtaatcc      720
caaatatcgg gtctagaccc tgggtaaggg gtgtctccag cataataagc atctattgga      780
caatagtaaa accgggagac atactttga ttaacagcac agggaatcta attgcccctc      840
ggggttactt caaattacaa agtggaaaaa gctcaataat gagatcagat gcacccattg      900
gcatctgcaa ttctgaatgc attactccaa atggaagcat tcccaacgac aaaccttttc      960
aaaatgtaaa caggatcact tatgggcct gtcccagata tgttaagcaa aacacctga     1020 aattggcaac aggaatgcgg aatgtaccag agaaacaaac cagaggcata tttggcgcaa     1080
tcgcaggttt catagaaaat ggttgggaag gatggtggga cggttggtac ggtttcaggc     1140
atcaaaattc tgaaggcaca ggacaagcag cagatcttaa aagcactcgt gcagcaatca     1200
accaaatcac cgggaaacta aatagagtaa tcaagaaaac gaacgagaaa ttccatcaga     1260
```

| | |
|---|---|
| tcgaaaaaga attctcagaa gtagaaggga gaattcagga cctagagaaa tacgttgaag | 1320 |
| acactaaaat agacctctgg tcttacaacg cggagcttct tgttgccctg gagaaccaac | 1380 |
| acacaattga tttaactgac tcagaaatga acaaactgtt cgaaagaaca agaaagcaat | 1440 |
| tgcgggaaaa tgctgaggac atgggcaatg gttgcttcaa aatataccac aaatgtgaca | 1500 |
| atgcctgcat aggatcaatc agaaatggaa cttatgacca tgatgtatac agagatgagg | 1560 |
| cattaaacaa tcggttccag atcaaaggtg ttcagctgaa gtcaggatac aaagattgga | 1620 |
| tcctatggat ttcctttgcc atatcatgct ttttgctttg tgttgttctg ctggggttca | 1680 |
| ttatgtgggc ctgccaaaaa ggcaacatta ggtgcaacat ttgcatttga gtgcattaat | 1740 |
| taaaaacacc cttgtttcta ct | 1762 |

<210> SEQ ID NO 89
<211> LENGTH: 1465
<212> TYPE: DNA
<213> ORGANISM: swine influenza virus

<400> SEQUENCE: 89

| | |
|---|---|
| agcaaaagca ggagtaaaga tgaatccaaa tcaaaagata ataacaattg gctctgtttc | 60 |
| tctcctcatt gccacaatat gcttccttat gcaaattgcc atcctggtaa ctactgtaac | 120 |
| attgcatttc aagcagcatg attgcaactc ctccccaaac aaccaagtaa tgctgtgtga | 180 |
| accaacaata atagaaagaa acacaacaga gattgtgtat ctgaccaaca taactataga | 240 |
| gaaggaaata tgccccaaac tagcagaata cagaaaattgg tcaaagcctc aatgtaacat | 300 |
| tacaggattt gcacctttct ctaaggacaa ttcgattcgg cttttccgctg gcggggacat | 360 |
| ctgggtgaca agagaacctt atgtgtcgtg cgatcctgac aagtgttatc aatttgccct | 420 |
| tgggcaggga acaacactaa acaacggtca ttcaaatgac actgtacatg ataggacccc | 480 |
| ttaccgaacc ctattgatga atgaattggg tgttccattt catttggga ccaggcaagt | 540 |
| gtgcatagca tggtccagct caagttgtca cgatggaaaa gcatggttgc atgtttgtat | 600 |
| aactggggat gataaaaatg caactgctag cttcatttac aatgggaggc ttgtagatag | 660 |
| tattggttca tggtccaaaa atatactcag aacccaggag tcggaatgcg tttgtatcaa | 720 |
| tggaacttgt acagtagtaa tgactgatgg gagcgcttca ggaaaagctg atactaaagt | 780 |
| actattcatt gaggagggaa aaatcgttca tattagcaca ttgtcaggaa gtgctcagca | 840 |
| tgtcgaggag tgctcctgtt atcctcgata tcctggtgtc agatgtgtct gtagagacaa | 900 |
| ctggaaaggc tccaacaggc ccatcgtaga cataaatgta aaggattata gtattgtttc | 960 |
| cagttatgta tgctcaggac ttgttggaga cacacccaga aaaacgaca gattcagcag | 1020 |
| tagccattgc caagatccta acaatgagga aggaggtcat ggggtgaaag gctgggcctt | 1080 |
| tgatgatgga aatgacgtgt ggatgggaag aacgatcaac gagaaattac gctcaggtta | 1140 |
| tgaaaccttc aaagtcatcg aaggctggtc caaacctaac tccaaattac agacaaatag | 1200 |
| gcaagtcata gttgaaagag gtaacaggtc cggttattct ggtattttct ccgttgaagg | 1260 |
| caaaagctgc atcaatcggt gttttttatgt ggagttgata aggggaagga aagaggaaac | 1320 |
| taaagtctgg tggacctcaa acagtattgt tgtgctttgt ggcacctcag gtacatatgg | 1380 |
| aacaggctca tggcctgatg gggcggatat caatctcatg cctatataac tttcgcaatt | 1440 |
| ttagaaaaaa ctccttgttt ctact | 1465 |

<210> SEQ ID NO 90

<211> LENGTH: 709
<212> TYPE: DNA
<213> ORGANISM: artificial sequence
<220> FEATURE:
<223> OTHER INFORMATION: NS-DO of TRIG H1N1 CDS + 5' and 3'UTR

<400> SEQUENCE: 90
agcaaaagca gggtgacaaa gacataatgg actccaatac tgtgtcaagc tttcaggtag 60
actgtttcct ttggcacatc cgcaaacgat ttgcagacaa tggattgggt gatgccccat 120
tccttgatcg gctccgccga gatcaaaaat cgttaaaagg acgtggaaat acgttatcgt 180
tagatataga aacggcgacg ctagtcggaa aacaaatagt cgaatggata ttaaaagaag 240
aatcgtcgga tatattaaaa atgacgatag cgtcggtccc gacgtcgcgt tatttagcgg 300
atatgacgtt agaagaaatg tcgcgtgatt ggtttatgtt aatgccgcgt caaaaaataa 360
taggaccgtt atgtgtccgt gtcgatcaag cgataatgga aaaaaatata atattaaaag 420
cgaatttttc ggtcatattt aatcgtttag aaacgttaat attattacgt gcgtttacgg 480
aggagggagc aatcgttgga gaaatttcac cattacctta tcttccagga catactaatg 540
aggatgtcaa aaatgcagtt ggggtcctca tcggagggct tgaatggaat ggtaacacgg 600
ttcgaggctc tgaaaatcta cagagattcg cttggagaaa ccataatgag gatgggagat 660
cttcactacc tccagaacag aaatgataaa aaacaccctt gtttctact 709

<210> SEQ ID NO 91
<211> LENGTH: 1778
<212> TYPE: DNA
<213> ORGANISM: artificial sequence
<220> FEATURE:
<223> OTHER INFORMATION: HA-DO of H1N1 CDS + 5' and 3'UTR

<400> SEQUENCE: 91
agcaaaagca ggggaaaata aaagcaacca aaatgaaggc aatactagta gttctgctat 60
atacatttgc aacctcaaat gcagacacat tatgtatagg ttatcatgcg aacaattcaa 120
cagatacggt cgatacggtc ttagaaaaaa atgtcacggt cacgcattcg gtcaatttat 180
tagaagataa acataatgga aaattatgta aattacgtgg agtcgcgccg ttacatttag 240
gaaaatgtaa tatagcggga tggatattag gaaatccgga atgtgaatcg ttatcgacgg 300
cgtcgtcgtg gtcgtatata gtcgaaacgt cgtcgtcggg aaatggaacg tgttatccgg 360
gagattttat agattatgaa gaattacgtg aacaattatc gtcggtctcg tcgtttgaac 420
gttttgaaat atttccgaaa acgtcgtcgt ggccgaatca tgaatcgaat aaaggagtca 480
cggcggcgtg tccgcatgcg ggagaaaaat cgttttataa aaatttaata tggctagtca 540
aaaaaggaaa ttcgtatccg aaattatcga aatcgtatat aaatgataaa ggaaaagaag 600
tcttagtctt atggggaata catcatccgt cgacgtcggc ggatcaacaa tcgttatatc 660
aaaatgcgga tgcgtatgtc tttgtcggaa cgtcgcgtta ttcgaaaaaa tttaaaccgg 720
aaatagcgat acgtccgaaa gtccgtgatc aagaaggacg catgaattat tattggacgc 780
tagtcgaacc gggagataaa ataacgtttg aagcgacggg aaatttagtc gtcccgcgtt 840
atgcgtttgc gatggaacgt aatgcgggat cgggaataat aatatcggat acgccggtcc 900
atgattgtaa tacgacgtgt caaacgccga aaggagcgat aaatacgtcg ttaccgtttc 960
aaaatataca tccgataacg ataggaaaat gtccgaaata tgtcaaatcg acgaaattac 1020
gtttagcgac gggattacgt aatgtcccgt cgatacaatc gcgtggatta tttggagcga 1080
tagcgggatt tatagaagga ggatggacgg gaatggtcga tggatggtat ggatatcatc 1140

```
atcaaaatga acaaggatcg ggatatgcgg cggatttaaa atcgacgcaa aatgcgatag      1200
atgaaataac gaataaagtc aattcggtca tagaaaaaat gaatacgcaa tttacggcgg      1260
tcggaaaaga atttaatcat ttagaaaaac gtatagaaaa tttaaataaa aaagtcgatg      1320
atggattttt agatatatgg acgtataatg cggaattatt agtcttatta gaaaatgaac      1380
gtacgttaga ttatcatgat tcgaatgtca aaaatttata tgaaaaagtc cgttcgcaat      1440
taaaaaataa tgcgaaagaa ataggaaatg gatgttttga atttatcat aaatgtgata       1500 atacgtgtat ggaatcggtc aaaaatggaa cgtatgatta ccgaaatat tcggaagaag       1560 cgaaattaaa tcgtgaagaa atagatgag tcaaattaga atcgacgcgt atatatcaaa       1620
tattagcgat atattcgacg gtcgcgtcgt cattggtact ggtagtctcc ctgggggcaa      1680
tcagtttctg gatgtgctct aatgggtctc tacagtgtag aatatgtatt taacattagg     1740
atttcagaaa catgagaaaa aacacccttg tttctact                              1778
```

<210> SEQ ID NO 92
<211> LENGTH: 1458
<212> TYPE: DNA
<213> ORGANISM: artificial sequence
<220> FEATURE:
<223> OTHER INFORMATION: NA-DO of H1N1 CDS + 5' and 3'UTR

<400> SEQUENCE: 92
agcaaaagca ggagtttaaa atgaatccaa accaaaagat aataaccatt ggttcggtct 60
gtatgacaat tggaatggct aacttaatat tacaaattgg aaacataatc tcaatatgga 120
tttcgcattc gatacaatta ggaaatcaaa atcaaataga aacgtgtaat caatcggtca 180
taacgtatga aaataatacg tgggtcaatc aaacgtatgt caatatatcg aatacgaatt 240
ttgcggcggg acaatcggtc gtatcggtca aattagcggg aaattcgtcg ttatgtccgg 300
tctcgggatg ggcgatatat tcgaaagata attcggtccg tataggatcg aaaggagatg 360
tctttgtcat acgtgaaccg tttatatcgt gttcgccgtt agaatgtcgt acgttttttt 420
taacgcaagg agcgttatta aatgataaac attcgaatgg aacgataaaa gatcgttcgc 480
cgtatcgtac gttaatgtcg tgtccgatag gagaagtccc gtcgccgtat aattcgcgtt 540
ttgaatcggt cgcgtggtcg gcgtcggcgt gtcatgatgg aataaattgg ttaacgatag 600
gaatatcggg accggataat ggagcggtcg cggtcttaaa atataatgga ataataacgg 660
atacgataaa atcgtggcgt aataatatat tacgtacgca agaatcggaa tgtgcgtgtg 720
tcaatggatc gtgttttacg gtcatgacgg atggaccgtc gaatggacaa gcgtcgtata 780
aaatatttcg tatagaaaaa ggaaaaatag tcaaatcggt cgaaatgaat gcgccgaatt 840
atcattatga agaatgttcg tgttatccgg attcgtcgga aataacgtgt gtctgtcgtg 900
ataattggca tggatcgaat cgtccgtggg tctcgtttaa tcaaaattta gaatatcaaa 960
taggatatat atgttcggga atatttggag ataatccgcg tccgaatgat aaaacgggat 1020
cgtgtggacc ggtctcgtcg aatggagcga atggagtcaa aggattttcg tttaaatatg 1080
gaaatggagt ctggatagga cgtacgaaat cgatatcgtc gcgtaatgga tttgaaatga 1140
tatgggatcc gaatggatgg acgggaacgg ataataattt ttcgataaaa caagatatag 1200
tcggaataaa tgaatggtcg ggatattcgg gatcgtttgt ccaacatccg gaattaacgg 1260
gattagattg tatacgtccg tgtttttggg tcgaattaat acgtggacgt ccgaaagaaa 1320
atacgatatg gactagcggg agcagcatat ccttttgtgg tgtaaacagt gacactgtgg 1380

```
gttggtcttg gccagacggt gctgagttgc catttaccat tgacaagtaa tttgttcaaa    1440
aaactccttg tttctact                                                  1458

<210> SEQ ID NO 93
<211> LENGTH: 1776
<212> TYPE: DNA
<213> ORGANISM: artificial sequence
<220> FEATURE:
<223> OTHER INFORMATION: HA-DO of H1N2 CDS + 5' and 3'UTR

<400> SEQUENCE: 93
agcaaaagca ggggaaaaat aaaagcaacc aaaatgaaag taaaactaat ggttctgtta      60
tgtacattta cagctacata tgcagacaca atatgtgtag ctaccatgc caacaactca     120 actgatacgg tcgatacggt cttagaaaaa atgtcacgg tcacgcattc ggtcaattta     180
ttagaagatt cgcataatgg aaaattatgt ttattaaaag aatagcgcc gttacaatta     240 ggatcgtgtt cggtcgcggg atggatatta ggaaatccgg aatgtgaatt attaatatcg     300
aaagaatcgt ggtcgtatat agtcgaaacg ccgaatccgg aaaatggaac gtgttatccg     360
ggatatttta cggattatga agaattacgt gaacaattat cgtcggtctc gtcgtttaaa     420
cgttttgaaa tatttccgaa agaatcgtcg tggccgaatc atacggtcac gggagtctcg     480
tcgtcgtgtt cgcataatgg aaaatcgtcg ttttatcgta atttattatg gttaacggtc     540
aaaaatggat tatatccgaa tttatcgaaa tcgtatacga ataaaaaga aaagaagtc     600 ttagtcttat ggggagtcca tcatccgtcg aatataggag atcaacgtgc gttatatcat     660
acggaaaatg cgtatgtctc ggtcgtatcg tcgcattatt cgcgtcgttt tacgccggaa     720
atagcgaaac gtccgaaagt ccgtaatcaa gaaggacgta taaattatta ttggacgtta     780
ttagaaccgg gagatacgat aatatttgaa gcgaatggaa atttaatagc gccgcgttat     840
gcgtttgaat tatcgaaagg atttggatcg ggaataataa cgtcgaatgc gccgatggga     900
gaatgtaatg cgaaatgtca aacgccgcaa ggagcgataa attcgtcgtt accgtttcaa     960
aatgtccatc cggtcacgat aggagaatgt ccgaaatatg tcaaatcggc gaaattacgt    1020
atggtcacgg gattacgtaa tacgccgtcg atacaatcgc gtggattatt tggagcgata    1080
gcgggattta tagaaggagg atggacggga atggtcgatg gatggtatgg atatcatcat    1140
caaaatgaac aaggatcggg atatgcggcg gatcaacaat cgacgcaaaa tgcgataaat    1200
ggaataacga ataaagtcaa ttcggtcata gaaaaaatga atacgcaatt tacggcggtc    1260
ggaaaagaat ttaataaatt agaacgtcgt atggaaaatt taaataaaaa agtcgatgat    1320
ggatttttag atatatggac gtataatgcg gaattattag tcttattaga aaatgaacgt    1380
acgttagatt tcatgattc gaatgtcaaa aattttatatg aaaaagtcaa atcgcaatta    1440
aaaaataatg cgaaagaaat aggaaatgga tgttttgaat tttatcataa atgtaatgat    1500
gaatgtatgg aatcggtcaa aaatggaacg tatgattatc cgaaatattc ggaagaatcg    1560
aaattaaatc gtgaaaaaat agatggagtc aaattagaat cgatgggagt ctataatata    1620
ttagcgatat attcgacggt cgcgtcgtcc ctagttcttt tagtctccct gggggcaatc    1680
agcttctgga tgtgttccaa tgggtcttta cagtgtagaa tatgcatcta agaccagaat    1740
ttcagaaata taaggaaaaa caccccttgtt tctact                             1776

<210> SEQ ID NO 94
<211> LENGTH: 1458
<212> TYPE: DNA
<213> ORGANISM: artificial sequence
```

```
<220> FEATURE:
<223> OTHER INFORMATION: NA-DO of H1N2 CDS + 5' and 3'UTR

<400> SEQUENCE: 94
agcaaaagca ggagtttaaa atgaatccaa atcaaaagat aataacgatt ggctctgttt      60
ctcttactat tgccacaatg tgcttcctta tgcaaattgc catcctggta actaatgtaa     120
cattgcactt caatcaatat gaatgtaatt atccgccgaa taatcaagtc atattatgtg     180
aaccgacgat aatagaacgt aatataacgg aaatagtcta tttaacgaat acgacgatag     240
aaaaagaaat atgtccgaaa ttagcggaat atcgtaattg gtcgaaaccg caatgtaaaa     300
taacgggatt tgcgccgttt tcgaaagata attcgatacg tttatcggcg ggaggagata     360
tatgggtcac gcgtgaaccg tatgtctcgt gtgatccgga taaatgttat caatttgcgt     420
taggacaagg aacgacgtta aataatcgtc attcgaatga tacggtccat gatcgtacgc     480
cgtatcgcac gttattaatg aatgaattag gaataccgtt tcatttagga acgaaacaag     540
tctgtatagc gtggtcgtcg tcgtcgtgtc atgatggaaa agcgtggtta catgtctgta     600
taacgggaca tgatgaaaat gcgacggcgt cgataatata taatggacgt ttagtcgatt     660
cgataggatc gtggtcgaaa aaaatattac gtacgcaaga atcggaatgt gtctgtataa     720
atggaacgtg tacggtcgtc atgacggatg gatcggcgtc gggaatagcg gatacgaaaa     780
tattatttat agaagaagga aaaatagtcc atatatcgcc gttattagga tcggcgcaac     840
atgtcgaaga atgttcgtgt tatccgcgtt atccgggagt ccgttgtata tgtcgtgata     900
attggaaagg atcgaatcgt ccggtcgtcg atataaatgt caaagattat tcgatagtct     960
cgtcgtatgt ctgttcggga ttagtcggag atacgccgcg taaagatgat cgttcgtcgt    1020
cgtcggattg tttaaatccg aataatgaag aggaggaaca tggagtcaaa ggatgggcgt    1080
ttgatgatgg aaatgatgtc tggatgggac gtacgataaa tgaaacgtta cgttcgggat    1140
atgaaacgtt taaagtcata gaaggatggt cgaaaccgaa ttcgaaatta caaataaatc    1200
gtcaagtcat agtcgaacgt ggagatcgtt cgggatattc gggaatattt tcggtcgaag    1260
gaaaatcgtg tataaatcgt tgtttttatg tcgaattaat acgtggacgt aaacaagaaa    1320
ctgcagtatg gtggacgtca aacagtattg ttgtgttttg tggcacctca ggtacatatg    1380
gaacaggctc atggcctgat ggggcgaaca tcaatctcat gcctgtataa tttattcaaa    1440
aaactccttg tttctact                                                  1458

<210> SEQ ID NO 95
<211> LENGTH: 1762
<212> TYPE: DNA
<213> ORGANISM: artificial sequence
<220> FEATURE:
<223> OTHER INFORMATION: HA-DO of H3N2 CDS + 5' and 3'UTR

<400> SEQUENCE: 95
agcaaaagca ggggatattt ctattaacca tgaagactat cattgctttt agctgcgttt      60
tatgtttgat tttcgctcaa aaacttcccg gaagtgacaa cagcatggca acgctgtgct     120
taggacatca tgcggtcccg aatggaacgt tagtcaaaac gataacggat gatcaaatag     180
aagtcacgaa tgcgacggaa ttagtccaat cgtcgtcgac gggacgtata tgtaattcgc     240
cgcatcaaat attagatgga aaaattgta cgttaataga tgcgttatta ggagatccgc     300
attgtgatga ttttcaaaat aaagaatggg atttatttgt cgaacgttcg acggcgtatt     360
cgaattgtta tccgtattat gtcccggatt atgcgtcgtt acgttcgtta gtcgcgtcgt     420
```

```
cgggaacgtt agaatttacg caagaatcgt ttaattggac gggagtcgcg caagatggat    480
cgtcgtatgc gtgtcgtcgt gaatcggtca attcgttttt ttcgcgttta aattggttac    540
ataaattaga ttataaatat ccggcgttaa aagtcacgat gccgaataat gataaatttg    600
ataaattata tatatgggga gtccatcatc cgggaacgga tcgtgatcaa acgaatttat    660
atgtccaaac gtcgggacgt gtcacggtct cgacgaaacg ttcgcaacaa acggtcatac    720
cgaatatagg atcgcgtccg tgggtccgtg gagtctcgtc gataatatcg atatattgga    780
cgatagtcaa accgggagat atattattaa taaattcgac gggaaattta atagcgccgc    840
gtggatattt taaattacaa tcgggaaaat cgtcgataat gcgttcggat gcgccgatag    900
gaatatgtaa ttcggaatgt ataacgccga atggatcgat accgaatgat aaaccgtttc    960
aaaatgtcaa tcgtataacc tatggagcgt gtccgcgtta tgtcaaacaa atacgttaa   1020 aattagcgac gggaatgcgt aatgtcccgg aaaaacaaac gcgtggaata tttggagcga   1080
tagcgggatt tatagaaaat ggatgggaag aatggtcga tggatggtat ggatttcgtc   1140
atcaaaattc ggaaggaacg ggacaagcgg cggatttaaa atcgacgcgt gcggcgataa   1200
atcaaataac gggaaaatta aatcgtgtca taaaaaaac gaatgaaaaa tttcatcaaa   1260
tagaaaaaga attttcggaa gtcgaaggac gtatacaaga tttagaaaaa tatgtcgaag   1320
atacgaaaat agatttatgg tcgtataatg cggaattatt agtcgcgtta gaaaatcaac   1380
atacgataga tttaacggat tcggaaatga ataaattatt gaacgtacg cgtaaacaat   1440 tacgtgaaaa tgcggaagat atgggaaatg gatgttttaa aatatatcat aaatgtgata   1500
atgcgtgtat aggatcgata cgtaatggaa cgtatgatca tgatgtctat cgtgatgaag   1560
cgttaaataa tcgttttcaa ataaaaggag tccaattaaa atcgggatat aaagattgga   1620
tattatggat atcgtttgcg atatcgtgct ttttgctttg tgttgttctg ctggggttca   1680
ttatgtgggc ctgccaaaaa ggcaacatta ggtgcaacat ttgcatttga gtgcattaat   1740
taaaaacacc cttgtttcta ct                                             1762

<210> SEQ ID NO 96
<211> LENGTH: 1465
<212> TYPE: DNA
<213> ORGANISM: artificial sequence
<220> FEATURE:
<223> OTHER INFORMATION: NA-DO of H3N2 CDS + 5' and 3'UTR

<400> SEQUENCE: 96
agcaaaagca ggagtaaaga tgaatccaaa tcaaaagata ataacaattg gctctgtttc      60
tctcctcatt gccacaatat gcttccttat gcaaattgcc atcctggtaa ctactgtaac    120
attgcatttc aaacaacatg attgtaattc gtcgccgaat aatcaagtca tgttatgtga    180
accgacgata atagaacgta atacgacgga aatagtctat ttaacgaata taacgataga    240
aaaagaaata tgtccgaaat tagcggaata tcgtaattgg tcgaaaccgc aatgtaatat    300
aacgggattt gcgccgtttt cgaaagataa ttcgatacgt ttatcggcgg gaggagatat    360
atgggtcacg cgtgaaccgt atgtctcgtg tgatccggat aaatgttatc aatttgcgtt    420
aggacaagga acgacgttaa ataatggaca ttcgaatgat acggtccatg atcgtacgcc    480
gtatcgcacg ttattaatga atgaattagg agtcccgttt catttaggaa cgcgtcaagt    540
ctgtatagcg tggtcgtcgt cgtcgtgtca tgatggaaaa gcgtggttac atgtctgtat    600
aacgggagat gataaaaatg cgacggcgtc gtttatatat aatggacgtt tagtcgattc    660
gataggatcg tggtcgaaaa atatattacg tacgcaagaa tcggaatgtg tctgtataaa    720
```

```
tggaacgtgt acggtcgtca tgacggatgg atcggcgtcg ggaaaagcgg atacgaaagt    780
cttatttata gaagaaggaa aaatagtcca tatatcgacg ttatcgggat cggcgcaaca    840
tgtcgaagaa tgttcgtgtt atccgcgtta tccgggagtc cgttgtgtct gtcgtgataa    900
ttggaaagga tcgaatcgtc cgatagtcga tataaatgtc aaagattatt cgatagtctc    960
gtcgtatgtc tgttcgggat tagtcggaga tacgccgcgt aaaaatgatc gttttcgtc    1020 gtcgcattgt caagatccga ataatgaaga aggaggacat ggagtcaaag gatgggcgtt    1080
tgatgatgga aatgatgtct ggatgggacg tacgataaat gaaaaattac gttcgggata    1140
tgaaacgttt aaagtcatag aaggatggtc gaaaccgaat tcgaaattac aaacgaatcg    1200
tcaagtcata gtcgaacgtg aaatcgttc gggatattcg gaatatttt cggtcgaagg    1260 aaaatcgtgt ataaatcgtt gttttatgt cgaattaata cgtggacgta agaagaaac    1320 taaagtctgg tggacctcaa acagtattgt tgtgctttgt ggcacctcag gtacatatgg    1380
aacaggctca tggcctgatg gggcggatat caatctcatg cctatataac tttcgcaatt    1440
ttagaaaaaa ctccttgttt ctact                                         1465
```

<210> SEQ ID NO 97
<211> LENGTH: 28
<212> TYPE: DNA
<213> ORGANISM: Artificial Sequence
<220> FEATURE:
<223> OTHER INFORMATION: Bm-HA-Forward Primer

<400> SEQUENCE: 97
tattcgtctc agggagcaaa agcagggg                                          28

<210> SEQ ID NO 98
<211> LENGTH: 21
<212> TYPE: DNA
<213> ORGANISM: Artificial Sequence
<220> FEATURE:
<223> OTHER INFORMATION: 3' Reverse Primer

<400> SEQUENCE: 98
gtagcctaca catattgtgt c                                                 21

<210> SEQ ID NO 99
<211> LENGTH: 47
<212> TYPE: DNA
<213> ORGANISM: Artificial Sequence
<220> FEATURE:
<223> OTHER INFORMATION: 5' Forward Primer

<400> SEQUENCE: 99
gacacaatat gtgtaggcta cgatatctta gcgatatatt cgacggt                     47

<210> SEQ ID NO 100
<211> LENGTH: 35
<212> TYPE: DNA
<213> ORGANISM: Artificial Sequence
<220> FEATURE:
<223> OTHER INFORMATION: Bm-HA-R

<400> SEQUENCE: 100
atatcgtctc gtattagtag aaacaagggt gtttt                                  35

<210> SEQ ID NO 101
<211> LENGTH: 29
<212> TYPE: DNA

```
<213> ORGANISM: Artificial Sequence
<220> FEATURE:
<223> OTHER INFORMATION: H3 Ecto Domain Forward Primer

<400> SEQUENCE: 101
ctacatatgc acaaaaactt cccggaagt                                      29

<210> SEQ ID NO 102
<211> LENGTH: 26
<212> TYPE: DNA
<213> ORGANISM: Artificial Sequence
<220> FEATURE:
<223> OTHER INFORMATION: H3 Ecto Domain Reverse Primer

<400> SEQUENCE: 102
taagatatct ttatatcccg atttta                                         26

<210> SEQ ID NO 103
<211> LENGTH: 21
<212> TYPE: DNA
<213> ORGANISM: Artificial Sequence
<220> FEATURE:
<223> OTHER INFORMATION: Overlapping sequence of SEQ ID NOs: 98 & 99.

<400> SEQUENCE: 103
gacacaatat gtgtaggcta c                                              21

<210> SEQ ID NO 104
<211> LENGTH: 325
<212> TYPE: DNA
<213> ORGANISM: Artificial Sequence
<220> FEATURE:
<223> OTHER INFORMATION: 3'UTR, signal sequence (SS), transmembrane
      domain (TMD), cytoplasmic tail domain (CTD), and 5'UTR of HA
      segment (H1N2-DO)

<400> SEQUENCE: 104
tattcgtctc agggagcaaa agcaggggaa aaataaaagc aaccaaaatg aaagtaaaac     60
taatggttct gttatgtaca tttacagcta catatgcaga cacaatatgt gtaggctacg    120
atatcttagc gatatattcg acggtttagc gatatattcg acggtcgcgt cgtccctagt    180
tcttttagtc tccctggggg caatcagctt ctggatgtgt tccaatgggt ctttacagtg    240
tagaatatgc atctaagacc agaatttcag aaatataagg aaaaacaccc ttgtttctac    300
taatacgaga cgatatatcg gatcc                                          325

<210> SEQ ID NO 105
<211> LENGTH: 2100
<212> TYPE: DNA
<213> ORGANISM: Artificial Sequence
<220> FEATURE:
<223> OTHER INFORMATION: HA-DO (H1-H3 chimera) - Nucleotides 351 to 2450
      of pHW2000

<400> SEQUENCE: 105
ggctaactag agaacccact gcttactggc ttatcgaaat taatacgact cactataggg     60
agacccaagc tgttaacgct agcagttaac cggagtactg gtcgacctcc gaagttgggg    120
gggagcaaaa gcaggggaaa aataaaagca accaaaatga aagtaaaact aatggttctg    180
ttatgtacat ttacagctac atatgcacaa aaacttcccg gaagtgacaa cagcatggca    240
acgctgtgct taggacatca tgcggtcccg aatggaacgt tagtcaaaac gataacggat    300
gatcaaatag aagtcacgaa tgcgacggaa ttagtccaat cgtcgtcgac gggacgtata    360
```

-continued

```
tgtaattcgc cgcatcaaat attagatgga aaaaattgta cgttaataga tgcgttatta    420
ggagatccgc attgtgatga ttttcaaaat aaagaatggg atttatttgt cgaacgttcg    480
acggcgtatt cgaattgtta tccgtattat gtcccggatt atgcgtcgtt acgttcgtta    540
gtcgcgtcgt cgggaacgtt agaatttacg caagaatcgt ttaattggac gggagtcgcg    600
caagatggat cgtcgtatgc gtgtcgtcgt gaatcggtca attcgttttt ttcgcgttta    660
aattggttac ataaattaga ttataaatat ccggcgttaa aagtcacgat gccgaataat    720
gataaatttg ataaattata tatatgggga gtccatcatc cgggaacgga tcgtgatcaa    780
acgaatttat atgtccaaac gtcgggacgt gtcacggtct cgacgaaacg ttcgcaacaa    840
acggtcatac cgaatatagg atcgcgtccg tgggtccgtg gagtctcgtc gataatatcg    900
atatattgga cgatagtcaa accgggagat atattattaa taaattcgac gggaaattta    960
atagcgccgc gtggatattt taaattacaa tcgggaaaat cgtcgataat gcgttcggat   1020
gcgccgatag gaatatgtaa ttcggaatgt ataacgccga atggatcgat accgaatgat   1080
aaaccgtttc aaaatgtcaa tcgtataacc tatggagcgt gtccgcgtta tgtcaaacaa   1140
aatacgttaa aattagcgac gggaatgcgt aatgtcccgg aaaaacaaac gcgtggaata   1200
tttggagcga tagcgggatt tatagaaaat ggatgggaag gaatggtcga tggatggtat   1260
ggatttcgtc atcaaaattc ggaaggaacg ggacaagcgg cggatttaaa atcgacgcgt   1320
gcggcgataa atcaaataac gggaaaatta aatcgtgtca taaaaaaaac gaatgaaaaa   1380
tttcatcaaa tagaaaaaga attttcggaa gtcgaaggac gtatacaaga tttagaaaaa   1440
tatgtcgaag atacgaaaat agatttatgg tcgtataatg cggaattatt agtcgcgtta   1500
gaaaatcaac atacgataga tttaacggat tcggaaatga ataaattatt tgaacgtacg   1560
cgtaaacaat tacgtgaaaa tgcggaagat atgggaaatg gatgttttaa aatatatcat   1620
aaatgtgata atgcgtgtat aggatcgata cgtaatggaa cgtatgatca tgatgtctat   1680
cgtgatgaag cgttaaataa tcgttttcaa ataaaaggag tccaattaaa atcgggatat   1740
aaagatatct tagcgatata ttcgacggtc gcgtcgtccc tagttctttt agtctccctg   1800
ggggcaatca gcttctggat gtgttccaat gggtctttac agtgtagaat atgcatctaa   1860
gaccagaatt tcagaaatat aaggaaaaac acccttgttt ctactaataa cccggcggcc   1920
caaaatgccg actcggagcg aaagatatac ctcccccggg gccgggaggt cgcgtcaccg   1980
accacgccgc cggcccaggc gacgcgcgac acggacacct gtccccaaaa acgccaccat   2040
cgcagccaca cacggagcgc ccggggccct ctggtcaacc ccaggacaca cgcgggagca   2100
```

<210> SEQ ID NO 106
<211> LENGTH: 567
<212> TYPE: PRT
<213> ORGANISM: Artificial Sequence
<220> FEATURE:
<223> OTHER INFORMATION: HA-DO (H1-H3 chimera)

<400> SEQUENCE: 106

```
Met Lys Val Lys Leu Met Val Leu Leu Cys Thr Phe Thr Ala Thr Tyr
1               5                   10                  15

Ala Gln Lys Leu Pro Gly Ser Asp Asn Ser Met Ala Thr Leu Cys Leu
            20                  25                  30

Gly His His Ala Val Pro Asn Gly Thr Leu Val Lys Thr Ile Thr Asp
        35                  40                  45

Asp Gln Ile Glu Val Thr Asn Ala Thr Glu Leu Val Gln Ser Ser Ser
    50                  55                  60
```

```
Thr Gly Arg Ile Cys Asn Ser Pro His Gln Ile Leu Asp Gly Lys Asn
 65                  70                  75                  80

Cys Thr Leu Ile Asp Ala Leu Leu Gly Asp Pro His Cys Asp Asp Phe
                 85                  90                  95

Gln Asn Lys Glu Trp Asp Leu Phe Val Glu Arg Ser Thr Ala Tyr Ser
            100                 105                 110

Asn Cys Tyr Pro Tyr Tyr Val Pro Asp Tyr Ala Ser Leu Arg Ser Leu
        115                 120                 125

Val Ala Ser Ser Gly Thr Leu Glu Phe Thr Gln Glu Ser Phe Asn Trp
    130                 135                 140

Thr Gly Val Ala Gln Asp Gly Ser Ser Tyr Ala Cys Arg Arg Glu Ser
145                 150                 155                 160

Val Asn Ser Phe Phe Ser Arg Leu Asn Trp Leu His Lys Leu Asp Tyr
                165                 170                 175

Lys Tyr Pro Ala Leu Lys Val Thr Met Pro Asn Asn Asp Lys Phe Asp
            180                 185                 190

Lys Leu Tyr Ile Trp Gly Val His His Pro Gly Thr Asp Arg Asp Gln
        195                 200                 205

Thr Asn Leu Tyr Val Gln Thr Ser Gly Arg Val Thr Val Ser Thr Lys
    210                 215                 220

Arg Ser Gln Gln Thr Val Ile Pro Asn Ile Gly Ser Arg Pro Trp Val
225                 230                 235                 240

Arg Gly Val Ser Ser Ile Ile Ser Ile Tyr Trp Thr Ile Val Lys Pro
                245                 250                 255

Gly Asp Ile Leu Leu Ile Asn Ser Thr Gly Asn Leu Ile Ala Pro Arg
            260                 265                 270

Gly Tyr Phe Lys Leu Gln Ser Gly Lys Ser Ser Ile Met Arg Ser Asp
        275                 280                 285

Ala Pro Ile Gly Ile Cys Asn Ser Glu Cys Ile Thr Pro Asn Gly Ser
    290                 295                 300

Ile Pro Asn Asp Lys Pro Phe Gln Asn Val Asn Arg Ile Thr Tyr Gly
305                 310                 315                 320

Ala Cys Pro Arg Tyr Val Lys Gln Asn Thr Leu Lys Leu Ala Thr Gly
                325                 330                 335

Met Arg Asn Val Pro Glu Lys Gln Thr Arg Gly Ile Phe Gly Ala Ile
            340                 345                 350

Ala Gly Phe Ile Glu Asn Gly Trp Glu Gly Met Val Asp Gly Trp Tyr
        355                 360                 365

Gly Phe Arg His Gln Asn Ser Glu Gly Thr Gly Gln Ala Ala Asp Leu
    370                 375                 380

Lys Ser Thr Arg Ala Ala Ile Asn Gln Ile Thr Gly Lys Leu Asn Arg
385                 390                 395                 400

Val Ile Lys Lys Thr Asn Glu Lys Phe His Gln Ile Glu Lys Glu Phe
                405                 410                 415

Ser Glu Val Glu Gly Arg Ile Gln Asp Leu Glu Lys Tyr Val Glu Asp
            420                 425                 430

Thr Lys Ile Asp Leu Trp Ser Tyr Asn Ala Glu Leu Leu Val Ala Leu
        435                 440                 445

Glu Asn Gln His Thr Ile Asp Leu Thr Asp Ser Glu Met Asn Lys Leu
    450                 455                 460

Phe Glu Arg Thr Arg Lys Gln Leu Arg Glu Asn Ala Glu Asp Met Gly
465                 470                 475                 480
```

```
Asn Gly Cys Phe Lys Ile Tyr His Lys Cys Asp Asn Ala Cys Ile Gly
                485                 490                 495

Ser Ile Arg Asn Gly Thr Tyr Asp His Asp Val Tyr Arg Asp Glu Ala
            500                 505                 510

Leu Asn Asn Arg Phe Gln Ile Lys Gly Val Gln Leu Lys Ser Gly Tyr
            515                 520                 525

Lys Asp Ile Leu Ala Ile Tyr Ser Thr Val Ala Ser Ser Leu Val Leu
            530                 535                 540

Leu Val Ser Leu Gly Ala Ile Ser Phe Trp Met Cys Ser Asn Gly Ser
545                 550                 555                 560

Leu Gln Cys Arg Ile Cys Ile
                565
```

<210> SEQ ID NO 107
<211> LENGTH: 3259
<212> TYPE: DNA
<213> ORGANISM: Artificial Sequence
<220> FEATURE:
<223> OTHER INFORMATION: pHW2000 plasmid

<400> SEQUENCE: 107

| | | |
|---|---|---|
| actcactata gggagaccca agctgttaac gctagcagtt aaccggagta ctggtcgacc | 60 |
| tccgaagttg ggggggagga gacggtaccg tctccaataa cccggcggcc caaaatgccg | 120 |
| actcggagcg aaagatatac ctcccccggg gccggggagg cgcgtcaccg accacgccgc | 180 |
| cggcccaggc gacgcgcgac acggacacct gtccccaaaa acgccaccat cgcagccaca | 240 |
| cacggagcgc ccggggcccct ctggtcaacc ccaggacaca cgcgggagca cgccggggcc | 300 |
| ggggacgccc tcccggcggt cacctaaatg ctagagctcg ctgatcagcc tcgactgtgc | 360 |
| cttctagttg ccagccatct gttgtttgcc cctcccccgt gccttccttg accctggaag | 420 |
| gtgccactcc cactgtcctt tcctaataaa atgaggaaat tgcatcgcat tgtctgagta | 480 |
| ggtgtcattc tattctgggg ggtggggtgg gcaggacag caaggggag gattgggaag | 540 |
| acaatagcag gcatgctggg gatgcggtgg gctctatggc ttctgaggcg gaaagaacca | 600 |
| gctgcattaa tgaatcggcc aacgcgcggg gagaggcggt ttgcgtattg ggcgctcttc | 660 |
| cgcttgatga cctctagcta gagcttggcg taatcatggt catagctgtt tcctgtgtga | 720 |
| aattgttatc cgctcacaat tccacacaac atacgagccg gaagcataaa gtgtaaagcc | 780 |
| tggggtgcct aatgagtgag ctaactcaca ttaattgcgt tgcgctcact gcccgctttc | 840 |
| cagtcgggaa acctgtcgtg ccagctgcat taatgaatcg gccaacgcgc ggggagaggc | 900 |
| ggtttgcgta ttgggcgctc ttccgcttcc tcgctcactg actcgctgcg ctcggtcgtt | 960 |
| cggctgcggc gagcggtatc agctcactca aaggcggtaa tacggttatc cacagaatca | 1020 |
| ggggataacg caggaaagaa catgtgagca aaaggccagc aaaaggccag gaaccgtaaa | 1080 |
| aaggccgcgt tgctggcgtt tttccatagg ctccgccccc ctgacgagca tcacaaaaat | 1140 |
| cgacgctcaa gtcagaggtg gcgaaacccg acaggactat aaagatacca ggcgtttccc | 1200 |
| cctggaagct ccctcgtgcg ctctcctgtt ccgaccctgc cgcttaccgg atacctgtcc | 1260 |
| gcctttctcc cttcgggaag cgtggcgctt tctcatagct cacgctgtag gtatctcagt | 1320 |
| tcggtgtagg tcgttcgctc caagctgggc tgtgtgcacg aacccccccgt tcagcccgac | 1380 |
| cgctgcgcct tatccggtaa ctatcgtctt gagtccaacc cggtaagaca cgacttatcg | 1440 |
| ccactggcag cagccactgg taacaggatt agcagagcga ggtatgtagg cggtgctaca | 1500 |
| gagttcttga agtggtggcc taactacggc tacactagaa gaacagtatt tggtatctgc | 1560 |

```
gctctgctga agccagttac cttcggaaaa agagttggta gctcttgatc cggcaaacaa     1620
accaccgctg gtagcggtgg ttttttttgtt tgcaagcagc agattacgcg cagaaaaaaa     1680
ggatctcaag aagatccttt gatcttttct acggggtctg acgctcagtg gaacgaaaac     1740
tcacgttaag ggattttggt catgagatta tcaaaaagga tcttcaccta gatccttta      1800 aattaaaaat gaagttttaa atcaatctaa agtatatatg agtaaacttg gtctgacagt     1860
taccaatgct taatcagtga ggcacctatc tcagcgatct gtctatttcg ttcatccata     1920
gttgcctgac tccccgtcgt gtagataact acgatacggg agggcttacc atctggcccc     1980
agtgctgcaa tgataccgcg agacccacgc tcaccggctc cagatttatc agcaataaac     2040
cagccagccg gaagggccga gcgcagaagt ggtcctgcaa ctttatccgc ctccatccag     2100
tctattaatt gttgccggga agctagagta agtagttcgc cagttaatag tttgcgcaac     2160
gttgttgcca ttgctacagg catcgtggtg tcacgctcgt cgtttggtat ggcttcattc     2220
agctccggtt cccaacgatc aaggcgagtt acatgatccc ccatgttgtg caaaaaagcg     2280
gttagctcct tcggtcctcc gatcgttgtc agaagtaagt tggccgcagt gttatcactc     2340
atggttatgg cagcactgca taattctctt actgtcatgc catccgtaag atgcttttct     2400
gtgactggtg agtactcaac caagtcattc tgagaatagt gtatgcggcg accgagttgc     2460
tcttgcccgg cgtcaatacg ggataatacc gcgccacata gcagaacttt aaaagtgctc     2520
atcattggaa aacgttcttc ggggcgaaaa ctctcaagga tcttaccgct gttgagatcc     2580
agttcgatgt aacccactcg tgcacccaac tgatcttcag catcttttac tttcaccagc     2640
gtttctgggt gagcaaaaac aggaaggcaa aatgccgcaa aaaagggaat aagggcgaca     2700
cggaaatgtt gaatactcat actcttcctt tttcaatatt attgaagcat ttatcagggt     2760
tattgtctca tgagcggata catatttgaa tgtatttaga aaaataaaca ataggggtt      2820 ccgcgcacat ttccccgaaa agtgccacct gacgtcatcg ccacctgacg tcgatatgcc     2880
aagtacgccc cctattgacg tcaatgacgg taaatggccc gcctggcatt atgcccagta     2940
catgacctta tgggactttc ctacttggca gtacatctac gtattagtca tcgctattac     3000
catggtgatg cggttttggc agtacatcaa tgggcgtgga tagcggtttg actcacgggg     3060
atttccaagt ctccacccca ttgacgtcaa tgggagtttg ttttggcacc aaaatcaacg     3120
ggactttcca aaatgtcgta acaactccgc cccattgacg caaatgggcg gtaggcgtgt     3180
acggtgggag gtctatataa gcagagctct ctggctaact agagaaccca ctgcttactg     3240
gcttatcgaa attaatacg                                                  3259

<210> SEQ ID NO 108
<211> LENGTH: 4130
<212> TYPE: DNA
<213> ORGANISM: Artificial Sequence
<220> FEATURE:
<223> OTHER INFORMATION: pHW2000-TRIG-NS-DO

<400> SEQUENCE: 108
gaaaagtgcc acctgacgtc atcgccacct gacgtcgata tgccaagtac gccccctatt       60
gacgtcaatg acgtaaatg gcccgcctgg cattatgccc agtacatgac cttatgggac       120
tttcctactt ggcagtacat ctacgtatta gtcatcgcta ttaccatggt gatgcggttt       180
tggcagtaca tcaatgggcg tggatagcgg tttgactcac ggggatttcc aagtctccac       240
cccattgacg tcaatgggag tttgttttgg caccaaaatc aacgggactt tccaaaatgt       300
```

```
cgtaacaact ccgccccatt gacgcaaatg ggcggtaggc gtgtacggtg ggaggtctat      360
ataagcagag ctctctggct aactagagaa cccactgctt actggcttat cgaaattaat      420
acgactcact atagggagac ccaagctgtt aacgctagca gttaaccgga gtactggtcg      480
acctccgaag ttggggggga gcaaaagcag ggtgacaaag acataatgga ctccaatact      540
gtgtcaagct ttcaggtaga ctgtttcctt tggcacatcc gcaaacgatt tgcagacaat      600
ggattgggtg atgccccatt ccttgatcgg ctccgccgag atcaaaaatc gttaaaagga      660
cgtggaaata cgttatcgtt agatatagaa acggcgacgc tagtcggaaa acaaatagtc      720
gaatggatat aaaagaaga atcgtcggat atattaaaaa tgacgatagc gtcggtcccg       780
acgtcgcgtt atttagcgga tatgacgtta gaagaaatgt cgcgtgattg gtttatgtta      840
atgccgcgtc aaaaataat aggaccgtta tgtgtccgtg tcgatcaagc gataatggaa       900
aaaaatataa tattaaaagc gaattttttcg gtcatatttta atcgtttaga aacgttaata    960
ttattacgtg cgtttacgga ggagggagca atcgttggag aaatttcacc attaccttat     1020
cttccaggac atactaatga ggatgtcaaa aatgcagttg gggtcctcat cggagggctt     1080
gaatggaatg gtaacacggt tcgaggctct gaaaatctac agagattcgc ttggagaaac     1140
cataatgagg atgggagatc ttcactacct ccagaacaga aatgaaaagt ggcgagagca     1200
attgggacag aaatttgagg aaataagatg gttaattgaa gaaatacggc acagattgaa     1260
agcgacagaa aatagtttcg agcaaataac atttatgcaa gccttacaac tactgcttga     1320
agtagaacaa gagataagga ctttctcgtt tcagcttatt taatgataaa aaacacccctt    1380 gtttctacta ataacccggc ggcccaaaat gccgactcgg agcgaaagat atacctcccc     1440
cggggccggg aggtcgcgtc accgaccacg ccgccggccc aggcgacgcg cgacacggac     1500
acctgtcccc aaaaacgcca ccatcgcagc cacacacgga gcgcccgggg ccctctggtc     1560
aaccccagga cacacgcggg agcagcgccg ggccggggac gccctcccgg cggtcaccta     1620
aatgctagag ctcgctgatc agcctcgact gtgccttcta gttgccagcc atctgttgtt     1680
tgcccctccc ccgtgccttc cttgaccctg gaaggtgcca ctcccactgt cctttcctaa     1740
taaaatgagg aaattgcatc gcattgtctg agtaggtgtc attctattct ggggggtggg     1800
gtggggcagg acagcaaggg ggaggattgg gaagacaata gcaggcatgc tggggatgcg     1860
gtgggctcta tggcttctga ggcggaaaga accagctgca ttaatgaatc ggccaacgcg     1920
cggggagagg cggtttgcgt attgggcgct cttccgcttg atgacctcta gctagagctt     1980
ggcgtaatca tggtcatagc tgtttcctgt gtgaaattgt tatccgctca caattccaca    2040
caacatacga gccggaagca taaagtgtaa agcctggggt gcctaatgag tgagctaact    2100
cacattaatt gcgttgcgct cactgcccgc tttccagtcg ggaaacctgt cgtgccagct    2160
gcattaatga atcggccaac gcgcggggag aggcggtttg cgtattgggc gctcttccgc    2220
ttcctcgctc actgactcgc tgcgctcggt cgttcggctg cggcgagcgg tatcagctca    2280
ctcaaaggcg gtaatacggt tatccacaga atcaggggat aacgcaggaa agaacatgtg    2340
agcaaaaggc cagcaaaagg ccaggaaccg taaaaaggcc gcgttgctgg cgttttttcca   2400 taggctccgc cccctgacg agcatcacaa aaatcgacgc tcaagtcaga ggtggcgaaa     2460
cccgacagga ctataaagat accaggcgtt tccccctgga agctccctcg tgcgctctcc    2520
tgttccgacc ctgccgctta ccggatacct gtccgccttt ctcccttcgg gaagcgtggc    2580
gctttctcat agctcacgct gtaggtatct cagttcggtg taggtcgttc gctccaagct    2640
gggctgtgtg cacgaacccc ccgttcagcc cgaccgctgc gccttatccg gtaactatcg    2700
```

| | |
|---|---|
| tcttgagtcc aacccggtaa gacacgactt atcgccactg gcagcagcca ctggtaacag | 2760 |
| gattagcaga gcgaggtatg taggcggtgc tacagagttc ttgaagtggt ggcctaacta | 2820 |
| cggctacact agaagaacag tatttggtat ctgcgctctg ctgaagccag ttaccttcgg | 2880 |
| aaaaagagtt ggtagctctt gatccggcaa acaaaccacc gctggtagcg gtggtttttt | 2940 |
| tgtttgcaag cagcagatta cgcgcagaaa aaaggatct caagaagatc ctttgatctt | 3000 |
| ttctacgggg tctgacgctc agtggaacga aaactcacgt taagggattt tggtcatgag | 3060 |
| attatcaaaa aggatcttca cctagatcct tttaaattaa aaatgaagtt ttaaatcaat | 3120 |
| ctaaagtata tatgagtaaa cttggtctga cagttaccaa tgcttaatca gtgaggcacc | 3180 |
| tatctcagcg atctgtctat ttcgttcatc catagttgcc tgactccccg tcgtgtagat | 3240 |
| aactacgata cgggagggct taccatctgg ccccagtgct gcaatgatac cgcgagaccc | 3300 |
| acgctcaccg gctccagatt tatcagcaat aaaccagcca gccggaaggg ccgagcgcag | 3360 |
| aagtggtcct gcaactttat ccgcctccat ccagtctatt aattgttgcc gggaagctag | 3420 |
| agtaagtagt tcgccagtta atagtttgcg caacgttgtt gccattgcta caggcatcgt | 3480 |
| ggtgtcacgc tcgtcgtttg gtatggcttc attcagctcc ggttcccaac gatcaaggcg | 3540 |
| agttacatga tcccccatgt tgtgcaaaaa agcggttagc tccttcggtc ctccgatcgt | 3600 |
| tgtcagaagt aagttggccg cagtgttatc actcatggtt atggcagcac tgcataattc | 3660 |
| tcttactgtc atgccatccg taagatgctt ttctgtgact ggtgagtact caaccaagtc | 3720 |
| attctgagaa tagtgtatgc ggcgaccgag ttgctcttgc ccggcgtcaa tacgggataa | 3780 |
| taccgcgcca catagcagaa ctttaaaagt gctcatcatt ggaaaacgtt cttcggggcg | 3840 |
| aaaactctca aggatcttac cgctgttgag atccagttcg atgtaaccca ctcgtgcacc | 3900 |
| caactgatct tcagcatctt ttactttcac cagcgtttct gggtgagcaa aaacaggaag | 3960 |
| gcaaaatgcc gcaaaaaagg gaataagggc gacacggaaa tgttgaatac tcatactctt | 4020 |
| cctttttcaa tattattgaa gcatttatca gggttattgt ctcatgagcg gatacatatt | 4080 |
| tgaatgtatt tagaaaaata acaaataggg gttccgcgc acatttcccc | 4130 |

<210> SEQ ID NO 109
<211> LENGTH: 5018
<212> TYPE: DNA
<213> ORGANISM: Artificial Sequence
<220> FEATURE:
<223> OTHER INFORMATION: pHW2000-H1N1-HA-DO

<400> SEQUENCE: 109

| | |
|---|---|
| atagggttc cgcgcacatt tccccgaaaa gtgccacctg acgtcatcgc cacctgacgt | 60 |
| cgatatgcca agtacgcccc ctattgacgt caatgacggt aaatggcccg cctggcatta | 120 |
| tgcccagtac atgaccttat gggactttcc tacttggcag tacatctacg tattagtcat | 180 |
| cgctattacc atggtgatgc ggttttggca gtacatcaat gggcgtggat agcggtttga | 240 |
| ctcacgggga tttccaagtc tccacccat tgacgtcaat gggagtttgt tttggcacca | 300 |
| aaatcaacgg gactttccaa aatgtcgtaa caactccgcc ccattgacgc aaatgggcgg | 360 |
| taggcgtgta cggtggagg tctatataag cagagctctc tggctaacta gagaacccac | 420 |
| tgcttactgg cttatcgaaa ttaatacgac tcactatagg gagacccaag ctgttaacgc | 480 |
| tagcagttaa ccgagtact ggtcgacctc cgaagtggg ggggagcaaa agcagggga | 540 |
| aataaaagca accaaaatga aggcaatact agtagttctg ctatatacat ttgcaacctc | 600 |

```
aaatgcagac acattatgta taggttatca tgcgaacaat tcaacagata cggtcgatac    660
ggtcttagaa aaaaatgtca cggtcacgca ttcggtcaat ttattagaag ataaacataa    720
tggaaaatta tgtaaattac gtggagtcgc gccgttacat ttaggaaaat gtaatatagc    780
gggatggata ttaggaaatc cggaatgtga atcgttatcg acggcgtcgt cgtggtcgta    840
tatagtcgaa acgtcgtcgt cgggaaatgg aacgtgttat ccgggagatt ttatagatta    900
tgaagaatta cgtgaacaat tatcgtcggt ctcgtcgttt gaacgttttg aaatatttcc    960 gaaacgtcg tcgtggccga atcatgaatc gaataaagga gtcacggcgg cgtgtccgca   1020
tgcgggagaa aaatcgtttt ataaaaattt aatatggcta gtcaaaaaag gaaattcgta   1080
tccgaaatta tcgaaatcgt atataaatga taaaggaaaa gaagtcttag tcttatgggg   1140
aatacatcat ccgtcgacgt cggcggatca acaatcgtta tatcaaaatg cggatgcgta   1200
tgtctttgtc ggaacgtcgc gttattcgaa aaaatttaaa ccggaaatag cgatacgtcc   1260
gaaagtccgt gatcaagaag gacgcatgaa ttattattgg acgctagtcg aaccgggaga   1320
taaaataacg tttgaagcga cgggaaattt agtcgtcccg cgttatgcgt ttgcgatgga   1380
acgtaatgcg ggatcgggaa taataatatc ggatacgccg gtccatgatt gtaatacgac   1440
gtgtcaaacc ccgaaaggag cgataaatac gtcgttaccg tttcaaaata tacatccgat   1500
aacgatagga aaatgtccga atatgtcaa atcgacgaaa ttacgtttag cgacgggatt   1560
acgtaatgtc ccgtcgatac aatcgcgtgg attatttgga gcgatagcgg gatttataga   1620
aggaggatgg acgggaatgg tcgatggatg gtatggatat catcatcaaa atgaacaagg   1680
atcgggatat gcggcggatt taaaatcgac gcaaaatgcg atagatgaaa taacgaataa   1740
agtcaattcg gtcatagaaa aaatgaatac gcaatttacg gcggtcggaa aagaatttaa   1800
tcatttagaa aaacgtatag aaatttaaa taaaaaagtc gatgatggat ttttagatat   1860
atggacgtat aatgcggaat tattagtctt attagaaaat gaacgtacgt tagattatca   1920
tgattcgaat gtcaaaaatt tatatgaaaa agtccgttcg caattaaaaa ataatgcgaa   1980
agaaatagga aatggatgtt ttgaatttta tcataaatgt gataatacgt gtatggaatc   2040
ggtcaaaaat ggaacgtatg attatccgaa atattcggaa gaagcgaaat taaatcgtga   2100
agaaatagat ggagtcaaat tagaatcgac gcgtatatat caaatattag cgatatattc   2160
gacggtcgcg tcgtcattgg tactggtagt ctccctgggg gcaatcagtt tctggatgtg   2220
ctctaatggg tctctacagt gtagaatatg tatttaacat taggatttca gaaacatgag   2280
aaaaaacacc cttgtttcta ctaataaccc ggcggcccaa aatgccgact cggagcgaaa   2340
gatataccct ccccggggcc gggaggtcgc gtcaccgacc acgccgccgg cccaggcgac   2400
gcgcgacacg gacacctgtc cccaaaaacg ccaccatcgc agccacacac ggagcgcccg   2460
gggccctctg gtcaaccccca ggacacacgc gggagcagcg ccgggccggg gacgccctcc   2520
cggcggtcac ctaaatgcta gagctcgctg atcagcctcg actgtgcctt ctagttgcca   2580
gccatctgtt gtttgcccct cccccgtgcc ttccttgacc ctggaaggtg ccactcccac   2640
tgtcctttcc taataaaatg aggaaattgc atcgcattgt ctgagtaggt gtcattctat   2700 tctgggggt ggggtgggc aggacagcaa ggggaggat tgggaagaca atagcaggca   2760
tgctggggat gcggtgggct ctatggcttc tgaggcggaa agaaccagct gcattaatga   2820
atcggccaac gcgcgggag aggcggtttg cgtattgggc gctcttccgc ttgatgacct   2880
ctagctagag cttggcgtaa tcatggtcat agctgtttcc tgtgtgaaat tgttatccgc   2940
tcacaattcc acacaacata cgagccggaa gcataaagtg taaagcctgg ggtgcctaat   3000
```

```
gagtgagcta actcacatta attgcgttgc gctcactgcc cgctttccag tcgggaaacc   3060
tgtcgtgcca gctgcattaa tgaatcggcc aacgcgcggg gagaggcggt ttgcgtattg   3120
ggcgctcttc cgcttcctcg ctcactgact cgctgcgctc ggtcgttcgg ctgcggcgag   3180
cggtatcagc tcactcaaag gcggtaatac ggttatccac agaatcaggg gataacgcag   3240
gaaagaacat gtgagcaaaa ggccagcaaa aggccaggaa ccgtaaaaag gccgcgttgc   3300
tggcgttttt ccataggctc cgcccccctg acgagcatca caaaaatcga cgctcaagtc   3360
agaggtggcg aaacccgaca ggactataaa gataccaggc gtttccccct ggaagctccc   3420
tcgtgcgctc tcctgttccg accctgccgc ttaccggata cctgtccgcc tttctccctt   3480
cgggaagcgt ggcgctttct catagctcac gctgtaggta tctcagttcg gtgtaggtcg   3540
ttcgctccaa gctgggctgt gtgcacgaac cccccgttca gcccgaccgc tgcgccttat   3600
ccggtaacta tcgtcttgag tccaacccgg taagacacga cttatcgcca ctggcagcag   3660
ccactggtaa caggattagc agagcgaggt atgtaggcgg tgctacagag ttcttgaagt   3720
ggtggcctaa ctacggctac actagaagaa cagtatttgg tatctgcgct ctgctgaagc   3780
cagttacctt cggaaaaaga gttggtagct cttgatccgg caaacaaacc accgctggta   3840
gcggtggttt ttttgtttgc aagcagcaga ttacgcgcag aaaaaaagga tctcaagaag   3900
atcctttgat cttttctacg ggtctgacgc tcagtggaa cgaaaactca cgttaaggga   3960
ttttggtcat gagattatca aaaaggatct tcacctagat ccttttaaat taaaaatgaa   4020
gttttaaatc aatctaaagt atatatgagt aaacttggtc tgacagttac caatgcttaa   4080
tcagtgaggc acctatctca gcgatctgtc tatttcgttc atccatagtt gcctgactcc   4140
ccgtcgtgta gataactacg atacgggagg gcttaccatc tggccccagt gctgcaatga   4200
taccgcgaga cccacgctca ccggctccag atttatcagc aataaaccag ccagccggaa   4260
gggccgagcg cagaagtggt cctgcaactt tatccgcctc catccagtct attaattgtt   4320
gccgggaagc tagagtaagt agttcgccag ttaatagttt gcgcaacgtt gttgccattg   4380
ctacaggcat cgtggtgtca cgctcgtcgt ttggtatggc ttcattcagc tccggttccc   4440
aacgatcaag gcgagttaca tgatccccca tgttgtgcaa aaaagcggtt agctccttcg   4500
gtcctccgat cgttgtcaga agtaagttgg ccgcagtgtt atcactcatg gttatggcag   4560
cactgcataa ttctcttact gtcatgccat ccgtaagatg cttttctgtg actggtgagt   4620
actcaaccaa gtcattctga gaatagtgta tgcggcgacc gagttgctct tgcccggcgt   4680
caatacggga taataccgcg ccacatagca gaactttaaa agtgctcatc attggaaaac   4740
gttcttcggg gcgaaaactc tcaaggatct taccgctgtt gagatccagt tcgatgtaac   4800
ccactcgtgc acccaactga tcttcagcat cttttacttt caccagcgtt tctgggtgag   4860
caaaaacagg aaggcaaaat gccgcaaaaa agggaataag ggcgacacgg aaatgttgaa   4920
tactcatact cttcctttt  caatattatt gaagcattta tcagggttat tgtctcatga   4980
gcggatacat atttgaatgt atttagaaaa ataaacaa                           5018
```

<210> SEQ ID NO 110
<211> LENGTH: 4698
<212> TYPE: DNA
<213> ORGANISM: Artificial Sequence
<220> FEATURE:
<223> OTHER INFORMATION: pHW2000-H1N1-NA-DO

<400> SEQUENCE: 110

-continued

```
caaatagggg ttccgcgcac atttccccga aaagtgccac ctgacgtcat cgccacctga        60
cgtcgatatg ccaagtacgc ccctattga cgtcaatgac ggtaaatggc ccgcctggca       120
ttatgcccag tacatgacct tatgggactt tcctacttgg cagtacatct acgtattagt       180
catcgctatt accatggtga tgcggttttg gcagtacatc aatgggcgtg gatagcggtt       240
tgactcacgg ggatttccaa gtctccaccc cattgacgtc aatgggagtt tgttttggca       300
ccaaaatcaa cgggactttc caaaatgtcg taacaactcc gccccattga cgcaaatggg       360
cggtaggcgt gtacggtggg aggtctatat aagcagagct ctctggctaa ctagagaacc       420
cactgcttac tggcttatcg aaattaatac gactcactat agggagaccc aagctgttaa       480
cgctagcagt taaccggagt actggtcgac ctccgaagtt ggggggggagc aaaagcagga       540 gtttaaaatg aatccaaacc aaaagataat aaccattggt tcggtctgta tgacaattgg       600
aatggctaac ttaatattac aaattggaaa cataatctca atatggattt cgcattcgat       660
acaattagga aatcaaaatc aaatagaaac gtgtaatcaa tcggtcataa cgtatgaaaa       720
taatacgtgg gtcaatcaaa cgtatgtcaa tatatcgaat acgaattttg cggcgggaca       780
atcggtcgta tcggtcaaat tagcgggaaa ttcgtcgtta tgtccggtct cgggatgggc       840
gatatattcg aaagataatt cggtccgtat aggatcgaaa ggagatgtct ttgtcatacg       900
tgaaccgttt atatcgtgtt cgccgttaga atgtcgtacg tttttttaa cgcaaggagc       960 gttattaaat gataaacatt cgaatggaac gataaaagat cgttcgccgt atcgtacgtt      1020
aatgtcgtgt ccgataggag aagtcccgtc gccgtataat tcgcgttttg aatcggtcgc      1080
gtggtcggcg tcggcgtgtc atgatggaat aaattggtta acgataggaa tatcgggacc      1140
ggataatgga gcggtcgcgg tcttaaaata taatggaata ataacggata cgataaaatc      1200
gtggcgtaat aatatattac gtacgcaaga atcggaatgt gcgtgtgtca atggatcgtg      1260
ttttacggtc atgacggatg gaccgtcgaa tggacaagcg tcgtataaaa tatttcgtat      1320
agaaaaagga aaaatagtca atcggtcga atgaatgcg ccgaattatc attatgaaga      1380
atgttcgtgt tatccggatt cgtcggaaat aacgtgtgtc tgtcgtgata attggcatgg      1440
atcgaatcgt ccgtgggtct cgtttaatca aaatttagaa tatcaaatag gatatatatg      1500
ttcgggaata tttggagata atccgcgtcc gaatgataaa acgggatcgt gtggaccggt      1560
ctcgtcgaat ggagcgaatg gagtcaaagg attttcgttt aaatatggaa atggagtctg      1620
gataggacgt acgaaatcga tatcgtcgcg taatggattt gaaatgatat gggatccgaa      1680
tggatggacg ggaacggata ataattttc gataaaacaa gatatagtcg gaataaatga      1740
atggtcggga tattcgggat cgtttgtcca acatccggaa ttaacgggat tagattgtat      1800
acgtccgtgt ttttgggtcg aattaatacg tggacgtccg aaagaaaata cgatatggac      1860
tagcgggagc agcatatcct tttgtggtgt aaacagtgac actgtgggtt ggtcttggcc      1920
agacggtgct gagttgccat ttaccattga caagtaattt gttcaaaaaa ctccttgttt      1980
ctactaataa cccggcggcc caaaatgccg actcggagcg aaagatatac ctcccccggg      2040
gccgggaggt cgcgtcaccg accacgccgc cggcccaggc gacgcgcgac acggacacct      2100
gtccccaaaa acgccaccat cgcagccaca cacggagcgc ccggggcccct ctggtcaacc      2160 ccaggacaca cgcgggagca gcgccgggcc ggggacgccc tccggcggt cacctaaatg      2220 ctagagctcg ctgatcagcc tcgactgtgc cttctagttg ccagccatct gttgtttgcc      2280
cctcccccgt gccttccttg accctggaag gtgccactcc cactgtcctt tcctaataaa      2340
atgaggaaat tgcatcgcat tgtctgagta ggtgtcattc tattctgggg ggtggggtgg      2400
```

```
ggcaggacag caaggggag gattgggaag acaatagcag gcatgctggg gatgcggtgg    2460
gctctatggc ttctgaggcg gaaagaacca gctgcattaa tgaatcggcc aacgcgcggg    2520
gagaggcggt ttgcgtattg ggcgctcttc cgcttgatga cctctagcta gagcttggcg    2580
taatcatggt catagctgtt tcctgtgtga aattgttatc cgctcacaat tccacacaac    2640
atacgagccg gaagcataaa gtgtaaagcc tggggtgcct aatgagtgag ctaactcaca    2700
ttaattgcgt tgcgctcact gcccgctttc cagtcgggaa acctgtcgtg ccagctgcat    2760
taatgaatcg gccaacgcgc ggggagaggc ggtttgcgta ttgggcgctc ttccgcttcc    2820
tcgctcactg actcgctgcg ctcggtcgtt cggctgcggc gagcggtatc agctcactca    2880
aaggcggtaa tacggttatc cacagaatca ggggataacg caggaaagaa catgtgagca    2940
aaaggccagc aaaaggccag gaaccgtaaa aaggccgcgt tgctggcgtt tttccatagg    3000
ctccgccccc ctgacgagca tcacaaaaat cgacgctcaa gtcagaggtg gcgaaacccg    3060
acaggactat aaagatacca ggcgtttccc cctggaagct ccctcgtgcg ctctcctgtt    3120
ccgaccctgc cgcttaccgg atacctgtcc gcctttctcc cttcgggaag cgtggcgctt    3180
tctcatagct cacgctgtag gtatctcagt tcggtgtagg tcgttcgctc caagctgggc    3240
tgtgtgcacg aaccccccgt tcagcccgac cgctgcgcct tatccggtaa ctatcgtctt    3300
gagtccaacc cggtaagaca cgacttatcg ccactggcag cagccactgg taacaggatt    3360
agcagagcga ggtatgtagg cggtgctaca gagttcttga agtggtggcc taactacggc    3420
tacactagaa gaacagtatt tggtatctgc gctctgctga agccagttac cttcggaaaa    3480
agagttggta gctcttgatc cggcaaacaa accaccgctg gtagcggtgg tttttttgtt    3540
tgcaagcagc agattacgcg cagaaaaaaa ggatctcaag aagatccttt gatcttttct    3600
acggggtctg acgctcagtg gaacgaaaac tcacgttaag ggattttggt catgagatta    3660
tcaaaaagga tcttcaccta gatccttta aattaaaaat gaagttttaa atcaatctaa    3720
agtatatatg agtaaacttg gtctgacagt taccaatgct taatcagtga ggcacctatc    3780
tcagcgatct gtctatttcg ttcatccata gttgcctgac tccccgtcgt gtagataact    3840
acgatacggg agggcttacc atctggcccc agtgctgcaa tgataccgcg agacccacgc    3900
tcaccggctc cagatttatc agcaataaac cagccagccg gaagggccga gcgcagaagt    3960
ggtcctgcaa ctttatccgc ctccatccag tctattaatt gttgccggga agctagagta    4020
agtagttcgc cagttaatag tttgcgcaac gttgttgcca ttgctacagg catcgtggtg    4080
tcacgctcgt cgtttggtat ggcttcattc agctccggtt cccaacgatc aaggcgagtt    4140
acatgatccc ccatgttgtg caaaaaagcg gttagctcct tcggtcctcc gatcgttgtc    4200
agaagtaagt tggccgcagt gttatcactc atggttatgg cagcactgca taattctctt    4260
actgtcatgc catccgtaag atgcttttct gtgactggtg agtactcaac caagtcattc    4320
tgagaatagt gtatgcggcg accgagttgc tcttgcccgg cgtcaatacg ggataatacc    4380
gcgccacata gcagaacttt aaaagtgctc atcattggaa aacgttcttc ggggcgaaaa    4440
ctctcaagga tcttaccgct gttgagatcc agttcgatgt aacccactcg tgcacccaac    4500
tgatcttcag catcttttac tttcaccagc gtttctgggt gagcaaaaac aggaaggcaa    4560
aatgccgcaa aaaagggaat aagggcgaca cggaaatgtt gaatactcat actcttcctt    4620
tttcaatatt attgaagcat ttatcagggt tattgtctca tgagcggata catatttgaa    4680
tgtatttaga aaaataaa                                                   4698
```

<210> SEQ ID NO 111
<211> LENGTH: 5016
<212> TYPE: DNA
<213> ORGANISM: Artificial Sequence
<220> FEATURE:
<223> OTHER INFORMATION: pHW2000-H1N2-HA-DO

<400> SEQUENCE: 111 atagggggttc cgcgcacatt tccccgaaaa gtgccacctg acgtcatcgc cacctgacgt 60
cgatatgcca agtacgcccc ctattgacgt caatgacggt aaatggcccg cctggcatta 120
tgcccagtac atgaccttat gggactttcc tacttggcag tacatctacg tattagtcat 180
cgctattacc atggtgatgc ggttttggca gtacatcaat gggcgtggat agcggtttga 240
ctcacgggga tttccaagtc tccaccccat tgacgtcaat gggagtttgt tttggcacca 300
aaatcaacgg gactttccaa aatgtcgtaa caactccgcc ccattgacgc aaatgggcgg 360
taggcgtgta cggtgggagg tctatataag cagagctctc tggctaacta gagaacccac 420
tgcttactgg cttatcgaaa ttaatacgac tcactatagg gagacccaag ctgttaacgc 480
tagcagttaa ccggagtact ggtcgacctc cgaagttggg ggggagcaaa agcaggggaa 540
aaataaaagc aaccaaaatg aaagtaaaac taatggttct gttatgtaca tttacagcta 600
catatgcaga cacaatatgt gtaggctacc atgccaacaa ctcaactgat acggtcgata 660
cggtcttaga aaaaaatgtc acggtcacgc attcggtcaa tttattagaa gattcgcata 720
atggaaaatt atgtttatta aaaggaatag cgccgttaca attaggatcg tgttcggtcg 780
cgggatggat attaggaaat ccggaatgtg aattattaat atcgaaagaa tcgtggtcgt 840
atatagtcga aacgccgaat ccggaaaatg gaacgtgtta tccgggatat tttacggatt 900
atgaagaatt acgtgaacaa ttatcgtcgg tctcgtcgtt taaacgtttt gaaatatttc 960
cgaaagaatc gtcgtggccg aatcatacgg tcacgggagt ctcgtcgtcg tgttcgcata 1020
atggaaaatc gtcgttttat cgtaatttat tatggttaac ggtcaaaaat ggattatatc 1080
cgaatttatc gaaatcgtat acgaataaaa aagaaaaaga agtcttagtc ttatggggag 1140
tccatcatcc gtcgaatata ggagatcaac gtgcgttata tcatacggaa aatgcgtatg 1200
tctcggtcgt atcgtcgcat tattcgcgtc gttttacgcc ggaaatagcg aaacgtccga 1260
aagtccgtaa tcaagaagga cgtataaatt attattggac gttattagaa ccgggagata 1320
cgataatatt tgaagcgaat ggaaatttaa tagcgccgcg ttatgcgttt gaattatcga 1380
aaggatttgg atcgggaata ataacgtcga atgcgccgat gggagaatgt aatgcgaaat 1440
gtcaaacgcc gcaaggagcg ataaattcgt cgttaccgtt tcaaaatgtc catccggtca 1500
cgataggaga atgtccgaaa tatgtcaaat cggcgaaatt acgtatggtc acgggattac 1560
gtaatacgcc gtcgatacaa tcgcgtggat tatttggagc gatagcggga tttatagaag 1620
gaggatggac gggaatggtc gatggatggt atggatatca tcatcaaaat gaacaaggat 1680
cgggatatgc ggcggatcaa caatcgacgc aaaatgcgat aaatggaata acgaataaag 1740
tcaattcggt catagaaaaa atgaatacgc aatttacggc ggtcggaaaa gaatttaata 1800
aattagaacg tcgtatggaa aatttaaata aaaaagtcga tgatggattt ttagatatat 1860
ggacgtataa tgcggaatta ttagtcttat tagaaaatga acgtacgtta gattttcatg 1920
attcgaatgt caaaaattta tatgaaaaag tcaaatcgca attaaaaaat aatgcgaaag 1980
aaataggaaa tggatgtttt gaattttatc ataaatgtaa tgatgaatgt atggaatcgg 2040
tcaaaaatgg aacgtatgat tatccgaaat attcggaaga atcgaaatta aatcgtgaaa 2100

```
aaatagatgg agtcaaatta gaatcgatgg gagtctataa tatattagcg atatattcga    2160
cggtcgcgtc gtccctagtt cttttagtct ccctggggc aatcagcttc tggatgtgtt    2220
ccaatgggtc tttacagtgt agaatatgca tctaagacca gaatttcaga aatataagga    2280
aaaacaccct tgtttctact aataacccgg cggcccaaaa tgccgactcg gagcgaaaga    2340
tatacctccc ccggggccgg gaggtcgcgt caccgaccac gccgccggcc caggcgacgc    2400
gcgacacgga cacctgtccc caaaaacgcc accatcgcag ccacacacgg agcgccgggg    2460
gccctctggt caaccccagg acacacgcgg gagcagcgcc gggccgggga cgccctcccg    2520
gcggtcacct aaatgctaga gctcgctgat cagcctcgac tgtgccttct agttgccagc    2580
catctgttgt ttgcccctcc cccgtgcctt ccttgaccct ggaaggtgcc actcccactg    2640
tcctttccta ataaaatgag gaaattgcat cgcattgtct gagtaggtgt cattctattc    2700
tggggggtgg ggtggggcag gacagcaagg gggaggattg gaagacaat agcaggcatg    2760 ctggggatgc ggtgggctct atggcttctg aggcggaaag aaccagctgc attaatgaat    2820
cggccaacgc gcggggagag gcggtttgcg tattgggcgc tcttccgctt gatgacctct    2880
agctagagct tggcgtaatc atggtcatag ctgtttcctg tgtgaaattg ttatccgctc    2940
acaattccac acaacatacg agccggaagc ataaagtgta aagcctgggg tgcctaatga    3000
gtgagctaac tcacattaat tgcgttgcgc tcactgcccg ctttccagtc gggaaacctg    3060
tcgtgccagc tgcattaatg aatcggccaa cgcgcgggga gaggcggttt gcgtattggg    3120
cgctcttccg cttcctcgct cactgactcg ctgcgctcgg tcgttcggct gcggcgagcg    3180
gtatcagctc actcaaaggc ggtaatacgg ttatccacag aatcagggga taacgcagga    3240
aagaacatgt gagcaaaagg ccagcaaaag gccaggaacc gtaaaaaggc cgcgttgctg    3300 gcgttttttcc ataggctccg ccccctgac gagcatcaca aaaatcgacg ctcaagtcag    3360
aggtggcgaa acccgacagg actataaaga taccaggcgt ttccccctgg aagctccctc    3420
gtgcgctctc ctgttccgac cctgccgctt accggatacc tgtccgcctt tctcccttcg    3480
ggaagcgtgg cgctttctca tagctcacgc tgtaggtatc tcagttcggt gtaggtcgtt    3540
cgctccaagc tgggctgtgt gcacgaaccc cccgttcagc ccgaccgctg cgccttatcc    3600
ggtaactatc gtcttgagtc aacccggta agacacgact tatcgccact ggcagcagcc    3660
actggtaaca ggattagcag agcgaggtat gtaggcggtg ctacagagtt cttgaagtgg    3720
tggcctaact acggctacac tagaagaaca gtatttggta tctgcgctct gctgaagcca    3780
gttaccttcg gaaaaagagt tggtagctct tgatccggca acaaaccac cgctggtagc    3840 ggtggttttt ttgtttgcaa gcagcagatt acgcgcagaa aaaaggatc tcaagaagat    3900 cctttgatct tttctacggg gtctgacgct cagtggaacg aaaactcacg ttaagggatt    3960
ttggtcatga gattatcaaa aaggatcttc acctagatcc ttttaaatta aaatgaagt    4020 tttaaatcaa tctaaagtat atatgagtaa acttggtctg acagttacca atgcttaatc    4080
agtgaggcac ctatctcagc gatctgtcta tttcgttcat ccatagttgc ctgactcccc    4140
gtcgtgtaga taactacgat acgggagggc ttaccatctg gccccagtgc tgcaatgata    4200
ccgcgagacc cacgctcacc ggctccagat ttatcagcaa taaaccagcc agccggaagg    4260
gccgagcgca gaagtggtcc tgcaacttta tccgcctcca tccagtctat taattgttgc    4320
cgggaagcta gagtaagtag ttcgccagtt aatagtttgc gcaacgttgt tgccattgct    4380
acaggcatcg tggtgtcacg ctcgtcgttt ggtatggctt cattcagctc cggttcccaa    4440
```

```
cgatcaaggc gagttacatg atcccccatg ttgtgcaaaa aagcggttag ctccttcggt   4500
cctccgatcg ttgtcagaag taagttggcc gcagtgttat cactcatggt tatggcagca   4560
ctgcataatt ctcttactgt catgccatcc gtaagatgct tttctgtgac tggtgagtac   4620
tcaaccaagt cattctgaga atagtgtatg cggcgaccga gttgctcttg cccggcgtca   4680
atacgggata ataccgcgcc acatagcaga actttaaaag tgctcatcat tggaaaacgt   4740
tcttcggggc gaaaactctc aaggatctta ccgctgttga gatccagttc gatgtaaccc   4800
actcgtgcac ccaactgatc ttcagcatct tttactttca ccagcgtttc tgggtgagca   4860
aaaacaggaa ggcaaaatgc cgcaaaaaag ggaataaggg cgacacggaa atgttgaata   4920
ctcatactct tcctttttca atattattga agcatttatc agggttattg tctcatgagc   4980
ggatacatat ttgaatgtat ttagaaaaat aaacaa                             5016
```

<210> SEQ ID NO 112
<211> LENGTH: 4698
<212> TYPE: DNA
<213> ORGANISM: Artificial Sequence
<220> FEATURE:
<223> OTHER INFORMATION: pHW2000-H1N2-NA-DO

<400> SEQUENCE: 112

```
caaatagggg ttccgcgcac atttccccga aaagtgccac ctgacgtcat cgccacctga     60
cgtcgatatg ccaagtacgc cccctattga cgtcaatgac ggtaaatggc ccgcctggca    120
ttatgcccag tacatgacct tatgggactt tcctacttgg cagtacatct acgtattagt    180
catcgctatt accatggtga tgcggttttg gcagtacatc aatgggcgtg gatagcggtt    240
tgactcacgg ggatttccaa gtctccaccc cattgacgtc aatgggagtt tgttttggca    300
ccaaaatcaa cgggactttc caaaatgtcg taacaactcc gccccattga cgcaaatggg    360
cggtaggcgt gtacggtggg aggtctatat aagcagagct ctctggctaa ctagagaacc    420
cactgcttac tggcttatcg aaattaatac gactcactat agggagaccc aagctgttaa    480
cgctagcagt taaccggagt actggtcgac ctccgaagtt ggggggggagc aaaagcagga    540
gtttaaaatg aatccaaatc aaaagataat aacgattggc tctgtttctc ttactattgc    600
cacaatgtgc ttccttatgc aaattgccat cctggtaact aatgtaacat tgcacttcaa    660
tcaatatgaa tgtaattatc cgccgaataa tcaagtcata ttatgtgaac cgacgataat    720
agaacgtaat ataacggaaa tagtctattt aacgaatacg acgatagaaa aagaaatatg    780
tccgaaatta gcggaatatc gtaattggtc gaaaccgcaa tgtaaaataa cgggatttgc    840
gccgttttcg aaagataatt cgatacgttt atcggcggga ggagatatat gggtcacgcg    900
tgaaccgtat gtctcgtgtg atccggataa atgttatcaa tttgcgttag gacaaggaac    960
gacgttaaat aatcgtcatt cgaatgatac ggtccatgat cgtacgccgt atcgcacgtt   1020
attaatgaat gaattaggaa taccgtttca tttaggaacg aaacaagtct gtatagcgtg   1080
gtcgtcgtcg tcgtgtcatg atggaaaagc gtggttacat gtctgtataa cgggacatga   1140
tgaaaatgcg acggcgtcga taatatataa tggacgttta gtcgattcga taggatcgtg   1200
gtcgaaaaaa atattacgta cgcaagaatc ggaatgtgtc tgtataaatg gaacgtgtac   1260
ggtcgtcatg acggatggat cggcgtcggg aatagcggat acgaaaatat tatttataga   1320
agaaggaaaa atagtccata tatcgccgtt attaggatcg gcgcaacatg tcgaagaatg   1380
ttcgtgttat ccgcgttatc cgggagtccg ttgtatatgt cgtgataatt ggaaaggatc   1440
gaatcgtccg gtcgtcgata taaatgtcaa agattattcg atagtctcgt cgtatgtctg   1500
```

```
ttcgggatta gtcggagata cgccgcgtaa agatgatcgt tcgtcgtcgt cggattgttt   1560
aaatccgaat aatgaagaag gaggacatgg agtcaaagga tgggcgtttg atgatggaaa   1620
tgatgtctgg atgggacgta cgataaatga aacgttacgt tcgggatatg aaacgtttaa   1680
agtcatagaa ggatggtcga aaccgaattc gaaattacaa ataaatcgtc aagtcatagt   1740
cgaacgtgga gatcgttcgg gatattcggg aatattttcg gtcgaaggaa atcgtgtat    1800 aaatcgttgt ttttatgtcg aattaatacg tggacgtaaa caagaaactg cagtatggtg   1860
gacgtcaaac agtattgttg tgttttgtgg cacctcaggt acatatggaa caggctcatg   1920
gcctgatggg gcgaacatca atctcatgcc tgtataattt attcaaaaaa ctccttgttt   1980
ctactaataa cccggcggcc caaaatgccg actcggagcg aaagatatac ctcccccggg   2040
gccgggaggt cgcgtcaccg accacgccgc cggcccaggc gacgcgcgac acggacacct   2100
gtccccaaaa acgccaccat cgcagccaca cacggagcgc ccggggccct ctggtcaacc   2160
ccaggacaca cgcgggagca cgccggggcc ggggacgccc tcccggcggt cacctaaatg   2220
ctagagctcg ctgatcagcc tcgactgtgc cttctagttg ccagccatct gttgtttgcc   2280
cctcccccgt gccttccttg accctggaag gtgccactcc cactgtcctt tcctaataaa   2340
atgaggaaat tgcatcgcat tgtctgagta ggtgtcattc tattctgggg ggtggggtgg   2400
ggcaggacag caaggggag gattgggaag acaatagcag gcatgctggg gatgcggtgg   2460
gctctatggc ttctgaggcg gaaagaacca gctgcattaa tgaatcggcc aacgcgcggg   2520
gagaggcggt ttgcgtattg ggcgctcttc cgcttgatga cctctagcta gagcttggcg   2580
taatcatggt catagctgtt tcctgtgtga aattgttatc cgctcacaat tccacacaac   2640
atacgagccg gaagcataaa gtgtaaagcc tggggtgcct aatgagtgag ctaactcaca   2700
ttaattgcgt tgcgctcact gcccgctttc cagtcgggaa acctgtcgtg ccagctgcat   2760
taatgaatcg gccaacgcgc ggggagaggc ggtttgcgta ttgggcgctc ttccgcttcc   2820
tcgctcactg actcgctgcg ctcggtcgtt cggctgcggc gagcggtatc agctcactca   2880
aaggcggtaa tacggttatc cacagaatca ggggataacg caggaaagaa catgtgagca   2940
aaaggccagc aaaaggccag gaaccgtaaa aaggccgcgt tgctggcgtt tttccatagg   3000
ctccgccccc ctgacgagca tcacaaaaat cgacgctcaa gtcagaggtg gcgaaacccg   3060
acaggactat aaagatacca ggcgtttccc cctggaagct ccctcgtgcg ctctcctgtt   3120
ccgaccctgc cgcttaccgg atacctgtcc gcctttctcc cttcgggaag cgtggcgctt   3180
tctcatagct cacgctgtag gtatctcagt tcggtgtagg tcgttcgctc caagctgggc   3240
tgtgtgcacg aaccccccgt tcagcccgac cgctgcgcct tatccggtaa ctatcgtctt   3300
gagtccaacc cggtaagaca cgacttatcg ccactggcag cagccactgg taacaggatt   3360
agcagagcga ggtatgtagg cggtgctaca gagttcttga agtggtggcc taactacggc   3420
tacactagaa gaacagtatt tggtatctgc gctctgctga agccagttac cttcggaaaa   3480
agagttggta gctcttgatc cggcaaacaa accaccgctg gtagcggtgg ttttttttgtt   3540 tgcaagcagc agattacgcg cagaaaaaaa ggatctcaag aagatccttt gatcttttct   3600
acggggtctg acgctcagtg gaacgaaaac tcacgttaag ggattttggt catgagatta   3660
tcaaaaagga tcttcaccta gatcctttta aattaaaaat gaagttttaa atcaatctaa   3720
agtatatatg agtaaacttg gtctgacagt taccaatgct taatcagtga ggcacctatc   3780
tcagcgatct gtctatttcg ttcatccata gttgcctgac tccccgtcgt gtagataact   3840
```

```
acgatacggg agggcttacc atctggcccc agtgctgcaa tgataccgcg agacccacgc    3900
tcaccggctc cagatttatc agcaataaac cagccagccg aaagggccga gcgcagaagt    3960
ggtcctgcaa ctttatccgc ctccatccag tctattaatt gttgccggga agctagagta    4020
agtagttcgc cagttaatag tttgcgcaac gttgttgcca ttgctacagg catcgtggtg    4080
tcacgctcgt cgtttggtat ggcttcattc agctccggtt cccaacgatc aaggcgagtt    4140
acatgatccc ccatgttgtg caaaaaagcg gttagctcct tcggtcctcc gatcgttgtc    4200
agaagtaagt tggccgcagt gttatcactc atggttatgg cagcactgca taattctctt    4260
actgtcatgc catccgtaag atgcttttct gtgactggtg agtactcaac caagtcattc    4320
tgagaatagt gtatgcggcg accgagttgc tcttgcccgg cgtcaatacg ggataatacc    4380
gcgccacata gcagaacttt aaaagtgctc atcattggaa aacgttcttc ggggcgaaaa    4440
ctctcaagga tcttaccgct gttgagatcc agttcgatgt aacccactcg tgcacccaac    4500
tgatcttcag catctttttac tttcaccagc gtttctgggt gagcaaaaac aggaaggcaa    4560
aatgccgcaa aaaagggaat aagggcgaca cggaaatgtt gaatactcat actcttcctt    4620
tttcaatatt attgaagcat ttatcagggt tattgtctca tgagcggata catatttgaa    4680
tgtatttaga aaaataaa                                                  4698

<210> SEQ ID NO 113
<211> LENGTH: 5002
<212> TYPE: DNA
<213> ORGANISM: Artificial Sequence
<220> FEATURE:
<223> OTHER INFORMATION: pHW2000-H3N2-HA-DO

<400> SEQUENCE: 113
taaacaaata ggggttccgc gcacatttcc ccgaaaagtg ccacctgacg tcatcgccac      60
ctgacgtcga tatgccaagt acgcccccta ttgacgtcaa tgacggtaaa tggcccgcct     120
ggcattatgc ccagtacatg accttatggg actttcctac ttggcagtac atctacgtat     180
tagtcatcgc tattaccatg gtgatgcggt tttggcagta catcaatggg cgtggatagc     240
ggtttgactc acggggattt ccaagtctcc accccattga cgtcaatggg agtttgtttt     300
ggcaccaaaa tcaacgggac tttccaaaat gtcgtaacaa ctccgcccca ttgacgcaaa     360
tgggcggtag gcgtgtacgg tgggaggtct atataagcag agctctctgg ctaactagag     420
aacccactgc ttactggctt atcgaaatta atacgactca ctatagggag acccaagctg     480
ttaacgctag cagttaaccg gagtactggt cgacctccga gttgggggg gagcaaaagc     540 agggatatt tctattaacc atgaagacta tcattgcttt tagctgcgtt ttatgtttga     600
ttttcgctca aaaacttccc ggaagtgaca acagcatggc aacgctgtgc ttaggacatc     660
atgcggtccc gaatggaacg ttagtcaaaa cgataacgga tgatcaaata gaagtcacga     720
atgcgacgga attagtccaa tcgtcgtcga cgggacgtat atgtaattcg ccgcatcaaa     780
tattagatgg aaaaaattgt acgttaatag atgcgttatt aggagatccg cattgtgatg     840
attttcaaaa taaagaatgg gatttatttg tcgaacgttc gacggcgtat tcgaattgtt     900
atccgtatta tgtcccggat tatgcgtcgt tacgttcgtt agtcgcgtcg tcgggaacgt     960
tagaatttac gcaagaatcg tttaattgga cgggagtcgc gcaagatgga tcgtcgtatg    1020
cgtgtcgtcg tgaatcggtc aattcgtttt tttcgcgttt aaattggtta cataaattag    1080
attataaata tccggcgtta aaagtcacga tgccgaataa tgataaattt gataaattat    1140
atatatgggg agtccatcat ccgggaacgg atcgtgatca aacgaattta tatgtccaaa    1200
```

```
cgtcgggacg tgtcacggtc tcgacgaaac gttcgcaaca aacggtcata ccgaatatag    1260
gatcgcgtcc gtgggtccgt ggagtctcgt cgataatatc gatatattgg acgatagtca    1320
aaccgggaga tatattatta ataaattcga cgggaaattt aatagcgccg cgtggatatt    1380
ttaaattaca atcgggaaaa tcgtcgataa tgcgttcgga tgcgccgata ggaatatgta    1440
attcggaatg tataacgccg aatggatcga taccgaatga taaaccgttt caaaatgtca    1500
atcgtataac ctatggagcg tgtccgcgtt atgtcaaaca aaatacgtta aaattagcga    1560
cgggaatgcg taatgtcccg gaaaaacaaa cgcgtggaat atttggagcg atagcgggat    1620
ttatagaaaa tggatgggaa ggaatggtcg atggatggta tggatttcgt catcaaaatt    1680
cggaaggaac gggacaagcg gcggatttaa aatcgacgcg tgcggcgata aatcaaataa    1740
cgggaaaatt aaatcgtgtc ataaaaaaaa cgaatgaaaa atttcatcaa atagaaaaag    1800
aattttcgga agtcgaagga cgtatacaag atttagaaaa atatgtcgaa gatacgaaaa    1860
tagatttatg gtcgtataat gcggaattat tagtcgcgtt agaaaatcaa catacgatag    1920
atttaacgga ttcggaaatg aataaattat ttgaacgtac gcgtaaacaa ttacgtgaaa    1980
atgcggaaga tatgggaaat ggatgtttta aaatatatca taaatgtgat aatgcgtgta    2040
taggatcgat acgtaatgga acgtatgatc atgatgtcta tcgtgatgaa gcgttaaata    2100
atcgttttca aataaaagga gtccaattaa aatcgggata taaagattgg atattatgga    2160
tatcgtttgc gatatcgtgc ttttgctttt gtgttgttct gctggggttc attatgtggg    2220
cctgccaaaa aggcaacatt aggtgcaaca tttgcatttg agtgcattaa ttaaaaacac    2280
ccttgtttct actaataacc cggcggccca aaatgccgac tcggagcgaa agatatacct    2340 cccccgggc cgggaggtcg cgtcaccgac cacgccgccg gcccaggcga cgcgcgacac    2400
ggacacctgt ccccaaaaac gccaccatcg cagccacaca cggagcgccc ggggccctct    2460
ggtcaacccc aggacacacg cgggagcagc gccgggccgg ggacgccctc ccggcggtca    2520
cctaaatgct agagctcgct gatcagcctc gactgtgcct tctagttgcc agccatctgt    2580
tgtttgcccc tccccgtgc cttccttgac cctggaaggt gccactccca ctgtcctttc    2640
ctaataaaat gaggaaattg catcgcattg tctgagtagg tgtcattcta ttctgggggg    2700
tggggtgggg caggacagca agggggagga ttgggaagac aatagcaggc atgctgggga    2760
tgcggtgggc tctatggctt ctgaggcgga agaaccagc tgcattaatg aatcggccaa    2820
cgcgcgggga gaggcggttt gcgtattggg cgctcttccg cttgatgacc tctagctaga    2880
gcttggcgta atcatggtca tagctgtttc ctgtgtgaaa ttgttatccg ctcacaattc    2940
cacacaacat acgagccgga agcataaagt gtaaagcctg gggtgcctaa tgagtgagct    3000
aactcacatt aattgcgttg cgctcactgc ccgctttcca gtcgggaaac ctgtcgtgcc    3060
agctgcatta atgaatcggc caacgcgcgg ggagaggcgg tttgcgtatt gggcgctctt    3120
ccgcttcctc gctcactgac tcgctgcgct cggtcgttcg gctgcggcga gcggtatcag    3180
ctcactcaaa ggcggtaata cggttatcca cagaatcagg ggataacgca ggaaagaaca    3240
tgtgagcaaa aggccagcaa aaggccagga accgtaaaaa ggccgcgttg ctggcgtttt    3300
tccataggct ccgcccccct gacgagcatc acaaaaatcg acgctcaagt cagaggtggc    3360
gaaacccgac aggactataa agataccagg cgtttccccc tggaagctcc ctcgtgcgct    3420
ctcctgttcc gaccctgccg cttaccggat acctgtccgc cttctccct cgggaagcg    3480 tggcgctttc tcatagctca cgctgtaggt atctcagttc ggtgtaggtc gttcgctcca    3540
```

| | |
|---|---|
| agctgggctg tgtgcacgaa ccccccgttc agcccgaccg ctgcgcctta tccggtaact | 3600 |
| atcgtcttga gtccaacccg gtaagacacg acttatcgcc actggcagca gccactggta | 3660 |
| acaggattag cagagcgagg tatgtaggcg gtgctacaga gttcttgaag tggtggccta | 3720 |
| actacggcta cactagaaga acagtatttg gtatctgcgc tctgctgaag ccagttacct | 3780 |
| tcggaaaaag agttggtagc tcttgatccg gcaaacaaac caccgctggt agcggtggtt | 3840 |
| tttttgtttg caagcagcag attacgcgca gaaaaaaagg atctcaagaa gatcctttga | 3900 |
| tcttttctac ggggtctgac gctcagtgga acgaaaactc acgttaaggg attttggtca | 3960 |
| tgagattatc aaaaaggatc ttcacctaga tccttttaaa ttaaaaatga agttttaaat | 4020 |
| caatctaaag tatatatgag taaacttggt ctgacagtta ccaatgctta atcagtgagg | 4080 |
| cacctatctc agcgatctgt ctatttcgtt catccatagt tgcctgactc cccgtcgtgt | 4140 |
| agataactac gatacgggag ggcttaccat ctggccccag tgctgcaatg ataccgcgag | 4200 |
| acccacgctc accggctcca gatttatcag caataaacca gccagccgga agggccgagc | 4260 |
| gcagaagtgg tcctgcaact ttatccgcct ccatccagtc tattaattgt tgccgggaag | 4320 |
| ctagagtaag tagttcgcca gttaatagtt tgcgcaacgt tgttgccatt gctacaggca | 4380 |
| tcgtggtgtc acgctcgtcg tttggtatgg cttcattcag ctccggttcc caacgatcaa | 4440 |
| ggcgagttac atgatccccc atgttgtgca aaaaagcggt tagctccttc ggtcctccga | 4500 |
| tcgttgtcag aagtaagttg gccgcagtgt tatcactcat ggttatgca gcactgcata | 4560 |
| attctcttac tgtcatgcca tccgtaagat gcttttctgt gactggtgag tactcaacca | 4620 |
| agtcattctg agaatagtgt atgcggcgac cgagttgctc ttgcccggcg tcaatacggg | 4680 |
| ataataccgc gccacatagc agaactttaa aagtgctcat cattggaaaa cgttcttcgg | 4740 |
| ggcgaaaact ctcaaggatc ttaccgctgt tgagatccag ttcgatgtaa cccactcgtg | 4800 |
| cacccaactg atcttcagca tcttttactt tcaccagcgt ttctgggtga gcaaaaacag | 4860 |
| gaaggcaaaa tgccgcaaaa aagggaataa gggcgacacg gaaatgttga atactcatac | 4920 |
| tcttcctttt tcaatattat tgaagcattt atcagggtta ttgtctcatg agcggataca | 4980 |
| tatttgaatg tatttagaaa aa | 5002 |

<210> SEQ ID NO 114
<211> LENGTH: 4705
<212> TYPE: DNA
<213> ORGANISM: Artificial Sequence
<220> FEATURE:
<223> OTHER INFORMATION: pHW2000-H3N2-NA-DO

<400> SEQUENCE: 114

| | |
|---|---|
| tccgcgcaca tttccccgaa aagtgccacc tgacgtcatc gccacctgac gtcgatatgc | 60 |
| caagtacgcc ccctattgac gtcaatgacg gtaaatggcc cgcctggcat tatgcccagt | 120 |
| acatgacctt atgggacttt cctacttggc agtacatcta cgtattagtc atcgctatta | 180 |
| ccatggtgat gcggttttgg cagtacatca atgggcgtgg atagcggttt gactcacggg | 240 |
| gatttccaag tctccacccc attgacgtca atgggagttt gttttggcac caaaatcaac | 300 |
| gggactttcc aaaatgtcgt aacaactccg ccccattgac gcaaatgggc ggtaggcgtg | 360 |
| tacggtggga ggtctatata agcagagctc tctggctaac tagagaaccc actgcttact | 420 |
| ggcttatcga aattaatacg actcactata gggagaccca gctgttaac gctagcagtt | 480 |
| aaccggagta ctggtcgacc tccgaagttg ggggggagca aaagcaggag taaagatgaa | 540 |
| tccaaatcaa aagataataa caattggctc tgtttctctc ctcattgcca caatatgctt | 600 |

```
ccttatgcaa attgccatcc tggtaactac tgtaacattg catttcaaac aacatgattg    660
taattcgtcg ccgaataatc aagtcatgtt atgtgaaccg acgataatag aacgtaatac    720
gacggaaata gtctatttaa cgaatataac gatagaaaaa gaaatatgtc gaaattagc     780
ggaatatcgt aattggtcga aaccgcaatg taatataacg ggatttgcgc cgttttcgaa    840
agataattcg atacgtttat cggcgggagg agatatatgg gtcacgcgtg aaccgtatgt    900
ctcgtgtgat ccgataaat gttatcaatt tgcgttagga caaggaacga cgttaaataa     960
tggacattcg aatgatacgg tccatgatcg tacgccgtat cgcacgttat taatgaatga   1020
attaggagtc ccgtttcatt taggaacgcg tcaagtctgt atagcgtggt cgtcgtcgtc   1080
gtgtcatgat ggaaaagcgt ggttacatgt ctgtataacg ggagatgata aaaatgcgac   1140
ggcgtcgttt atatataatg gacgtttagt cgattcgata ggatcgtggt cgaaaaatat   1200
attacgtacg caagaatcgg aatgtgtctg tataaatgga acgtgtacgg tcgtcatgac   1260
ggatggatcg gcgtcgggaa aagcggatac gaaagtctta tttatagaag aaggaaaaat   1320
agtccatata tcgacgttat cgggatcggc gcaacatgtc gaagaatgtt cgtgttatcc   1380
gcgttatccg ggagtccgtt gtgtctgtcg tgataattgg aaaggatcga atcgtccgat   1440
agtcgatata aatgtcaaag attattcgat agtctcgtcg tatgtctgtt cgggattagt   1500
cggagatacg ccgcgtaaaa atgatcgttt ttcgtcgtcg cattgtcaag atccgaataa   1560
tgaagaagga ggacatggag tcaaaggatg ggcgtttgat gatggaaatg atgtctggat   1620
gggacgtacg ataaatgaaa aattacgttc gggatatgaa acgtttaaag tcatagaagg   1680
atggtcgaaa ccgaattcga aattacaaac gaatcgtcaa gtcatagtcg aacgtggaaa   1740
tcgttcggga tattcgggaa tattttcggt cgaaggaaaa tcgtgtataa atcgttgttt   1800
ttatgtcgaa ttaatacgtg gacgtaaaga agaaactaaa gtctggtgga cctcaaacag   1860
tattgttgtg ctttgtggca cctcaggtac atatggaaca ggctcatggc ctgatggggc   1920
ggatatcaat ctcatgccta tataactttc gcaattttag aaaaaactcc ttgtttctac   1980
taataacccg gcggcccaaa atgccgactc ggagcgaaag atatacctcc cccgggccg    2040
ggaggtcgcg tcaccgacca cgccgccggc ccaggcgacg cgcgacacgg acacctgtcc   2100
ccaaaaacgc caccatcgca gccacacacg gagcgcccgg ggccctctgg tcaaccccag   2160
gacacacgcg ggagcagcgc cgggccgggg acgccctccc ggcggtcacc taaatgctag   2220
agctcgctga tcagcctcga ctgtgccttc tagttgccag ccatctgttg tttgcccctc   2280
ccccgtgcct tccttgaccc tggaaggtgc cactcccact gtcctttcct aataaaatga   2340
ggaaattgca tcgcattgtc tgagtaggtg tcattctatt ctgggggtg gggtggggca    2400
ggacagcaag gggaggatt gggaagacaa tagcaggcat gctggggatg cggtgggctc     2460
tatggcttct gaggcggaaa gaaccagctg cattaatgaa tcggccaacg cgcgggaga     2520
ggcggtttgc gtattgggcg ctcttccgct tgatgacctc tagctagagc ttggcgtaat   2580
catggtcata gctgtttcct gtgtgaaatt gttatccgct cacaattcca cacaacatac   2640
gagccggaag cataaagtgt aaagcctggg gtgcctaatg agtgagctaa ctcacattaa   2700
ttgcgttgcg ctcactgccc gctttccagt cgggaaacct gtcgtgccag ctgcattaat   2760
gaatcggcca acgcgcgggg agaggcggtt tgcgtattgg gcgctcttcc gcttcctcgc   2820
tcactgactc gctgcgctcg gtcgttcggc tgcggcgagc ggtatcagct cactcaaagg   2880
cggtaatacg gttatccaca gaatcagggg ataacgcagg aaagaacatg tgagcaaaag   2940
```

| | |
|---|---|
| gccagcaaaa ggccaggaac cgtaaaaagg ccgcgttgct ggcgtttttc cataggctcc | 3000 |
| gcccccctga cgagcatcac aaaaatcgac gctcaagtca gaggtggcga acccgacag | 3060 |
| gactataaag ataccaggcg tttccccctg gaagctccct cgtgcgctct cctgttccga | 3120 |
| ccctgccgct taccggatac ctgtccgcct ttctcccttc gggaagcgtg gcgctttctc | 3180 |
| atagctcacg ctgtaggtat ctcagttcgg tgtaggtcgt tcgctccaag ctgggctgtg | 3240 |
| tgcacgaacc ccccgttcag cccgaccgct gcgccttatc cggtaactat cgtcttgagt | 3300 |
| ccaacccggt aagacacgac ttatcgccac tggcagcagc cactggtaac aggattagca | 3360 |
| gagcgaggta tgtaggcggt gctacagagt tcttgaagtg gtggcctaac tacggctaca | 3420 |
| ctagaagaac agtatttggt atctgcgctc tgctgaagcc agttaccttc ggaaaaagag | 3480 |
| ttggtagctc ttgatccggc aaacaaacca ccgctggtag cggtggtttt tttgtttgca | 3540 |
| agcagcagat tacgcgcaga aaaaaggat ctcaagaaga tcctttgatc ttttctacgg | 3600 |
| ggtctgacgc tcagtggaac gaaaactcac gttaagggat tttggtcatg agattatcaa | 3660 |
| aaaggatctt cacctagatc cttttaaatt aaaaatgaag ttttaaatca atctaaagta | 3720 |
| tatatgagta aacttggtct gacagttacc aatgcttaat cagtgaggca cctatctcag | 3780 |
| cgatctgtct atttcgttca tccatagttg cctgactccc cgtcgtgtag ataactacga | 3840 |
| tacgggaggg cttaccatct ggccccagtg ctgcaatgat accgcgagac ccacgctcac | 3900 |
| cggctccaga tttatcagca ataaaccagc cagccggaag ggccgagcgc agaagtggtc | 3960 |
| ctgcaacttt atccgcctcc atccagtcta ttaattgttg ccgggaagct agagtaagta | 4020 |
| gttcgccagt taatagtttg cgcaacgttg ttgccattgc tacaggcatc gtggtgtcac | 4080 |
| gctcgtcgtt tggtatggct tcattcagct ccggttccca acgatcaagg cgagttacat | 4140 |
| gatcccccat gttgtgcaaa aaagcggtta gctccttcgg tcctccgatc gttgtcagaa | 4200 |
| gtaagttggc cgcagtgtta tcactcatgg ttatggcagc actgcataat tctcttactg | 4260 |
| tcatgccatc cgtaagatgc ttttctgtga ctggtgagta ctcaaccaag tcattctgag | 4320 |
| aatagtgtat gcggcgaccg agttgctctt gcccggcgtc aatacgggat aataccgcgc | 4380 |
| cacatagcag aactttaaaa gtgctcatca ttggaaaacg ttcttcgggg cgaaaactct | 4440 |
| caaggatctt accgctgttg agatccagtt cgatgtaacc cactcgtgca cccaactgat | 4500 |
| cttcagcatc ttttactttc accagcgttt ctgggtgagc aaaaacagga aggcaaaatg | 4560 |
| ccgcaaaaaa gggaataagg gcgacacgga aatgttgaat actcatactc ttcctttttc | 4620 |
| aatattattg aagcatttat cagggttatt gtctcatgag cggatacata tttgaatgta | 4680 |
| tttagaaaaa taaacaaata ggggt | 4705 |

<210> SEQ ID NO 115
<211> LENGTH: 5022
<212> TYPE: DNA
<213> ORGANISM: Artificial Sequence
<220> FEATURE:
<223> OTHER INFORMATION: pHW2000-HA-DO (H1-H3 chimera)

<400> SEQUENCE: 115

| | |
|---|---|
| acctgacgtc gatatgccaa gtacgccccc tattgacgtc aatgacggta aatggcccgc | 60 |
| ctggcattat gcccagtaca tgaccttatg ggactttcct acttggcagt acatctacgt | 120 |
| attagtcatc gctattacca tggtgatgcg gttttggcag tacatcaatg ggcgtggata | 180 |
| gcggtttgac tcacggggat ttccaagtct ccaccccatt gacgtcaatg ggagtttgtt | 240 |
| ttggcaccaa aatcaacggg actttccaaa atgtcgtaac aactccgccc cattgacgca | 300 |

```
aatgggcggt aggcgtgtac ggtgggaggt ctatataagc agagctctct ggctaactag    360
agaacccact gcttactggc ttatcgaaat taatacgact cactataggg agacccaagc    420
tgttaacgct agcagttaac cggagtactg gtcgacctcc gaagttgggg gggagcaaaa    480 gcagggggaaa aataaaagca accaaaatga agtaaaact aatggttctg ttatgtacat    540
ttacagctac atatgcacaa aaacttcccg gaagtgacaa cagcatggca acgctgtgct    600
taggacatca tgcggtcccg aatggaacgt tagtcaaaac gataacggat gatcaaatag    660
aagtcacgaa tgcgacggaa ttagtccaat cgtcgtcgac gggacgtata tgtaattcgc    720
cgcatcaaat attagatgga aaaaattgta cgttaataga tgcgttatta ggagatccgc    780
attgtgatga ttttcaaaat aaagaatggg atttatttgt cgaacgttcg acggcgtatt    840
cgaattgtta ccgtattat gtcccggatt atgcgtcgtt acgttcgtta gtcgcgtcgt    900
cgggaacgtt agaatttacg caagaatcgt ttaattggac gggagtcgcg caagatggat    960
cgtcgtatgc gtgtcgtcgt gaatcggtca attcgttttt ttcgcgttta aattggttac   1020
ataaattaga ttataaatat ccggcgttaa aagtcacgat gccgaataat gataaatttg   1080
ataaattata tatatgggga gtccatcatc cgggaacgga tcgtgatcaa acgaatttat   1140
atgtccaaac gtcgggacgt gtcacggtct cgacgaaacg ttcgcaacaa acggtcatac   1200
cgaatatagg atcgcgtccg tgggtccgtg gagtctcgtc gataatatcg atatattgga   1260
cgatagtcaa accgggagat atattattaa taaattcgac gggaaattta atagcgccgc   1320
gtggatattt taaattacaa tcgggaaaat cgtcgataat gcgttcggat gcgccgatag   1380
gaatatgtaa ttcggaatgt ataacgccga atggatcgat accgaatgat aaaccgtttc   1440
aaaatgtcaa tcgtataacc tatggagcgt gtccgcgtta tgtcaaacaa atacgttaa    1500 aattagcgac gggaatgcgt aatgtcccgg aaaaacaaac gcgtggaata tttggagcga   1560
tagcgggatt tatagaaaat ggatgggaag aatggtcga tggatggtat ggatttcgtc    1620
atcaaaattc ggaaggaacg ggacaagcgg cggatttaaa atcgacgcgt gcggcgataa   1680
atcaaataac gggaaaatta aatcgtgtca taaaaaaaac gaatgaaaaa tttcatcaaa   1740
tagaaaaaga atttcggaa gtcgaaggac gtatacaaga tttagaaaaa tatgtcgaag    1800
atacgaaaat agatttatgg tcgtataatg cggaattatt agtcgcgtta gaaaatcaac   1860
atacgataga tttaacggat tcggaaatga ataaaattat tgaacgtacg cgtaaacaat   1920
tacgtgaaaa tgcggaagat atgggaaatg gatgttttaa aatatatcat aaatgtgata   1980
atgcgtgtat aggatcgata cgtaatggaa cgtatgatca tgatgtctat cgtgatgaag   2040
cgttaaataa tcgttttcaa ataaaggag tccaattaaa atcgggatat aaagatatct    2100
tagcgatata ttcgacggtc gcgtcgtccc tagttctttt agtctccctg ggggcaatca    2160
gcttctggat gtgttccaat gggtctttac agtgtagaat atgcatctaa gaccagaatt   2220
tcagaaatat aaggaaaaac acccttgttt ctactaataa cccggcggcc caaaatgccg   2280
actcggagcg aaagatatac ctcccccggg gccgggaggt cgcgtcaccg accacgccgc   2340
cggcccaggc gacgcgcgac acggacacct gtccccaaaa acgccaccat cgcagccaca   2400
cacggagcgc ccggggccct ctggtcaacc ccaggacaca cgcgggagca cgcccgggcc   2460
ggggacgccc tcccggcggt cacctaaatg ctagagctcg ctgatcagcc tcgactgtgc   2520
cttctagttg ccagccatct gttgtttgcc cctcccccgt gccttccttg acctggaag    2580 gtgccactcc cactgtcctt tcctaataaa atgaggaaat tgcatcgcat tgtctgagta    2640
```

```
ggtgtcattc tattctgggg ggtggggtgg ggcaggacag caaggggag gattgggaag      2700 acaatagcag gcatgctggg gatgcggtgg gctctatggc ttctgaggcg gaaagaacca     2760
gctgcattaa tgaatcggcc aacgcgcggg gagaggcggt ttgcgtattg ggcgctcttc     2820
cgcttgatga cctctagcta gagcttggcg taatcatggt catagctgtt tcctgtgtga    2880
aattgttatc cgctcacaat tccacacaac atacgagccg gaagcataaa gtgtaaagcc    2940
tggggtgcct aatgagtgag ctaactcaca ttaattgcgt tgcgctcact gcccgctttc    3000
cagtcgggaa acctgtcgtg ccagctgcat taatgaatcg gccaacgcgc ggggagaggc    3060
ggtttgcgta ttgggcgctc ttccgcttcc tcgctcactg actcgctgcg ctcggtcgtt    3120
cggctgcggc gagcggtatc agctcactca aaggcggtaa tacggttatc cacagaatca    3180
ggggataacg caggaaagaa catgtgagca aaaggccagc aaaaggccag gaaccgtaaa    3240
aaggccgcgt tgctggcgtt tttccatagg ctccgccccc ctgacgagca tcacaaaaat    3300
cgacgctcaa gtcagaggtg gcgaaacccg acaggactat aaagatacca ggcgtttccc    3360
cctggaagct ccctcgtgcg ctctcctgtt ccgaccctgc cgcttaccgg atacctgtcc    3420
gcctttctcc cttcgggaag cgtggcgctt tctcatagct cacgctgtag gtatctcagt    3480
tcggtgtagg tcgttcgctc caagctgggc tgtgtgcacg aaccccccgt tcagcccgac    3540
cgctgcgcct tatccggtaa ctatcgtctt gagtccaacc cggtaagaca cgacttatcg    3600
ccactggcag cagccactgg taacaggatt agcagagcga ggtatgtagg cggtgctaca    3660
gagttcttga agtggtggcc taactacggc tacactagaa gaacagtatt tggtatctgc    3720
gctctgctga agccagttac cttcggaaaa agagttggta gctcttgatc cggcaaacaa    3780
accaccgctg gtagcggtgg tttttttgtt tgcaagcagc agattacgcg cagaaaaaaa    3840
ggatctcaag aagatccttt gatcttttct acggggtctg acgctcagtg gaacgaaaac    3900
tcacgttaag ggattttggt catgagatta tcaaaaagga tcttcaccta gatcctttta    3960
aattaaaaat gaagttttaa atcaatctaa agtatatatg agtaaacttg gtctgacagt    4020
taccaatgct taatcagtga ggcacctatc tcagcgatct gtctatttcg ttcatccata    4080
gttgcctgac tccccgtcgt gtagataact acgatacggg agggcttacc atctggcccc    4140
agtgctgcaa tgataccgcg agacccacgc tcaccggctc cagatttatc agcaataaac    4200
cagccagccg aagggccga gcgcagaagt ggtcctgcaa ctttatccgc ctccatccag    4260
tctattaatt gttgccggga agctagagta agtagttcgc cagttaatag tttgcgcaac    4320
gttgttgcca ttgctacagg catcgtggtg tcacgctcgt cgtttggtat ggcttcattc    4380
agctccggtt cccaacgatc aaggcgagtt acatgatccc ccatgttgtg caaaaaagcg    4440
gttagctcct tcggtcctcc gatcgttgtc agaagtaagt tggccgcagt gttatcactc    4500
atggttatgg cagcactgca taattctctt actgtcatgc catccgtaag atgcttttct    4560
gtgactggtg agtactcaac caagtcattc tgagaatagt gtatgcggcg accgagttgc    4620
tcttgcccgg cgtcaatacg ggataatacc gcgccacata gcagaacttt aaaagtgctc    4680
atcattggaa aacgttcttc ggggcgaaaa ctctcaagga tcttaccgct gttgagatcc    4740
agttcgatgt aacccactcg tgcacccaac tgatcttcag catcttttac tttcaccagc    4800
gtttctgggt gagcaaaaac aggaaggcaa aatgccgcaa aaagggaat aagggcgaca    4860 cggaaatgtt gaatactcat actcttcctt tttcaatatt attgaagcat ttatcagggt    4920
tattgtctca tgagcggata catatttgaa tgtatttaga aaaataaaca atagggggtt    4980
ccgcgcacat ttccccgaaa agtgccacct gacgtcatcg cc                       5022
```

```
<210> SEQ ID NO 116
<211> LENGTH: 51
<212> TYPE: DNA
<213> ORGANISM: Artificial Sequence
<220> FEATURE:
<223> OTHER INFORMATION: pHW2000 5' cloning site (BsmBI) sequence

<400> SEQUENCE: 116
tccgaagttg gggggagga gacggtaccg tctccaataa cccggcggcc c         51

<210> SEQ ID NO 117
<211> LENGTH: 51
<212> TYPE: DNA
<213> ORGANISM: Artificial Sequence
<220> FEATURE:
<223> OTHER INFORMATION: pHW2000 3' cloning site (BsmBI) sequence

<400> SEQUENCE: 117
gggccgccgg gttattggag acggtaccgt ctcctccccc ccaacttcgg a         51
```

ATTENUATED SWINE INFLUENZA VACCINES AND METHODS OF MAKING AND USE THEREOF

CROSS-REFERENCE TO RELATED APPLICATIONS

This application claims priority to U.S. provisional application No. 62/428,062, filed 30 Nov. 2016, and incorporated herein by reference in its entirety.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents. All sequences referenced herein by GenBank Accession numbers are herein incorporated by reference in their entirety, and said sequences are as set forth in GenBank at as of the filing date of the present application.

FIELD OF THE INVENTION

The present invention relates generally to attenuated viral vaccines, particularly those providing broad, safe, and effective protection to porcines against infections/disease caused by swine influenza virus (SIV). The invention further relates to methods of producing, testing and releasing attenuated viruses, and to methods of using these attenuated SIV to elicit protective immunity in porcine animals in need thereof.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER 16-309p_ST25.txt. The text file is 326 KB; it was created on 16 Aug. 2016; and it is being submitted electronically via EFS-Web, concurrent with the filing of the specification.

SUMMARY OF THE INVENTION

Influenza virions include an internal ribonucleoprotein core (a helical nucleocapsid) containing the single-stranded RNA genome, and an outer lipoprotein envelope lined inside by a matrix protein (M1). The genome of influenza A virus consists of eight segmented negative sense single-stranded RNA molecules. Each segment possesses segment-specific RNA packaging signals which are composed of both the noncoding regions and short coding regions at both 5' and 3' ends. The eight segmented RNAs encode 11 viral proteins, including RNA-dependent RNA polymerase proteins (PB2, PB1 and PA) and nucleoprotein (NP) which form the nucleocapsid; the matrix membrane proteins (M1, M2); hemagglutinin (HA) and neuraminidase (NA), both surface glycoproteins which project from the lipid-containing envelope; the nonstructural protein (NS1), nuclear export protein (NEP, also termed NS2), the proapoptotic factor PB1-F2. HA is critical for virus binding and entry to the cells, and is the major neutralizing antibody target, whereas NA plays a role in progeny virus release and is essential for virus propagation. Transcription and replication of the genome take place in the nucleus and assembly occurs via budding on the plasma membrane.

Swine influenza (SI) is an acute respiratory disease of swine caused by type A and type C influenza viruses. Pigs also support the replication of both human and avian influenza A viruses and have been postulated to play an important role in interspecies transmission by acting as a "mixing vessel" for re-assortment between viruses specific to different hosts (Scholtissek, Eur. J. Epidemiol. (1994) 10:455-458). Multiple swine influenza virus (SIV) subtypes continue to circulate in swine populations despite available vaccines. Currently, H1N1, H3N2, and H1N2 are the dominant subtypes that cause disease in the North American swine population. SIVs of the subtype H3N2 were generated by re-assortment between human, avian and classical swine viruses, are undergoing rapid evolution and in general cause more severe disease than classical H1N1 SIV. Current SIV vaccines do not protect against multiple antigenic SIV variants.

One approach to producing new influenza vaccine strains has been to deoptimize one or more of the genes, to produce a recombinant/re-assortant influenza that does not cause disease, yet elicits an immunological response against subsequent virulent SIV challenge (see e.g. US 2012/026,9849, to the Research Foundation of the State University of New York). However, this approach has not been attempted for use in modifying swine influenza virus (SIV) to produce novel attenuated SIV vaccine strains. Thus, there remains a need for the development of effective strategies for the treatment and prevention of swine influenza infection.

An object of this invention is to provide attenuated swine influenza viruses (SIvs), safe and effective vaccines containing same, and methods for the treatment and prophylaxis of infection and disease caused by swine influenza virus (SIV). In some embodiments, the vaccines comprise attenuated influenza viruses, which have been modified to contain deoptimized coding sequences, relative to the corresponding parental strains from which they were derived. In a particular embodiment, the safe and effective SIV vaccine strains carry codon deoptimized hemagglutinin (HA-DO), neuraminidase (NA-DO), and optionally nonstructural (NS-DO) gene coding sequences.

Another object of this invention is to provide cDNA and/or plasmids for use in a reverse genetics system for producing attenuated influenza according to the instant disclosure. In an embodiment, the cDNA and/or plasmids comprise a deoptimized HA sequence having at least 70%, at least 80%, or at least 90% identity to a sequence as set forth in SEQ ID NO: 22, 29, 35 or 105; a deoptimized NA having at least 70%, at least 80%, or at least 90% identity to a sequence as set forth in SEQ ID NO: 25, 32 or 38; and optionally, a deoptimized NS sequence having at least 70%, at least 80%, or at least 90% identity to a sequence as set forth in SEQ ID NO:27.

In general, production of reassortant SIV using deoptimized HA, NA and optionally NS1 SIV coding sequences yields re-assortants having attenuated virulence when compared to the virulent wild type strains from which the HA, NA and optionally NS1 sequences were derived.

The present invention further relates to new attenuated strains of SIV, which provide safe, effective, and broad protective-including cross-protective-immunity, relative to parental H1N1, H1N2 and H3N2 SIV strains.

Thus, the invention provides mutant swine influenza viruses comprising silent mutations in one or more SIV HA, NA and optionally NS1 nucleic acid sequence, relative to the wild type/parental virus, which renders the mutant/re-assortant virus attenuated, relative to the parent virus. In some embodiments, parental SIVs comprise SIV HA, NA and NS1 nucleic acid molecules from wild type H1N1, H1N2 or H3N2 SIV strains, each sequence comprising wild type HA, NA and optionally NS1 coding sequences. In other embodiments, parental SIVs comprise SIV HA, NA and NS nucleic acid molecules from synthetically or naturally-attenuated H1N1, H1N2 or H3N2 SIV strains, each sequence comprising non-wild type SIV HA, NA and optionally NS1 coding sequences.

It is thus an important object of the invention to provide attenuated reassortant SIVs, which comprise a base set of SIV internal genes, in addition to deoptimized versions of HA, NA and optionally NS1 coding sequences.

Accordingly, applicants disclose herein, for the first time, that different sets of deoptimized HA, NA and optionally NS1 coding sequences may be combined with the same core set of TRIG backbone H1N1 SIV M, NP, PA, PB1, PB2 and optionally NS sequences, to produce safe and effective reassortant, attenuated SIV vaccine strains.

The invention further provides methods for inducing an immunological (or immunogenic) or protective response against Influenza, as well as methods for preventing or treating Influenza, or disease state(s) caused by Influenza, comprising administering the attenuated virus, or a composition comprising the attenuated virus to animals in need thereof.

Kits comprising at least the attenuated Influenza strain and instructions for use are also provided.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 2 is a table describing the sequences disclosed in this application;

FIG. 4 shows PCR amplicons of 3'UTR/signal sequences and transmembrane/tail domain/5'UTR of HA segment (H1 subtype);

FIG. 5 presents a graphical map of the sequence (SEQ ID NO:103) comprising a 3'UTR, signal sequence (SS), transmembrane domain (TMD), cytoplasmic tail domain (CTD), and a 5'UTR of HA segment (H1N2-DO);

FIG. 6 presents the cloning scheme for pHW2000-H1 SP-TM chimera;

FIG. 7 nucleotide sequence of H3 ectodomain PCR amplicon (indicated by the underlined section, corresponding to nucleotides 609-2147 of SEQ ID NO:113);

FIG. 9 presents the nucleotide sequence of pHW2000-HA-DO (H1-H3 chimera) (SEQ ID NO:105);

DETAILED DESCRIPTION OF THE INVENTION

Figure 1:
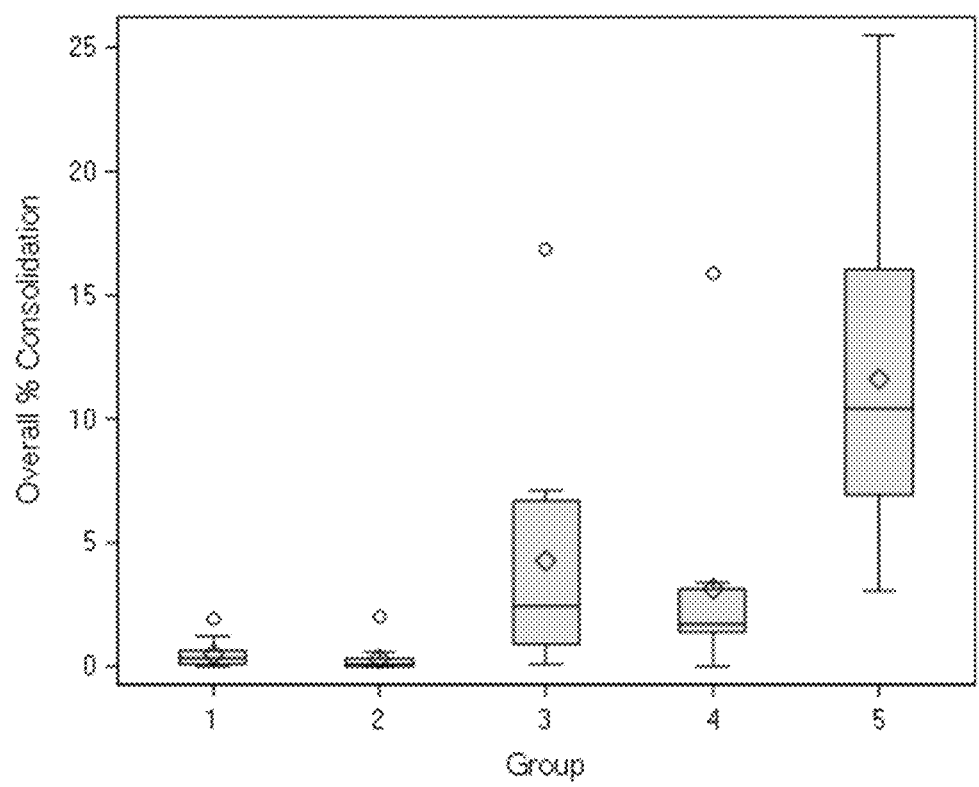
FIG. 1 is a graph showing overall % consolidation by group (1=vSIV01, 2=vSIV02, 3=vSIV05, 4=vSIV06, 5=Control)

The present invention provides nucleotide sequences and genes involved in the attenuation of a microorganism, such as virus, for instance, Influenza, products (e.g., proteins, antigens, immunogens, epitopes) encoded by the nucleotide sequences, methods for producing such nucleotide sequences, products, micro-organisms, and uses therefor, such as for preparing vaccine or immunogenic compositions or for eliciting an immunological or immune response or as a vector, e.g., as an expression vector (for instance, an in vitro or in vivo expression vector).

Mutations introduced into nucleotide sequences and genes of micro-organisms produce novel and nonobvious attenuated mutants. These mutants are useful for the production of live attenuated immunogenic compositions or live attenuated vaccines having a high degree of immunogenicity.

Identification of the mutations provides novel and nonobvious nucleotide sequences and genes, as well as novel and nonobvious gene products encoded by the nucleotide sequences and genes.

The invention is based in part upon the remarkable observation that pigs vaccinated with the disclosed attenuated SIV, and then challenged with virulent H1N2 SIV, had significantly reduced lung lesions and virus shedding from the respiratory tract as compared to unvaccinated pigs. Because vaccination with currently approved commercial inactivated products does not fully prevent transmission, the team recommends introduction of a new control strategy that involves the use of LAIV vaccines in conjunction with additional control measures in swine to limit shedding, transmission and zoonotic spillover. Such a strategy will minimize the risk of swine being the source of the next pandemic.

In some embodiments, the invention provides a new model for evaluating the ability of the attenuated SIV to reduce disease spillover/transmission. In some embodiments, animals are vaccinated with one more attenuated SIV according to the present disclosure. After a sufficient period of time for the animals to develop protective immunity has passed, the animals may be challenged with an effective amount of a virulent strain of SIV. Typically, the amount of challenge strain administered is sufficient to enable a skilled person to determine whether the vaccines have elicited protective immunity, including heterologous protective immunity, in vaccinates, relative to control/sham-vaccinates.

Once the animals have been challenged, they may be placed in proximity with sentinel animals, to evaluate the extent to which vaccination protects sentinels against SIV transmission. In some embodiments, the vaccinated and control animals may be placed in sufficiently close proximity to a group of sentinels such that if the animals are shedding a sufficient amount of virus, the sentinels will be exposed and infected. Each group of vaccinates and sentinels may be physically isolated from one another, such that sentinels housed with one group of vaccinates will not be exposed to challenge virus shed by another group of vaccinates or controls.

In an embodiment, the invention provides an attenuated swine influenza virus (SIV) strain capable of providing a safe and effective immune response in porcine against influenza or diseases caused by influenza.

In some embodiments, the deoptimized sequences were produced by providing wild type HA sequences having at least 70%, at least 80%, or at least 90% sequence identity to a sequence set forth in SEQ ID NO: 21, 28 or 34), wild type NA sequences having at least 70%, at least 80%, or at least 90% sequence identity to a sequence set forth in SEQ ID NO: 24, 31 or 37), and optionally an NS1 sequence having at least 70%, at least 80%, or at least 90% identity to a sequence set forth in SEQ ID NO: 1. In some embodiments, these wild type sequences are identical to wild type, virulent H1N1, H1N2 or H3N2 SIV strains.

In a particular embodiment, the mutant virus comprises vRNA nucleic acid sequences which correspond to (i.e. are reverse complementary and have uracils in place of thymidines) the deoptimized DNA sequences set forth in SEQ ID NO: 22, 29, 35 or 105 (HA-DO); SEQ ID NO: 25, 32 or 38 (NA-DO); and optionally, SEQ ID NO:27 (NS1-DO), which cause the mutant virus to be attenuated/non-virulent, relative to the virulent wild type/parental virus.

In some embodiments, the balance of the SIV gene segments (i.e. M, NP, PA, PB1, PB2 and optionally NS) comprise wild type coding sequences. In a particular embodiment, the wild type (i.e. non-deoptimized) sequences are H1N1 SIV M, NP, PA, PB1, PB2 and optionally NS sequences.

In some embodiments, the H1N1 NS1 wild type coding sequence comprises a sequence having at least 70%, at least 80%, or at least 90% identity to a sequence set forth in SEQ ID NO: 1. In some embodiments, the NS1 wild type coding sequence comprises the sequence set forth in SEQ ID NO: 1.

In some embodiments, the H1N1 M1 wild type coding sequence comprises a sequence having at least 70%, at least 80%, or at least 90% identity to a sequence set forth in SEQ ID NO: 3. In some embodiments, the M1 wild type coding sequence comprises the sequence set forth in SEQ ID NO: 3.

In some embodiments, the H1N1 M2 wild type coding sequence comprises a sequence having at least 70%, at least 80%, or at least 90% identity to a sequence set forth in SEQ ID NO: 5. In some embodiments, the M2 wild type coding sequence comprises the sequence set forth in SEQ ID NO: 5.

In some embodiments, the H1N1 NP wild type coding sequence comprises a sequence having at least 70%, at least 80%, or at least 90% identity to a sequence set forth in SEQ ID NO: 9. In some embodiments, the NP wild type coding sequence comprises the sequence set forth in SEQ ID NO: 9.

In some embodiments, the H1N1 PA wild type coding sequence comprises a sequence having at least 70%, at least 80%, or at least 90% identity to a sequence set forth in SEQ ID NO:13. In some embodiments, the PA wild type coding sequence comprises the sequence set forth in SEQ ID NO:13.

In some embodiments, the H1N1 PB1 wild type coding sequence comprises a sequence having at least 70%, at least 80%, or at least 90% identity to a sequence set forth in SEQ ID NO:15. In some embodiments, the PB1 wild type coding sequence comprises the sequence set forth in SEQ ID NO:15.

In some embodiments, the H1N1 PB2 wild type coding sequence comprises a sequence having at least 70%, at least 80%, or at least 90% identity to a sequence set forth in SEQ ID NO:17. In some embodiments, the PB2 wild type coding sequence comprises the sequence set forth in SEQ ID NO:17.

In other embodiments, the non-deoptimized coding sequences may also be taken from H1N2 or H3N2 SIV strain. For example, the HA, NA and optionally NS1 coding sequences, prior to deoptimization, may comprise sequences as set forth in 40, 42, 44, 46, 48, 50, 52, 54, 56, 58, 60, 62, 64, 66, 68, 70, 72, 74 or 76. Moreover, the base strains (i.e. the "wild type" H1N1, H1N2 or H3N2 SIV strains) may also themselves be synthetically or naturally attenuated versions of their more-virulent parental strains.

In another aspect, the invention provides immunological composition comprising attenuated influenza strains as detailed above. In one embodiment, the compositions may further comprise a pharmaceutically or veterinary acceptable vehicle, diluent or excipient.

In some embodiments, the immunological composition may include various components to improve its storage stability. Vaccines may be formulated and tested using, for example, accelerated stability studies. In some embodiments, the following combinations of ingredients may be used to produce stabile vaccine formulations according to the present invention:

sucrose, phosphate buffer, glutamatic acid, bovine serum albumin
soy peptone, dextran 70, glutamic acid, sucrose
gelatin, casein hydrolysate, sucrose
dextran 40, sorbitol, gelatin, casein hydrolysate, sucrose Accordingly, in some embodiments, suitable polymers may include Dextran 40, Dextran 70, PEG, povidone, or combinations thereof. Suitable animal proteins may include casein hydrolysate, gelatin, bovine serum albumin (BSA), lactalbumin hydrolysate, and non-animal proteins may include soy peptone. Suitable carbohydrate components may include sucrose, raffinose, lactose, and suitable buffers may include phosphate and histidine. Some advantageous formulation components include PEG and povidone, lactalbumin hydrolysate, raffinose and lactose, and histidine.

In some embodiments, the immunological composition may comprise any or all of the following stabilizing components: about 0.1% to about 2.5% of a polymer bulking agent (e.g. dextran, PEG, povidone, etc.), about 0.1 to about 4.5% of a sugar alcohol (e.g. sorbitol, mannitol, etc.), about 0.1% to about 2.5% of an animal protein (e.g. casein hydrosylate, gelatin, BSA, LAH, etc.), about 0.1% to about 2.5% of a vegetable protein (e.g. soy peptone, etc.), a phosphate buffer, a histidine buffer, about 1.0% to about 7.5% of a carbohydrate (e.g. lactose, raffinose, sucrose, combinations thereof, etc.).

In some embodiments, the immunological composition may comprise the following components, each expressed in w/v (g/100 mL) of the composition:

- About 0.5% to about 1.0% of a first protein type, about 0.5% to about 1.0% of a second protein type, and about 2.0% to about 5.0% of a non-reducing saccharide
- About 0.5% to about 1.0% gelatin, about 0.5% to about 1.0% casein hydrosylate (CH), and about 2.0% to about 5.0% sucrose
- About 1.0% to about 2.0% of a polymer, about 1.0% to about 2.0% of a non-animal sourced protein, and about 0.25% to about 0.5% of a glutamic acid salt, and about 2% to about 5% of a non-reducing sugar
- About 1.0% to about 2.0% of a dextran polymer, about 1.0% to about 2.0% of a soy peptone, and about 0.25% to about 0.5% 1-glutamic acid monopotassium salt, about 2% to about 5% sucrose
- About 1.0% to about 2.0% of BSA, about 0.05% $KH_2PO_4$, about 0.14% $K_2HPO_4$, about 0.03% to about 0.1% of a glutamic acid salt, and about 2% to about 5% sucrose
- About 1.2% to about 2.4% of a dextran polymer, about 1.2% to about 2.4% sorbitol, about 0.6% to about 1.2% CH, about 0.75% to about 1.5% gelatin, about 0.015% to about 0.031% $KH_2PO_4$, about 0.0375% to about 0.075% $K_2HPO_4$, and about 2% to about 5% sucrose In an embodiment, the composition provides a protective immune response in porcine against virulent swine influenza challenge. Protection may be homologous, heterologous or both. In some embodiments, the composition further comprises at least one additional antigen associated with a pathogen other than swine influenza.

In another embodiment, the at least one additional antigen is selected from *Mycoplasma hyopneumoniae* (*M. hyo*), PCV2, PRRSV, SIV or other pathogen capable of infecting and causing illness or susceptibility to illness in a porcine, or combinations thereof.

In some embodiments, combinations include a trivalent H1N1, H1N2, H3N2 vaccine composition. Such a composition may be administered to young pigs, for example, via the intranasal route. Other combinations include a one dose MLV in powder formulation for mucosal administration, a multi-dose sachet presentation for reconstitution at pig side, and a codon de-optimized, M2 gene negative SIV composition.

In an embodiment, the invention provides methods of vaccinating an animal comprising at least one administration of the attenuated SIV compositions. In another embodiment, the porcine is a sow or gilt from about 3 weeks to about 6 weeks prefarrowing. In yet another embodiment, the resulting piglets may have a reduced morbidity and/or mortality as compared to piglets coming from unvaccinated sows. In other embodiments, the animal to be vaccinated is a piglet. The piglet may be any age, including about 1 day old to about 30 days old. In some embodiments, the piglets are between about 1 day old and about 2 to 4 weeks old.

In an embodiment, the invention provides a method to prepare influenza virus, comprising: contacting a cell with one of the inventive compositions in an amount effective to yield infectious influenza virus. The method may further comprise isolating the virus.

In another embodiment, the invention provides a method to prepare a gene delivery vehicle, comprising: contacting cells with the inventive composition in an amount effective to yield influenza virus, and isolating the virus. The invention further provides a cell contacted with the inventive composition.

In an embodiment, the invention provides a vertebrate cell comprising a plurality of vectors for production of attenuated swine influenza including a vector comprising a promoter operably linked to influenza virus HA, NA and optionally NS1 coding sequences, wherein the HA, NA and optionally NS1 coding sequences are codon deoptimized, relative to non-deoptimized HA, NA and NS1 coding sequences present in virulent parental SIV strains.

The invention further encompasses gene products, which provide antigens, immunogens and epitopes, and are useful as isolated gene products.

Such isolated gene products, as well as epitopes thereof, are also useful for generating antibodies, which are useful in diagnostic applications.

Such gene products, which can provide or generate epitopes, antigens or immunogens, are also useful for immunogenic or immunological compositions, as well as vaccines.

In an aspect, the invention provides viruses containing an attenuating mutation in a nucleotide sequence or a gene wherein the mutation modifies the biological activity of a polypeptide or protein encoded by a gene, resulting in attenuated virulence of the virus.

In particular, the present invention encompasses attenuated swine influenza strains and vaccines comprising the same, which elicit an immunogenic response in an animal, particularly the attenuated swine influenza strains that elicit, induce or stimulate a response in a porcine.

Particular swine influenza attenuated strains of interest have mutations in genes, relative to wild type virulent parent strain, which are associated with virulence. It is recognized that, in addition to strains having the disclosed mutations, attenuated strains having any number of mutations in the disclosed virulence genes can be used in the practice of this invention.

In another aspect, the novel attenuated reassortant swine influenza strains are formulated into safe, effective vaccine against swine influenza and infections/diseases cause by swine influenza.

In an embodiment, the swine influenza vaccines further comprise an adjuvant. In a particular embodiment, the adjuvant is a mucosal adjuvant, such as chitosan, methylated chitosan, trimethylated chitosan, or derivatives or combinations thereof.

In an embodiment, the adjuvant comprises whole bacteria and/or viruses, including *H. parasuis*, clostridium, swine influenza virus (SIV), porcine circovirus 2 (PCV2), porcine reproductive and respiratory syndrome virus (PRRSV), Mannheimia, Pasteurella, Histophilus, Salmonella, *Escherichia coli*, or combinations and/or variations thereof. In several embodiments, the adjuvant increases the animal's production of IgM, IgG, IgA, and/or combinations thereof.

As used herein, the term "gene" will be used in a broad sense, and shall encompass both coding and non-coding sequences (i.e. upstream and downstream regulatory sequences, promoters, 5'/3' UTR, introns, and exons). Where reference to only a gene's coding sequence is intended, the term "gene's coding sequence" or "CDS" will be used interchangeably throughout this disclosure. When a specific nucleic acid is discussed, for example, the sequence as set forth in SEQ ID NO:17 (the DNA sequence equivalent of parental virus cRNA "sense" strand), the skilled person will instantly be in possession of all derivable forms of that sequence (mRNA, vRNA, cRNA, DNA, protein, etc.). For example, the influenza virus is a negative single strand RNA virus (ssRNA). To replicate, its negative ssRNA (defined herein as "vRNA") must be transcribed to positive or sense RNA (defined herein as "cRNA"). Host cell machinery is co-opted to use the cRNA to produce the viral proteins and vRNA. A skilled person using the well-known genetic code can routinely derive from a DNA sequence the vRNA, cRNA, and peptide sequences.

As used herein, "wild type" is intended to mean that a sequence or strain contains the same genetic sequence as it did when it was isolated from nature. For example, "field isolates" that have been recovered from the cells, tissues or organs of a virus-infected animal are "wild type" viruses. The gene segments contained within these field isolates contain wild type polynucleotide sequences, which encode for wild type polypeptides. "Non-wild type" strains and sequences are those that have been altered either using genetic engineering techniques, or by serially passaging wild type or modified viruses in cells, tissues or organs. Cell passaging is a well-known technique for producing attenuated viruses.

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) nonpolar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Compositions

The present invention relates to a swine influenza vaccine or composition which may comprise an attenuated swine influenza strain and a pharmaceutically or veterinarily acceptable carrier, excipient, or vehicle, which elicits, induces or stimulates a response in an animal.

The term "nucleic acid" and "polynucleotide" refers to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism.

The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

An "isolated" biological component (such as a nucleic acid or protein or organelle) refers to a component that has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, as described above.

The term "recombinant" means a polynucleotide with semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, 5'UTR, 3'UTR, transcription terminators, polyadenylation sites, additional transcription units under control of the same or a different promoter, sequences that permit cloning, expression, homologous recombination, and transformation of a host cell, and any such construct as may be desirable to provide embodiments of this invention.

Methods of Use and Article of Manufacture

The present invention includes the following method embodiments. In an embodiment, a method of vaccinating an animal comprising administering a composition comprising an attenuated swine influenza strain and a pharmaceutical or veterinarily acceptable carrier, excipient, or vehicle to an animal is disclosed. In one aspect of this embodiment, the animal is a porcine.

In one embodiment of the invention, a prime-boost regimen can be employed, which is comprised of at least one primary administration and at least one booster administration using at least one common polypeptide, antigen, epitope or immunogen. Typically the immunological composition or vaccine used in primary administration is different in nature from those used as a booster. However, it is noted that the same composition can be used as the primary administration and the booster administration. This administration protocol is called "prime-boost".

A prime-boost regimen comprises at least one prime-administration and at least one boost administration using at least one common polypeptide and/or variants or fragments thereof. The vaccine used in prime-administration may be different in nature from those used as a later booster vaccine. The prime-administration may comprise one or more administrations. Similarly, the boost administration may comprise one or more administrations.

In some embodiments, the prime-vaccination may be performed with one of the disclosed reassortant attenuated SIV vaccine formulations. In such embodiments, the boost may be performed using the same attenuated SIV vaccine formulation, or, it may performed using a different attenuated SIV vaccine formulation. In other embodiments, the prime-vaccination may performed with an autogenous vaccine (i.e. a vaccine based upon or derived from the strain currently circulating in a population of porcine animals). In such embodiments, the boost-vaccination may be performed with either the same autogenous vaccine, or, with one or more of the attenuated SIV vaccine formulations disclosed herein. Other effective combinations of prime and boost will be readily apparent to the skilled person, now that the invention has been disclosed.

The dose volume of compositions for target species that are mammals, e.g., the dose volume of pig or swine compositions, based on viral antigens, is generally between about 0.1 to about 2.0 ml, between about 0.1 to about 1.0 ml, and between about 0.5 ml to about 1.0 ml.

The efficacy of the vaccines may be tested about 2 to 4 weeks after the last immunization by challenging animals, such as porcine, with a virulent strain of swine influenza. Both homologous and heterologous strains are used for challenge to test the efficacy of the vaccine. The animal may be challenged by IM or SC injection, spray, intra-nasally, intra-ocularly, intra-tracheally, and/or orally. Samples from joints, lungs, brain, and/or mouth may be collected before and post-challenge and may be analyzed for the presence of swine influenza-specific antibody.

The compositions comprising the attenuated viral strains of the invention used in the prime-boost protocols are contained in a pharmaceutically or veterinary acceptable vehicle, diluent or excipient. The protocols of the invention protect the animal from swine influenza and/or prevent disease progression in an infected animal.

The various administrations are preferably carried out 1 to 6 weeks apart. In particular embodiments, the time interval is from about 3 to about 5 weeks. In more particular embodiments, the interval is about 4 weeks, and an annual booster is also envisioned. The porcine animals may be at least about 3-4 weeks of age at the time of the first administration, or, they may even be as young as 1 day old.

In some embodiments, the disclosed attenuated SIV vaccine formulations may be administered during each gestation. Accordingly, in some embodiments, sows may be vaccinated between about 2 to about 3 times per year (i.e. about 4 to about 6 times per year, in the case where a prime-boost vaccination regimen is used). A particularly useful route of administration for sow is intramuscular (IM).

It should be understood by one of skill in the art that the disclosure herein is provided by way of example and the present invention is not limited thereto. From the disclosure herein and the knowledge in the art, the skilled artisan can determine the number of administrations, the administration route, and the doses to be used for each injection protocol, without any undue experimentation.

Another embodiment of the invention is a kit for performing a method of eliciting or inducing an immunological or protective response against swine influenza in an animal comprising an attenuated swine influenza immunological composition or vaccine and instructions for performing the method of delivery in an effective amount for eliciting an immune response in the animal.

Another embodiment of the invention is a kit for performing a method of inducing an immunological or protective response against swine influenza in an animal comprising a composition or vaccine comprising an attenuated swine influenza strain of the invention, and instructions for performing the method of delivery in an effective amount for eliciting an immune response in the animal.

Yet another aspect of the present invention relates to a kit for prime-boost vaccination according to the present invention as described above. The kit may comprise at least two vials: a first vial containing a vaccine or composition for the prime-vaccination according to the present invention, and a second vial containing a vaccine or composition for the boost-vaccination according to the present invention. The kit may advantageously contain additional first or second vials for additional prime-vaccinations or additional boost-vaccinations.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on page 147 of "Vaccine Design, The Subunit and Adjuvant Approach" published by M. Powell, M. Newman, Plenum Press 1995, and the emulsion MF59 described on page 183 of the same work, (4) cationic lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

In an embodiment, adjuvants include those which promote improved absorption through mucosal linings. Some examples include MPL, LTK63, toxins, PLG microparticles and several others (Vajdy, M. Immunology and Cell Biology (2004) 82, 617-627). In an embodiment, the adjuvant may be a chitosan (Van der Lubben et al. 2001; Patel et al. 2005; Majithiya et al. 2008; U.S. Pat. No. 5,980,912).

In some embodiments, the invention provides a vaccine comprising an attenuated swine influenza virus (SIV), which comprises a nucleic acid molecule encoding a deoptimized SIV hemagglutinin (HA) gene, a deoptimized SIV neuraminidase (NA) gene, non-deoptimized SIV M, NP, PA, PB1 and PB2 genes, and optionally, a deoptimized SIV NS1 gene; wherein, it is the presence in the SIV of the deoptimized genes, relative to a corresponding virulent parental SIV strain, which contains wild type versions of the deoptimized genes, which is responsible for the attenuated phenotype.

In some embodiments, the attenuated SIV strain comprises a deoptimized SIV NS1 gene.

In some embodiments, the virulent parental SIV strain is a natural SIV isolate. In some embodiments, the virulent parental strain is an H1N1, H1N2 or H3N2 strain.

In some embodiments, the deoptimized HA gene comprises a nucleic acid molecule having the sequence as set forth in SEQ ID NO:22, 29 or 105; and, the deoptimized NA gene comprises a nucleic acid molecule having the sequence as set forth in SEQ ID NO:25, 32 or 38.

In some embodiments, the deoptimized HA and NA genes comprise nucleic acid molecules having the sequences as set forth in SEQ ID NO:22 & 25, respectively; 29 & 32, respectively; or 105 & 38, respectively.

In some embodiments, the deoptimized NS1 gene comprises a nucleic acid sequence having the sequence as set forth in SEQ ID NO:27.

In some embodiments, the non-deoptimized M, NP, PA, PB1 and PB2 are:
  a) SIV H1N1 genes, each gene having at least 70%, at least 80%, or at least 90% identity to the sequences as set forth in SEQ ID NOs: 19 (M), 9 (NP), 13 (PA), 15 (PB1) and 17 (PB2); or
  b) SIV H1N2 genes, each gene having at least 70%, at least 80%, or at least 90% identity to the sequences as set forth in SEQ ID NOs: 44 (M), 48 (NP), 52 (PA), 54 (PB1) and 56 (PB2); or
  c) SIV H3N2 genes, each gene having at least 70%, at least 80%, or at least 90% identity to the sequences as set forth in SEQ ID NOs: 62 (M1), 64 (M2), 68 (NP), 72 (PA), 74 (PB1) and 76 (PB2).

In some embodiments, the non-deoptimized M, NP, PA, PB1 and PB2 are:
  a) SIV H1N1 genes, each gene comprising the sequences as set forth in SEQ ID NOs: 19 (M), 9 (NP), 13 (PA), 15 (PB1) and 17 (PB2); or
  b) SIV H1N2 genes, each gene comprising the sequences as set forth in SEQ ID NOs: 44 (M), 48 (NP), 52 (PA), 54 (PB1) and 56 (PB2); or
  c) SIV H3N2 genes, each gene comprising the sequences as set forth in SEQ ID NOs: 62 (M1), 64 (M2), 68 (NP), 72 (PA), 74 (PB1) and 76 (PB2).

In another aspect, the invention provides a vaccine composition, for inducing a protective immune response in a porcine animal, comprising one or more attenuated swine influenza viruses according to the present disclosure, and wherein the protective response is elicited within about three (3) weeks after vaccination.

In some embodiments, the vaccine composition comprises one or more attenuated SIV(s), which comprise at least one nucleic acid molecule encoding a deoptimized SIV hemagglutinin (HA) gene, a deoptimized SIV neuraminidase (NA) gene, non-deoptimized SIV M, NP, PA, PB1 and PB2 genes, and optionally, a deoptimized SIV NS1 gene. In the cases where the attenuated SIV comprises a non-deoptimized NS gene, said SIV does not contain also a deoptimized NS1 gene.

In some embodiments, it is the presence of the deoptimized genes in the reassortant SIV, relative to a corresponding parental SIV, which contains wild type versions of the deoptimized genes, which is responsible for the attenuated phenotype. In some embodiments, the attenuated SIV strain comprises a deoptimized SIV NS1 gene, a deoptimized HA gene and a deoptimized NA gene segment, with the proviso that the remaining SIV gene segments are non-deoptimized.

In some embodiments, the vaccine composition further comprises a pharmaceutically or veterinary acceptable vehicle, diluent or excipient. In some embodiments, the vaccine provides a protective immune response in porcine against virulent swine influenza challenge. In some embodiments, the protection is homologous. In other embodiments, the protection is both homologous and heterologous. In still other embodiments, vaccine comprises multiple subtype attenuated reassortant SIV, and elicits protective immune responses in porcines against virulent challenge and/or subsequent exposure to virulent SIV H1N1, H1N2 and H3N2 subtypes.

In some embodiments, the vaccine composition further comprises at least one additional antigen associated with or derived from a porcine pathogen other than swine influenza.

In some embodiments, the at least one or more additional antigen(s) is capable of eliciting in a porcine an immune response against *Mycoplasma hyopneumoniae* (*M. hyo*), porcine circovirus 2 (PCV2), porcine respiratory and reproductive syndrome virus (PRRSV) or other pathogen capable of infecting and causing illness or susceptibility to illness in a porcine.

In another aspect, the invention provides a method of eliciting a protective immune response in a porcine subject comprising administering to the subject a prophylactically or therapeutically effective dose of the disclosed vaccine compositions, which minimally comprise an attenuated SIV according to the present disclosure.

In some embodiments, the method further comprises administering to the subject at least one adjuvant.

In another aspect, the invention provides a method of vaccinating an animal comprising at least one administration of at least vaccine composition according to this disclosure.

In some embodiments of the method, the porcine is a sow from about 3 weeks to about 6 weeks prefarrowing.

In some embodiments of the method, the resulting piglets have a reduced morbidity and/or mortality as compared to piglets coming from unvaccinated sows.

In another aspect, the invention provides a vaccine-producing composition comprising a plurality of vectors for the production of attenuated reassortant swine influenza viruses (SIVs) including vectors comprising promoters operably linked to SIV HA, NA and optionally NS1 cDNAs, wherein the HA, NA and optionally NS1 cDNAs encode deoptimized coding sequences, relative to the corresponding virulent SIV strain's HA, NA and NS1 coding sequences. As used herein, "vaccine-producing composition" means that when the composition is transfected into a suitable host cell, for example, an HEK cell, a re-assortant influenza vaccine strain will be produced.

In some embodiments, the composition comprises plasmids comprising deoptimized HA and NA genes comprise nucleic acid molecules having the sequences as set forth in SEQ ID NO:22 & 25, respectively; 29 & 32, respectively; or 105 & 38, respectively; and optionally, wherein the deoptimized NS1 gene comprises a nucleic acid sequence having the sequence as set forth in SEQ ID NO:27.

In some embodiments, the deoptimized HA and NA genes comprise nucleic acid molecules having the sequences as set forth in SEQ ID NO:91 & 92, respectively; 93 & 94, respectively; or 105 & 96, respectively; and optionally, wherein the deoptimized NS1 gene comprises a nucleic acid sequence having the sequence as set forth in SEQ ID NO:90.

In some embodiments, the vectors comprise the following TRIG gene segments: NS (SEQ ID NO:83), M (SEQ ID NO:82), NP (SEQ ID NO:81), PA (SEQ ID NO:80), PB1 (SEQ ID NO:79), PB2 (SEQ ID NO:78).

In some embodiments, the vectors comprise the following TRIG gene segments: NS (SEQ ID NO:83), M (SEQ ID NO:82), NP (SEQ ID NO:81), PA (SEQ ID NO:80), PB1 (SEQ ID NO:79), PB2 (SEQ ID NO:78).

In some embodiments, the plasmids have the sequences as set forth in: a) SEQ ID NOs:109 and 110; b) SEQ ID NOs:108, 109 and 110; c) SEQ ID NOs:111 and 112; d) SEQ ID NOs:108, 111 and 112; e) SEQ ID NOs:115 and 114; or f) SEQ ID NOs:108, 115 and 114.

In some embodiments, when the plasmids are transfected into suitable, virus-producing cells, attenuated, reassortant viruses selected from vSIV01, vSIV02, vSIV03, vSIV04, vSIV05 and vSIV06 are produced and are rescuable.

In another aspect, the invention provides a method to prepare influenza virus, comprising: contacting a cell with an amount of the composition of any one of claims 19 to 26 that is effective to yield reassortant, attenuated, infectious influenza virus.

In another aspect, the invention provides a cell comprising the composition comprising the disclosed plurality of reverse genetic vectors encoding SIV gene segments.

In still another aspect, the invention provides a bi-valent attenuated SIV vaccine, comprising an effective amount of an attenuated H1N1 SIV and an effective amount an attenuated H3N2 SIV.

In some embodiments, the bi-valent attenuated SIV vaccine comprises an effective amount of an attenuated H1N2 SIV and an effective amount of an attenuated H3N2 SIV.

In some embodiments, the invention provides a tri-valent attenuated SIV vaccine, comprising an effective amount of an attenuated H1N1 SIV, an effective amount of an attenuated H1N2, and an effective amount of an attenuated H3N2 SIV.

REFERENCES

Coleman J R et al. Virus attenuation by genome-scale changes in codon pair bias. Science 2008. 320(5884): 1784-1787. PMID: 18583614

Mueller S et al. Live attenuated influenza virus vaccines by computer-aided rational design. Nat. Biotechn. 2010. 28:723-727. PMID: 20543832

Yang C et al. Deliberate reduction of hemagglutinin and neuraminidase expression of influenza virus leads to an ultra-protective influenza vaccine in mice. Proc. Natl., Acad. Sci. USA 2013. 110:9481-9486. PMID: 23690603

Le Nouën C et al. Attenuation of Human Respiratory Syncytial Virus by Genome Scale Codon-Pair Deoptimization. Proc. Natl. Acad. Sci. USA Aug. 25, 2014. pii: 201411290. PMID: 25157129

Altschul S F, Madden T L. 1997. Gapped BLAST and PSI-BLAST: a new generation of protein database search programs. Nucleic Acids Res. 25:3389-3402.

Bragstad K et al. 2008. The evolution of human influenza A viruses from 1999 to 2006: A complete genome study. Virology J. 5:40.

Cai Z et al. 2010. A computational framework for influenza antigenic cartography. PLoS Computational Biology, 6(10):e1000949.

Cottey R et al. 2001. Influenza virus. Curr. Protoc. Immunol. 19.11:1-32.

Das S R et al. 2011. Fitness costs limit influenza A virus hemagglutinin glycosylation as an immune evasion strategy. Proc. Natl. Acad. Sci. 108:E1417-E1422.

Desselberger U et al. 1978. Biochemical evidence that "new" influenza virus strains in nature may arise by recombination (reassortment). Proc. Natl. Acad. Sci. 75:3341-3345.

Hause B M et al. 2011. Genetic and antigenic characterization of recent human-like H1 (8-cluster) swine influenza virus isolates. J. Swine Health Prod. 19:268-276.

Hause B M et al. 2010. Antigenic categorization of contemporary H3N2 swine influenza virus isolates using a high-throughput serum neutralization assay. J. Vet. Diagn. Invest. 22:352-359.

Hay A J et al. 2001. The evolution of human influenza viruses. Philos. T. R. Soc. B. 356:1861-1870.

Hensley S E et al. 2011. Influenza A virus hemagglutinin antibody escape promotes neuraminidase antigenic variation and drug resistance. PLoS ONE 6:e15190.

Hoffmann E et al. 2001. Universal primer set for the full length amplification of al influenza viruses. Arch. Virol. 146:2275-2289.

Hoffmann E et al. 2000. A DNA transfection system for generation of influenza A virus from eight plasmids. Proc. Natl. Acad. Sci. 97:6108-6113.

Karasin A I et al. 2006. Identification of human H1N2 and human-swine reassortant H1N2 and H1N1 influenza A viruses among pigs in Ontario, Canada (2003-2005). J. Clin. Microbiol. 44:1123-1126.

Long J et al. 2011. Evolution of H3N2 influenza virus in a guinea pig model. PLoS ONE 6:e20130.

Lorusso A et al. 2012. Contemporary epidemiology of North American lineage triple reassortant influenza A viruses in pigs. Curr. Top. Microbiol. Immunol. January 22 [epub ahead of print].

Sali A, Potterton L. 1995. Evaluation of comparative protein modeling by MODELLER." Proteins 23: 318-326.

Schild G et al. 1974. Antigenic variation in current influenza A viruses: evidence for a high frequency of antigenic 'drift' for the Hong Kong virus. Bull. World Health Organ. 51:1-11.

Strengell M et al. 2011. Minor changes in the hemagglutinin of influenza A(H1N1)2009 virus alter its antigenic properties. PLoS ONE 6:e25848.

Vincent A L et al. 2009. Characterization of a newly emerged genetic cluster of H1N1 and H1N2 swine influenza virus in the United States. Virus Genes 39:176-185.

The invention will now be further described by way of the following non-limiting examples.

EXAMPLES

Example 1—Construction of Deoptimized Swine Influenza Viruses

Materials/Methods.

Briefly, beginning with a triple reassortant internal gene (TRIG) swine influenza virus (SIV) (A/swine/North Carolina/3793/08 (H1N1)) "base genome," reassortant Modified Live Attenuated (MLV) Influenza Viruses (LAIVs) were produced using a standard eight plasmid reverse genetics approach (Hoffman, 2003; U.S. Pat. No. 9,216,211 (to Merial, Inc.)). To make the reassortant LAIVs, the TRIG sequences were added to codon deoptimized HA (SEQ ID NOs:22, 29, 35 or 105), NA (SEQ ID NOs:25, 32 or 38) and NS (SEQ ID NO:27). The deoptimized sequences were produced beginning with the following base sequences: H1N1 HA (SEQ ID NO:21), H1N2 HA (SEQ ID NO:28), and H3N2 HA (SEQ ID NO:-34); H1N1 NA (SEQ ID NO:24), H1N2 NA (SEQ ID NO:31), and H3N2 NA (SEQ ID NO:37). The base CDS were subjected to computer-assisted codon deoptimization, without altering the originally encoded amino acids. The CDS content of the LAIV constructs is summarized in Table 1.

sequences remained the same, such that SEQ ID NOs:34 & 35 both encode for the amino acid sequence set forth in SEQ ID NO:36; and, SEQ ID NOs:37 & 38 both encode the amino acid sequence set forth in SEQ ID NO:39. Additionally, the coding sequence of the NS1 gene (SEQ ID NO: 1) of A/swine/NC/3793/2008 (H1N1) was codon deoptimized to produce NS1-DO (SEQ ID NO:27.

Figure 3A:
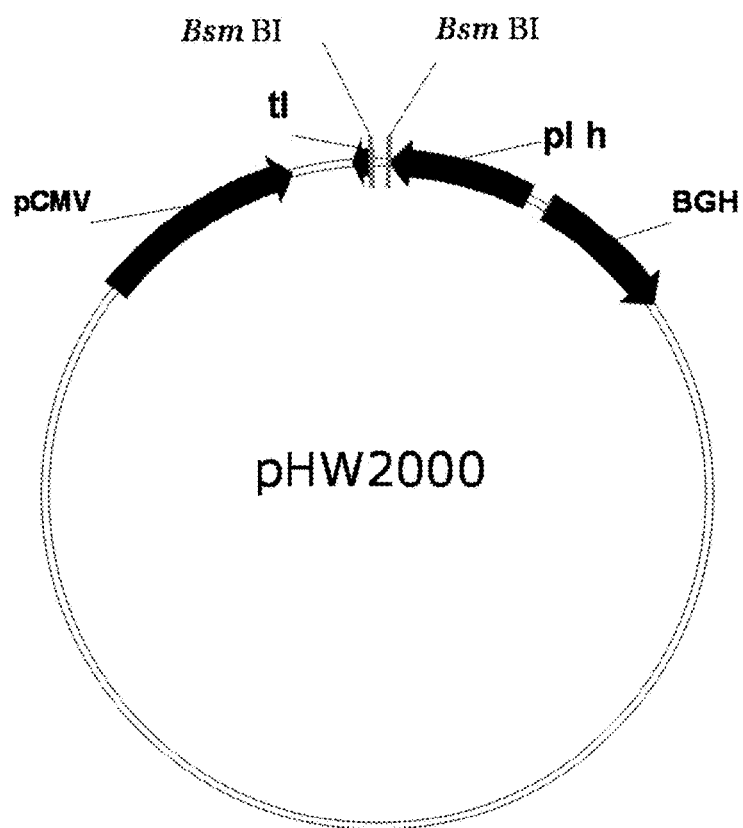
FIG. 3A is a map of the pHW2000 cloning vector, used to carry gene segments for producing infectious, re-assortant, reverse genetics-produced swine influenza viruses (rgSIV)
Figure 3B:
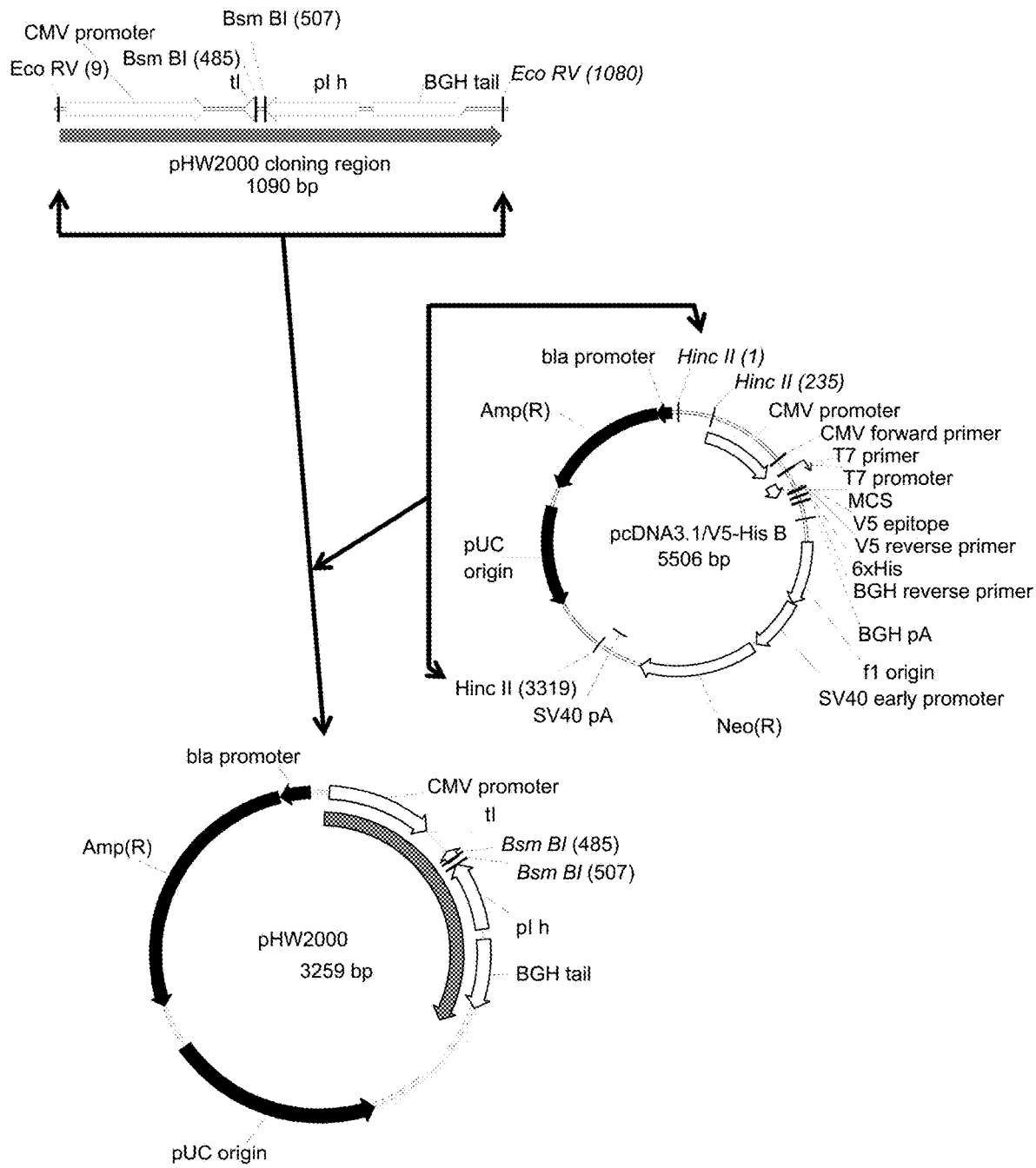
FIG. 3B schematizes the construction of pHW2000, beginning with a synthesized pHW2000 cloning region and the pcDNA3.1/V5-His B plasmid.

Six internal gene segments from A/swine/North Carolina/3793/2008 (H1N1) were cloned into the pHW2000 cloning vector (FIG. 3A) (SEQ ID NO:107), to produce: pHW2000-PB2, pHW2000-PB1, pHW2000-PA, pHW2000-NP, pHW2000-M, pHW2000-NS. pHW2000 itself was produced by synthesizing a dual promoter-tail cassette, pHW2000 cloning region, including 5' and 3' EcoRV restriction sites (see Virology 267, 310-317, 2000, which is herein incorporated by reference in its entirety). Then, the antibiotics resistance gene cassette and pUC origin were taken from pCDNA3.1/V5-His B by cutting out the HincII restriction fragment, and ligating said fragment together with the dual promoter-containing EcoRV fragment. The resulting plasmid was pHW2000, the construction of which is schematize in FIG. 3B.

A plurality of plasmids, each containing the dual promoter cassette (pCMV-tI-restriction site-pIh-BGH tail) and one or

TABLE 1

CDS present in vSIV01, vSIV02, vSIV05 and vSIV06.

| rgSIV | Subtype | Deoptimized Gene CDS | TRIG Gene CDS |
|---|---|---|---|
| vSIV01 | H1N2 | HA-DO (SEQ ID NO: 29); NA-DO (SEQ ID NO: 32) | NS (SEQ ID NO: 20), M (SEQ ID NO: 19), NP (SEQ ID NO: 9), PA (SEQ ID NO: 13), PB1 (SEQ ID NO: 15), PB2 (SEQ ID NO: 17) |
| vSIV02 | H1N2 | HA-DO (SEQ ID NO: 29); NA-DO (SEQ ID NO: 32); NS1-DO (SEQ ID NO: 27) | M (SEQ ID NO: 19), NP (SEQ ID NO: 9), PA (SEQ ID NO: 13), PB1 (SEQ ID NO: 15), PB2 (SEQ ID NO: 17) |
| vSIV05 | H1N1 | HA-DO (SEQ ID NO: 22); NA-DO (SEQ ID NO: 25) | NS (SEQ ID NO: 20), M (SEQ ID NO: 19), NP (SEQ ID NO: 9), PA (SEQ ID NO: 13), PB1 (SEQ ID NO: 15), PB2 (SEQ ID NO: 17) |
| vSIV06 | H1N1 | HA-DO (SEQ ID NO:-22); NA-DO (SEQ ID NO: 25); NS1-DO (SEQ ID NO: 27) | M (SEQ ID NO: 19), NP (SEQ ID NO: 9), PA (SEQ ID NO: 13), PB1 (SEQ ID NO: 15), PB2 (SEQ ID NO: 17) |

When the TRIG sequences were combined with the HA-DO, NA-DO and NS1-DO from either wild type H1N1 or wild type H1N2 SIV strains, infectious re-assortant SIV virions were recovered. In contrast, when the TRIG sequences were combined with the HA-DO, NA-DO and NS1-DO from an H3N2 SIV strain, infectious re-assortant SIV virions were not recovered. Accordingly, applicants have demonstrated the broad principle that HA, NA and NS1 genes, from either H1N1 or H1N2 influenza strains—but not one specific H3N2 strain—may be successfully combined with the H1N1-based TRIG genes to produce attenuated reassortant SIV.

In order to address the unforeseen problem that the H3N2-derived HA-DO, NA-DO and NS1-DO sequences did not successfully combine with the TRIG sequences to produce infectious virions, applicants devised and constructed chimeric versions of the H3N2 codon deoptimized HA genes. Briefly, wild type H3N2 HA (SEQ ID NO:34) and NA (SEQ ID NO:37) gene coding sequences were subjected to codon de-optimization (Codagenix) to produce codon de-optimized H3N2 HA-DO (SEQ ID NO:35) and H3N2 NA-DO (SEQ ID NO:38). The encoded amino acid more influenza virus gene segment(s), may be transfected into cells to produce infectious influenza virus particles (see, e.g., US 2005/0186563 A1, to St. Jude Children's Research Hospital, which is also incorporated herein by reference in its entirety).

Now that the inventive sequences and combinations of SIV reassortant viruses have been disclosed, the skilled person will appreciate that any suitable reverse genetics system may be employed to produce influenza particles disclosed herein. For example, the disclosed deoptimized and TRIG sequences could be expressed to produce intact, infectious reassortant virions using the eight-plasmid system (U.S. Pat. No. 6,951,754 B2, to St. Jude) or the single plasmid system (U.S. Pat. No. 9,163,219 B2, to Arizona Board of Regents), both publications herein incorporated by reference in their entirety.

The complete "TRIG" H1N1 segments have the following sequence designations: PB2 (SEQ ID NO:78); PB1 (SEQ ID NO:79); PA (SEQ ID NO:80); NP (SEQ ID NO:81); M (SEQ ID NO:82); NS (SEQ ID NO:83). The HA and NA have the following sequence designations: HA of H1N1 (SEQ ID NO:84); NA of H1N1 (SEQ ID NO:85); HA of H1N2 (SEQ ID NO:86); NA of H1N2 (SEQ ID NO:87); HA of H3N2 (SEQ ID NO:88); and NA of H3N2 (SEQ ID NO:89).

To produce the H3N2 re-assortant SIV, codon deoptimized H3N2 HA (HA-DO) (SEQ ID NO:95) and NA (NA-DO) (SEQ ID NO:96) gene segments were chemically synthesized (GenScript) and cloned into pHW2000 by subcloning: pHW2000-H3N2-HA-DO (SEQ ID NO:113); and pHW2000-H3N2-NA-DO (SEQ ID NO:114). The pHW2000-TRIG-NS-DO (SEQ ID NO:108) was similarly constructed, and contains a codon deoptimized NS1 gene (SEQ ID NO:90).

Virus Rescue.

Co-transfection of eight (8) reverse genetics plasmids, consisting of internal segment plasmids (PB2, PB1, PA, NP, M, NS or NS-DO) from TRIG (H1N1) and codon deoptimized HA, NA segment from H3N2 was conducted with Lipofectamine 2000CD (Invitrogen) as per the manufacturer's protocol (Tables 2 and 3). However, three independent attempts of transfection/passage were not successful to rescue the infectious virus.

TABLE 2

Reverse genetics plasmids for H3N2 HA, NA deoptimized virus

|   | Segment | SEQ ID NO | Strain | Subtype |
|---|---------|-----------|--------|---------|
| 1 | PB2     | 78        | 3793   | H1N1    |
| 2 | PB1     | 79        | 3793   | H1N1    |
| 3 | PA      | 80        | 3793   | H1N1    |
| 4 | HA-DO   | 95        | 14-3037| H3N2    |
| 5 | NP      | 81        | 3793   | H1N1    |
| 6 | NA-DO   | 96        | 14-3037| H3N2    |
| 7 | M       | 82        | 3793   | H1N1    |
| 8 | NS      | 83        | 3793   | H1N1    |

TABLE 3

Reverse genetics plasmids for H3N2 HA, NA, NS deoptimized virus

|   | Segment | SEQ ID NO | Strain | Subtype |
|---|---------|-----------|--------|---------|
| 1 | PB2     | 78        | 3793   | H1N1    |
| 2 | PB1     | 79        | 3793   | H1N1    |
| 3 | PA      | 80        | 3793   | H1N1    |
| 4 | HA-DO   | 95        | 14-3037| H3N2    |
| 5 | NP      | 81        | 3793   | H1N1    |
| 6 | NA-DO   | 96        | 14-3037| H3N2    |
| 7 | M       | 82        | 3793   | H1N1    |
| 8 | NS-DO   | 90        | 3793   | H1N1    |

Transfection with Different NA Segments.

Since the deoptimized H3N2 virus could not be rescued, a codon deoptimized NA segment (H1N2 NA-DO; SEQ ID NO:94; from A/Swine/NC/0036-2/2010 (H1N2)) was used instead of H3N2 NA-DO (Tables 4 & 5). The H1N2-NA-DO supports the codon deoptimized H1N2 virus rescue with the same protocol (i.e. the H1N2 re-assortant virus with HA-DO, NA-DO, NS1-DO was recovered easily). Since NA has an important role in the release of SIV from cells, Applicants tried to recover the H3 virus using H1N2-NA-DO. Further, this approach seemed plausible, since both NAs are N2 sub-types, and have about 92% amino acid identity. However, no H3/H1N2-NA-DO re-assortant virus was recoverable. This indicated that HA might be the problem, but not NA. Therefore, a chimeric HA segment was devised and constructed.

TABLE 4

Transfection for codon deoptimized H3N2 with H1N2 NA segment

|   | Segment | SEQ ID NO | Strain  | Subtype |
|---|---------|-----------|---------|---------|
| 1 | PB2     | 78        | 3793    | H1N1    |
| 2 | PB1     | 79        | 3793    | H1N1    |
| 3 | PA      | 80        | 3793    | H1N1    |
| 4 | HA-DO   | 95        | 14-3037 | H3N2    |
| 5 | NP      | 81        | 3793    | H1N1    |
| 6 | NA-DO   | 94        | 0036-2  | H1N2    |
| 7 | M       | 82        | 3793    | H1N1    |
| 8 | NS      | 83        | 3793    | H1N1    |

TABLE 5

Transfection for codon deoptimized H3N2 with H1N2 NA segment

|   | Segment | SEQ ID NO | Strain  | Subtype |
|---|---------|-----------|---------|---------|
| 1 | PB2     | 78        | 3793    | H1N1    |
| 2 | PB1     | 79        | 3793    | H1N1    |
| 3 | PA      | 80        | 3793    | H1N1    |
| 4 | HA-DO   | 95        | 14-3037 | H3N2    |
| 5 | NP      | 81        | 3793    | H1N1    |
| 6 | NA-DO   | 94        | 0036-2  | H1N2    |
| 7 | M       | 82        | 3793    | H1N1    |
| 8 | NS-DO   | 90        | 3793    | H1N1    |

Unfortunately (and unpredictably), rescue of infectious reassortant virus was not achieved using the codon deoptimized H1N2 NA segment (pHW2000-H1N2-NA-DO). Thus, the combination of TRIG PB2, PB1, PA, NP, M, (NS) and H3N2 HA-DO, (TRIG NS-DO) did not yield rescuable amounts of infectious virus. In a further effort to produce a reassortant H3N2 SIV, combinations of different deoptimized HA or NA segments were used to examine the compatibility of H3N2 HA and NA segment with backbone plasmids (Tables 6 & 7). Nevertheless, no infectious virus was rescued despite multiple attempts.

TABLE 6

Transfection for virus rescue with different HA segment

|   | Segment | SEQ ID NO | Strain  | Subtype |
|---|---------|-----------|---------|---------|
| 1 | PB2     | 78        | 3793    | H1N1    |
| 2 | PB1     | 79        | 3793    | H1N1    |
| 3 | PA      | 80        | 3793    | H1N1    |
| 4 | HA-DO   | 93        | 0036-2  | H1N2    |
| 5 | NP      | 81        | 3793    | H1N1    |
| 6 | NA-DO   | 96        | 14-3037 | H3N2    |
| 7 | M       | 82        | 3793    | H1N1    |
| 8 | NS      | 83        | 3793    | H1N1    |

TABLE 7

Transfection for virus rescue with different NA segment

|   | Segment | SEQ ID NO | Strain  | Subtype |
|---|---------|-----------|---------|---------|
| 1 | PB2     | 78        | 3793    | H1N1    |
| 2 | PB1     | 79        | 3793    | H1N1    |
| 3 | PA      | 80        | 3793    | H1N1    |
| 4 | HA-DO   | 95        | 14-3037 | H3N2    |
| 5 | NP      | 81        | 3793    | H1N1    |
| 6 | NA-DO   | 92        | 14-0081 | H1N1    |
| 7 | M       | 82        | 3793    | H1N1    |
| 8 | NS      | 83        | 3793    | H1N1    |

Construction of Chimeric HA.

Because reassortant SIV could not be rescued using H3N2 HA-DO or H3N2 NA-DO, chimeric HA-DO segments were constructed in which the ectodomain domain of H3N2 was fused to signal sequences (SS) and transmembrane domain (TMD)/cytoplasmic tail domain (CTD) of an H1N2 HA-DO protein (SEQ ID NO:86). Thus, the polynucleotide sequence encoding the ecto-domain of HA (H3N2) was cloned into pHW2000 containing SS, TMD and CTD of H1N2 HA protein (pHW2000-H1 SP-TM).

Construction of pHW2000-H1 SP-TM.

The 3'UTR/signal sequences of HA segment were amplified by PCR with Bm-HA-F and 3-Rev primer sets from pUC57-Kan-H1N2-HA-DO (Table 8, FIG. 4). Also, the TMD, CTD, and 5'UTR of the HA segment were amplified by PCR from pUC57-Kan-H1N2-HA-DO using 5-For and Bm-HA-R primer sets (Table 8, FIG. 4). Two PCR amplicons had overlapping sequences (21 nt, 5'-GACACAATAT-GTGTAGGCTAC-3') (SEQ ID NO:103), which allowed amplification of the entire region. A mixture of two PCR amplicons was used as template to amplify the 3'UTR/SS/TMD/CTD/5'UTR of the HA segment (H1 chimeric PCR amplicon) with Bm-HA-Forward and Bm-HA-Reverse primer set (FIG. 5).

TABLE 8

Primers used to construct pHW2000-H1 SP-TM

| primer | Sequences (5' to 3') | SEQ ID NO |
|---|---|---|
| Bm-HA-F | TATTCGTCTCAGGGAGCAAAAGCAGGGG | 97 |
| 3-Rev | GTAGCCTACACATATTGTGTC | 98 |
| 5-For | GACACAATATGTGTAGGCTACGATATCTTAGCGATATATTCGACGGT | 99 |
| Bm-HA-R | ATATCGTCTCGTATTAGTAGAAACAAGGGTGTTTT | 100 |
| H3ectFP | CTACATATGCACAAAAACTTCCCGGAAGT | 101 |
| H3ectRP | TAAGATATCTTTATATCCCGATTTTA | 102 |

Construction of pHW2000-H1 SP-TM.

The H1 chimeric PCR amplicons were cloned into pHW2000 by BsmBI restriction site (FIG. 6).

PCR Amplification of H3 Ecto-Domain and Cloning into pHW2000-H1-SP-TM Chimera.

Figure 8:
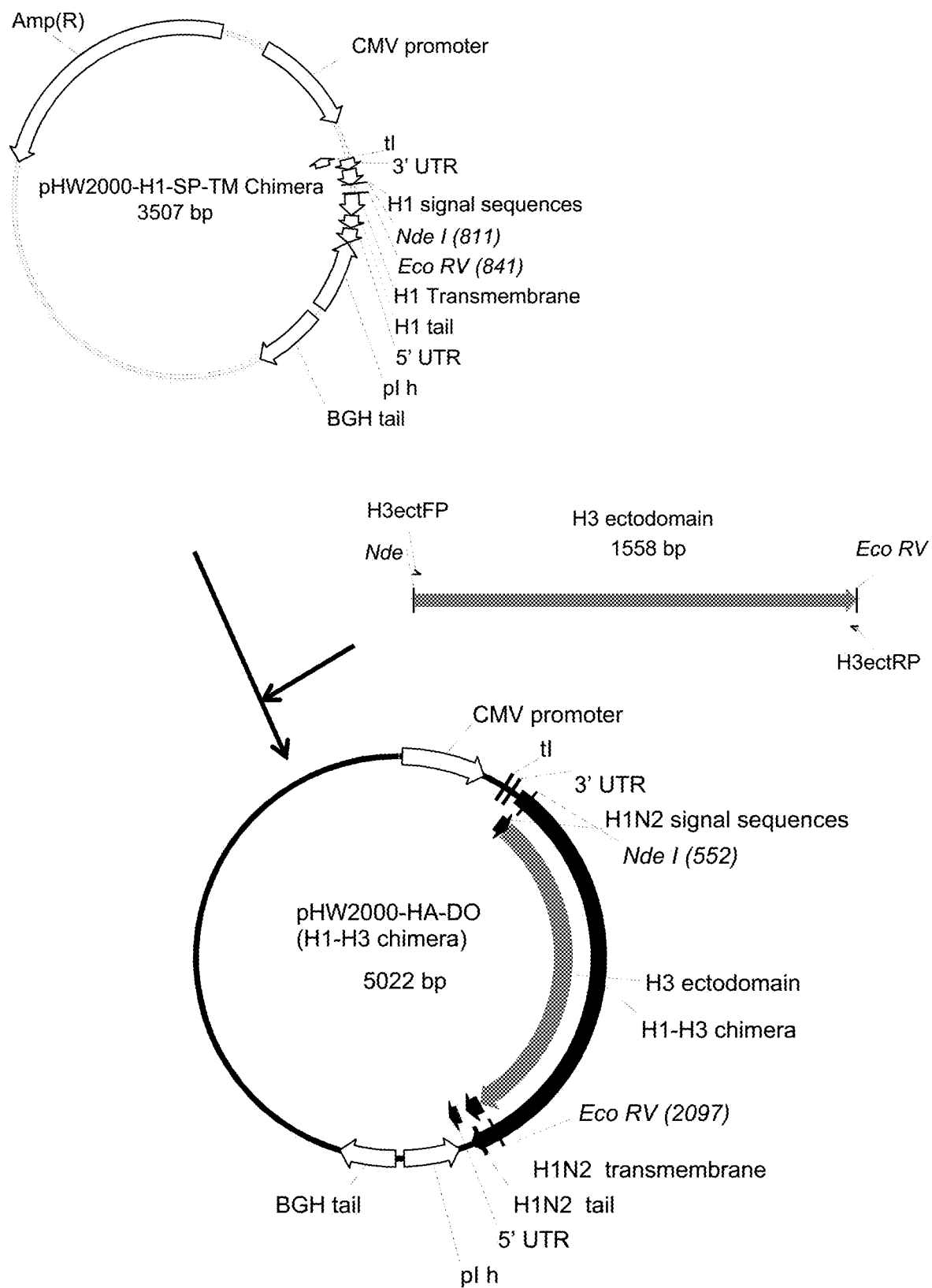
FIG. 8 shows the cloning scheme for production of pHW2000-HA-DO (H1-H3 chimera)
Figure 10:
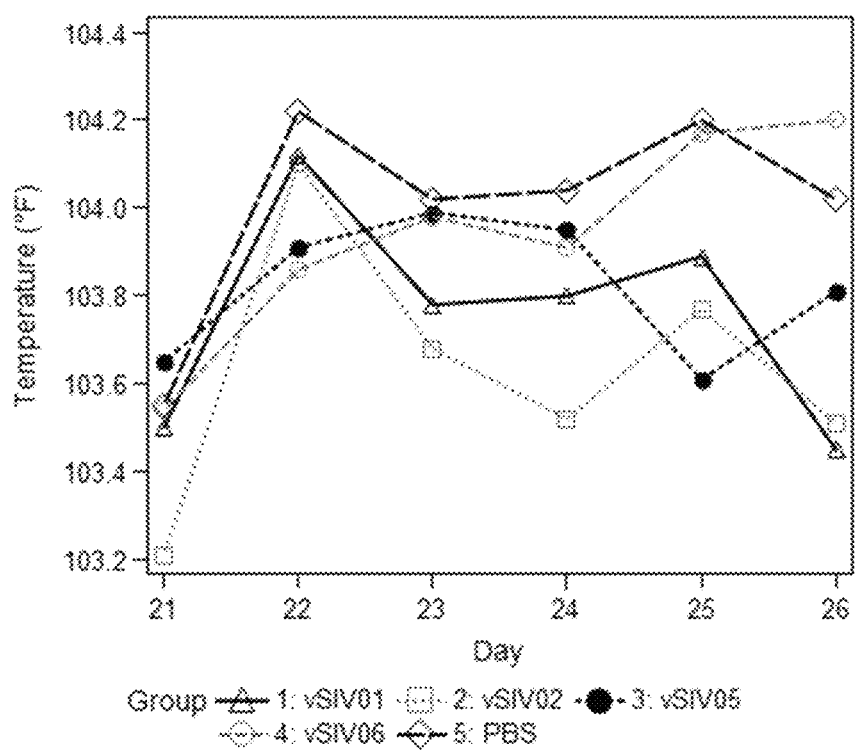
FIG. 10 is a graph showing group mean vaccinate temperature post-challenge.
Figure 11:
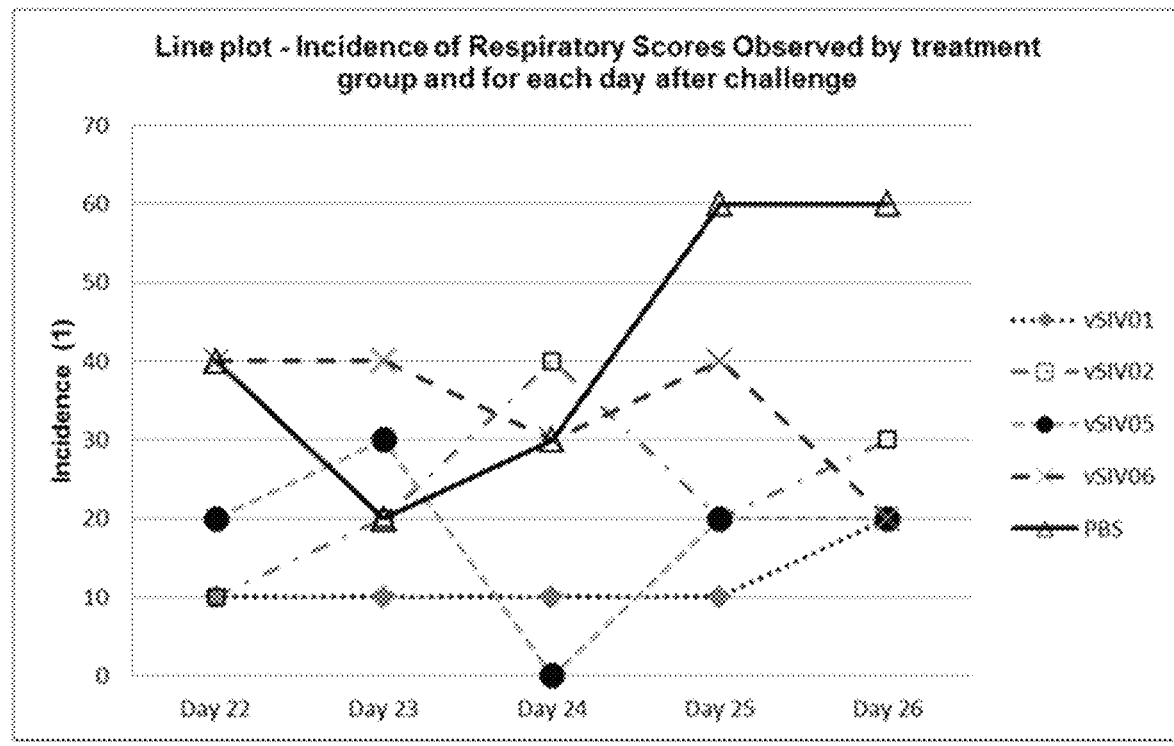
FIG. 11 is a graph showing the incidence of respiratory scores observed by treatment group and for each day after challenge.
Figure 12:
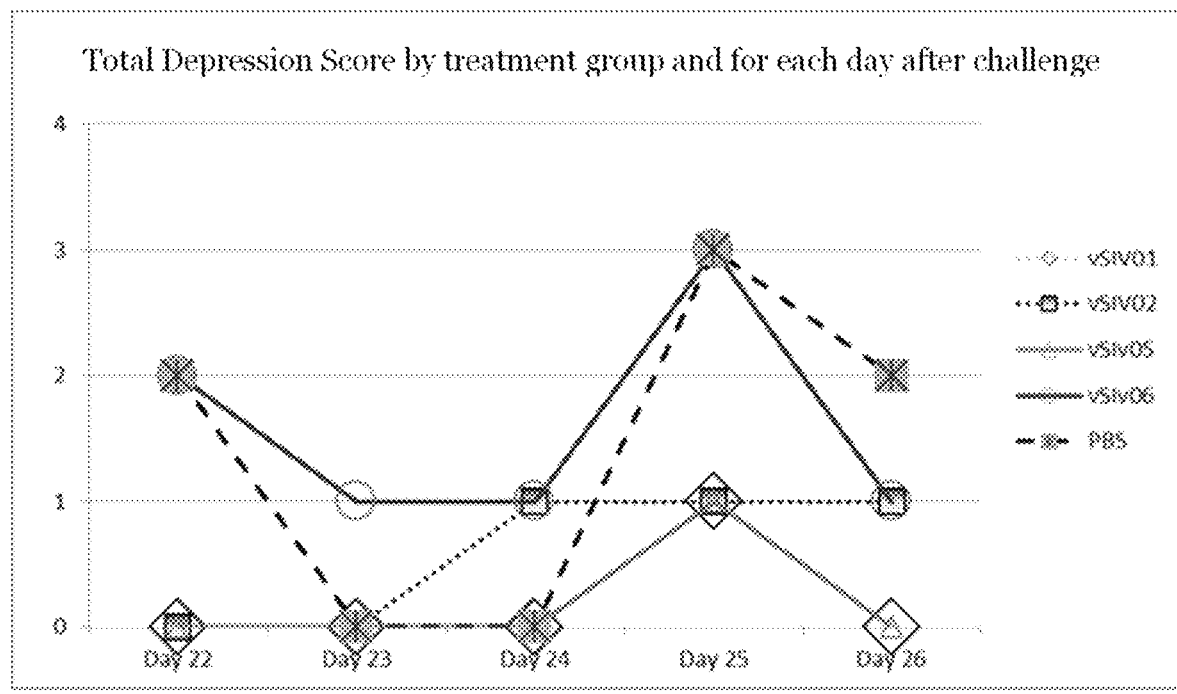
FIG. 12 is a graph showing total depression score by treatment group and for each day after challenge.
Figure 13:
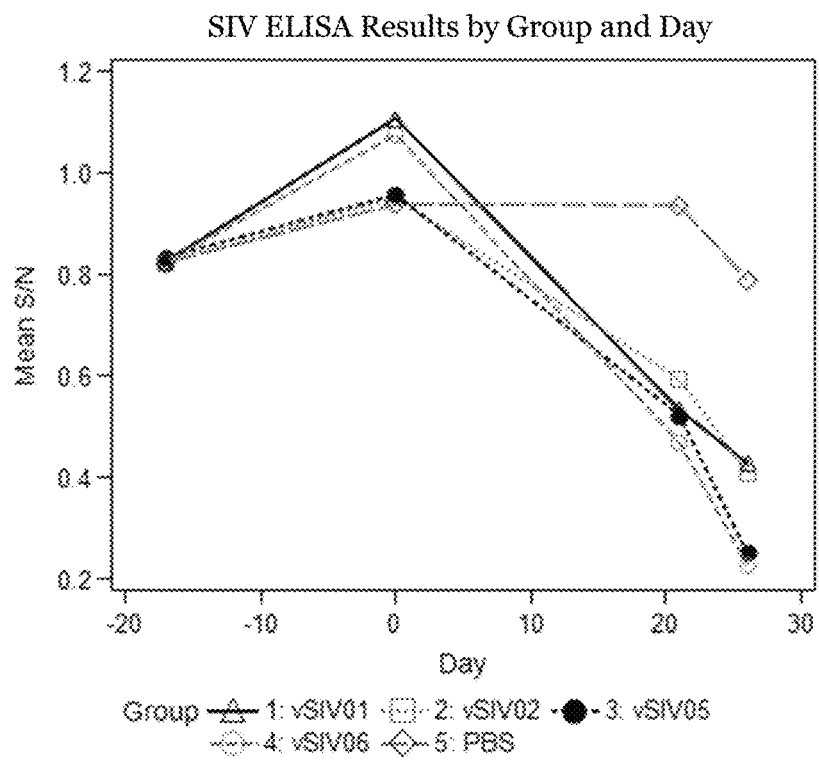
FIG. 13 is a graph showing SIV ELISA results by group and day.

The ecto-domain of HA (H3N2) was amplified from pUC57-Kan-H3N2-HA-DO (FIG. 7) using H3ectFP (SEQ ID NO:101) and H3ectRP (SEQ ID NO:102) primers. Next, the H3 ectodomain PCR amplicons (FIG. 7) were cloned into pHW2000-H1 SP-TM Chimera by NdeI and EcoRV restriction site (FIG. 8). The nucleotide sequences of resulting plasmid were confirmed by sequencing analysis (FIG. 9).

H3N2 Virus Rescue.

Co-transfection of reverse genetics plasmids including internal segment plasmids, pHW2000-HA-DO (H1-H3 chimera) and pHW2000-H3N2-NA-DO or pHW2000-H1N2-NA-DO, pHW2000-H1N1-NA-DO was conducted with by Lipofectamine 2000CD as detailed above and summarized below (Tables 9, 10 & 11).

TABLE 9

Reverse genetics plasmids for codon deoptimized HA-DO-H1-H3/H3N2 NA-DO virus

| | Segment | SEQ ID NO | Strain | Subtype |
|---|---|---|---|---|
| 1 | PB2 | 78 | 3793 | H1N1 |
| 2 | PB1 | 79 | 3793 | H1N1 |
| 3 | PA | 80 | 3793 | H1N1 |
| 4 | HA-DO-H1-H3 | 105 | 14-3037 | H1N2-H3N2 |
| 5 | NP | 81 | 3793 | H1N1 |
| 6 | NA-DO | 96 | 14-3037 | H3N2 |
| 7 | M | 82 | 3793 | H1N1 |
| 8 | NS | 83 | 3793 | H1N1 |

TABLE 10

Reverse genetics plasmids for codon deoptimized HA-DO-H1-H3/H1N2 NA-DO virus

| | Segment | SEQ ID NO | Strain | Subtype |
|---|---|---|---|---|
| 1 | PB2 | 78 | 3793 | H1N1 |
| 2 | PB1 | 79 | 3793 | H1N1 |
| 3 | PA | 80 | 3793 | H1N1 |
| 4 | HA-DO-H1-H3 | 105 | 14-3037 | H1N2-H3N2 |
| 5 | NP | 81 | 3793 | H1N1 |
| 6 | NA-DO | 94 | 0036-2 | H1N2 |
| 7 | M | 82 | 3793 | H1N1 |
| 8 | NS | 83 | 3793 | H1N1 |

TABLE 11

Reverse genetics plasmids for codon deoptimized HA-DO-H1-H3/H1N1 NA-DO virus

| | Segment | SEQ ID NO | Strain | Subtype |
|---|---|---|---|---|
| 1 | PB2 | 78 | 3793 | H1N1 |
| 2 | PB1 | 79 | 3793 | H1N1 |
| 3 | PA | 80 | 3793 | H1N1 |
| 4 | HA-DO-H1-H3 | 105 | 14-3037 | H1N2-H3N2 |
| 5 | NP | 81 | 3793 | H1N1 |
| 6 | NA-DO | 92 | 14-0081-1 | H1N1 |
| 7 | M | 82 | 3793 | H1N1 |
| 8 | NS | 83 | 3793 | H1N1 |

All three viruses were recovered from transfection in HEK cells and passages in MDCK cells. The recovered virus with codon deoptimized HA H1-H3 chimera (SEQ ID NO:105), and codon deoptimized NA segment (H3N2) (SEQ ID NO:96) was designated as vSIV03. In addition, deoptimized NS segment with deoptimized HA and NA segment viruses were recovered with same protocol (Tables 12 & 13).

TABLE 12

Reverse genetics plasmids for codon deoptimized H3 virus

| | Segment | SEQ ID NO | Strain | Subtype |
|---|---|---|---|---|
| 1 | PB2 | 78 | 3793 | H1N1 |
| 2 | PB1 | 79 | 3793 | H1N1 |
| 3 | PA | 80 | 3793 | H1N1 |
| 4 | HA-DO-H1-H3 | 105 | 14-3037 | H1N2-H3N2 |
| 5 | NP | 81 | 3793 | H1N1 |
| 6 | NA-DO | 96 | 14-3037 | H3N2 |
| 7 | M | 82 | 3793 | H1N1 |
| 8 | NS-DO | 90 | 3793 | H1N1 |

TABLE 13

Reverse genetics plasmids for codon deoptimized H3 virus

| | Segment | SEQ ID NO | Strain | Subtype |
|---|---|---|---|---|
| 1 | PB2 | 78 | 3793 | H1N1 |
| 2 | PB1 | 79 | 3793 | H1N1 |
| 3 | PA | 80 | 3793 | H1N1 |
| 4 | HA-DO-H1-H3 | 105 | 14-3037 | H1N2-H3N2 |
| 5 | NP | 81 | 3793 | H1N1 |
| 6 | NA-DO | 92 | 14-0081-1 | H1N1 |
| 7 | M | 82 | 3793 | H1N1 |
| 8 | NS-DO | 90 | 3793 | H1N1 |

By using H1-H3 chimeric HA segment, infectious influenza viruses with codon deoptimized HA, NA segments or codon deoptimized HA, NA, NS segments were successfully recovered and propagated. The recovered virus with codon deoptimized HA H1-H3 chimera (SEQ ID NO:105), codon deoptimized NA (SEQ ID NO:96), and codon deoptimized NS segment (SEQ ID NO:90) was designated as vSIV04.

Accordingly, six (6) sets of eight (8) pHW2000-based, reverse genetics plasmids were used to produce vSIV01, vSIV02, vSIV03, vSIV04, vSIV05 and vSIV06, as described and tested herein. Table 14 summarizes the gene segments used to produce these reassortant SIV.

TABLE 14

Gene segments used to produce vSIV01, vSIV02, vSIV03, vSIV04, vSIV05 and vSIV06

| rgSIV | Subtype | Deoptimized Gene Segments | "TRIG" Gene Segments |
|---|---|---|---|
| vSIV01 | H1N2 | HA-DO (SEQ ID NO: 93); NA-DO (SEQ ID NO: 94) | NS (SEQ ID NO: 83), M (SEQ ID NO: 82), NP (SEQ ID NO: 81), PA (SEQ ID NO: 80), PB1 (SEQ ID NO: 79), PB2 (SEQ ID NO: 78) |
| vSIV02 | H1N2 | HA-DO (SEQ ID NO: 93); NA-DO (SEQ ID NO: 94); NS1-DO (SEQ ID NO: 90) | M (SEQ ID NO: 82), NP (SEQ ID NO: 81), PA (SEQ ID NO: 80), PB1 (SEQ ID NO: 79), PB2 (SEQ ID NO: 78) |
| vSIV03 | H3N2 | HA-DO H1-H3 chimera (SEQ ID NO: 105); NA-DO (H3N2) (SEQ ID NO: 96) | NS (SEQ ID NO: 83), M (SEQ ID NO: 82), NP (SEQ ID NO: 81), PA (SEQ ID NO: 80), PB1 (SEQ ID NO: 79), PB2 (SEQ ID NO: 78) |
| vSIV04 | H3N2 | HA-DO H1-H3 chimera (SEQ ID NO: 105); NA-DO (SEQ ID NO: 96); NS1-DO (SEQ ID NO: 90) | M (SEQ ID NO: 82), NP (SEQ ID NO: 81), PA (SEQ ID NO: 80), PB1 (SEQ ID NO: 79), PB2 (SEQ ID NO: 78) |
| vSIV05 | H1N1 | HA-DO (SEQ ID NO: 91); NA-DO (SEQ ID NO: 92) | NS (SEQ ID NO: 83), M (SEQ ID NO: 82), NP (SEQ ID NO: 81), PA (SEQ ID NO: 80), PB1 (SEQ ID NO: 79), PB2 (SEQ ID NO: 78) |
| vSIV06 | H1N1 | HA-DO (SEQ ID NO: 91); NA-DO (SEQ ID NO: 92); NS1-DO (SEQ ID NO: 90) | M (SEQ ID NO: 82), NP (SEQ ID NO: 81), PA (SEQ ID NO: 80), PB1 (SEQ ID NO: 79), PB2 (SEQ ID NO: 78) |

Example 2—Protection Efficacy of Attenuated Swine Influenza Vaccines in Piglets Against H1N2 Subtype Challenge Materials & Methods.

The study included fifty Yorkshire crossbred pigs consisting of females and castrated males, confirmed SIV ELISA negative, and approximately four weeks of age on Day 0. Piglets were sourced from Midwest Research Swine, Princeton Sow herd. All pigs had full access to a commercial pelleted pig ration suitable for their size and age and had full access to the water supply through automatic drinkers. Piglets were housed by treatment group in different pens within the same room with no nose-to-nose contact.

On Day 0 all animals were vaccinated intranasally (IN) with 2 mL (1 mL each nostril) of their respective test vaccine. On Day 21 all animals were challenged intranasally with 2 mL SIV H1N2 subtype (1 mL each nostril). Appropriate precautions, techniques and safety practices were followed when handling and administering the experimental products. Blood was collected from pigs for serum titer analysis prior to the start of the study for screening purposes and on Days 0, 21 and 26. Nasal swabs were collected from pigs on Days 1, 7, 22, 24 and 26, and used to detect virus replication by qRT-PCR. On Days 21 (pre-challenge) through 26, rectal body temperatures were collected from pigs. Daily General Health Observations were made and recorded from Day −7 to Day 26. Post-challenge clinical observations were made and recorded from Day 22 to Day 26. All lungs were visually accessed for pathology with an estimate of percent consolidation/pneumonic involvement per lung lobe, by a veterinarian that was blinded to treatment assignment as derived from the following formula and recorded in the raw data.

$$\text{Overall Percent Consolidation}=[(\% \, LA*0.05)+(\% \, LC*0.06)+(\% \, LD*0.29)+(\% \, RA*0.11)+(\% \, RC*0.10)+(\% \, RD*0.34)+(\%1*0.05)]*100$$

A sample of the right middle lobe of each lung was fixed in 10% formalin and assessed for immunohistochemistry (IHC) scores. Also, a similar section of each lung was kept fresh and analyzed by RT-PCR testing.

TABLE 15

Experimental Vaccine Details ("DO" = deoptimized sequence); PBS negative control;
challenged with SIV 10-0036-1 051515 (H1N2) at 6.0 log 10 TCID50/mL

| vSIV | Subtype | Surface Genes (SG) | Backbone (IG) | Titer (TCID50/mL) | Genetic analysis | Sterility test |
|---|---|---|---|---|---|---|
| vSIV01 | H1N2 | HA- and NA-DO | TRIG | P.2 = 6.10 (6.03/6.16)H/C | HA, NA, NS confirmed | Pass |
| vSIV02 | H1N2 | HA- and NA-DO | TRIG-NS1 DO | P.2 = 6.09 (6.07/6.12) | HA, NA, NS confirmed | Pass |
| vSIV05 | H1N1 | HA- and NA-DO | TRIG | P.2 = 6.55 (6.49/6.62) | HA, NA, NS confirmed | Pass |
| vSIV06 | H1N1 | HA- and NA-DO | TRIG-NS1 DO | P.2 = 6.59 (6.70/6.49) | HA, NA, NS confirmed | Pass |

TABLE 16

Study Groups

| Group | Vaccine | Dose Volume | Route of Administration | Dose in (log10) in 1 mL | Number of animals | Challenge D21 |
|---|---|---|---|---|---|---|
| 1 | vSIV01 (H1N2.2) | 2 mL | IN | 6.0 | 10 | H1N2 |
| 2 | vSIV02 (H1N2.3) | 2 mL | IN | 6.0 | 10 | H1N2 |
| 3 | vSIV05 (H1N1.2) | 2 mL | IN | 6.0 | 10 | H1N2 |
| 4 | vSIV06 (H1N1.3) | 2 mL | IN | 6.0 | 10 | H1N2 |
| 5 | PBS | 2 mL | IN | N/A | 10 | H1N2 |

Results.

FIG. 1 shows the boxplot showing overall % consolidation by group. For the purpose of obtaining an incidence assessment for pneumonic tissue, a piglet with percent pneumonic tissue scores≥10% was categorized as positive and a piglet with percent pneumonic tissue scores<10% was categorized as negative. Importantly, rgSIV containing deoptimized HA (HA-DO) and NA deoptimized (NA-DO) genes (Groups 1, 2, 3 and 4) provide significant protection from lung lesion, as compared to PBS control.

Moreover, the rgSIV containing HA-DO, NA-DO and NS1-DO (Groups 2 and 4) show a trend of enhanced protection over their corresponding rgSIV having only their HA and NA genes deoptimized (Groups 1 and 3, respectively). It is also important to note that since the challenge strain was virulent H1N2 the rgSIV administered to Groups 1 and 2 were essentially being evaluated for their ability to elicit homologous protection, whereas the rgSIV administered to Groups 3 and 4 were essentially being evaluated for their ability to elicit heterologous protection. This explains, at least in part, why the protection elicited in Group 3 and 4 animals was significant when compared to that elicited in Group 5 animals (i.e. the control group), but not so strong as the protection elicited in Group 1 and 2 animals.

Applicants envision that many different combinations deoptimized HA, NA and/or NS1 may be employed in the practice of the invention. For example, if protection from H1N2 is desired, deoptimized HA, NA, and NS1 may be added to the other five TRIG segments (or even added to another SIV backbone strain, as desired), to produce highly effective attenuated H1N2 deoptimized rgSIV.

TABLE 17

Incidence of positive Pneumonic Tissue score

| Group Name | N | Negative | Positive | P-value (Fisher's Exact Test) | Prevented Fraction (95% CI) |
|---|---|---|---|---|---|
| PBS | 10 | 5 | 5 | 0.0325 | 1.00 |
| vSIV01 | 10 | 10 | 0 | | (0.32, 1.00) |
| PBS | 10 | 5 | 5 | 0.0325 | 1.00 |
| vSIV02 | 10 | 10 | 0 | | (0.32, 1.00) |
| PBS | 10 | 5 | 5 | 0.1409 | 0.80 |
| vSIV05 | 10 | 9 | 1 | | (−0.001, 0.98) |
| PBS | 10 | 5 | 5 | 0.1409 | 0.80 |
| vSIV06 | 10 | 9 | 1 | | (−0.001, 0.98) |

TABLE 18

Viral load

| Vaccine | N | Mean | P-value (Wilcoxon Two-sided Z Test) | Mitigated Fraction (95% CI) |
|---|---|---|---|---|
| PBS | 10 | 162341186 | 0.0002 | 100% |
| vSIV01 | 10 | 32745 | | (100%, 100%) |
| PBS | 10 | 162341186 | 0.0003 | 96% |
| vSIV02 | 10 | 177374 | | (87%, 100%) |
| PBS | 10 | 162341186 | 0.0017 | 84% |
| vSIV05 | 10 | 2084421 | | (61%, 100%) |
| PBS | 10 | 162341186 | 0.0022 | 82% |
| vSIV06 | 10 | 3618562 | | (58%, 100%) |

TABLE 19

Incidences of Positive PCR Results by Group

| Group Name | N | Negative | Positive | P-value (Fisher's Exact Test) | Prevented Fraction (95% CI) |
|---|---|---|---|---|---|
| PBS | 10 | 0 | 10 | 0.0325 | 0.50 |
| vSIV01 | 10 | 5 | 5 | | (0.20, 0.79) |
| PBS | 10 | 0 | 10 | 0.0325 | 0.50 |
| vSIV02 | 10 | 5 | 5 | | (0.20, 0.79) |
| PBS | 10 | 0 | 10 | 1.0000 | 0.10 |
| vSIV05 | 10 | 1 | 9 | | (−0.27, 0.41) |
| PBS | 10 | 0 | 10 | 0.4737 | 0.20 |
| vSIV06 | 10 | 2 | 8 | | (−0.18, 0.55) |

TABLE 20

Incidences Summary Statistics, p-value of the Wilcoxon tests, and Mitigated Fractions for the Comparison of PCR Results of the Vaccinated Groups against the Placebo Group

| Vaccine | N | Mean | P-value (Wilcoxon Two-sided Z Test) | Mitigated Fraction (95% CI) |
|---|---|---|---|---|
| PBS | 10 | 412000 | 0.0002 | 100% |
| vSIV01 | 10 | 763 | | (100%, 100%) |
| PBS | 10 | 412000 | 0.0002 | 100% |
| vSIV02 | 10 | 1029 | | (100%, 100%) |
| PBS | 10 | 412000 | 0.0002 | 100% |
| vSIV05 | 10 | 4588 | | (100%, 100%) |
| PBS | 10 | 412000 | 0.0003 | 96% |
| vSIV06 | 10 | 24586 | | (87%, 100%) |

TABLE 21

Least Square Means (LSM) of SIV Serology by Day and Group

| Day | Vaccine | LSM ± StdErr |
|---|---|---|
| 21 | PBS | 0.93 ± 0.05 |
| | vSIV01 | 0.53 ± 0.05 |
| | vSIV02 | 0.6 ± 0.04 |
| | vSIV05 | 0.49 ± 0.05 |
| | vSIV06 | 0.47 ± 0.05 |
| 26 | PBS | 0.79 ± 0.05 |
| | vSIV01 | 0.43 ± 0.05 |
| | vSIV02 | 0.42 ± 0.04 |
| | vSIV05 | 0.22 ± 0.05 |
| | vSIV06 | 0.23 ± 0.05 |

Conclusions.

The post-challenge lung lesion scores were significantly lower for all treatment groups. Groups vSIV01 and vSIV02 aided in the prevention of lung lesions, whereas Groups vSIV05 and vSIV06 aided in the control of lung lesions. For vSIV01 and vSIV02, the mitigated fraction was 100%, demonstrating a complete protection from homologous challenge. Promisingly, the mitigated fractions of vSIV05 and vSIV06 were 70% and 82%, respectively, showing a significant level of cross-protection from lung lesions against a heterologous challenge. Such levels are unpredictable in view of the state of art understanding at the time Applicants developed the disclosed invention. Finally, no abnormal post-vaccination reactions were observed, including depression and anaphylaxis.

Example 3—Protection Efficacy of Attenuated Swine Influenza Vaccines in Piglets Against H1N1 or H3N2 Subtype Challenge This study was generally conducted using the methods described in Example 2, unless otherwise stated (details summarized in Table 22). Briefly, piglets were allocated to one of six (6) treatment groups using litter as a randomization factor. After vaccination, but before challenge, piglets in Groups 1, 2, 4, and 5 were housed in a separate room(s) (all vaccinates in one/two room(s)) separate from the controls. Pigs from different vaccinate groups did not have nose to nose contact. Groups 1 and 4 were housed together prior to challenge however.

Prior to challenge on Day 21, piglets assigned to Groups 1, 2, and 3 were comingled and housed together and piglets assigned to Groups 4, 5, and 6 were comingled and housed together until the end of the study.

TABLE 22

Study Design

| Group | Vaccine | Challenge | Route | Dose | Frequency | No. of Animals |
|---|---|---|---|---|---|---|
| 1 | Trivalent (MLV IAV vSIV02(H1N2) + vSIV04(H3N2) + vSIV06(H1N1)) | H1N1 | IN | 1 mL | Once on D0 | 10-12 |
| 2 | H1N1 (MLV IAV vSIV06) | H1N1 | IN | 1 mL | Once on D0 | 10-12 |
| 3 | Control (PBS) | H1N1 | IN | 1 mL | Once on D0 | 10-12 |
| 4 | Trivalent (MLV IAV vSIV02(H1N2) + vSIV04(H3N2) + vSIV06(H1N1)) | H3N2 | IN | 1 mL | Once on D0 | 10-12 |
| 5 | H3N2 (MLV IAV vSIV04) | H3N2 | IN | 1 mL | Once on D0 | 10-12 |
| 6 | Control (PBS) | H3N2 | IN | 1 mL | Once on D0 | 10-12 |

In view of the protective efficacy demonstrated by the results presented in Example 2, it was expected that the Group 1, 2, 4 and 5 vaccines would elicit protective immunity that is significantly greater than respective control vaccines, 3 and 6.

Results.

Figure 14:
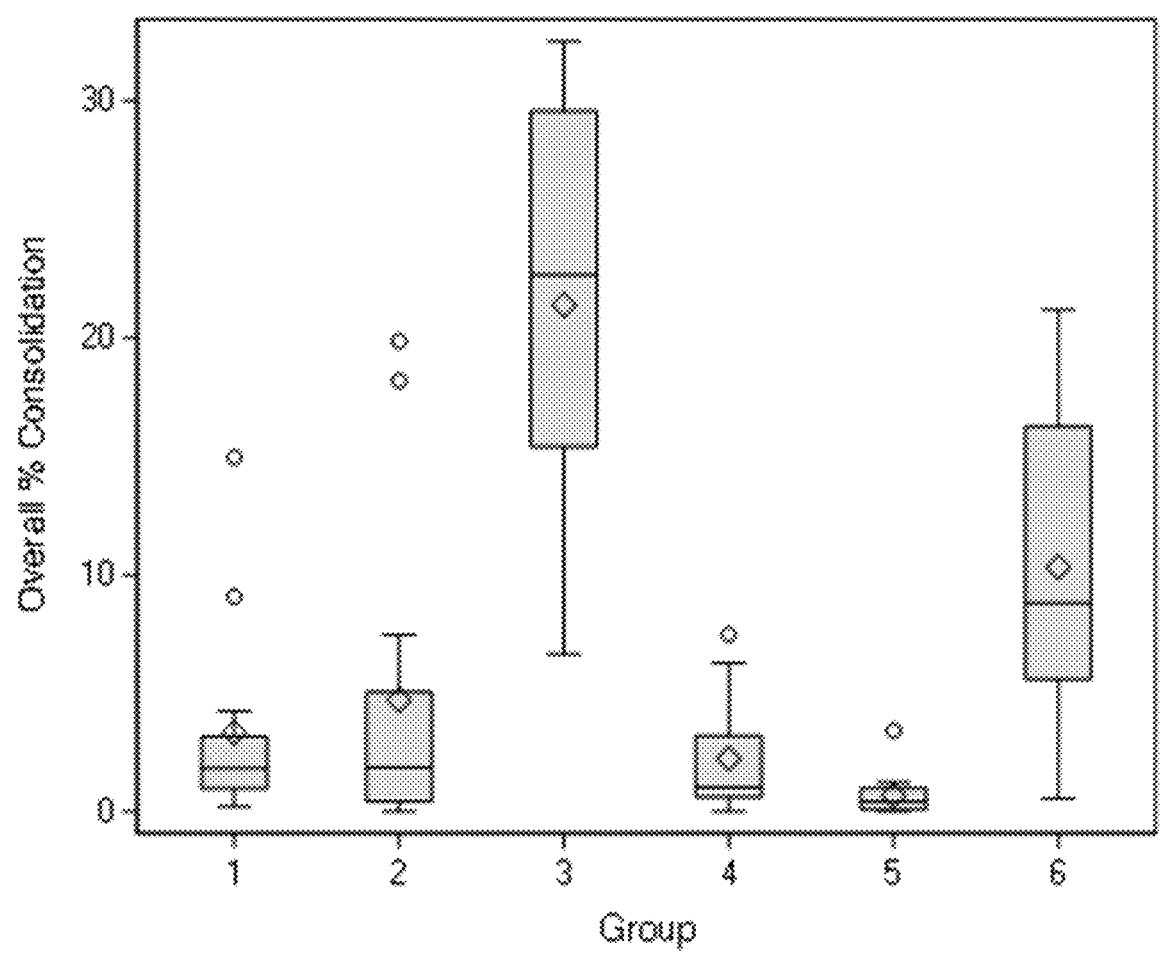
FIG. 14 is a boxplot showing post-challenge lung lesion scores as indicated by overall % consolidation by group.

FIG. 14 shows the boxplot showing overall % consolidation by group.

TABLE 23

P-value of the Wilcoxon test and Mitigated Fractions for the comparison of the overall percent consolidation of Vaccinate Groups against the Control Groups

| Group | Group Name | N | Mean | Min | 25th Pctl | Median | 75th Pctl | Max | P-value (Wilcoxon Two-sided Z Test) | Mitigated Fraction (95% CI) |
|---|---|---|---|---|---|---|---|---|---|---|
| 1 | Trivalent | 12 | 3.3 | 0.2 | 1.0 | 1.8 | 3.2 | 15.0 | 0.0001 | 93% |
| 3 | Control | 12 | 21.4 | 6.7 | 15.4 | 22.6 | 29.6 | 32.5 | | (82%, 100%) |
| 2 | H1N1 | 12 | 4.7 | 0.0 | 0.4 | 1.8 | 5.0 | 19.9 | 0.0005 | 85% |
| 3 | Control | 12 | 21.4 | 6.7 | 15.4 | 22.6 | 29.6 | 32.5 | | (64%, 100%) |
| 4 | Trivalent | 12 | 2.2 | 0.0 | 0.6 | 1.0 | 3.2 | 7.5 | 0.0024 | 74% |
| 6 | Control | 12 | 10.3 | 0.5 | 5.6 | 8.8 | 16.2 | 21.2 | | (44%, 100%) |
| 5 | H3N2 | 12 | 0.7 | 0.0 | 0.1 | 0.4 | 1.0 | 3.4 | 0.0001 | 93% |
| 6 | Control | 12 | 10.3 | 0.5 | 5.6 | 8.8 | 16.2 | 21.2 | | (81%, 100%) |

TABLE 24

P-value of the Wilcoxon test and Mitigated Fractions for the comparison of the microscopic lung IAV lesions of Vaccinate Groups against the Control Groups

| Group | Group Name | N | Mean | Min | 25th Pctl | Median | 75th Pctl | Max | P-value (Wilcoxon Two-sided Z Test) | Mitigated Fraction (95% CI) |
|---|---|---|---|---|---|---|---|---|---|---|
| 1 | Trivalent | 12 | 1.3 | 0.0 | 0.5 | 1.0 | 2.0 | 3.0 | 0.0013 | 74% |
| 3 | Control | 12 | 2.6 | 2.0 | 2.0 | 3.0 | 3.0 | 3.0 | | (49%, 100%) |
| 2 | H1N1 | 12 | 1.4 | 0.0 | 1.0 | 1.0 | 2.0 | 3.0 | 0.0012 | 74% |
| 3 | Control | 12 | 2.6 | 2.0 | 2.0 | 3.0 | 3.0 | 3.0 | | (49%, 100%) |
| 4 | Trivalent | 12 | 1.6 | 0.0 | 1.0 | 1.5 | 2.0 | 3.0 | 0.1984 | 29% |
| 6 | Control | 12 | 2.0 | 1.0 | 2.0 | 2.0 | 2.0 | 3.0 | | (−12%, 71%) |
| 5 | H3N2 | 12 | 0.7 | 0.0 | 0.0 | 0.0 | 1.5 | 2.0 | 0.0015 | 72% |
| 6 | Control | 12 | 2.0 | 1.0 | 2.0 | 2.0 | 2.0 | 3.0 | | (46%, 99%) |

TABLE 25

P-value of the Wilcoxon test and Mitigated Fractions for the comparison of the lung IAV IHC Score of Vaccinate Groups against the Control Groups

| Group | Group Name | N | Mean | Min | 25th Pctl | Median | 75th Pctl | Max | P-value (Wilcoxon Two-sided Z Test) | Mitigated Fraction (95% CI) |
|---|---|---|---|---|---|---|---|---|---|---|
| 1 | Trivalent | 12 | 1.1 | 0.0 | 0.0 | 1.0 | 2.0 | 3.0 | 0.0142 | 58% |
| 3 | Control | 12 | 2.2 | 1.0 | 1.5 | 2.0 | 3.0 | 3.0 | | (24%, 91%) |
| 2 | H1N1 | 12 | 0.9 | 0.0 | 0.5 | 1.0 | 1.0 | 2.0 | 0.0019 | 72% |
| 3 | Control | 12 | 2.2 | 1.0 | 1.5 | 2.0 | 3.0 | 3.0 | | (46%, 97%) |
| 4 | Trivalent | 12 | 1.0 | 0.0 | 0.5 | 1.0 | 1.5 | 2.0 | 0.7888 | −6% |
| 6 | Control | 12 | 0.9 | 0.0 | 0.0 | 1.0 | 1.0 | 2.0 | | (−47%, 35%) |
| 5 | H3N2 | 12 | 0.5 | 0.0 | 0.0 | 0.0 | 1.0 | 2.0 | 0.0815 | 39% |
| 6 | Control | 12 | 0.9 | 0.0 | 0.0 | 1.0 | 1.0 | 2.0 | | (−4%, 81%) |

TABLE 26

P-value of the Fisher's exact test and Prevented Fractions
for the comparison of the incidence of viral load in the nasal passage,
post-challenge of Vaccinate Groups against the Control Groups

| Group | Group Name | N | Negative | Positive | P-value (Fisher's exact test) | Prevented Fraction (95% CI) |
|---|---|---|---|---|---|---|
| 1 | Trivalent | 12 | 9 | 3 | 0.0003 | 75% |
| 3 | Control | 12 | 0 | 12 | | (45%, 93%) |
| 2 | H1N1 | 12 | 8 | 4 | 0.0013 | 67% |
| 3 | Control | 12 | 0 | 12 | | (38%, 88%) |
| 4 | Trivalent | 12 | 5 | 7 | 0.0373 | 42% |
| 6 | Control | 12 | 0 | 12 | | (14%, 71%) |
| 5 | H3N2 | 12 | 9 | 3 | 0.0003 | 75% |
| 6 | Control | 12 | 0 | 12 | | (45%, 93%) |

Conclusions.

A significant vaccine effect was observed for gross lung lesions for both monovalent vaccines and the trivalent vaccine when compared to the control groups. This was also true for microscopic lesions with the exception of the Group 4 (Trivalent/H3N2 Challenge) which did not show a significant decrease. The score was lower in this group compared to the control group and could be a product of selection bias, however this observation is consistent with the IHC scores observed in the same group described below.

For lung colonization, there was a significant vaccine effect observed with Groups 1 and 2 when compared to the control group challenged with H1N1. A vaccine affect was not observed in Groups 4 and 5 when compared with the controls challenged with H3N2. For nasal shedding, a significant vaccine effect was observed in all vaccinated groups which prevented shedding when compared to the controls. For groups receiving an H1N1 challenge, the clinical respiratory character was lower in the vaccinates than the controls in 4 of 6 observation days. For those groups receiving H3N2 challenge the clinical respiratory character was lower in the vaccinates in 2 of 6 observation days. Depression scores were lower in vaccinates receiving H1N1 challenge when compared to controls, however, for those receiving H3N2 challenge depression was observed in very few pigs and therefore cannot be adequately assessed. Temperatures post-challenge were lower in all vaccinated groups when compared to controls. Finally, no abnormal post-vaccination reactions were observed, including depression and anaphylaxis.

Example 4—Development and Implementation of Sentinel Model for Evaluating Effect of Vaccination on Challenge Virus Transmission This study is generally conducted using the methods described in Example 3, with the addition of positive control sentinel animal comingling, unless otherwise stated (details summarized in Table 27).

In order to evaluate actual virus transmission, instead of merely measuring virus shed (e.g. via nasal swabs and virus detection), it was necessary to develop a Sentinel Model. Applicants contemplated that it could not be predicted with certainty whether the optimal conditions would be produced by comingling control and vaccinated animals with sentinels immediately post challenge, or sometime after challenge. Understanding that peak SIV shedding normally occurred at about 48 hours post exposure to a virulent challenge SIV strain, Applicants reasoned that a good time to begin comingling would be from about 12 hours to about 36 hours. A 24 hour delay was selected for this study. This delay in comingling would allow the challenge virus a sufficient time to be absorbed and dispersed into the housing environment. Alternatively, the animals may be comingled immediately after challenge.

TABLE 27

Study Design - Sentinel Model Conditions

| Group | Vaccine | Challenge | Room placement after challenge |
|---|---|---|---|
| 1 | Trivalent (MLV IAV vSIV02(H1N2) + vSIV04(H3N2) + vSIV06(H1N1)) | H1N1 | 1 |
| 2 | Transmission Negative Control Sentinel (no vaccine; PBS only) | — | 1 |
| 3 | Trivalent (MLV IAV vSIV02(H1N2) + vSIV04(H3N2) + vSIV06(H1N1)) | — | 2 |
| 4 | Transmission Positive Control Sentinel (no vaccine; PBS only) | H1N1 | 2 |
| 5 | H1N1 (MLV IAV vSIV06) | H1N1 | 3 |
| 6 | Transmission Negative Control Sentinel (no vaccine; PBS only) | — | 3 |
| 7 | H1N1 (MLV IAV vSIV06) | — | 4 |
| 8 | Transmission Positive Control Sentinel (no vaccine; PBS only) | H1N1 | 4 |
| 9 | Trivalent (MLV IAV vSIV02(H1N2) + vSIV04(H3N2) + vSIV06(H1N1)) | H3N2 | 5 |
| 10 | Transmission Negative Control Sentinel (no vaccine; PBS only) | — | 5 |
| 11 | Trivalent (MLV IAV vSIV02(H1N2) + vSIV04(H3N2) + vSIV06(H1N1)) | — | 6 |
| 12 | Transmission Positive Control Sentinel (no vaccine; PBS only) | H3N2 | 6 |
| 13 | H3N2 (MLV IAV vSIV04) | H3N2 | 7 |
| 14 | Transmission Negative Control Sentinel (no vaccine; PBS only) | — | 7 |
| 15 | H3N2 (MLV IAV vSIV04) | — | 8 |
| 16 | Transmission Positive Control Sentinel (no vaccine; PBS only) | H3N2 | 8 |

Vaccines are demonstrated to reduce transmission in the following cases:

(a) Comingled Groups 1 & 2

Now that Applicants have developed this approach, any number of vaccines may be tested for their ability to reduce challenge virus transmission. The important difference between the Sentinel Model study design and the study designs disclosed in Examples 2 and 3 is the inclusion of the positive control group (i.e. for each vaccine, there are 2 groups per airspace/housing environment). This feature, along with the option to delay the time between challenge and comingling, allows the Sentinel Model to measure the impact of any SIV vaccine on virus transmission.

Example 5—Genetic Stability of the Modified Live Vaccines

Objective.

To evaluate the genetic stability of the modified live vaccine following in vivo co-inoculation with wild-type virus and assess the potential occurrence of VAERD in pigs using an IAV vaccine. Table 28 presents the overall study design.

Primary Variables.

The following were evaluated: 1) genetic stability of the codon de-optimized HA, NA and NS1 genes of the vaccine virus recovered following in vivo passage of the co-inoculated vaccine and challenge viruses; 2) Vaccine Associated Enhanced Respiratory Disease (VAERD) based on assessment of lung lesions and viral shedding from pigs receiving the MLV IAV vaccine following in vivo passage; and 3) efficacy of the test vaccines.

Vaccination & Challenge.

Piglets received 2 doses of the vaccine in the right nare on Day 0 and on Day 21. All piglets received a dose of the appropriate challenge material in the left nare on Day 21.

Daily Clinical Observations: All piglets were observed daily for general well-being and signs of IAV disease (fever, lethargy, dyspnea).

TABLE 28

Study Design

| Group | No. Animals | Vaccination | Route | Frequency | Dose Vol. | Challenge |
|---|---|---|---|---|---|---|
| 1 | 10 | H1N1 | IN | Days 0 & 21 | 1 mL | H1N1 |
| 2 | 10 | H1N2 | IN | Days 0 & 21 | 1 mL | H1N1 |
| 3 | 10 | Placebo | IN | Days 0 & 21 | 1 mL | H1N1 |
| 4 | 10 | H3N2 | IN | Days 0 & 21 | 1 mL | H3N2 |
| 5 | 10 | Placebo | IN | Days 0 & 21 | 1 mL | H3N2 |

Example 6—In Vitro Genetic Stability of the Modified Live Vaccines

Vaccines were serially passed in ST cells and as indicated in Table 29, vSIV01, 02, 05 and 06 remained quite stable.

TABLE 29

Sequence analysis indicated that the vSIV remained stable after 10 passages in ST cells

| Gene | vSIV01 | vSIV02 | VSIV05 | vSIV06 |
|---|---|---|---|---|
| HA | No change | No change | No change | 1 nt/aa |
| NA | No change | No change | No change | No change |
| NS | No change | No change | No change | No change |

Example 7—Vaccines Formulated as Fine-Grained Powders

Three Master Seed Viruses (MSVs), SIV02 (H1N2), SIV 04 (H3N2) and SIV06 (H1N1), were generated on canine cell line MDCK. Viruses were combined with stabilizing components and lyophilized and/or vitrified using previously-described techniques (see e.g. US 2013/0040370 & US 2016/0256554, both to Merial, Inc.). The desiccated biological materials were then subjected to milling to produce a fine-grained powder. The powders were assayed for stability over time.

TABLE 30

Stability of monovalent SIV04 (H3N2), formulated as a powder

| Harvest Titer SIV-04 H3N2 | Blend Titer Pre-Lyo | Post Lyo Process/Post Mill | Storage Conditions | Stability 1 month | Stability 2 month |
|---|---|---|---|---|---|
| Pre Blend 7.5 $TCID_{50}$ | 7.0 $TCID_{50}$ | 7.0 $TCID_{50}$ | 4° C. | 7.0 $TCID_{50}$ | 7.16 $TCID_{50}$ |

TABLE 31

Stability of trivalent SIV02 (H1N2) SIV04 (H3N2) SIV06 (H1N1), formulated as a powder

| Harvest Titer Trivalent Formulation | Blend Titer Pre-Lyo | Post Lyo Process (no loss) | Storage Conditions | Stability 1 month | Stability 2 month | Stability 3 month |
|---|---|---|---|---|---|---|
| Pre Blend ~7.4 $TCID_{50}$ | 6.4 $TCID_{50}$ | 6.5 $TCID_{50}$ | 4° C. | 6.5 $TCID_{50}$ | 6.5 $TCID_{50}$ | 6.2 $TCID_{50}$ |

Accordingly, immunological compositions of the present invention are stable when formulated as a dry, fine-grained powder.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A vaccine comprising a pharmaceutically or veterinary acceptable vehicle, diluent or excipient and an effective amount of an attenuated swine influenza virus (SIV), wherein the SIV comprises:
   a) an HA gene segment having at least 90% sequence identity to SEQ ID NO: 93, and an NA gene segment having at least 90% sequence identity to SEQ ID NO: 94, or
   b) an HA gene segment having at least 90% sequence identity to SEQ ID NO: 93, an NA gene segment having at least 90% sequence identity to SEQ ID NO: 94, and an NS1 gene segment having at least 90% sequence identity to SEQ ID NO: 90, or
   c) an HA gene segment having at least 90% sequence identity to SEQ ID NO: 105, and an NA gene segment having at least 90% sequence identity to SEQ ID NO: 96, or
   d) an HA gene segment having at least 90% sequence identity to SEQ ID NO: 105, an NA gene segment having at least 90% sequence identity to SEQ ID NO: 96, and an NS1 gene segment having at least 90% sequence identity to SEQ ID NO: 90, or
   e) an HA gene segment having at least 90% sequence identity to SEQ ID NO: 91, and an NA gene segment having at least 90% sequence identity to SEQ ID NO: 92, or
   f) an HA gene segment having at least 90% sequence identity to SEQ ID NO: 91, an NA gene segment having at least 90% sequence identity to SEQ ID NO: 92, and an NS1 gene segment having at least 90% sequence identity to SEQ ID NO: 90.

2. A vaccine comprising a pharmaceutically or veterinary acceptable vehicle, diluent or excipient and an effective amount of an attenuated swine influenza virus (SIV), wherein the SIV comprises:
   a) an HA gene segment having SEQ ID NO: 93, and an NA gene segment having SEQ ID NO: 94, or
   b) an HA gene segment having SEQ ID NO: 93, an NA gene segment having SEQ ID NO: 94, and an NS1 gene segment having least 90% sequence identity to SEQ ID NO: 90, or
   c) an HA gene segment having SEQ ID NO: 105, and an NA gene segment having SEQ ID NO: 96, or
   d) an HA gene segment having SEQ ID NO: 105, an NA gene segment having SEQ ID NO: 96, and an NS1 gene segment having least 90% sequence identity to SEQ ID NO: 90, or
   e) an HA gene segment having least 90% sequence identity to SEQ ID NO: 91, and an NA gene segment having SEQ ID NO: 92, or
   f) an HA gene segment having SEQ ID NO: 91, an NA gene segment having SEQ ID NO: 92, and an NS1 gene segment having SEQ ID NO: 90.

3. The vaccine according to claim 2 comprising SIV a).
4. The vaccine according to claim 2 comprising SIV b).
5. The vaccine according to claim 2 comprising SIV c).
6. The vaccine according to claim 2 comprising SIV d).
7. The vaccine according to claim 2 comprising SIV e).
8. The vaccine according to claim 2 comprising SIV f).
9. The vaccine according to claim 1 wherein SIV a), c) and e) further comprise an NS gene segment having SEQ ID NO:83, an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.
10. The vaccine according to claim 2 wherein SIV a), c) and e) further comprise an NS gene segment having SEQ ID NO:83, an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78; or, wherein the SIV comprises vSIV01, vSIV03, or vSIV05.
11. The vaccine according to claim 3 wherein SIV a) further comprises an NS gene segment having SEQ ID NO:83, an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.
12. The vaccine according to claim 5 wherein SIV c) further comprises an NS gene segment having SEQ ID NO:83, an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.

13. The vaccine according to claim 7 wherein SIV e) further comprises an NS gene segment having SEQ ID NO:83, an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.

14. The vaccine according to claim 1 wherein SIV b), d) and f) further comprise an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.

15. The vaccine according to claim 2 wherein SIV b), d) and f) further comprise an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78; or wherein the SIV comprises vSIV02, vSIV04, or vSIV06.

16. The vaccine according to claim 4 wherein SIV b) further comprises an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.

17. The vaccine according to claim 6 wherein SIV d) further comprises an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.

18. The vaccine according to claim 8 wherein SIV f) further comprises an M gene segment having SEQ ID NO:82, an NP gene segment having SEQ ID NO:81, a PA gene segment having SEQ ID NO:80, a PB1 gene segment having SEQ ID NO:79, and a PB2 gene segment having SEQ ID NO:78.

19. The vaccine of claim 1, further comprising at least one additional antigen associated with or derived from a porcine pathogen other than swine influenza.

20. The vaccine of claim 19, wherein the at least one or more additional antigen(s) is capable of eliciting in a porcine an immune response against *Mycoplasma hyopneumoniae* (*M hyo*), porcine circovirus 2 (PCV2), or porcine respiratory and reproductive syndrome virus (PRRSV).

21. The vaccine of claim 1, further comprising an adjuvant.

22. The vaccine of claim 20, further comprising an adjuvant.

23. A method of eliciting a protective immune response in a porcine subject comprising administering to the porcine subject a prophylactically or therapeutically effective dose of the vaccine of claim 1.

24. A method of eliciting a protective immune response in a porcine subject comprising administering to the porcine subject a prophylactically or therapeutically effective dose of the vaccine of claim 21.

25. A method of vaccinating a porcine animal comprising at least one administration of the vaccine of claim 1.

26. The method of claim 25, wherein the porcine animal is a sow from about 3 weeks to about 6 weeks prefarrowing.

27. The method of 26, wherein the resulting piglets have a reduced morbidity and/or mortality as compared to piglets coming from unvaccinated sows.

28. A vaccine according to claim 1, wherein the vaccine comprises a bivalent vaccine comprising
 (i) (1) SIV e) or SIV f) and (2) SIV c) or SIV d), or
 (ii) (1) SIV a) or SIV b) and (2) SIV c) or SIV d), or
 (iii) (1) SIV e) or SIV f) and (2) SIV c) or SIV d) and (3) SIV a) or SIV b), or
 (iv) (1) vSIV05 or vSIV06 and (2) vSIV03 or vSIV04, or
 (v) (1) vSIV01 or vSIV02 and (2) vSIV03 or vSIV04, or
 (vi) (1) vSIV05 or vSIV06, (2) vSIV03 or vSIV04, and (3) vSIV01 or vSIV02.

29. A composition for producing the vaccine of claim 1 comprising:
 (A) vectors comprising (i) the HA gene segment operably linked to a promoter, and (ii) the NA gene segment operably linked to a promoter, or
 (B) vectors comprising (i) the HA gene segment operably linked to a promoter, (ii) the NA gene segment operably linked to a promoter, (iii) the NS gene segment operably linked to a promoter, (iv) the M gene segment operably linked to a promoter, (v) the NP gene segment operably linked to a promoter, (vi) the PA gene segment operably linked to a promoter, (vii) the PB1 gene segment operably linked to a promoter, and (viii) the PB2 gene segment operably linked to a promoter, or
 (C) vectors comprising (i) the HA gene segment operably linked to a promoter, (ii) the NA gene segment operably linked to a promoter, and, (iii) the NS gene segment operably linked to a promoter.

30. A method of preparing an attenuated swine influenza virus (SIV) vaccine strain, comprising: contacting a cell with an amount of the composition of claim 28 that is effective to yield reassortant, attenuated, infectious influenza virus particles.

31. An isolated cell comprising the composition of claim 28.

* * * * *